US009783804B2

(12) United States Patent
Burnett et al.

(10) Patent No.: US 9,783,804 B2
(45) Date of Patent: Oct. 10, 2017

(54) COMPOSITIONS AND METHODS FOR INHIBITION OF NUCLEIC ACIDS FUNCTION

(71) Applicant: LIFE TECHNOLOGIES CORPORATION, Carlsbad, CA (US)

(72) Inventors: Christopher Burnett, Austin, TX (US); Nitin Puri, Pleasanton, CA (US); Susan Magdaleno, Austin, TX (US); Alexander Vlassov, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/217,007

(22) Filed: Jul. 22, 2016

(65) Prior Publication Data

US 2017/0009232 A1    Jan. 12, 2017

Related U.S. Application Data

(62) Division of application No. 14/564,573, filed on Dec. 9, 2014, now Pat. No. 9,410,153, which is a division of application No. 13/085,878, filed on Apr. 13, 2011, now Pat. No. 9,145,556.

(60) Provisional application No. 61/323,664, filed on Apr. 13, 2010, provisional application No. 61/430,005, filed on Jan. 5, 2011.

(51) Int. Cl.
| A61K 31/70 | (2006.01) |
| C07H 21/02 | (2006.01) |
| C07H 21/04 | (2006.01) |
| C12N 15/113 | (2010.01) |
| C12N 15/11 | (2006.01) |
| A61K 31/713 | (2006.01) |
| A61K 47/48 | (2006.01) |
| C12N 5/00 | (2006.01) |

(52) U.S. Cl.
CPC .......... *C12N 15/113* (2013.01); *A61K 31/713* (2013.01); *A61K 47/48* (2013.01); *C12N 15/111* (2013.01); *C12N 2310/113* (2013.01); *C12N 2310/141* (2013.01); *C12N 2310/321* (2013.01); *C12N 2310/322* (2013.01); *C12N 2310/3231* (2013.01); *C12N 2310/332* (2013.01); *C12N 2310/3515* (2013.01); *C12N 2310/3519* (2013.01); *C12N 2310/51* (2013.01); *C12N 2310/531* (2013.01); *C12N 2330/31* (2013.01)

(58) Field of Classification Search
None
See application file for complete search history.

(56) References Cited

U.S. PATENT DOCUMENTS

| 5,500,357 A * | 3/1996 | Taira .................... C12N 15/113 |
| | | 435/252.3 |
| 5,919,965 A | 7/1999 | Gentles et al. |
| 7,217,807 B2 | 5/2007 | Bentwich |
| 7,232,806 B2 | 6/2007 | Tuschl et al. |
| 7,307,067 B2 | 12/2007 | Sarnow et al. |
| 7,575,863 B2 | 8/2009 | Chen et al. |
| 7,592,435 B2 | 9/2009 | Milton et al. |
| 7,592,441 B2 | 9/2009 | Bentwich et al. |
| 7,595,301 B2 | 9/2009 | Kunugiza et al. |
| 7,683,036 B2 | 3/2010 | Esau et al. |
| 7,687,616 B1 | 3/2010 | Bentwich et al. |
| 7,709,616 B2 | 5/2010 | Bentwich et al. |
| 7,723,030 B2 | 5/2010 | Croce et al. |
| 7,723,510 B1 | 5/2010 | Tuschl et al. |
| 7,759,319 B2 | 7/2010 | Lollo et al. |
| 7,759,478 B1 | 7/2010 | Bentwich |
| 7,777,022 B2 | 8/2010 | Bentwich et al. |
| 7,795,419 B2 | 9/2010 | Bentwich et al. |
| 7,838,658 B2 | 11/2010 | MacLachlan et al. |
| 8,241,854 B2 | 8/2012 | Yin et al. |
| 9,145,556 B2 | 9/2015 | Burnett et al. |
| 9,410,153 B2 | 8/2016 | Burnett et al. |
| 2003/0143732 A1 | 7/2003 | Fosnaugh et al. |
| 2004/0058886 A1 | 3/2004 | Scaringe |
| 2005/0261218 A1 | 11/2005 | Esau et al. |
| 2006/0211000 A1 | 9/2006 | Sorge et al. |
| 2006/0223777 A1 | 10/2006 | Vermeulen et al. |
| 2007/0065840 A1 | 3/2007 | Naguibneva et al. |
| 2008/0085869 A1 | 4/2008 | Yamada et al. |
| 2009/0092980 A1 | 4/2009 | Arenz et al. |
| 2009/0136957 A1 | 5/2009 | Ivanovska et al. |
| 2010/0035233 A1 | 2/2010 | Yin et al. |
| 2011/0130327 A1 | 6/2011 | Houston, Jr. et al. |
| 2011/0190445 A1 | 8/2011 | Anro et al. |

FOREIGN PATENT DOCUMENTS

| WO | WO 94/01550 | 1/1994 |
| WO | WO 95/06731 | 3/1995 |
| WO | WO 2004/015075 | 2/2004 |

(Continued)

OTHER PUBLICATIONS

Bolcato-Bellemin et al., "Sticky Overhangs Enhance siRNA-Mediated Gene Silencing", *Proceedings of the National Academy of Sciences*, vol. 104, No. 41, Oct. 9, 2007, 16050-16055.

(Continued)

*Primary Examiner* — Sean McGarry

(57) ABSTRACT

The invention relates generally to compositions and methods for inhibiting the function of target nucleic acids by sequence specific binding. The compositions and methods can be used for inhibition of micro RNAs and other relatively short non-coding RNAs.

20 Claims, 32 Drawing Sheets

(56) References Cited

FOREIGN PATENT DOCUMENTS

| WO | WO 2005/013901 | 2/2005 |
|----|----|----|
| WO | WO 2005/054494 | 6/2005 |
| WO | WO 2005/079397 | 9/2005 |
| WO | WO 2005/111238 | 11/2005 |
| WO | WO 2007/095387 | 8/2007 |
| WO | WO 2007/143086 | 12/2007 |
| WO | WO 2010/033247 | 3/2010 |
| WO | WO 2011/130371 | 10/2011 |

OTHER PUBLICATIONS

Boutla et al., "Developmental Defects by Antisense-Mediated Inactivation of Micro-RNAs 2 and 13 in *Drosophila* and the Identification of Putative Target Genes", *Nucleic Acids Research*, vol. 31, No. 17, Sep. 1, 2003, 4793-4980.
Clusel et al., "Ex Vivo Regulation of Specific Gene Expression by Nanomolar Concentration ofDouble-Stranded Dumbbell Oligonucleotides", *Nucleic Acids Research*, vol. 21, No. 15, Jul. 25, 1993, 3405-3411.
Davis et al., "Improved Targeting of miRNA with Antisense Oligonucleotides", *Nucleic Acids Research*, vol. 34, No. 8, May 2006, 2294-2304.
Ebert et al., "MicroRNA Sponges: Competitive Inhibitors of Small RNAs in Mammalian Cells", *Nature Methods*, vol. 4, No. 9, Sep. 2007, 721-726.
Elmen et al., "LNA-Mediated MicroRNA Silencing in Non-Human Primates", *Nature*, vol. 452, No. 7189, Apr. 17, 2008, 896-899.
EP11715836.0, Examination Report dated May 16, 2014, 1-5.
EP11715836.0, Examination Report dated, Mar. 20, 2013, 1-6.
Esau et al., "MicroRNA-143 Regulates Adipocyte Differentiation", *The Journal of Biological Chemistry*, vol. 279, No. 50, Dec. 10, 2004, 52361-52365.
Esau et al., "mIR-122 Regulation of Lipid Metabolism Revealed by In Vivo Antisense Targeting", *Cell Metabolism*, vol. 3, No. 4, Feb. 2006, 87-89.
Grimm, "Small silencing RNAs: State-of-the-art", *Advanced Drug Delivery Reviews*, vol. 61, No. 9, Jul. 25, 2009, 672-703.
Horwich, et al., "Design and Delivery of Antisense Oligonucleotides to Block microRNA Function in Cultured *Drosophila* and Human Cells", *Nature Protocol*, vol. 3, No. 10, Jan. 1, 2008, 1537-1549.
Hutvagner, et al., "Sequence-Specific Inhibition of Small RNA Function", *PLoS Biology Journal*, vol. 2, No. 4, Apr. 2004, 465-475.
Intl PCT/US2011/032257, International Preliminary Report on Patentability dated Oct. 26, 2012, 1-7.
Intl PCT/US2011/032257, International Search Report dated Aug. 4, 2011, 1-5.
Intl PCT/US2011/032257,Written Opinion dated Aug. 4, 2011, 1-5.
Jinek et al., "A Three-Dimensional View of the Molecular Machinery of RNA Interference", *Nature*, vol. 457, No. 7228, Jan. 22, 2009, 405-412.
Krutzfeldt et al., "Specificity, Duplex Degradation and Subcellular Localization of Antogomirs", *Nucleic Acids Research*, vol. 35, No. 9, May 2007, 2885-2892.
Lecellier et al., "A Cellular MicroRNA Mediates Antiviral Defense in Human Cells", *Science*, vol. 308, No. 5721, Apr. 22, 2005, 557-560.
Meister et al., "Sequence-Specific Inhibition of MicroRNA- and siRNA-Induced RNA Silencing", *RNA*, vol. 10, No. 3, Mar. 2004, 544-550.
Pils et al., "Flexible non-nucleotide linkers as loop replacements in short double helical RNAs", *Nucleic Acids Research*, vol. 28, No. 9, May 1, 2000, 1859-1863.
Vermeulen et al., "Double-Stranded Regions are Essential Design Components of Potent Inhibitors of RISC Function", *RNA*, vol. 13, No. 5, with Supp Material, May 2007, 723-730.

\* cited by examiner

COMPOSITIONS AND METHODS FOR INHIBITION OF NUCLEIC ACIDS FUNCTION

This application is a divisional of U.S. application Ser. No. 14/564,573 filed Dec. 9, 2014, which is divisional of U.S. application Ser. No. 13/085,878 filed Apr. 13, 2011 (now U.S. Pat. No. 9,145,556), which is a non provisional of and claims the benefit of U.S. Provisional Application Nos. 61/323,664 filed Apr. 13, 2010 and 61/430,005 filed Jan. 5, 2011. The priority applications are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Apr. 4, 2011, is named LT0183US.txt and is 77,601 bytes in size.

FIELD OF THE INVENTION

The invention relates generally to compositions and methods for inhibiting the function of target nucleic acids by sequence specific binding. The compositions and methods can be used for inhibition of micro RNAs and other short non-coding RNAs.

BACKGROUND INFORMATION

Recent evidence suggests that the human transcriptome is not only significantly larger than previously recognized but also it is primarily composed of functional RNA transcripts which are not translated into proteins known as non-coding RNAs (ENCODE Project Consortium, Nature 2007, v. 447, p. 799-816). Among the more intensely studied class of endogenously expressed non-coding RNAs are the microRNAs (miRNAs). Mature miRNAs are relatively small (21-23 nucleotides) RNA duplexes that act as translational repressors of protein expression. The guide strand of a miRNA unites with Argonaute family proteins (Ago) to form RNA-Induced Silencing Complexes (RISC) in the cell. These sequence-specific ribonucleoprotein complexes bind target mRNAs typically in the 3'UTR and can subsequently silence gene expression either through directed mRNA degradation or by simply sequestering the target mRNA in an ineffectual form (Lee et al., *Cell* 1993, v. 75, p. 843-854; Bartel, *Cell* 2009 v. 136, p. 215-233). It has been demonstrated that miRNA based regulation plays a significant role in routine cellular processes including metabolism (Esau et al, *Cell Met.* 2006, v. 3, p 87-98), development (Carthew et al., *Cell* 2009, v. 137, p. 273-282), and even apoptosis (Cheng et al, *Nucl. Acids Res.* 2005, v. 33, p 1290-1297). Further research has revealed that miRNAs play critical roles in diverse disease processes such as hepatitis C (Jopling et al., *Science* 2005, v. 309, p. 1577-1581), diabetes (Poy et al., *Nature* 2004, v. 432, p. 226-230), and most notably multiple cancer types (Hammond, Can. Chemo. Pharma. 2006 v. 58, s63-s68; Calin et al., *Cancer Res.* 2006, v. 66, p. 7390-7394) including leukemia (Calin et al., *PNAS* 2002, v. 101, p. 2999-3004) and glioma (Corsten et al., *Cancer Res.* 2007, v. 67, p. 8994-9000). In addition, miRNA discovery has far surpassed miRNA phenotypic identification thus creating a "validation gap" for miRNA function (Griffiths-Jones et al., *Nucl. Acids Res.* 2006, v. 34, p. D141-D144). Over one thousand miRNAs have now been identified in animals, but only a few individual miRNAs have been linked to specific functions.

Given the range and degree of effects that miRNAs have on cellular processes and that a single miRNA can modulate multiple gene products (Selbach et al., *Nature* 2008, v. 455, p. 58-63), miRNAs have become attractive targets both for loss of function studies in vitro (to study miRNA function and mechanism) and potential therapeutic applications in vivo. To this end, research groups both public and private have sought to develop highly potent miRNA inhibitors (antisense oligos which bind to complementary miRNAs and selectively block silencing in cell extracts, in cultured cells, and in vivo) by utilizing one of three basic approaches: (i) antisense (AS)-based oligonucleotides that employ chemically modified sugars, bases, phosphate backbones, and/or terminal conjugates (Krutzfeldt et al., *Nucl. Acids Res.* 2007 v. 35, p. 2885-2892, Horwich et al., *Nat. Protocols,* 2008 v. 3, p. 1537-1549, Davis et al., *Nucl. Acids Res.* 2006, v. 34, p. 2294-2304); (ii) long (>34 nucleotides) oligonucleotides wherein the reverse complement (AS) strand to the miRNA is flanked on both the 3' and 5' end with 12-16 nucleotides which are intended to form hairpin loops (Vermeulen et al., *RNA* 2007, v. 13, p. 723-730); and (iii) Tandemic antisense RNA produced from DNA vectors with multiple miRNA binding sites per unit which behave as decoy targets for endogenous miRNAs ("miRNA sponges", Ebert et al, *Nature Methods* 2007, v. 4, p. 721-726). Further, 2'O-Me oligonucleotides have been produced to be resistant to cleavage by RISC and other cellular ribonucleases (Hutvágner, et al., *PloS Biol.* 2004, v. 2, p. E98; Meister, et al., *RNA* 2004, v. 10, p. 544-550). Oligonucleotides have also been made that combine 2'-deoxy and locked nucleic acid (LNA) nucleotides (Lecellier et al., *Science* 2005, v. 308, p. 557-560). Oligonucleotides have been made that contain all 2'-O-methoxyethyl nucleotides and oligonucleotides incorporating pyrimidines bearing 2'-O-fluoromodifications (Essau et al., *Cell Metab.* 2006, v. 3, p. 87-89; Davis et al, *Nucleic Acids Res.* 2006, v. 34, p. 2294-2304). Further, nuclease resistant phosphorothioate backbone linkages in combination with ribose modifications have also been employed in cultured cells and in vivo in mice and non-human primates (Essau et al., *Cell Metab.* 2006, v. 3, p. 87-89; Elmén et al., *Nature,* 2008, v. 452, p. 896-899).

Life Technologies currently offers miRNA inhibitors with proprietary modifications (AntiMiRs), Exiqon offers LNA-modified short antisense inhibitors, and Dharmacon/ThermoFisher offers 2'-OMe antisense inhibitors with hairpin structure motifs at both the 3' and 5' ends (>55 nt). The invention discussed herein offers several novel and unique designs for miRNA inhibitors that enable superior miRNA inhibition.

SUMMARY OF THE INVENTION

This disclosure provides compositions and methods for inactivating nucleic acid molecules. Methods of the invention involve, in part, the use of molecules with nucleic acid regions with sequence complementarity to the nucleic acid molecules which is the subject of desired inactivation (i.e., a target nucleic acid molecule). Methods of the invention can be used for inactivation of relatively short regulatory non-coding RNAs, such as micro RNAs (miRNAs), Piwi-interacting RNAs (piRNAs), snoRNAs, snRNAs, moRNAs, PARs, sdRNAs, tel-sRNAs, crasiRNAs, and small interfering RNAs (siRNAs). Methods of the invention can also be used for long non-coding RNAs (long ncRNAs), traditional non-coding tRNAs and ribosomal RNA (rRNA).

In general methods of the invention include those which comprise one or more of the following steps: contacting the target RNA or DNA molecule with one or more of the composite nucleic acid inhibitory molecules set out below:

Some embodiments of the invention are directed to composite nucleic acid inhibitory molecules which comprise one or more of the following regions: (a) a first homologous region, (b) a loop, (c) a second homologous region, and (d) a target binding nucleic acid segment which is greater than 6 nucleotides in length, wherein the loop connects the first homologous region and the second homologous region and is of sufficient length to allow for the first homologous region and the second homologous region to hybridize to one another to form a double-stranded structure, and wherein the first homologous region and the second homologous region share sufficient sequence homology to allow for hybridization under physiological conditions. In some embodiments, the target is a long non-coding RNA or a short non-coding RNA. In some embodiments, the short non-coding RNA is chosen from a microRNA (miRNA), a Piwi-interacting RNA (piRNA), and a small interfering RNA (siRNA). In some embodiments, the loop is a non-nucleotide loop. In some embodiments, the target binding nucleic acid segment is about 60 to about 100% complementary to all or a portion of at least one target nucleic acid. In some embodiments, the first homologous region or the second homologous region is between from about 3 nucleotides to about 30 nucleotides in length. In some embodiments, the first homologous region is between about 4 and about 10 nucleotides in length. In some embodiments, the backbone of the loop comprises covalently bonded carbon atoms. In some embodiments, the backbone of the loop comprises covalently bonded carbon and oxygen atoms. In some embodiments, the loop is chosen from polyethylene glycol, C2-C18 alkane diol, styrene, stilbene, triazole, tetrazole, nucleic acid, poly abasic nucleoside, polysaccharide, peptide, polyamide, hydrazone, oxyimine, polyester, disulfide, polyamine, polyether, peptide nucleic acid, cycloalkane, polyalkene, aryl, derivatives thereof and any combination thereof. In some embodiments, the homologous region is separated from the target binding nucleic acid segment by at least one nucleotide having a purine base, a pyrimidine base, or no base (abasic). In some embodiments, the nucleotides that comprise the target-binding nucleic acid segment are modified and those modifications are chosen from, DNA, RNA, 2'OMe, 2'OAllyl, 2'O-propargyl, 2'O-alkyl, 2'fluoro, 2'arabino, 2' xylo, 2'fluoro arabino, phosphorothioate, phosphorodithioate, phosphoroamidates, 2'Amino, 5-alkyl-substituted pyrimidine, 5-halo-substituted pyrimidine, alkyl-substituted purine, halo-substituted purine, bicyclic nucleotides, 2'MOE, LNA, LNA-like molecules and derivatives thereof. In some embodiments, the polyethylene glycol is a polyethylene glycol derivative and wherein the polyethylene glycol derivative is hexa-ethylene glycol or penta-ethylene glycol. In some embodiments, the loop is C12 alkane diol. In some embodiments, the molecule is modified and the modification adds at least one amine, imine, guanidine, or aromatic amino heterocycle. In some embodiments, the nucleotides in the homologous region and/or spacer comprises at least one 2' O-alkyl, LNA, 2'fluoro, arabino, 2' xylo, 2'fluoro arabino, phosphorothioate, phosphorodithioate, 2'amino, bicyclic nucleotide, 5-alkyl-substituted pyrimidine, 5-halo-substituted pyrimidine, alkyl-substituted purine, or halo-substituted purine, halo-substituted purine, bicyclic nucleotides, 2'MOE, LNA, and derivatives thereof. In some embodiments, the target binding nucleic acid segment is between from about 10 nucleotides to about 100 nucleotides in length. In some embodiments, the target binding nucleic acid segment is between from about 15 to about 25 nucleotides in length. In some embodiments, the first homologous region, the second homologous region and the loop form a stem loop structure and the stem loop structure is on the 5' end of the nucleic acid inhibitory molecule. In some embodiments, the first homologous region, the second homologous region and the loop form a stem loop structure and the stem loop structure is on the 3' end of the nucleic acid inhibitory molecule. In some embodiments, the composite nucleic acid inhibitory molecule also includes a second stem loop structure at the 5' end of the nucleic acid inhibitory molecule. In some embodiments, the entire molecule is between about 20 and about 150 nucleotides in length. In some embodiments, the inhibitory molecule is modified and the modification is a covalently linked conjugate that enhances cell penetration, endocytosis, facilitated diffusion, tissue localization, inhibitor detection, or cellular trafficking of the modified nucleic acid inhibitory molecule. In some embodiments, the inhibitory molecule further comprises one or more nucleotides on either end of the molecule.

Some embodiments of the invention are directed to multimeric nucleic acid inhibitory molecules which comprises at least one or more of the following regions: (a) a first oligonucleotide and (b) a second oligonucleotide, wherein the first oligonucleotide comprises a target nucleic acid molecule binding region, and two regions which will not hybridize to the target nucleic acid molecule, wherein the second oligonucleotide comprises two regions which will hybridize under physiological conditions to at least two of the two regions of the first oligonucleotides which will not hybridize to the target nucleic acid molecule, and wherein the multimeric nucleic acid inhibitory molecule comprises both single-stranded and double-stranded regions. In some embodiments, the sequence that will not hybridize to the target nucleic acid molecule is separated from the target binding nucleic acid segment by at least one nucleotide having a purine base, a pyrimidine base, or no base (abasic). In some embodiments, the target nucleic acid molecule is a long non-coding RNA or a short non-coding RNA. In some embodiments, the first oligonucleotide is between from about 30 nucleotides to about 200 nucleotides in length. In some embodiments, the second oligonucleotide is between from about 6 nucleotides to about 50 nucleotides in length. In some embodiments, the single-stranded region is capable of binding a target nucleic acid molecule under physiological conditions.

In some embodiments, the single-stranded region is complementary to all or a portion of the target nucleic acid. In some embodiments, the short non-coding RNA is chosen from a microRNA (miRNA), Piwi-interacting RNA, and small interfering RNA, a messenger RNA, and a ribosomal RNA. In some embodiments, the nucleic acid molecule comprises at least one modification chosen from, DNA, RNA, 2'OMe, 2'OAllyl, 2'O-propargyl, 2'O-alkyl, 2'fluoro, 2'arabino, 2' xylo, 2'fluoro arabino, phosphorothioate, phosphorodithioate, 2'amino, 5-alkyl-substituted pyrimidine, 5-halo-substituted pyrimidine, alkyl-substituted purine, halo-substituted purine, bicyclic nucleotides, 2'MOE, LNA, and derivatives thereof. In some embodiments, the molecule further comprises one or more nucleotides on either end of the molecule. In some embodiments, the target binding nucleic acid segment is about 60 to about 100% complementary to all or a portion of at least one target nucleic acid.

A further aspect of the invention is a method for inhibiting the function of a target RNA or DNA molecule, the method comprising contacting the target RNA or DNA molecule with at least one composite nucleic acid inhibitory molecule which comprises the following regions: a first homologous region, a loop, a second homologous region, and a target binding nucleic acid segment which is greater than 6 nucleotides in length, wherein the loop connects the first homologous region and the second homologous region and is of sufficient length to allow for the first homologous region and the second homologous region to hybridize to one another to form a double-stranded structure, and wherein the first homologous region and the second homologous region share sufficient sequence homology to allow for hybridization under physiological conditions.

A further aspect of the invention is a method for inhibiting the function of a target RNA or DNA molecule, the method comprising contacting the target RNA or DNA molecule with at least one multimeric nucleic acid inhibitory molecule having at least a first oligonucleotide and a second oligonucleotide. In many instances, the first oligonucleotide comprises a target nucleic acid molecule binding region and two regions which will not hybridize to the target nucleic acid molecule, wherein the second oligonucleotide comprises two regions which will hybridize under physiological conditions to at least two of the two regions of the first oligonucleotides which will not hybridize to the target nucleic acid molecule, and wherein the multimeric nucleic acid inhibitory molecule comprises both single-stranded and double-stranded regions.

A further aspect of the invention is a method for producing a multimeric nucleic acid inhibitory molecule, including obtaining at least a first oligonucleotide and a second oligonucleotide, wherein the first oligonucleotide comprises a target nucleic acid molecule binding region, and two or more regions which will not hybridize to the target nucleic acid molecule, wherein the second oligonucleotide comprises two regions which will hybridize under physiological conditions to at least two of the two or more regions of the first oligonucleotide which will not hybridize to the target nucleic acid molecule; admixing equal amounts of the first and second oligonucleotides in an appropriate buffer and allowing annealing of the two molecules, wherein the resulting multimeric nucleic acid inhibitory molecule comprises both single-stranded and double-stranded regions.

A further aspect of the invention is a composite nucleic acid inhibitory molecule which includes a 5' and/or 3' non-nucleotide loop, and a target binding nucleic acid segment which is greater than 6 nucleotides in length, wherein the target binding nucleic acid segment is modified to increase binding affinity to its target. In some embodiments, the non-nucleotide loop is chosen from polyethylene glycol (PEG3-PEG10), C2-C18 alkane diol, styrene, stilbene, triazole, tetrazole, nucleic acid, poly abasic nucleoside, polysaccharide, peptide, polyamide, hydrazone, oxyimine, polyester, disulfide, polyamine, polyether, peptide nucleic acid, cycloalkane, polyalkene, aryl, any combination thereof, and derivatives thereof. In some embodiments, the loop is separated from the target binding nucleic acid segment by at least one nucleotide having a purine base, a pyrimidine base, or no base (abasic). In some embodiments, the target nucleic acid molecule is a long non-coding RNA or a short non-coding RNA. In some embodiments, the short non-coding RNA is chosen from a microRNA (miRNA), a Piwi-interacting RNA (piRNA), and a small interfering RNA (siRNA), snoRNAs, snRNAs, moRNAs, PARs, sdRNAs, tel-sRNAs, crasiRNAs, and small interfering RNAs (siRNAs). Methods of the invention can also be used for long non-coding RNAs (long ncRNAs), traditional non-coding tRNAs and ribosomal RNA (rRNA).

In some embodiments, the nucleotides in the target binding nucleic acid segment comprises at least one 2' O-alkyl, LNA, 2'fluoro, 2' arabino, 2' xylo, 2'fluoro arabino, phosphorothioate, phosphorodithioate, 2'amino, bicyclic nucleotide, 5-alkyl-substituted pyrimidine, 5-halo-substituted pyrimidine, alkyl-substituted purine, or halo-substituted purine, halo-substituted purine, bicyclic nucleotides, 2'MOE, LNA, and derivatives thereof. In some embodiments, the target binding nucleic acid segment is about 60 to about 100% complementary to all or a portion of at least one target nucleic acid.

A further aspect of the invention is a method for inhibiting the function of a target RNA or DNA molecule, the method comprising contacting the target RNA or DNA molecule with at least one composite nucleic acid inhibitory molecule which includes a 5' and/or 3' non-nucleotide loop, and a target binding nucleic acid segment which is greater than 6 nucleotides in length, wherein the target binding nucleic acid segment is modified to increase binding affinity to its target.

A further aspect of the invention is a method for treatment of a disease, comprising administering at least one composite nucleic acid inhibitory molecule which includes a 5' and/or 3' non-nucleotide loop, and a target binding nucleic acid segment which is greater than 6 nucleotides in length, wherein the target binding nucleic acid segment is modified to increase binding affinity to its target, in an amount effective to treat a disease, wherein treatment of the disease comprises reducing the symptoms of a disease. In some embodiments, the method also includes complexing the inhibitory molecule with a cellular delivery agent. In some embodiments, the disease is chosen from cancer, Alzheimer's disease, diabetes, and viral infections.

A further aspect of the invention is a method for treatment of a disease, comprising administering at least one composite nucleic acid inhibitory molecule which comprises the following regions: a first homologous region, a loop, a second homologous region, and a target binding nucleic acid segment which is greater than 6 nucleotides in length, wherein the loop connects the first homologous region and the second homologous region and is of sufficient length to allow for the first homologous region and the second homologous region to hybridize to one another to form a double-stranded structure, and wherein the first homologous region and the second homologous region share sufficient sequence homology to allow for hybridization under physiological conditions, in an amount effective to treat a disease, wherein treatment of the disease comprises reducing the symptoms of a disease. In some embodiments, the method also includes complexing the inhibitory molecule with a cellular delivery agent. In some embodiments, the disease is chosen from cancer, Alzheimer's disease, diabetes, and viral infections.

A further aspect of the invention is a method for treatment of a disease, comprising administering at least one a multimeric nucleic acid inhibitory molecule having at least a first oligonucleotide and a second oligonucleotide, wherein the first oligonucleotide comprises a target nucleic acid molecule binding region, and two regions which will not hybridize to the target nucleic acid molecule, wherein the second oligonucleotide comprises two regions which will hybridize under physiological conditions to at least two of the two regions of the first oligonucleotides which will not hybridize to the target nucleic acid molecule, and wherein the multimeric nucleic acid inhibitory molecule comprises both single-stranded and double-stranded regions, in an amount effective to treat a disease, wherein treatment of the disease comprises reducing the symptoms of a disease. In some embodiments, the method also includes complexing the molecule with a cellular delivery agent. In some embodiments, the disease is chosen from cancer, Alzheimer's disease, diabetes, and viral infections.

BRIEF DESCRIPTION OF THE DRAWINGS

FIG. 3A: miR21 target; FIG. 3B: let7c target. The expression induced by miRNA inhibition is the Average fold change and is calculated in the following way: (fLuc activity anti-miR/βGal activity anti-miR)/(fLuc activity negative/βGal activity negative). Note: the higher the bars—the stronger the miRNA inhibition. All experiments were performed in triplicate.

FIG. 4A: miR21 target. Concentrations of miRNA inhibitors upon transfection: 3 nM (solid bar) and 0.3 nM (open bar). FIG. 4B: let7c target. Concentration of miRNA inhibitors upon transfection: 0.3 nM. Average fold change is calculated in the following way: (fLuc activity anti-miR/βGal activity anti-miR)/(fLuc activity negative/ βGal activity negative). All experiments were performed in triplicate.

FIG. 6A: let-7c target. FIG. 6B: miR-21 target. Concentration of miRNA inhibitors upon transfection: 3 and 30 nM. Decrease of the free miRNA levels (available for primer hybridization and thus detection) is shown relative to negative control-transfected samples. All experiments were performed in triplicate.

FIG. 7A: miR21 target; FIG. 7B: let7a target; FIG. 7C: let7c target. Concentrations of miRNA inhibitors upon transfection: 30, 3 and 0.3 nM. Average fold change is calculated in the following way: (fLuc activity anti-miR/βGal activity anti-miR)/(fLuc activity negative/βGal activity negative). Note: the higher the bars—the stronger the miRNA inhibition. All experiments were performed in triplicate.

FIG. 8A: miR21 target; FIG. 8B: let7a target; FIG. 8C: let7c target. Concentration of miRNA inhibitors upon transfection: 3 nM. Average fold change is calculated in the following way: (fLuc activity anti-miR/ βGal activity anti-miR)/(fLuc activity negative/βGal activity negative). Note: the higher the bars—the stronger the miRNA inhibition. All experiments were performed in triplicate.

FIG. 19A: miR21 target; FIG. 19B: let7a target.

FIG. 20A: miR23a target; FIG. 20B: miR21 target. The expression induced by miRNA inhibition is the Average fold change and is calculated in the following way: (fLuc activity anti-miR/βGal activity anti-miR)/(fLuc activity negative/βGal activity negative). The concentration of miRNA inhibitors upon transfection: 0.3 and 3 nM. All experiments were performed in triplicate.

DETAILED DESCRIPTION OF THE INVENTION

Definitions

Figure 1:
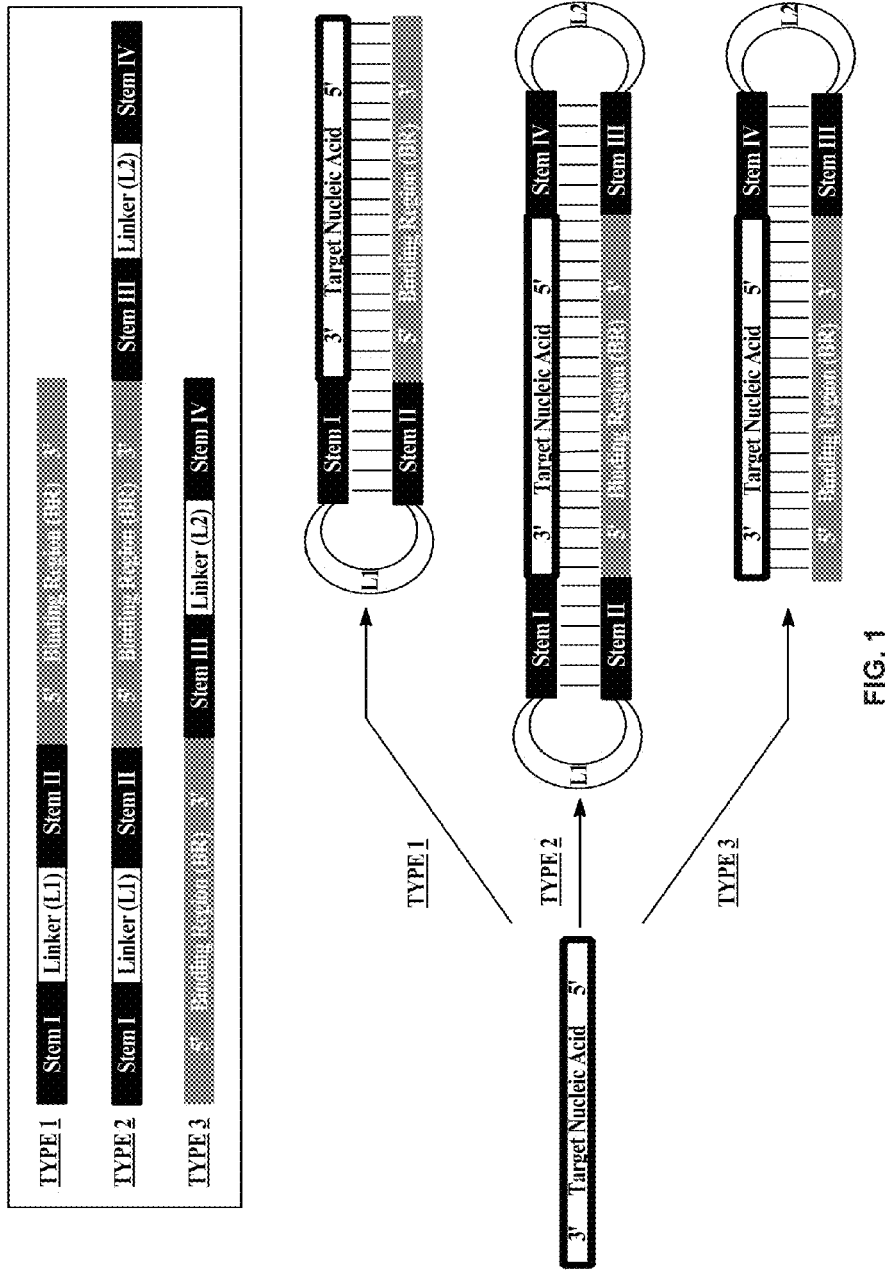
FIG. 1 shows schematic structures of the hairpin (HP)-based miRNA inhibitors (anti-miRs) used in Examples 1-6. Two types of loops were used: one all nucleotide and the other non-nucleotide (e.g., PEG3). The top part of the figure shows the nucleic acid molecules before hybridization. The bottom part of the figure shows the structure when bound to the target nucleic acid (e.g., a miRNA). As shown in the figure, type 1 has a 5' stem loop, type 2 has both a 5' and 3' stem loop, and Type 3 has a 3' stem loop. All experiments were performed in triplicate.

The term "siRNA," and "short interfering RNA" are interchangeable and refer to unimolecular nucleic acids and to nucleic acids comprised of two separate strands that are capable of inducing RNA interference. SiRNA molecules typically have a duplex region that is between 18 and 30 base pairs in length.

The term "microRNA", "miRNA", and MiR" are interchangeable and refer to endogenous non-coding RNAs that are capable of regulating gene expression. It is believed that miRNAs function via RNA interference. When used herein in the context of inactivation, the use of the term microRNAs is intended to include also long non-coding RNAs, piRNAs, siRNAs, and the like. Endogenous (e.g., naturally occurring) miRNAs are typically expressed from RNA polymerase II promoters and are generated from a larger transcript.

As used herein "piRNAs" refer to Piwi-interacting RNAs, a class of small RNAs that are believed to be involved in transcriptional silencing.

As used herein "microRNA inhibitors," "miRNA inhibitors," "antisense inhibitors" "anti-miRs" and "anti-miRNAs" are interchangeable and refer to molecules that inhibit the action of miRNAs and the like.

As used herein "alkyl" refers to a hydrocarbyl moiety that can be saturated or unsaturated (alkenyl or alkynyl), and substituted or unsubstituted. It can comprise moieties that are linear, branched, cyclic and/or heterocyclic, and contain functional groups such as ethers, ketones, aldehydes, carboxylates, etc. Exemplary alkyl groups include but are not limited to substituted and unsubstituted groups of methyl, ethyl, propyl, butyl, pentyl, hexyl, heptyl, octyl, nonyl, decyl, undecyl, dodcecyl, tridecyl, tetradecyl, pentadecyl, hexadecyl, heptadecyl, octadecyl, nonadecyl, eicosyl and alkyl groups of higher number of carbons as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. The term alkyl also encompasses alkenyl groups, such as vinyl, allyl, aralkyl, and alkynyl groups.

The term "homologous region" refers to a region of nucleic acid with homology to another nucleic acid region. Thus, whether a "homologous region" is present in a nucleic acid molecule is determined with reference to another nucleic acid region in the same or different molecule. Further, since nucleic acid is often double-stranded, the term "homologous, region", as used herein refers to the ability of nucleic acid molecules to be capable of hybridizing to each other. As an example, a single-stranded nucleic acid molecule can have two homologous regions which are capable of hybridizing to each other. Thus, the term "homologous region" includes nucleic acid segments with complementary sequence. Homologous regions may be of a variety of lengths but will typically be between 4 and 40 (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.) nucleotides in length.

As used herein "chimeric" refers to a mixture of parts from different origins. As used herein, the term can refer to an inhibitor having combined parts of the formats shown herein, including at least one or more of any of parts designated as, but not limited to, BR's, NBR's, S's, HR1 and HR2's, NBR1 and NBR2's, and loops. Further, "chimeric" can refer to various types of nucleic acids combined into an inhibitor (such as deoxy-, ribo- or various modified nucleotides). A chimera may also refer to combinations of hairpin inhibitors, conjugated antisense inhibitors and multimeric inhibitors. Another example would be a nucleic acid molecule which contains one region from a mouse chromosome and another region generated by chemical synthesis and representing a nucleotide sequence not known to exist in nature.

The term "sequence identity" refers to the extent to which two sequences have the same nucleotide at equivalent positions in a comparison of nucleic acid usually expressed as a percentage. Thus, two nucleic acid molecules which differ by one nucleotide over a stretch of 100 nucleotides would be said to share 99% sequence identity.

The term "hybridization" refers to the formation of a double-stranded nucleic acid (or region) from two single-stranded nucleic acid molecules or two regions of one nucleic acid molecule.

The term "physiological conditions" refers to environmental conditions which are not deleterious to cells such as mammalian cells and includes conditions found, for example, in the cytoplasm of cells. Many of the molecules described herein are designed to function inside cells. Examples of conditions which are not considered to be physiological are temperatures above 45° C. and pH levels above 9 and below 4. Thus, conditions inside some cellular vacuoles would not necessarily be considered to be "physiological", as that term is used herein.

The term "hairpin" and "stem-loop" can be used interchangeably and refer to stem-loop structures. The stem results from two sequences of nucleic acid or modified nucleic acid annealing together to generate a duplex. The loop lies between the two strands comprising the stem.

The term "loop" refers to the part of the stem-loop between the two homologous regions (the stem) that can loop around to allow base-pairing of the two homologous regions. The loop can be composed of nucleic acid (e.g., DNA or RNA) or non-nucleic acid material(s), referred to herein as nucleotide or non-nucleotide loops. A non-nucleotide loop can also be situated at the end of a nucleotide molecule with or without a stem structure.

The term "target" refers to a range of molecules including but not limited to a miRNA (or pre-miRNAs), an siRNA, a piRNA, a long non-coding RNA, an mRNA, rRNA, tRNA, hnRNA, cDNA, genomic DNA, and long noncoding RNA (ncRNA).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

As used herein, the "reverse complement" or "RC" refers to a sequence that will anneal/basepair or substantially anneal/basepair to a second oligonucleotide according to the rules defined by Watson-Crick base pairing and the antiparallel nature of the DNA-DNA, RNA-RNA, and RNA-DNA double helices. Thus, as an example, the reverse complement of the RNA sequence 5'-AAUUUGC-3' (SEQ ID NO:142) would be 5'GCAAAUU-3' (SEQ ID NO:143). Alternative base pairing schemes including but not limited to G-U pairing can also be included in reverse complements.

The term "multimeric" refers to a nucleic acid molecule composed of several identical or different subunits held together. As used herein, the term refers to a multimeric nucleic acid molecule made up of several different sections, some single-stranded, and some double stranded.

As used herein, the term "composite" refers to a structure or an entity made up of distinct components, such as distinct sections of nucleic acid.

As used herein, the term "nucleotide" or "nt" refers to a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, 2'OMe, 2'halo such as 2'fluoro or 2'bromo, LNA, ENA, or 7-deaza such as 7-deaza-dGTP or 7-deaza-dATP. The term nucleotide as used herein also refers to dideoxyribonucleoside triphosphates (ddNTPs) and their derivatives. Examples of dideoxyribonucleoside triphosphates include, but are not limited to, ddATP, ddCTP, ddGTP, ddITP, and ddTTP.

As used herein, the phrase "nucleic acid molecule" refers to a sequence of contiguous nucleotides (riboNTPs, dNTPs or ddNTPs, or combinations thereof) of any length which can encode a full-length polypeptide or a fragment of any length thereof, or which can be non-coding. As used herein, the terms "nucleic acid molecule" and "polynucleotide" can be used interchangeably and include both RNA and DNA.

As used herein, the term "oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

As used herein the term "binding affinity" refers to the affinity between two complementary nucleic acid molecules or regions within one nucleic acid molecule. Binding affinity between two complementary nucleic acids will vary with a number of factors including, length, and AT/CG content.

I. Overview

The invention relates to compositions and methods for inactivating nucleic acid targets. Methods of the invention involve, in part, the use of molecules (e.g., composite inhibitory molecules) with nucleic acid regions with sequence complementarity to the nucleic acid molecule which is the subject of desired inactivation (e.g., a target nucleic acid molecule). Compositions described herein can be used for inactivation of targets that are relatively short non-coding RNAs including regulatory RNAs. Compositions described herein can be used for the inactivation of short non-coding RNAs and long non-coding RNAs. Compositions described herein can be used for the inactivation of short non-coding RNAs, such as microRNAs (miRNAs), Piwi-interacting RNAs (piRNAs), and small interfering RNAs (siRNAs). Thus, compositions of the invention can include the composite nucleic acid molecules that are microRNA inhibitors (anti-miRs). In some embodiments, compositions of the invention include at least one miRNA inhibitor and the miRNA inhibitor is produced to target all or a portion of a target nucleic acid. Though they will be referred to as miRNA inhibitors (and anti-miRs), composite nucleic acids can also act to inhibit any target including miRNAs, siRNAs, piRNAs, mRNAs, and rRNAs. Either strand of a duplexed target RNA can be targeted by miRNA inhibitors provided herein.

In general methods of the invention include the use of nucleic acid molecules (e.g., composite nucleic acid molecules) that inactivate and/or inhibit miRNAs and other short non-coding RNAs. In some embodiments, methods of the invention involve using inhibitors of three distinct formats: hairpin inhibitors, conjugated antisense inhibitors and multimeric inhibitors. Also envisioned are mixtures and chimera thereof. In many instances, all of the formats can be specific for one or more target nucleic acid molecules (e.g., miRNA).

In some embodiments, target nucleic acid molecules can be obtained from a sample. Samples can be derived from any number of sources. Since methods and compositions described herein can be used to inhibit the activity of miRNAs and the like, most samples will either be known or suspected to contain one or more target nucleic acid segments (i.e., miRNAs). Samples can be from viruses, virally infected cells or eukaryotic sources such as protozoa, algae, fungi (yeast and molds), plants, invertebrates (worms), insects (flies), vertebrates, fish, mammals, rodents and primates. Other sources include culture media, either cell free or cell containing as well as cell storage media. Thus, nucleic acid molecules of the invention (e.g., miRNA inhibitors) can be produced to any target within a sample and/or source.

In some embodiments, mixtures of different nucleic acid molecules of the invention (e.g., miRNA inhibitors) that target one or more specific targets can be used. In some embodiments, mixtures of different formats disclosed herein can be used to target one or multiple targets (e.g., one, two, three, four, five, six, seven, eight targets and/or from about two to about fifteen, from about two to about twelve, from about two to about ten, from about two to about eight, from about two to about six, from about three to about fifteen, from about three to about seven, etc. targets). For example, a mixture including a hairpin inhibitory molecule and a mixture that includes a conjugated antisense inhibitory molecule can be used. Mixtures of inhibitors can also include other types of miRNA inhibitors known in the art. In some embodiments, a mixture of various hairpin inhibitors (5' hairpin, 3' hairpin, and 5' and 3' hairpin), conjugated antisense inhibitors, and/or multimeric inhibitors can be used to target a single target. In some embodiments, a mixture of various hairpin inhibitors (5' hairpin and 3' hairpin) and/or multimeric inhibitors can be used to target multiple targets. In some embodiments, a single miRNA inhibitor can be used that is a chimera of a hairpin inhibitor and a multimeric inhibitor, for example, having some multimeric regions and a 3' or 5' hairpin on the same miRNA inhibitory molecule. In some embodiments, a single miRNA inhibitor can be used for multiple targets. For example, the target binding region can include sequences complementary to two different targets. Alternatively, a multimer can include numerous target binding regions that are complementary to one or more targets.

As one skilled in the art would understand, similar embodiments of the invention may comprise or employ inhibitory molecules which do not inhibit the function of miRNAs. In other words, while reference is made herein to miRNAs inhibitors, the invention includes inhibitors of other classes of nucleic acid molecules. In most instances, inhibitory molecules will associate a corresponding target by hybridization. Thus, the invention includes methods by which a first molecule (e.g., a nucleic acid molecule) binds to a second molecule (e.g., a target nucleic acid molecule) and inhibits a function (e.g., transcription, translation, RNA interference, etc.) of the second nucleic acid molecule, as well as compositions of matter used in such methods.

In some embodiments, the miRNA inhibitors, and other inhibitory molecules of the invention, reduce the amount and/or activity of one or more targets. In some embodiments, the miRNA inhibitors reduce the amount and/or activity of one or more miRNAs. In some embodiments, the miRNA inhibitors, and other inhibitory molecules of the invention, reduce the amount and/or activity of the target from about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including but not limited to 15%, 20%, 25%, 30%, 35%, 40%, 45%, 50%, 55%, 60%, 65%, 70%, 75%, 80%, 85%, 90%, 95%, 96%, 97%, 98%, and 99%. In some embodiments, the miRNA inhibitors, and other inhibitory molecules of the invention, act to reduce the symptoms of a disease. In some embodiments, the miRNA inhibitors, and other inhibitory molecules of the invention, act to change a phenotype of a cell, such as a developmental phenotype.

Exemplary inhibitory molecule formats including hairpin inhibitors, multimeric inhibitors, conjugated antisense inhibitors, mixtures thereof, and chimeric inhibitors thereof are explained in more detail with reference to FIG. 1 and FIG. 9.

TABLE 1A

Codes for Formats in Tables 1B-1D

| Base | Code |
|---|---|
| RNA A | A |
| RNA C | C |
| RNA G | G |
| RNA U | U |
| DNA A | a |
| DNA C | c |
| DNA G | g |
| DNA T | t |
| 2'Ome A | *A* (ital) |
| 2'Ome C | *C* (ital) |
| 2'Ome G | *G* (ital) |
| 2'Ome U | *U* (ital) |
| LNA A | A (bold) |
| LNA methyl C | C (bold) |
| LNA G | G (bold) |
| LNA T | T (bold) |
| 2'F C | $C_f$ |
| 2'F U | $U_f$ |
| phosphorothioate | ACGt (underlined) |

TABLE 1A-continued

Codes for Formats in Tables 1B-1D

| Base | Code |
|---|---|
| C6 amino | N |
| 2'O-Propargyl G | Y |

II. Inhibitory Molecule Formats

Embodiments of inhibitory molecule formats can include hairpin inhibitors, conjugated inhibitors, multimeric inhibitors, mixtures and chimera thereof. With reference to FIG. 9, the inhibitors and chimera will be discussed generally. Then each format will be discussed in more detail in the following sections A-D.

Figure 9:
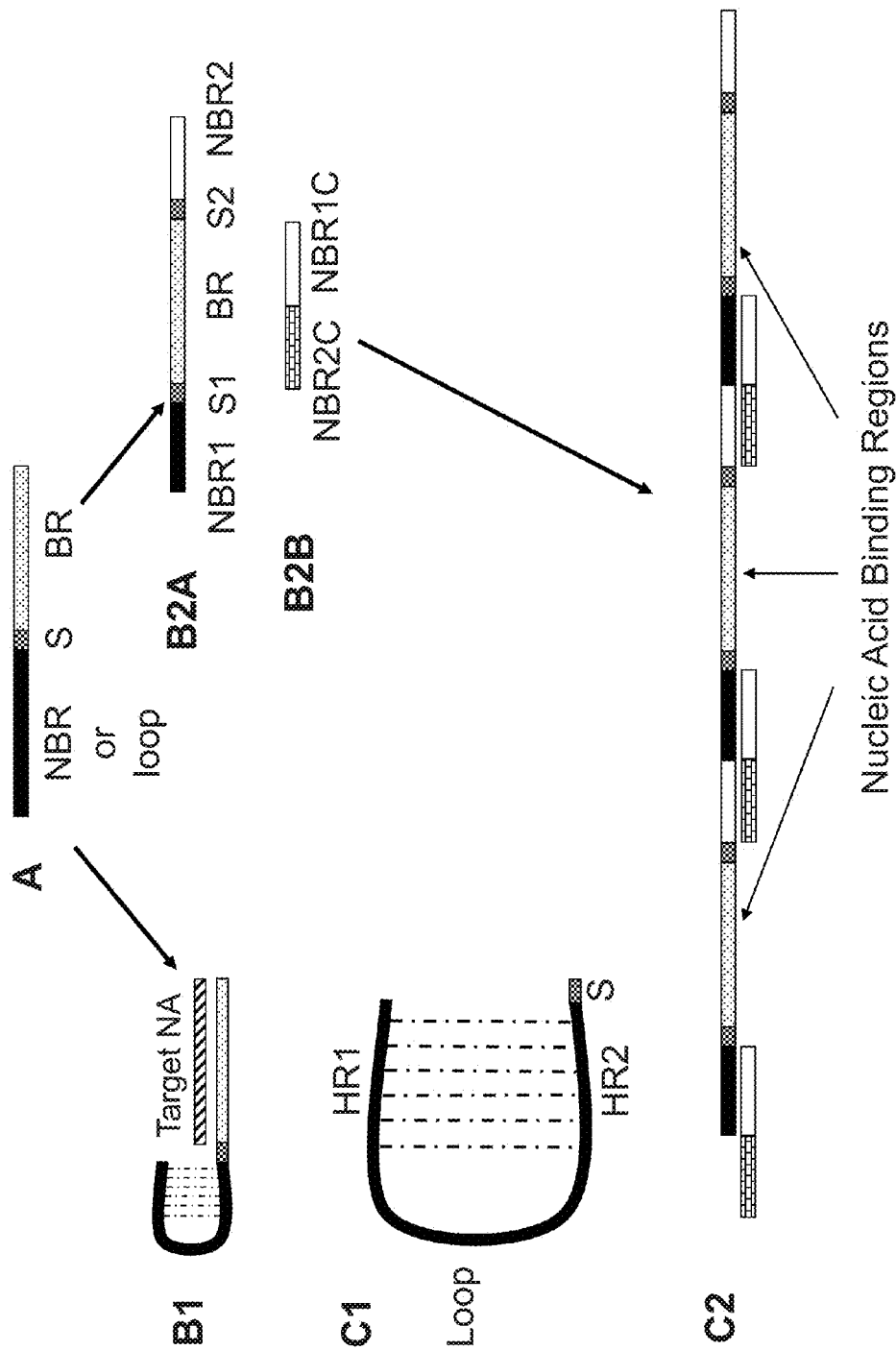
FIG. 9 is a schematic showing formats of embodiments and inter-relationships of the inhibitors herein including hairpin inhibitors (B1 and C1) and multimeric inhibitors (B2A, B2B, and C2). Regions of the inhibitors are designated as follows: NBR=non-binding region, S=Spacer, BR=binding region, HR=homology region, Loop=nucleotide or non-nucleotide loop. All experiments were performed in triplicate.

FIG. 9 shows a schematic of certain formats of the inventions as well as the inter-relationships of the formats. The formats include a hairpin inhibitor (format B1 and C1), a conjugated antisense inhibitor (format A conjugated to at least one non-nucleic acid moiety, for example), and a multimeric inhibitor (format C2). All of the formats are based on a generic structure "A" in FIG. 9, including at least one binding region (BR), an optional spacer (S), and at least one non-binding region (NBR or loop). The at least one non-binding region (NBR) may also be a nucleotide or non-nucleotide loop and can be at the 5' and/or 3' end of the binding region (BR) or both the 5' and 3' end.

With reference to the generic format "A" in FIG. 9, the binding region (BR) is the region that binds to the target and is also referred to as the target binding region, the target binding nucleic acid segment, the target binding segment and the target binding nucleic acid. The target can be any nucleic acid discussed herein as a target, including any short, non-coding nucleic acid (e.g., microRNA). The binding region can be a reverse complement (RC) to one or more target molecule(s) of interest (e.g., miRNA). In some embodiments, the length of the target binding region is optimized to obtain maximum specificity for the target (e.g., the miRNA) while retaining potency. In some embodiments, the target binding nucleic acid segment is complementary to all or a portion of at least one target, such that it will bind to the target (See FIG. 9, Target NA in format B1). In some embodiments the portion of the target includes at least a part of the 5' UTR or the 3' UTR. In some embodiments the portion of the target includes at least a part of a coding region. In some embodiments the target binding nucleic acid segment is complementary to two or more targets. By complementary, the target binding nucleic acid segment can have between about 40% to about 100% complementarity with one or more targets, including about 40% to about 100% complementarity with one or more targets, including about 60% to 100% complementarity with one or more targets, including but not limited to 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99% complementarity. In some embodiments, the target binding region can have 80-100% complementarity with one target and 60% or more complementarity with at least a second target. In some embodiments, the target binding region can have 100% complementarity to a portion of a single target and 60% complementarity to the rest of the target. In some embodiments, the target binding nucleic acid segment is at least 6 or more nucleotides in length. In some embodiments, the target binding nucleic acid segment is between about 6 and about 200 nucleotides in length. In some embodiments, the target binding nucleic acid segment is between about 6 and 50 nucleotides in length, including between about 9 and 25 nucleotides in length, including, but not limited to: 10 nt, 11 nt, 12 nt, 13 nt, 14 nt, 15 nt, 16 nt, 17 nt, 18 nt, 19 nt, 20 nt, 21 nt, 22 nt, 23 nt, 24 nt and 25 nt in length. In some embodiments, the target binding nucleic acid segment is between about 15 nt and about 25 nucleotides in length. In some embodiments, the target binding nucleic acid segment is between about 20 and about 23 nucleotides in length. The target binding region (BR) can be modified in any way known in the art and/or discussed herein (see section entitled "Modification"). In some embodiments, the target binding region is between about 20 and about 200 nucleotides in length and the target is a long non-coding RNA.

A spacer (S in FIG. 9) can be used to separate the stem loop, loop or NBR from the target binding nucleic acid segment. The spacer can be one or more nucleotides. In some embodiments, the spacer is one or more nucleotides having a purine base, a pyrimidine base, or no base (e.g., abasic). In some embodiments, the spacer is a single nucleotide with the base A, C, G, U or T. In some embodiments the spacer is at least one universal and/or a modified base. In some embodiments, the spacer is at least one nucleotide but can be between 0 and 10 nucleotides, including, but not limited to, 1, 2, 3, 4, 5, 6, 7, 8, and 9 nucleotides. In some embodiments, the spacer is one or more nucleotides and can include purine bases, a pyrimidine bases, and/or no base (e.g., abasic). One or more nucleotides in the spacer can also be modified (see "Modification" section below). Thus, for example, a conjugated antisense inhibitor can include a spacer to separate the binding region (BR) from the non-nucleotide loop (See A in FIG. 9). For the hairpin inhibitor, the spacer can separate the stem loop from the binding region (see B1 and C1 in FIG. 9). For the multimeric inhibitor, the spacer can separate the binding regions from one or more non-binding regions (see NBR in FIG. 9). The spacer can function to reduce or eliminate the charge repulsion of the 5' end of the NBR or stem (homology region 1) in the respective formats for the target nucleic acid. Thus, for example, with reference to FIG. 9, B1, the 5' end of the target nucleic acid-bearing phosphate when bound to the binding region (BR) may be repulsed. A spacer can reduce this repulsion. The sequence of spacer S1 may be the same as the sequence of spacer S2 or the sequences may be different.

The non-binding region (NBR) in FIG. 9 can be any nucleic acid segment that does not bind to the target (a loop, a homology region, a stem loop, or a homology region for the double-stranded part of the multimeric inhibitor). In the case of the conjugated antisense inhibitor, the NBR can be a non-nucleotide loop (see format A in FIG. 9) and the loop can be attached directly to the inhibitory molecule (with or without a spacer). In the case of the hairpin inhibitor, the non-binding region can be a stem loop (see format B1 and C1 in FIG. 9). The loop of the stem loop can be a non-nucleotide loop or a nucleotide loop. Alternatively, the NBR (non binding region) can be the part of the multimeric inhibitory molecule that is double-stranded (see NBR1 and NBR2 in FIG. 9, B2A). In this case, while the NBR does not bind to the target, it can bind to a reverse complement NBR (NBR2C and NBR1C) to create the final multimeric molecule with single stranded regions (BR) and double stranded regions (NBR1 bound to NBR1C and NBR2 bound to NBR2C). A chimeric version of a multimeric inhibitory molecule (see C2 in FIG. 9) can also be envisioned to contain one or more loops—either stem loops or non-nucleotide loops as non-binding regions.

The loop in the hairpin inhibitor (see "loop" in drawing C1) functions to connect the two homology regions (HR1 and HR2 in FIG. 9) or stem regions to produce a stem loop. In some embodiments, the inhibitor contains 2 or more loops. In some embodiments, the 2 or more loops can be nucleotide loops, non-nucleotide loops and/or mixtures thereof.

When the loop (see drawing "C1") is composed of nucleic acid, this nucleic acid can be chemically modified and can be DNA or RNA. Further, the length of the loop can be adjusted to allow for association and binding between homologous regions (e.g., "HR1" and "HR2" in FIG. 1 "C1"). Typically, nucleotide loops will be between about 3 and about 50 nucleotides in length (e.g., from about 4 to about 50, from about 6 to about 50, from about 8 to about 50, from about 10 to about 50, from about 4 to about 40, from about 4 to about 30, from about 4 to about 25, from about 4 to about 20, from about 4 to about 15, from about 5 to about 30, from about 5 to about 15, from about 6 to about 50, from about 6 to about 20, from about 8 to about 20, etc. nucleotides).

In some embodiments, the loop (in the hairpin inhibitor) is composed of non-nucleotide polymers and derivatives thereof. Briefly, the non-nucleotide loop can be of sufficient length and/or of sufficient materials to enable effective intramolecular hybridization between the homologous regions (to form a stem). The length of the loop will typically be a length which is at least the length spanned by at least 8-50 atoms (e.g., from about 8 to about 50, from about 8 to about 40, from about 8 to about 30, from about 8 to about 25, from about 8 to about 20, from about 10 to about 30, from about 12 to about 30, etc. atoms), while not being so long as to interfere with the pairing of the oligonucleotides capable of hybridizing to each other. In some embodiments, the length of the loop is the length spanned by between about 18 and about 22 atoms. In some embodiments, the loop has a backbone of covalently bonded atoms chosen from: carbon, oxygen, sulfur, phosphate, and nitrogen. In some embodiments, the non-nucleotide loop has a backbone composed of covalently bonded carbon atoms. In some embodiments, the backbone of the loop comprises covalently bonded carbon and oxygen atoms. In some embodiments, the loop is chosen from polyethylene glycol (PEG3-PEG10), C2-C18 alkane diol, styrene, stilbene, triazole, tetrazole, nucleic acid, poly abasic nucleoside, polysaccharide, peptide, polyamide, hydrazone, oxyimine, polyester, disulfide, polyamine, polyether, peptide nucleic acid, cycloalkane, polyalkene, aryl, derivatives thereof and any combination thereof. In some embodiments, the non-nucleotide loop is a fluorescent dye. In some embodiments, the fluorescent dye is CYANINE™ 5 dye, CYANINE™ 3 dye, or an Alexa Fluor emitter. In some embodiments, the non-nucleotide loop is selected from one of the structures in Table 2. In some embodiments, the non-nucleotide loop is composed of polyethylene glycol (PEG). In some embodiments, the non-nucleotide loop is composed of a polyethylene glycol (PEG) derivative. In some embodiments, the non-nucleotide loop is composed of a polyethylene glycol (PEG) derivative and the polyethylene glycol (PEG) derivative is penta-ethylene glycol or hexa-ethylene glycol. In some embodiments, the non-nucleotide loop is modified by attaching an amine, thiol, NGS ester, alkyne or other functional handle that could partake in a reaction post synthesis, such as labeling with a dye or biotin. Other modifications can be found in references such as: Beaucage, et al, 1992, Tetrahedron, v. 48, p. 2223-2311; Beaucage, et al, 1993, Tetrahedron, v. 49, p. 1925-1963, p 6123-6194, and p. 10441-10488, herein incorporated by reference. Derivatives of non-nucleotide loops can include modified non-nucleotide loops, sidechains, and cycloalkanes addition.

TABLE 2

| Linker | Structure | Name |
| --- | --- | --- |
| L1 | 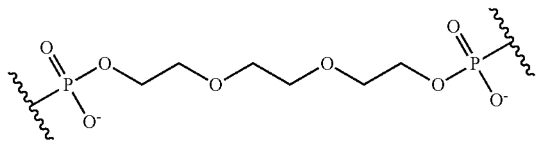 [SMILES: *P(=O)([O-])OCCOCCOCCOP(*)(=O)[O-]] | Triethylene glycol bis-phosphate (TEG) |
| L2 | 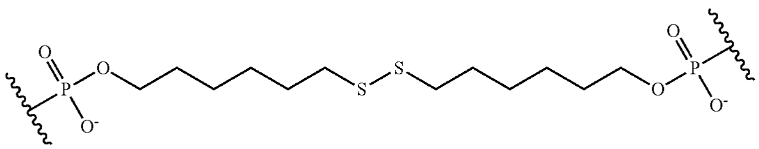 [SMILES: *P(=O)([O-])OCCCCCCSSCCCCCCOP(*)(=O)[O-]] | Bis-hexanol disulfide bis-phosphate |
| L3 | 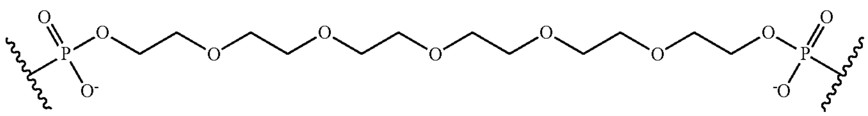 | Hexaethylene glycol bis-phosphate |
| L4 | 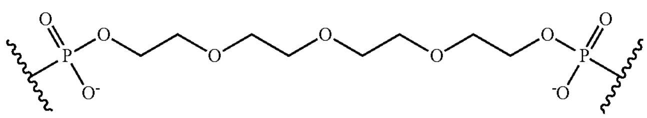 | Tetraethylene glycol bis-phosphate |
| L5 | 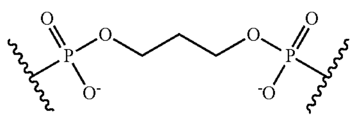 | Propane diol bis-phosphate |
| L6 | 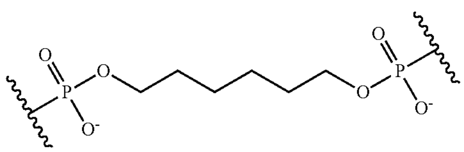 [SMILES: *P(=O)([O-])OCCCCCCOP(*)(=O)[O-]] | Hexane diol bis-phosphate |
| L7 | 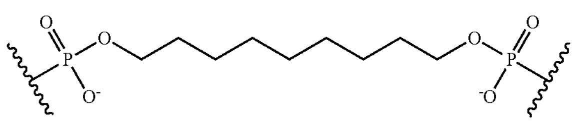 | Nonane diol bis-phosphate |
| L8 | 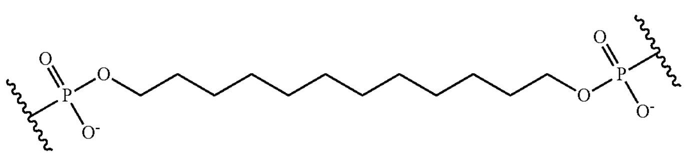 [SMILES: *P(=O)([O-])OCCCCCCCCCCCCOP(*)(=O)[O-]] | Dodecyl diol bis-phosphate |
| L10 | 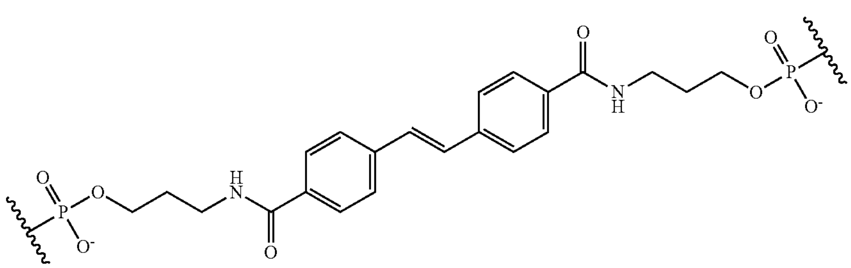 [SMILES: *P(=O)([O-])OCCCNC(=O)c1ccc(/C=C/c2ccc(C(=O)NCCCOP(*)(=O)[O-])cc2)cc1] | Bis-propyl-amido stilbene bis-phosphate |
| L11 | 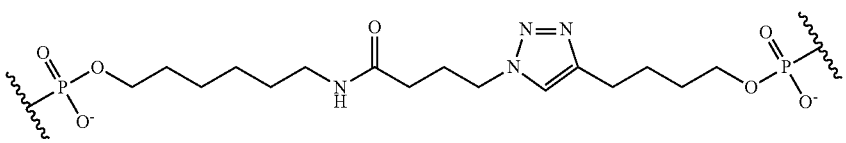 [SMILES: *P(=O)([O-])OCCCCCCNC(=O)CCCn1cc(CCCCOP(*)(=O)[O-])nn1] | 4-(hydroxybutyl)-1H-1,2,3-triazol-1-yl)-N-(6-hydroxy-hexyl)butanamide bis-phosphate |

TABLE 2-continued

Non-Nucleotide Loop Structures

| Linker | Structure | Name |
| --- | --- | --- |
| L12 | 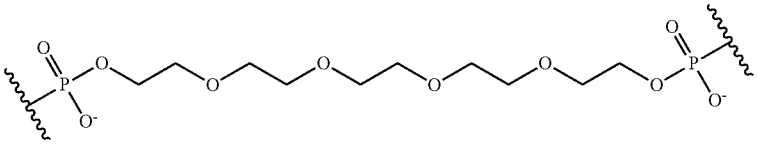 [SMILES: *P(=O)([O-])OCCOCCOCCOCCOCCOP(*)(=O)[O-]] | Pentaethylene glycol bis-phosphate |

In some embodiments, (the conjugated antisense inhibitor), the non-nucleotide loop (NBR or loop in format A, FIG. 9) can be any material without limitation and the size is not limiting as long as it does not interfere with binding of the binding region (BR) to its target. Thus, when the loop is on the 5' or 3' end of the conjugated antisense inhibitor, it can be composed of any of the materials used for a nucleotide loop or for a non-nucleotide loop on the hairpin inhibitor.

In some embodiments, the basic format A inhibitory molecule can also include a second non-binding region (NBR2) and can be separated from the binding region (BR) by an optional spacer (S) (see format B2A). With reference to format B2A, the NBR1 and NBR2 can be any sequence as long as it does not interfere with binding of the target to the binding region (BR). Further, the NBR1 and NBR2 can be any sequence as long as NBR1 does not hybridize to NBR2. In some embodiments, the NBR1 and/or NBR2 is between from about 30 nucleotides to about 200 nucleotides in length, including about 30 to about 100 nucleotides in length, and about 30 to about 50 nucleotides in length. In some embodiments, the NBR1 and/or NBR2 is from 5 nts to 100 nts in length, or from 5 nts to 50 nts in length or from 5 to 20 nts in length. The length of NBR1 can be the same as or different than the length of NBR2.

Inhibitory molecules can also include a second oligonucleotide (see B2B in FIG. 9) that is capable of binding to the B2A oligonucleotide as follows. The B2B oligonucleotide can contain a region that is capable of hybridizing to NBR1 (NBR1C) and a region that is capable of hybridizing to NBR2 (NBR2C). The B2B segment will be the reverse complement of these sequences and, as such, will be approximately the same length as the sequences. However, the B2B segment can be any length as long as it does not interfere with the target binding to the binding region (BR).

With reference to format C2 (the multimeric inhibitor) in FIG. 9, the B2A molecules can be multimerized in a head to tail manner to create the top strand in the final C2 molecule. Further, the B2B segments can be added to a mixture containing the B2A molecule and allowed to hybridize such that the resulting C2 molecule has some single-stranded regions (the BR with or without the spacer) and some double stranded regions (the B2A segment and the B2B segment). Any of the regions within the multimeric inhibitor (C2) can be modified as discussed in the section below entitled "Modification". For example, the binding region can be modified to enhance binding to its target, and the NBR1 and NBR2 can be modified to promote binding to the NBR1C and NBR2C regions. Modifications can also be included in any part of the multimeric inhibitor, for example, to increase stability or to enhance cell uptake.

In some embodiments, the length of the B2A portion of a multimeric miRNA inhibitor is from about 30 to about 150 nt in length, including about 30 to about 100 nt in length, including about 30 to about 45 nucleotides in length, including, but not limited to, about 31 nt, 32 nt, 33 nt, 34 nt, 35 nt, 36 nt, 37 nt, 38 nt, 39 nt, 40 nt, 41 nt, 42 nt, 43 nt, 44 nt, and 45 nt. In some embodiments, the length of the B2A portion of a multimeric miRNA inhibitor is from 30 nt, 40 nt, 50 nt, 60 nt, 66 nt, 70 nt, 80 nt, 90 nt, 100 nt, or more nucleotides to 175 nt, 200 nt, 250 nt, 300 nt, 350 nt, 400 nt, 500 nt, or 660 nucleotides, or any range therebetween. For example the length of the miRNA inhibitor may be from 30 nt to 250 nt, from 45 to 150 nt, from 50 to 100 nt, from 66 nt to 660 nt, from 80 to 500 nt, from 90 to 400 nt, from 100 to 300 nt, from 100 to 200 nt, or about 85, 86, 87, 88, 89, 90, 91, 92, 93, 94, 95, 96, 97, 98, or 100 nucleotides.

In some embodiments, a multimeric miRNA inhibitor is made by mixing B2A and B2B molecules in various molar ratios and allowing the molecules to anneal. Because of this, the length of the final multimeric inhibitor can vary dramatically, from a single B2A molecule to hundreds of B2A molecules long. In some embodiments, the multimeric molecules are a pool of various lengths.

In some embodiments, chimeric molecules can be envisioned which contain various parts of the formats shown herein, including but not limited to, BR's, NBR's, S's, HR1 and HR2's, NBR1 and NBR2's, and loops. Further, the formats can include nucleotide loops or non-nucleotide loops as part of a stem-loop structure or attached at the 3' or 5' ends directly. The formats can also include multimers of any of the above formats and can include single and double-stranded regions such as those shown in format C2. The chimeric molecules of the invention can also include any of the modifications discussed herein and/or under the heading "Modifications" below.

Figure 10:
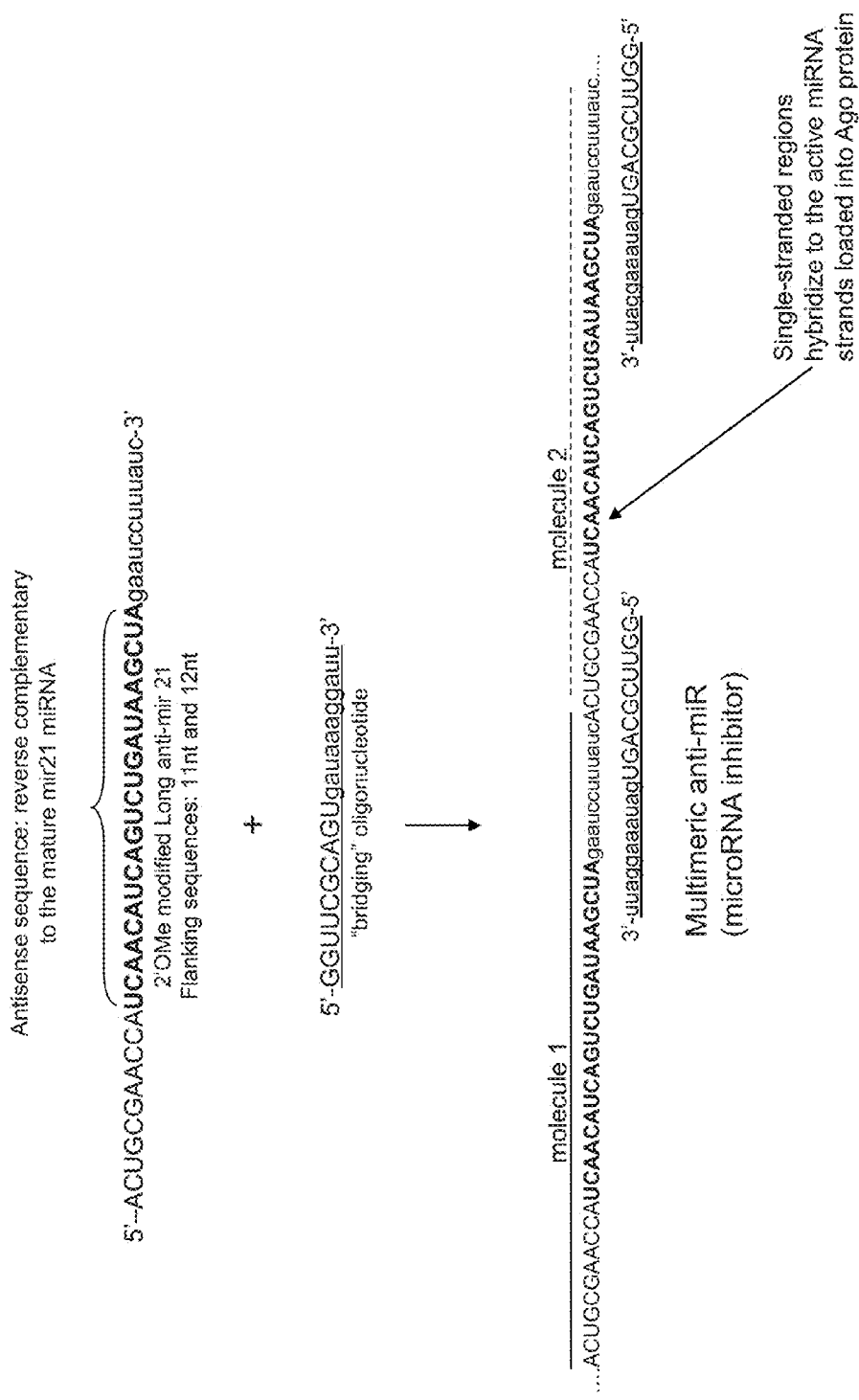
FIG. 10 shows the formation of inhibitors used in the Example 7 experiment in which the formation of multimeric inhibitor complexes was evaluated. The long 2'-OMe modified anti-miRs (elongated at 3' and 5' ends—11 nt at the 5' end and 12 nt at the 3' end) and "bridging" oligonucleotide (21 nt) were combined and heated in the annealing buffer, followed by slow cooling to RT. The top sequence is the 2'OMe modified long anti-mir21 (SEQ ID NO:139), the middle sequence is the "bridging" oligonucleotide (SEQ ID NO:140), the bottom sequence is the multimeric strand containing the target binding sequences (SEQ ID NO:141), and the "bridging" oligonucleotide (SEQ ID NO:140). All experiments were performed in triplicate.

Further, the miRNA inhibitors can include a composition comprising mixtures of various formats shown in FIG. 1, FIG. 9 and FIG. 10 and/or discussed herein.

MiRNA inhibitors can target one or more targets. Thus, each specific binding region can be complementary to one or more targets. Alternatively, multimers can be made that contain mixtures of B2A molecules with multiple binding regions each complementary to one or more targets.

The various formats of the inhibitors shown in FIG. 9 will now be discussed in more detail under the headings "A. hairpin inhibitors," "B. conjugated antisense inhibitors," "C. multimeric inhibitors," and "D. chimeric inhibitors" below:

A. Hairpin Inhibitory Molecules

Without being limited to a single hypothesis, the hairpin structure acts to "stabilize" one terminus and makes the antisense region more accessible for hybridization. Other possibilities are that the double-stranded stem region of the hairpin inhibitor (See FIG. 1 and "B1" in FIG. 9) provides an opportunity for a thermodynamically favorable base-stacking interaction between the inhibitory molecule and the target miRNA. This feature can enhance the ability of inhibitory molecules to retain the hybridization to the target brought about by the canonical Watson-Crick complementarity of the strands. However, base stacking is not the only and may not be the major factor. miRNA guide strands are contained within Ago2 proteins or more sophisticated protein complexes of the RNAi machinery. When inhibitors approach the miRNA strand, hybridization is likely not the major factor; presumably the protein has a governing role. Its natural target is long and structured mRNA, so rather than binding the short antisense sequences (even though they are chemically modified and have high melting temperature) they prefer to bind longer nucleic acids. Hairpin inhibitors seem to work by acting more like the long and structured mRNA with respect to the Ago protein. Hairpin inhibitors with non-nucleotide loops have the added advantage that they are less expensive to produce than those with nucleotide loops, because during oligonucleotide synthesis, one coupling reaction is needed for a non-nucleotide loop whereas nucleotide based loops need multiple (e.g., 4-5) coupling reactions.

With reference to FIG. 9 B1 and C1, embodiments of hairpin inhibitors include at least one loop (either nucleotide or non-nucleotide loop), a first homologous region (HR1), a second homologous region (HR2), and a target binding nucleic acid segment (BR) which is greater than 6 nucleotides in length (a composite nucleic acid). The loop (L) functions to connect the first nucleotide (HR1) and second nucleotide homologous regions (HR2) to form a double-stranded structure (a stem loop) (see C1 in FIG. 9). The loop can be composed of nucleotides. Alternatively, the loop can be composed of any type of non-nucleotide material. In either case, the loop is of sufficient length to allow for the first and the second homologous region to hybridize to one another to form the double stranded structure (a stem). In some embodiments, the first and second homologous regions are able to hybridize under physiological conditions. In some embodiments, the stem-loop is on the 3' end of the nucleic acid molecule (3' hairpin). In some embodiments, the stem-loop is on the 5' end of the nucleic acid molecule (5' hairpin). In some embodiments, the hairpin inhibitors include at least a second loop (either nucleotide or non-nucleotide loop), and a second stem region (including a third homologous region, and a fourth homologous region). In some embodiments, the hairpin inhibitor has a single stem-loop region either at the 3' end or the 5' end of the molecule. In some embodiments, the stem-loop is on the 5' end and there is an addition of at least one nucleotide between the stem and the target binding nucleic acid segment (a spacer). In some embodiments, the stem-loop is on the 3' end and there is an addition of at least one nucleotide between the stem and the target binding nucleic acid segment (a spacer). In some embodiments, the hairpin inhibitors are asymmetric structures including a single stem-loop.

When the loop is composed of nucleic acid, this nucleic acid can be chemically modified and can be DNA or RNA. Further, the length of the loop can be adjusted to allow for association and binding between homologous regions (e.g., "HR1" and "HR2" in FIG. 1 and FIG. 9). Typically, nucleotide loops will be between 4 and 50 nucleotides in length (e.g., from about 4 to about 50, from about 6 to about 50, from about 8 to about 50, from about 10 to about 50, from about 4 to about 40, from about 4 to about 30, from about 4 to about 25, from about 4 to about 20, from about 4 to about 15, from about 5 to about 30, from about 5 to about 15, from about 6 to about 50, from about 6 to about 20, from about 8 to about 20, etc. nucleotides). In some embodiments, the loop has a 2' position substituted with a molecule chosen from O-alkyl, fluoro, OH and H. Alternatively, the nucleic acid loop can include any of the modifications discussed herein (see section entitled "Modifications")

The non-nucleotide loops (see "loop" in FIG. 9, C1) can be used to connect the homologous nucleic acid segments (HR1 and HR2 in FIG. 9, C1). Briefly, the non-nucleotide loop can be of sufficient length and/or have a sufficient number of monomers and/or a sufficient number of atoms to enable effective intramolecular hybridization between the homologous regions (to form a stem). In some embodiments, the loop (see "loop" in FIG. 9, C1) is composed of non-nucleotide polymers. The length of the loop will typically be a length which is at least the length spanned by at least 8-50 atoms (e.g., from about 8 to about 50, from about 8 to about 40, from about 8 to about 30, from about 8 to about 25, from about 8 to about 20, from about 10 to about 30, from about 12 to about 30, etc. atoms), while not being so long as to interfere with the pairing of the oligonucleotides capable of hybridizing to each other. In some embodiments, the length of the loop is the length spanned by between about 18 and about 22 atoms. In some embodiments, the loop has a backbone of covalently bonded atoms chosen from: Carbon, Oxygen, sulfur, phosphate, and nitrogen. In some embodiments, the non-nucleotide loop has a backbone composed of covalently bonded carbon atoms. In some embodiments, the loop is composed of one of the molecules listed in Table 2. In some embodiments, the backbone of the loop comprises covalently bonded carbon and oxygen atoms. In some embodiments, the loop is chosen from polyethylene glycol (e.g., PEG3, PEG4, PEG5, PEG6, PEG7, PEG8, PEG9, or PEG10), C2-C18 alkane diol, styrene, stilbene, triazole, tetrazole, nucleic acid, poly abasic nucleoside, polysaccharide, peptide, polyamide, hydrazone, oxyimine, polyester, disulfide, polyamine, polyether, peptide nucleic acid, cycloalkane, polyalkene, aryl, derivatives thereof and any combination thereof. In some embodiments, the non-nucleotide loop is a fluorescent dye. In some embodiments, the fluorescent dye is CYANINE™ 5 dye, CYANINE™ 3 dye, or an Alexa Fluor emitter. In some embodiments, the non-nucleotide loop is composed of polyethylene glycol (PEG). In some embodiments, the non-nucleotide loop is composed of a polyethylene glycol (PEG) derivative. In some embodiments, the non-nucleotide loop is composed of a polyethylene glycol (PEG) derivative and the polyethylene glycol (PEG) derivative is tri-, tetra-, penta-, hexa-, hepta-, octa-, nona-, or deca-, ethylene glycol ethylene glycol. In some embodiments, the non-nucleotide loop is C12 alkane diol.

In some embodiments, the loop can be separated from the target binding nucleic acid segment by one or more nucleotide spacers (see FIG. 9, format A, designated as an S). The spacer can be one or more nucleotides. In some embodiments, the spacer is a single nucleotide having a purine base, a pyrimidine base, or no base (e.g., abasic). In some embodiments, the spacer is a single nucleotide with the base A, C, G, U or T. In some embodiments, the spacer is at least one nucleotide but can be between 0 and 10 nucleotides, including, but not limited to, 1, 2, 3, 4, 5, 6, 7, 8, and 9 nucleotides. In some embodiments, the spacer is one or more nucleotides and can include universal bases, purine bases, a pyrimidine bases, and/or no base (e.g., abasic). One or more nucleotides in the spacer can also be modified (see "Modification" section below). The spacer can function to reduce the possibility that when the target strand binds to the binding region of the inhibitor, there will be charge repulsion between the end of the homologous region (the 3'phosphate) and the 5' end of the target.

The first and second homologous regions are of an equivalent length such that a stem-like structure can be formed when the two regions bind (see FIG. 1 and FIG. 9, HR1 and HR2). In some embodiments, the length of the first and second homologous regions is between about 3 and 30 nt in length, including but not limited to 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt and 30 nt in length. In some embodiments, the length of the first and second homologous regions is between about 4 and about 10 nucleotides. In some embodiments, the length of the first and second homologous regions is between about 4 and about 8 nucleotides. In some embodiments, the first and second homologous regions are complementary to each other such that they can hybridize under physiological conditions. In some embodiments, the first and second homologous regions have between about 40% to about 100% complementarity with one or more targets, including about 40% to about 100% complementarity with one or more targets, including about 60% to 100% complementarity with one or more targets, including 70%, 80%, 90%, 95% and 99%. In some embodiments, the first and second homologous regions are not the same length.

The target binding nucleic acid segment shown as "BR" in FIG. 1 and FIG. 9, can be a reverse complement (RC) to the target molecule of interest (e.g., miRNA). In some embodiments, the length of the target binding region is optimized to obtain maximum specificity for the target (e.g., the miRNA) while retaining potency. The target can be any nucleic acid discussed herein as a target, including any short, non-coding nucleic acid (e.g., microRNA). The binding region can be a reverse complement (RC) to one or more target molecule(s) of interest (e.g., miRNA). In some embodiments, the target binding nucleic acid segment is complementary to all or a portion of at least one target, such that it will bind to the target (see FIG. 9, Target NA in format B1). By complementary, the target binding nucleic acid segment can have between about 40% to about 100% complementarity with one or more targets, including about 60% to 100% complementarity with one or more targets, including but not limited to 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99% complementarity. In some embodiments the target binding region can be complementary to more than one target. In some embodiments, the binding region can be complementary to two or more targets. In some embodiments the target binding region is 100% complementary to two or more targets. In some embodiments, the target binding region can have 80-100% complementarity with one target and 60% or more complementarity with at least a second target. In some embodiments, the target binding region can have 100% complementarity to a portion of the target and 60% complementarity to the rest. In some embodiments, the target binding nucleic acid segment is at least 6 or more nucleotides in length. In some embodiments, the target binding nucleic acid segment is between about 6 and about 200 nucleotides in length. In some embodiments, the target binding nucleic acid segment is between about 6 and 50 nucleotides in length, including between about 9 and 25 nucleotides in length, including, but not limited to: 10 nt, 11 nt, 12 nt, 13 nt, 14 nt, 15 nt, 16 nt, 17 nt, 18 nt, 19 nt, 20 nt, 21 nt, 22 nt, 23 nt, 24 nt and 25 nt in length. In some embodiments, the target binding nucleic acid segment is between about 15 nt and about 25 nucleotides in length In some embodiments, the target binding nucleic acid segment is between about 20 nt and about 23 nucleotides in length.

The target binding region (BR) can be modified in any way known in the art and/or discussed herein (see section entitled "Modification"). In some embodiments, the target binding region is between about 20 and about 200 nucleotides in length and the target is a long non-coding RNA.

In some embodiments, the composite nucleic acid inhibitor (hairpin) molecule can include one or more nucleotides on the 5' or 3' end. In some embodiments, the extra nucleotides can be selected from a purine base, a pyrimidine base or no base (e.g., abasic). In some embodiments, the extra nucleotides can be from 0 to 30 nucleotides, including but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, and 29 nucleotides. In some embodiments, the composite nucleic acid inhibitory (hairpin) molecule can include a non-nucleotide loop on the 5' or 3' end. The non-nucleotide loop can be any material discussed herein as long as it does not interfere with binding to the target nucleic acid.

In some embodiments, the total composite nucleic acid inhibitory molecule (hairpin inhibitor) in total is between about 28 and about 200 nucleotides in length, including between about 28 and about 100 nucleotides in length. In some embodiments, the composite nucleic acid molecule is between about 28 and about 40 nucleotides in length. In some embodiments the composite nucleic acid molecule is between about 34 and about 36 nucleotides in length. In some embodiments, the length does not include the non-nucleotide loop.

In some embodiments, the composite nucleic acid molecule (hairpin inhibitor) includes modifications in any part of the hairpin inhibitor, including the target binding nucleic acid ("BR" in FIG. 9), the stem ("HR1" and "HR2" in FIG. 9), the loop ("Loop" in FIG. 9), the spacer ("S" in FIG. 9), the 5' end and the 3' end. Such modifications can be any modifications that do not preclude binding to the target (e.g., the miRNA). In some embodiments, the modifications increase binding to the target. Modifications can include, without limitations, an alkyl, an amine, imine, guanidine, aromatic amino heterocycle. Modifications can include DNA, RNA, 2'OMe, 2'OAllyl, 2'O-propargyl, 2'O-alkyl, 2'fluoro, arabino, 2'-xylo, 2'fluoro arabino, phosphorothioate, phosphorodithioate, 2'amino, 5-alkyl-substituted pyrimidine, 5-halo-substituted pyrimidine, alkyl-substituted purine, halo-substituted purine, bicyclic nucleotides, 2'MOE, LNA, ENA (e.g. aza-ENA and carbo-ENA), combinations thereof and derivatives thereof. Modifications of these types, as well as other modifications, are disclosed in US Patent Publ. Nos. 2008/0146788, 2009/0192302, and 2010/0087387, the entire disclosures of which are incorporated herein by reference.

Alternatively, modifications can include modifications to the nucleotides in the target binding region, particularly modifications that increase binding of the nucleotides to their target. For example, LNA-like molecules are sugar structures that are 3'endo and are fixed in a certain conformation that is effective to bind to RNA. Exemplary modifications include at least one 2'O-alkyl, LNA (and LNA-like molecules), 2'fluoro, phosphorothioate, phosphoroamidates, 5-alkyl- or halo substituted pyrimidines and alkyl or halo-substituted purine bases. Further exemplary modifications include DNA, RNA, 2'OMe, 2'OAllyl, 2'O-propargyl, 2'O-alkyl, 2'-xylo, 2'fluoro, 2' arabino, 2'fluoro arabino, phosphorothioate, phosphorodithioate, 2'Amino, 5-alkyl-substituted pyrimidine, 5-halo-substituted pyrimidine, alkyl-substituted purine, halo-substituted purine, bicyclic nucleotides, 2'MOE, LNA, combinations thereof and modifications thereof. In some embodiments, the modifications can include addition of a 3' alkyl amino group. In some embodiments, the addition of the 3' alkyl amino group enhances potency of the microRNA inhibitor at lower concentrations. Exemplary modifications include LNA (and LNA-like molecules) and 2'-OMe, but many other modifications can be included. In some embodiments, the nucleotides are LNA modified at every position. In some embodiments the nucleotides are LNA modified at every other position. In some embodiments, the target binding region is 2'OMe modified. See more about modification in the section entitled "Modifications" below.

With reference to FIG. 1, the hairpin inhibitors can be included in a composition as 3'hairpins (having the stem loop at the 3' end), 5' hairpins (having the stem loop at the 5' end), 3' and 5' double hairpins and/or combinations of the three. Further, hairpin inhibitors of the invention can be included in compositions with other types of inhibitors, including multimeric and/or conjugated antisense inhibitors of the invention. The asymmetric design can also allow for specificity modulation. The ability to have two (5' loop or 3' loop) highly potent inhibitory molecules for each target miRNA provides not only a means for target validation but also a mechanism for studies of specificity within and among members of closely related miRNA families. 5' inhibitors reinforce duplex formation at the 3' end of the miRNA which can contribute to inter-familial specificity. Alternatively, 3' inhibitors reinforce duplex formation at the 5' end of the miRNA presumably reinforcing intra-familial specificity. Thus, mixtures can have a number of advantages. With reference herein to a 22 nt miRNA inhibitor control with complete 2'-OMe modification (2'-OMe), the first 3'-nucleotide for hairpin inhibitors is unmodified as shown in tables and drawings herein.

B. Conjugated Antisense Inhibitors

In some embodiments conjugated antisense inhibitors are envisioned. With reference to format A in FIG. 9, the conjugated antisense inhibitors include a target binding nucleic acid segment (BR) and at least one loop (NBR or loop), wherein the loop is not nucleic acid. In some embodiments, the loop is located at the 3' end of the antisense inhibitor. In some embodiments, the loop is located at the 5' end of the antisense inhibitor. In some embodiments, the loop is located at both ends of the antisense inhibitor. In some embodiments, when there are two loops, they are the same non-nucleotide loop. In some embodiments, when there are two loops, they are different non-nucleotide loops.

The target binding nucleic acid segment (see "BR" in FIG. 9, format A) can be a reverse complement (RC) to the target molecule of interest (e.g., miRNA). In some embodiments, the length of the target binding region is optimized to obtain maximum specificity for the target (e.g., the miRNA) while retaining potency. The target can be any nucleic acid discussed herein as a target, including any short, non-coding nucleic acid (e.g., microRNA). The binding region can be a reverse complement (RC) to one or more target molecule(s) of interest (e.g., miRNA). In some embodiments, the target binding nucleic acid segment is complementary to all or a portion of at least one target, such that it will bind to the target (see FIG. 9, Target NA in format B1). By complementary, the target binding nucleic acid segment can have between about 40% to about 100% complementarity with one or more targets, including about 60% to 100% complementarity with one or more targets, including but not limited to 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99% complementarity. In some embodiments the target binding region can be complementary to more than one target. In some embodiments, the binding region can be complementary to two or more targets. In some embodiments the target binding region is 100% complementary to two or more targets. In some embodiments, the target binding region can have 80-100% complementarity with one target and 60% or more complementarity with at least a second target. In some embodiments, the target binding region can have 100% complementarity to a portion of the target and 60% complementarity to the rest.

In some embodiments, the target binding nucleic acid segment is at least 6 or more nucleotides in length. In some embodiments, the target binding nucleic acid segment is between about 6 and about 200 nucleotides in length. In some embodiments, the target binding nucleic acid segment is between about 6 and 50 nucleotides in length, including between about 9 and 25 nucleotides in length, including, but not limited to: 10 nt, 11 nt, 12 nt, 13 nt, 14 nt, 15 nt, 16 nt, 17 nt, 18 nt, 19 nt, 20 nt, 21 nt, 22 nt, 23 nt, 24 nt and 25 nt in length. In some embodiments, the target binding nucleic acid segment is between about 15 nt and about 25 nucleotides in length In some embodiments, the target binding nucleic acid segment is between about 20 nt and about 23 nucleotides in length. The target binding region (BR) can be modified in any way known in the art and/or discussed herein (see section entitled "Modification"). In some embodiments, the target binding nucleic acid segment is between about 20 and about 200 nucleotides in length and the target is a long non-coding RNA.

In some embodiments, the loop (see NBR or Loop in FIG. 9, format A) can be separated from the target binding nucleic acid segment by a one or more nucleotide spacer (see FIG. 9, format A, designated as an "S"). The spacer can be one or more nucleotides. In some embodiments, the spacer is a single nucleotide having a purine base, a pyrimidine base, or no base (e.g., abasic). In some embodiments, the spacer is a single nucleotide with the base A, C, G, U or T. In some embodiments, the spacer is at least one nucleotide but can be between 0 and 10 nucleotides, including, but not limited to, 1, 2, 3, 4, 5, 6, 7, 8, and 9 nucleotides. In some embodiments, the spacer is one or more nucleotides and can include universal bases, purine bases, a pyrimidine bases, and/or no base (e.g., abasic). One or more nucleotides in the spacer can also be modified (see "Modification" section below).

In some embodiments, the composite nucleic acid molecule in total (conjugated antisense inhibitor) is between about 15 and about 50 nucleotides in length, including between about 20 and about 40 nucleotides in length. In some embodiments, the composite nucleic acid molecule is between about 20 and about 30 nucleotides in length. In some embodiments the composite nucleic acid molecule is between about 20 and about 25 nucleotides in length. In some embodiments, the length does not include the non-nucleotide loop.

In some embodiments, the loop (see "NBR" in FIG. 9, format A) is composed of one or more non-nucleotide polymers. In some embodiments, the loop is composed of one of the compounds listed in Table 2. In some embodiments, the non-nucleotide loop has a backbone composed of covalently bonded carbon atoms. In some embodiments, the loop has a backbone of covalently bonded atoms chosen from: carbon, oxygen, sulfur, phosphate, and nitrogen. In some embodiments, the backbone of the loop comprises covalently bonded carbon and oxygen atoms. In some embodiments, the loop is chosen from polyethylene glycol (e.g., PEG3, PEG4, PEG5, PEG6, PEG7, PEG8, PEG9, and PEG10), C2-C18 alkane diol, styrene, stilbene, triazole, tetrazole, nucleic acid, poly abasic nucleoside, polysaccharide, peptide, polyamide, hydrazone, oxyimine, polyester, disulfide, polyamine, polyether, peptide nucleic acid, cycloalkane, polyalkene, aryl derivatives thereof and any combination thereof. In some embodiments, the non-nucleotide loop is a fluorescent dye. In some embodiments, the fluorescent dye is CYANINE™ 5 dye, CYANINE™ 3 dye, or an Alexa Fluor emitter. In some embodiments, the non-nucleotide loop is composed of polyethylene glycol (PEG). In some embodiments, the non-nucleotide loop is composed of a polyethylene glycol (PEG) derivative. In some embodiments, the non-nucleotide loop is composed of a polyethylene glycol (PEG) derivative and the polyethylene glycol (PEG) derivative is a tri-, tetra-, penta-, hexa-, hepta-, octa-, nona-, or deca-, ethylene glycol. In some embodiments, the non-nucleotide loop is C12 alkane diol.

In some embodiments, the composite nucleic acid inhibitory (conjugated antisense) molecule can include one or more nucleotides on the 5' or 3' end. In some embodiments, the extra nucleotides can be selected from a purine base, a pyrimidine base or no base (e.g., abasic). In some embodiments, the extra nucleotides can be from 0 to 30 nucleotides, including but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, and 29 nucleotides.

C. Multimeric Inhibitors

Without being limited to a single hypothesis, a multimeric inhibitor can act by mimicking the mRNA and thus, promoting stronger interaction with the microRNA. Multimeric inhibitors have the further advantage of not having secondary structure (in contrast to long single-stranded tandem anti-miRs, which could be chemically synthesized or transcribed in vitro) which can complicate complex formation with miRNAs. In addition, the termini of multimeric inhibitors will inherently have extra protection from RNases, and packaging and in vitro delivery of these multimers will be more efficient with many commercially available reagents because the complexes are long and rigid.

Embodiments of multimeric inhibitors include at least a first oligonucleotide (e.g., B2A in FIG. 9) and a second oligonucleotide (e.g., B2B in FIG. 9), wherein the first oligonucleotide comprises a target nucleic acid molecule binding region, and two or more regions which will not hybridize to the target nucleic acid molecule, wherein the second oligonucleotide comprises two regions which will hybridize under physiological conditions to at least two of the two or more regions of the first oligonucleotides which will not hybridize to the target nucleic acid molecule, and wherein the multimeric nucleic acid molecule comprises both single-stranded and double-stranded regions. In some embodiments, the single-stranded region is capable of binding to a target nucleic acid molecule under physiological conditions. In some embodiments, the target nucleic acid is a short non-coding RNA. In some embodiments, the target nucleic acid molecule is chosen from a microRNA, a piwi-interacting RNA, a small interfering RNA, a messenger RNA, and a ribosomal RNA.

With reference to FIG. 9, an embodiment of a multimeric inhibitory molecule C2 is shown that is made up of a multimer of molecules B2A with three molecules of B2B hybridized thereto. Thus, a multimeric inhibitor can be made up of at least one first oligonucleotide (B2A) that comprises a target nucleic acid molecule binding region (BR), and two or more regions which will not hybridize to the target nucleic acid molecule (NBR1 and NBR2) and at least one second oligonucleotide (B2B) that comprises two regions which will hybridize under physiological conditions (NBR2C and NBR1C) to at least two of the two or more regions of the first oligonucleotides which will not hybridize to the target nucleic acid molecule (NBR1 and NBR2), and wherein the multimeric nucleic acid molecule (C2) comprises both single-stranded and double-stranded regions. Multimeric nucleic acid molecule inhibitors are therefore comprised of individual molecules that assemble into a multimeric structure. The number of individual molecules may be from 2, 3, 4, 5, to 20 or to 100 or more, or any integer range therebetween. Multimeric inhibitors may contain nicks where hybridization of two ends to a complementary nucleic acid occurs.

With reference to FIG. 9 and in more detail, the first oligonucleotide B2A comprises at least one binding region (BR), and at least two non-binding regions (NBR1 and NBR2). The non-binding regions, while they do not bind to the target nucleic acid, can bind to other regions of the second oligonucleotide (B2B). Thus, the NBR1 is complementary to the NBR1C of the second oligonucleotide (B2B) and the NBR2 is complementary to the NBR2C of the second oligonucleotide. In some embodiments, the length of the non-binding regions is between about 3 and 30 nt in length, including but not limited to 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt and 30 nt in length. In some embodiments, the length of the non-binding regions is between about 4 and about 10 nucleotides. In some embodiments, the length of the non-binding regions is between about 4 and about 8 nucleotides. In some embodiments, the non-binding regions of the first oligonucleotide are complementary to the non-binding regions on the second oligonucleotide such that they can hybridize under physiological conditions. In some embodiments, the non-binding region for the first oligonucleotide and the non-binding region on the second oligonucleotide are about 80% to about 100% complementary to each other. In some embodiments, the non-binding regions on the first oligonucleotide are complementary to the non-binding regions on the second oligonucleotide but are not the same length.

Although it is not necessary to include spacer regions, in some embodiments, the binding region (BR) of the first oligonucleotide can be separated from the one or more non-binding regions (NBR1 and/or NBR2) of the first oligonucleotide by a one or more nucleotide spacer (see FIG. 9, B2A, designated as an "S1" and "S2"). The spacer can be one or more nucleotides. In some embodiments, the spacer is a single nucleotide having a purine base, a pyrimidine base, or no base (e.g., abasic). In some embodiments, the spacer is a single nucleotide with the base A, C, G, U or T. In some embodiments, the spacer is at least one nucleotide but can be between 0 and 10 nucleotides, including, but not limited to, 1, 2, 3, 4, 5, 6, 7, 8, and 9 nucleotides. In some embodiments, the spacer is one or more nucleotides and can include universal bases, purine bases, a pyrimidine bases, and/or no base (e.g., abasic). One or more nucleotides in the spacer can also be modified (see "Modification" section below). The spacer can function in this inhibitory molecule to ensure that there is no charge repulsion from the 3' phosphate of the second oligonucleotide when the target binds to the binding region (BR).

In some embodiments, the binding region binds one or more targets. The target can be any nucleic acid discussed herein as a target, including any short, non-coding nucleic acid (e.g., microRNA). The binding region can be a reverse complement (RC) to one or more target molecule(s) of interest (e.g., miRNA). In some embodiments, the length of the target binding region is optimized to obtain maximum specificity for the target (e.g., the miRNA) while retaining potency. In some embodiments, the target binding nucleic acid segment is complementary to all or a portion of at least one target, such that it will bind to the target (See FIG. 9, Target NA in format B1). By complementary, the target binding nucleic acid segment can have between about 40% to about 100% complementarity with one or more targets, including about 60% to 100% complementarity with one or more targets, including but not limited to 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99% complementarity. In some embodiments the target binding region can be complementary to more than one target. In some embodiments, the binding region can be complementary to two or more targets. In some embodiments the target binding region is 100% complementary to two or more targets. In some embodiments, the target binding region can have 80-100% complementarity with one target and 60% or more complementarity with at least a second target. In some embodiments, the target binding region can have 100% complementarity to a portion of the target and 60% complementarity to the rest. In some embodiments, the target binding nucleic acid segment is at least 6 or more nucleotides in length. In some embodiments, the target binding nucleic acid segment is between about 9 and 50 nucleotides in length, including between about 10 and 25 nucleotides in length, including, but not limited to: 11 nt, 12 nt, 13 nt, 14 nt, 15 nt, 16 nt, 17 nt, 18 nt, 19 nt, 20 nt, 21 nt, 22 nt, 23 nt, 24 nt and 25 nt in length. In some embodiments, the target binding nucleic acid segment is between about 15 nt and about 25 nucleotides in length In some embodiments, the target binding nucleic acid segment is between about 20 nt and about 23 nucleotides in length. The target binding region (BR) can be modified in any way known in the art and/or discussed herein (see section entitled "Modification").

In some embodiments, multimers of B2A are linked to form the multimeric top strand of the multimeric inhibitor C2 in FIG. 9. The multimers of the B2A molecule include binding regions (BR) separated from other binding regions (BR) by one or more non-binding regions (NBR1, NBR2, and NBR1NBR2). The binding regions may also be separated from the non-binding regions by at least one spacer. Thus, C2 shows one exemplary format of a multimeric top strand, but other embodiments can be envisioned that contain more or fewer B2A molecules and/or spacers. In some embodiments, some of the B2A molecules linked to create the multimeric top strand in C2 can contain spacers and some may not contain spacers. In some embodiments, there are one or more Binding Regions (BR), including but not limited to, two, three, four, five, six, seven, eight, nine, and ten. In some embodiments there are between two and five binding regions.

In some embodiments, the first oligonucleotide is between from about 30 nucleotides to about 200 nucleotides in length, including about 30 to about 100 nucleotides in length, and about 30 to about 50 nucleotides in length.

In some embodiments, the second oligonucleotide is between from about 10 nucleotides to about 50 nucleotides in length, including about 10 to about 30 nucleotides in length, and about 10 to about 20 nucleotides in length. In some embodiments, the second oligonucleotide does not overlap the binding region of the first oligonucleotide. In some embodiments, the second oligonucleotide is the same length as the one or more non-binding regions of the first oligonucleotide that it binds to. It is understood that if the first oligonucleotide includes one or more spacer regions that are, for example, 4 nucleotides in length, the second oligonucleotide could be one or two nucleotides longer (could bind partially to the spacer region and would not interfere with binding of the target molecule.

In some embodiments, because of the way the multimers are formed, the total length of the multimeric anti-microRNA molecule (not including the second oligonucleotide) can vary from the length of a single B2A molecule to the length of 100-300 B2A molecules. Thus, depending on the annealing buffer, the number of monomers (B2A and B2B molecules) that multimerize can vary. Further, depending on the molar ratio of B2A:B2B molecules, the number that multimerize can vary. While the difference in size should not affect the performance, the size can be controlled, if desired, by addition of "stoppers/blockers". The "stoppers/blockers" can be oligonucleotides that are added with the B2A and B2B molecules during annealing. The "stoppers/blockers" can contain only one part of the bridging oligo (e.g., only NBR2C without NBR1C). Optionally, a "stopper/blocker" can be a hairpin structure at the 5' or 3' end of the B2A molecule. Such blockers could be added to the complexes at different concentrations and restrict the average length of the complexes formed.

FIG. 10 shows a schematic of the production of a multimeric inhibitor. With reference to FIG. 10, the top strand is the B2A molecule shown in FIG. 9. The middle strand is the B2B molecule shown in FIG. 9 and the bottom molecule is C2 in FIG. 9. Without being limited to a specific theory, the single-stranded regions of multimeric inhibitors are believed to hybridize to the active miRNA strands loaded onto the Ago protein. The multimeric inhibitor in FIG. 10 shows two binding regions (the single-stranded regions), but could contain many more depending on how many B2A molecules multimerize.

In some embodiments, modifications are included that allow for strong interactions with the target and/or strong interactions between the first and second oligonucleotides (B2A and B2B in FIG. 9). Exemplary modifications include LNA (and LNA-like molecules) and 2'-OMe, but many other modifications can be included. In some embodiments, the nucleotides are LNA modified at every other position. In some embodiments, the first oligonucleotide and/or the target binding region is 2'OMe modified.

In some embodiments, the composite nucleic acid inhibitory (multimeric inhibitor) molecule can include one or more nucleotides on the 5' or 3' end. In some embodiments, the extra nucleotides can be selected from a purine base, a pyrimidine base or no base (e.g., abasic). In some embodiments, the extra nucleotides can be from 0 to 30 nucleotides, including but not limited to, 1, 2, 3, 4, 5, 6, 7, 8, 9, 10, 11, 12, 13, 14, 15, 16, 17, 18, 19, 20, 21, 22, 23, 24, 25, 26, 27, 28, and 29 nucleotides. In some embodiments, the composite nucleic acid inhibitory (multimeric inhibitor) molecule can include a non-nucleotide loop on the 5' or 3' end. The non-nucleotide loop can be any material discussed herein as long as it does not interfere with binding to the target nucleic acid.

In some embodiments, the multimeric molecules are formed by mixing various amounts of the long strand containing the target molecule binding region (the first oligonucleotide) with the smaller oligonucleotide (the second oligonucleotide). In some embodiments, the first and second oligonucleotides are mixed in an appropriate buffer (such as an annealing buffer) at a temperature for a time long enough to anneal. In some embodiments, the first and second oligonucleotides are denatured followed by a cool down for an amount of time to allow annealing of the two molecules. For example, a typical annealing buffer includes 10 mM Tris pH 7.4, 100 mM NaCl. A typical denaturing temperature is 95° C. for 3 min. A typical cool down temperature is 37° C. for 1 hour. In some embodiments, the first and second oligonucleotides are added in equal amounts. In some embodiments, the two are added such that there is a molar excess of the first oligonucleotide. In some embodiments, the two are added such that there is a molar excess of the second oligonucleotide. In some embodiments, the multimers spontaneously anneal to produce the final multimerized inhibitory molecules. In some embodiments, the multimers anneal to form molecules having a variety of sizes (a pool of sizes). In some embodiments, the sizes can be, from a single multimer (the length of one B2A molecule) to 100 s of multimers (100 s of B2A molecules in length).

D. Chimera of Inhibitors

In some embodiments, chimeric molecules can be envisioned which contain various parts of the formats shown herein, including but not limited to, BR's, NBR's, S's, HR1 and HR2's, NBR1 and NBR2's, and loops (see FIG. 9). Further, the formats can include nucleotide loop or non-nucleotide loops as part of a stem-loop structure or attached at the 3' or 5' ends directly. The formats can be produced as multimers and can include single and double-stranded regions such as those shown in format C2. The chimeric molecules of the invention can also include any of the modifications discussed herein and/or under the heading "Modifications".

In some embodiments, chimeric miRNA inhibitors are produced that have parts of conjugated antisense inhibitors coupled with parts of multimeric inhibitors. For example, parts of the multimeric inhibitor can be combined with a 3' or 5' non-nucleotide loop. Further, chimeric inhibitors having parts of the hairpin inhibitors mixed with parts of the multimeric inhibitors are envisioned. For example, multimeric inhibitors having 5' or 3' hairpin structures can be produced and used for inhibition of the microRNAs in the cell. In some embodiments, chimeric inhibitors can target one or more targets within a cell or sample.

E. Mixtures of Inhibitors

Compositions of miRNA inhibitors for use in miRNA inhibition can include any combinations or mixtures of the formats discussed herein. For example, combinations can include hairpin inhibitors (with nucleotide or non-nucleotide loops) mixed with conjugated antisense inhibitors and/or multimeric inhibitors. Further, combinations can include mixtures of different types of hairpin inhibitors that are complementary to the same target. In some embodiments, mixtures of miRNA inhibitors with a 5' loop (5' hairpin) and miRNA inhibitors with a 3' loop (3' hairpin) can be used. Having the loop at the 5' end of the hairpin inhibitors can provide certain advantages over having the loop at the 3' end of the hairpin inhibitor (and vice versa). Thus, having a mixture of the two can be particularly advantageous in some circumstances.

II. Modifications

The composition of the nucleic acid inhibitory molecules of the invention can vary greatly and can include homogeneous nucleic acids (e.g., all RNA), heterogeneous nucleic acids, (e.g., RNA and DNA), modified nucleic acids, and unmodified nucleic acids. In some embodiments, the nucleic acid molecules of the invention include a mixture of modified and unmodified RNA and/or DNA.

Any modification without limitation can be used for the nucleic acid inhibitory molecules of the invention provided they do not inactivate the inhibitory molecules. The position of the modification can vary with respect to the following: The position or positions within the strand (i.e., the nucleotide position or positions within the strand or strands), the positions of the nucleotide(s) that are modified (e.g. the sugar and/or the base), the region of the inhibitory nucleic acid that is modified (e.g., the target binding region), the number of modifications in a specific nucleic acid molecule, and what the modification accomplishes (e.g., increased binding, stability, resistance to RNase, etc.).

In some embodiments, modifications can enhance binding of nucleic acid inhibitory molecules to their target sequences. In some embodiments, modifications can enhance cellular uptake (e.g., endocytosis) of the nucleic acid inhibitor. In some embodiments, modifications can cause specific cellular uptake to a specific cell or tissue. In some embodiments, modifications can enhance cell penetration of the nucleic acid inhibitor. In some embodiments, modifications can enhance cell or tissue localization of the nucleic acid inhibitor. In some embodiments, modifications can enhance facilitated diffusion of the nucleic acid inhibitor. In some embodiments, modifications can enhance cellular trafficking of the nucleic acid inhibitor. In some embodiments, modifications can enhance binding of the stem structure, thus creating a stable stem loop structure. In some embodiments, modifications can reduce the chance of degradation of the nucleic acid inhibitor within a cell or tissue. In some embodiments, modifications can reduce non-specific binding of the nucleic acid inhibitor. In some embodiments, modifications can enhance binding of the double stranded regions of a multimeric inhibitor. In some embodiments, modifications can enhance inhibitor detection of the nucleic acid inhibitor, for example, by adding a tag or detection agent, such as a fluorophore or a radioactive moiety.

In some embodiments, modifications can be found on any one or more regions on the nucleic acid inhibitory molecule. With reference to FIG. 9, these can include, but are not limited to: a non-binding region (NBR), a binding region (BR), a spacer (S), a homology region (HR), or a loop (nucleotide or non-nucleotide). In some embodiments, modifications are a 5' and/or 3' modification. In some embodiments, modifications are nucleoside modifications. In some embodiments, modifications are base modifications. In some embodiments, modifications are modifications to a non-nucleotide loop. In some embodiments, modifications are to 1 or more nucleotides within one or more regions within the nucleic acid inhibitory molecule. For example, for a 25 nt binding region, the modification may be to between 1 and 25 nucleotides, including 2, 3, 4, 5, 6, 7, 8, 9, 10, 11, 12, 13, 14, 15, 16, 17, 18, 19, 20, 21, 22, 23, and 24 nucleotides. In some embodiments, modifications are to every other nucleotide. In some embodiments, every nucleotide in the specified region is modified. For example, in some embodiments, all of the nucleotides of the spacer region (see FIG. 9) are modified. In some embodiments, all of the nucleotides that comprise both the homologous regions and the target binding regions are modified. In some embodiments, all of the nucleotides that comprise both the homologous regions and the target binding regions are 2'OMe modified.

In some embodiments, modifications include the addition of a nucleotide or non-nucleotide loop. In some embodiments, when a nucleotide loop is added, it is included as a stem-loop structure. In some embodiments, a non-nucleotide loop is composed of one or more of the following: polyethylene glycol (e.g., PEG3, PEG4, PEG5, PEG6, PEG7, PEG8, PEG9, or PEG10), C2-C18 alkane diol, styrene, stilbene, triazole, tetrazole, nucleic acid, poly abasic nucleoside, polysaccharide, peptide, polyamide, hydrazone, oxyimine, polyester, disulfide, polyamine, polyether, peptide nucleic acid, cycloalkane, polyalkene, aryl, derivatives thereof and any combination thereof. In some embodiments, the non-nucleotide loop contains a fluorescent dye. In some embodiments, the fluorescent dye is CYANINE™ 5 dye, CYANINE™ 3 dye, or an Alexa Fluor emitter. In some embodiments, the non-nucleotide loop is composed of polyethylene glycol (PEG), fluorescent dye, and a steroid.

In some embodiments, nucleic acid molecules of the invention can include one or more modifications, including but not limited to: 2'-O-alkyl modifications such as 2'-O-methyl modifications, 2'-orthoester modifications, 2' halogen modifications (2'-fluoro), LNAs (locked nucleic acids), LNA derivatives (LNA-like molecules), dithiol, amino acids, peptides, polypeptides, proteins, sugars, carbohydrates, lipids (e.g., cholesterol) polymers (e.g., PEG), nucleotides, polynucleotides, phosphorothioates, targeted small molecules, fluorescent tags, radioactive labels, derivatives thereof and combinations thereof. In some embodiments, the modification adds an amine, imine, guanidine, or aromatic amino heterocycle. In some embodiments, nucleic acid molecules can include modifications chosen from DNA, RNA, 2'OMe, 2'Oallyl, 2'O-propargyl, 2'O-alkyl, 2'fluoro, 2'arabino, 2'xylo, 2'fluoroarabino, phosphorothioate, phosphorodithioate, 2'amino, 5-alkyl-substituted pyrimidine, 5-halo-substituted pyrimidine, alkyl-substituted purine, halo-substituted purine, bicyclic nucleotides, 2'MOE, LNA, combinations thereof and derivatives thereof.

In some embodiments, the modification comprises at least one or more alkyl groups. Alkyl groups can comprise moieties that are linear, branched, cyclic and/or heterocyclic, and contain functional groups such as ethers, ketones, aldehydes, carboxylates, etc. Exemplary alkyl groups include but are not limited to substituted and unsubstituted groups of methyl, ethyl, propyl, butyl, pentyl, hexyl, heptyl, octyl, nonyl, decyl, undecyl, dodcecyl, tridecyl, tetradecyl, pentadecyl, hexadecyl, heptadecyl, octadecyl, nonadecyl, eicosyl and alkyl groups of higher number of carbons as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and derivatives thereof. The term alkyl also encompasses alkenyl groups, such as vinyl, allyl, aralkyl and alkynyl groups.

Substitutions within alkyl groups, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The alkyl groups can by way of example also comprise modifications such as azo groups, keto groups, aldehyde groups, carboxyl groups, nitro, nitrosos or nitrile groups, heterocycles such as imidazole, hydrazino or hydroxylamino groups, isocyanate or cyanate groups, and sulfur containing groups such as sulfoxide, sulfone, sulfide, and disulfide. Unless otherwise specified, alkyl groups do not comprise halogens, sulfurs, thiols, thioethers, thioesters, amines, amides, ethers, esters, alcohols, oxygen, derivatives thereof and/or the modifications listed above.

Further, alkyl groups can also contain hetero substitutions, which are substitutions of carbon atoms, by for example, nitrogen, oxygen or sulfur. Heterocyclic substitutions refer to alkyl rings having one or more heteroatoms. Examples of heterocyclic moieties include but are not limited to morpholine, imidazole, and pyrrolidino.

In some embodiments, modifications can enhance binding to the target nucleic acid molecule. In some embodiments, such modifications are within the target binding region of the inhibitory molecules of the invention. In some embodiments, the binding of the nucleic acid inhibitor is enhanced as compared to binding of the unmodified nucleic acid inhibitory molecule to its target. In some embodiments, binding is increased compared to binding to its RNA target. In some embodiments, binding is increased compared to binding to its DNA target. Examples of modifications that can enhance the binding of an RNA or DNA to its target include but are not limited to: 2'-O-alkyl modified ribonucleotides, 2'-O-methyl ribonucleotides, 2'-orthoester modifications (including but not limited to 2'-bis(hydroxyl ethyl), and 2' halogen modifications and locked nucleic acids (LNAs and LNA-like molecules). However, it is also to be understood that binding can be enhanced by changing the sequence of a region, for example, by including more G and C bases. Thus, binding can be increased by increasing the CG content of a region. For example, to increase binding of the stem area of the stem-loop and/or the double-stranded region of the multimeric inhibitor, the sequence can be changed to include more cytosines and more guanines.

In some embodiments, modifications can enhance cellular uptake of the nucleic acid inhibitor, specifically or nonspecifically. For example, a 3'-terminal cholesterol group appears to aid delivery of inhibitors to cells (Forstemann, et al., 2007, *Cell*, v. 130, p. 287-297). Further, cholesterol conjugation may also have properties that further enhance inhibitor activity, such as improved intracellular escape from lipsomes, relocalization of the targeted miRNAs or enhancement of inhibitor stability. Exemplary modifications that can enhance cellular uptake include but are not limited to: 3'Chl$_A$ (3' cholesterol), 3' Chl$_P$ (3' cholesterol), or phosphorothioates. Antisense inhibitors with complete phosphorothioate backbones have been used previously and show no toxicity in mice or primates (Elmén et al, 2008, Nature, v. 452, p. 896-900; Elmén et al, 2008, *Nucl. Acids Res.*, v. 36, p. 1153-1162).

The invention thus includes inhibitory molecules which are capable of crossing cell membranes. Such molecules will typically be nucleic acid molecules that are associated with one or more non-nucleic acid molecules. One example would be a nucleic acid molecule with a double-stranded region wherein the complementary regions are connected by a hydrophilic chemical group or collection of groups. In a specific embodiment, a loop region of a miRNA inhibitor may (1) be hydrophilic and/or (2) contain hydrophilic groups and/or regions. For example, the loop may be composed of polyethylene glycol covalently linked to one or more (e.g., one, two, three, four, five, six, seven, eight, etc.) steroid molecules (e.g., cholesterol, ergosterol, lanosterol, etc., as well as derivatives thereof). Further, instead of or in addition to steroid molecules, other hydrophobic molecules may be present (e.g., lipids such as fatty acyls, sphingolipids, prenol lipids, etc.). Thus, the invention includes methods for delivering inhibitory molecules to cells, as well as the inhibitory molecules themselves. Typically, such inhibitory molecules will contain a hydrophobic group and/or region.

Additional lipophilic moieties which can be used for delivery of inhibitory molecules include oleyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. Additional compounds, and methods of use, are set out in US Patent Publication Nos. 2010/0076056, 2009/0247608 and 2009/0131360, the entire disclosures of which are incorporated herein by reference.

In some embodiments, modifications can enhance resistance to cellular enzymes, such as RNases and DNases. For example, 2'-O-Me oligonucleotides have been shown to be resistant to cleavage by RNase A, RISC and other cellular ribonucleases (Hutvagner et al., 2004, *PLoS Biol.* v. 2, p. E98; Meister et al., 2004, *RNA*, v. 10, p. 544-550). Modifications providing resistance of the nucleic acid inhibitors to nucleases include, but are not limited to, 2'-O-Me, phosphorothioates, LNA (LNA-like molecules), ENA, 2'-MOE, 2'-F, and FANA.

In some embodiments, one or more nucleotide and/or nucleic acid molecules can be detectably labeled by well known techniques. Detectable labels include, for example, radioactive isotopes, fluorescent labels, chemiluminescent labels, bioluminescent labels and enzyme labels. Such labeled nucleic acid molecules can be used as controls to determine uptake efficiency. In many instances, the detectable label is a fluorescent molecule. In some instances, the detectable label is a fluorescent (e.g., FITC) or chemiluminescent fluorophore. Fluorescent labels, nucleic acid molecules, and methods suitable for determining, for example, transfection efficiency are disclosed in US Patent Publication No. 2006/0009409, the entire disclosures of which is incorporated herein by reference.

III. Mode of Action

In some embodiments, inhibitory molecules (e.g., inhibitory nucleic acid molecules) can act as miRNA inhibitors and/or inactivators in a variety of ways. Without being bound by any one theory as to why inhibitors of the invention perform as inhibitors, they can act by preventing transcription cleavage and/or by inhibiting translation attenuation. For example, a target miRNA can silence its respective target gene by inducing either transcript cleavage (e.g., in cases where the mature miRNA and target sequence are 100% complementary) or translation attenuation (e.g., in cases where the mature miRNA and target sequence are less than 100% complementary). Thus, the miRNA inhibitors of the invention can act by inhibiting either of these actions by the miRNA.

IV. Synthesis of miRNA Inhibitors

The inhibitory molecules (e.g., inhibitory nucleic acid molecules) can be synthesized by any method that is now known, will be identified in the future, or is included in this disclosure a person of ordinary skill in the art would appreciate would be useful to synthesize the embodiments taught herein. For example, inhibitory molecules of the invention can be chemically synthesized using compositions and methods described in U.S. Pat. Nos. 5,889,136, 6,008,400, 6,111,086, and 6,590,093, which are all incorporated by reference herein.

Synthesis methods can include nucleoside base protected 5'-O-silyl-2'-O-orthoester-3'-O-phosphoramidites to assemble the desired unmodified oligonucleotide sequences on a solid support in the 3' to 5' direction. miRNA inhibitors can be chemically synthesized using standard phosphoramidite-based nucleoside monomers and established solid phase oligomerization cycles according to Beaucage, S. L. and Iyer, R. P. (*Tetrahedron*, 1993 (49) 6123; *Tetrahedron*, 1992 (48) 2223). Purification of the individual oligonucleotides for in vitro screening can be carried out using high throughput desalting and alcohol precipitation techniques. Purification of the individual oligonucleotides for in vivo screening can be performed with either anion exchange or reverse-phase prep HPLC and oligonucleotides can be desalted using a semi-permeable membrane. Analytical HPLC (ion exchange or reverse-phase) can be used for determining single strand purity, MALDI mass spectrometry can be used for determining oligonucleotide identity, and UV spectroscopy can be used for quantitative determination of inhibitors. When a cytidine (C) nucleoside is modified as a bicyclo-sugar, the substituted nucleobase can be a 5'methylated cytidine residue. When a uridine (U) nucleoside is modified as a bicyclo-sugar, the substituted nucleobase can be a thymine (T) residue.

In addition, as partially explained above, inhibitory molecules can be synthesized with an array of conjugates for enhancing delivery or allowing visualization of the molecule in a cell or organism. Exemplary conjugates for delivery include, but are not limited to: cholesterol, folate, PET, peptides, proteins, sugars, carbohydrates, and moieties or combinations of moieties that enhance cellular uptake. Additional conjugates can include fluorescent labels, such as fluoroscein, lissamine, phycoerythrin, etc., radioactive labels, or mass labels. All of the before-mentioned conjugates or labels can be associated with the 5' or 3' end of the inhibitory molecule or can be conjugated to internal regions.

V. General Methods of Using Inhibitory Molecules/Applications

Inhibitory molecules of the invention can be used for inhibiting or inactivating short non-coding RNAs. In some embodiments, inhibitory molecules of the invention can be used for inhibiting or inactivating long non-coding RNAs, and small non-coding RNAs (e.g., miRNAs, piRNAs, and/or siRNAs) in any cell, tissue, or organism. Inhibitory molecules can be used in basic research, for treatment of a disease, and for modeling a disease. Inhibitory molecules can be used to inhibit miRNA and/or piRNAs of the human genome implicated in diseases, such as diabetes, Alzheimer's and cancer, and miRNA and/or piRNAs associated with the genomes of pathogens (e.g., viruses, bacteria, protozoa).

Additionally, inhibitory molecules of the invention can be used in RNA interference applications, such as diagnostics, prophylactics, and therapeutics. This can include using inhibitors in the manufacture of a medicament for prevention and/or treatment of animals, such as mammals (e.g., humans). In particular, inhibitory molecules of the invention can be used to reverse the action of long non-coding RNAs, siRNAs, miRNAs, or piRNAs in disease or therapy.

Inhibitory molecules of the invention can be used in a diverse set of applications, including basic research. For example, inhibitory molecules can be used to validate whether one or more miRNAs or targets of miRNA can be involved in cell maintenance, cell differentiation, development, or a target for drug discovery or development. Inhibitory molecules that are specific for inhibiting a particular miRNA are introduced into a cell or organism and the cell or organism is maintained under conditions that allow for specific inhibition of the targeted molecule. The extent of any decreased expression or activity of the target is then measured along with the effect of such decreased expression or activity, and a determination is made that if expression or activity is decreased, then the target is an agent for drug discovery or development. In this manner, phenotyically desirable effects can be associated with inhibition of particular targets, and in appropriate cases toxicity and pharmacokinetic studies can be undertaken and therapeutic preparations developed.

Inhibitory molecules of the invention can be used for loss of function studies in any cell type or tissue to identify if certain targets are involved in disease and/or differentiation.

Inhibitory molecules can be used with diverse cell types, such as primary cells, germ cell lines, and somatic cells. For example, the cell types can be embryonic cells, oocytes, sperm cells, adipocytes, fibroblasts, myocytes, cardiomyocytes, endothelium, neurons, glia, blood cells, megakaryocytes, lymphocytes, macrophages, neutrophyls, eosinophils, basophils, mast cells, leukocytes, granulocytes, keratinocytes, chondrocytes, osteoblasts, osteoclasts, hepatocytes and cells of the endocrine or exocrine glands.

Inhibitory molecules of the invention can be used in vivo using methods and modifications known to those of skill in the art. When used in vivo, inhibitory molecules can contain modifications that aid delivery, uptake, and/or survival intracellularly. Methods of modifying inhibitory molecules for use in vivo are presented in the section entitled "Modifications." Further delivery reagents can be used to enhance uptake and/or delivery of the inhibitors, such as cationic lipids, and lipid-like delivery agents (Semple, et al, 2010, *Nature Biotech*. January 17, p. 1-7; Love et al, 2010, *PNAS*, v. 107, p. 1-6).

Inhibitory molecules can be used as a diagnostic or characterization tool. For diagnostics, miRNA inhibitors (inhibitory molecules which block miRNA function) can be used to treat a sample from a patient that is believed to have the disease. Based on the cellular consequences to the sample, the presence of the disease can be determined. Alternatively, miRNA inhibition of a sample of primary cells from a patient can be used to identify the best course of treatment for the specific patient.

VI. Methods of Using Inhibitory Molecules to Treat Disease

Advantageously, inhibitory molecules can be used to inhibit a broad range of miRNAs, piRNAs, long non-coding RNAs and siRNAs. For example, inhibitory molecules can be used to inhibit miRNA and/or piRNAs of the human genome implicated in diseases, such as diabetes (Poy et al., *Nature* 2004, v. 432, p. 226-230), Alzheimer's and cancer, and miRNA and/or piRNAs associated with the genomes of pathogens (e.g., pathogenic viruses).

Because a growing body of evidence implicates miRNAs in cancer development, maintenance and metastasis, it is envisioned that inhibitory molecules discussed herein can be used to treat cancers. For example, Matsuhara et al. (*Oncogene* 2007, v. 26, p. 6099-6015) found that blocking miR-20a and miR-17-5p with antisense oligonucleotides reduced cell viability and increased the proportion of sub G1 cells. Similarly, Bommer et al. and colleagues (*Curr. Biol.*, 2007, v. 17, p. 1290-1307) used propidium iodide stain and FACS to show that miR-34 inhibition resulted in increased viability of colon cancer cells. Ma et al. (*Nature* 2007, v. 449, p. 682-688) found that miR-10b expression enhanced metastasis; invasive breast cancer cells failed to migrate as far when treated with a miR-10b antisense oligonucleotide. Antisense oligonucleotides have also been used in xenograft cancer models to demonstrate that some miRNAs affect metastatic potential and in vivo growth of tumors. Corsten et al. (*Cancer Res.* 2007, v. 67, p. 8994-9000) saw that transplanted gliomas treated with miR-21-specific antisense oligonucleotides were sensitized to a chemotherapeutic agent. Other studies showed the involvement of miRNAs in multiple cancer types (Hammond, et al., *Can. Chemo. Pharma.* 2006, v. 58, s63-s68; Calin et al., *Cancer Res* 2006, v. 66, p. 7390-7394) including leukemia (Calin et al., *PNAS* 2002, v. 101, p. 2999-3004) and glioma (Corsten et al., *Cancer Res.* 2007, v. 67, p. 8994-9000).

Further, multiple studies using antisense oligonucleotides suggest roles for endogenous miRNAs in viral defense or replication. Thus, it is envisioned that the miRNA inhibitors discussed herein can be used alone or in combination with an antiviral drug to treat viral infections. For example, Lecellier et al. (*Science* 2005, v. 308, p. 557-560) found that antisense oligonucleotide inhibition of miR-32, a miRNA with potential target sites in primate foamy cell virus genes, permitted enhanced production of viral RNA in human tissue culture cells. Similarly, inhibition of interferon-β-induced miRNAs permited Hepatitis C viral production. However, antisense oligonucleotide inhibition of liver-specific miR-122 in cultured hepatocytes crippled Hepatitis C replication, suggesting its requirement in the Hepatitis C viral life cycle. These antisense oligonucleotide studies suggest that combinatorial expression of pro- or antiviral miRNAs may affect tissue tropism of some viruses.

Inhibitory molecules of the invention can be used to inhibit single or multiple targets simultaneously. This can be affected by introducing pools of inhibitory molecules targeting different molecules to inhibit different targets. Alternatively, this can be affected by including more than one target in the target binding region of a single inhibitor. Different types of inhibitors can be pooled together, e.g., (i) miRNA inhibitory molecules of one design (e.g., hairpin) can be pooled with miRNA inhibitory molecules of another design (e.g., multimer), (ii) miRNA inhibitors with siRNAs, shRNA, or antisense oligos, or ribozymes, and/or deoxyribozymes can be pooled, (iii) inhibitors targeting microRNAs and inhibitors targeting other short non-coding RNAs can be pooled. Inhibitory molecules of the invention can be used to inhibit targets including but not limited to: miR-20a, miR-17-5p, miR-34, miR-10b, miR-21, miR-32, miR15, miR34a, miR29abc, miR16, let7, miR33, miR221, miR222, miR26a and miR-122. Other disease-related targets can be found via a human miRNA-associated disease database (HMDD), which contains miRNA names, disease names, dysfunction, evidence, and PubMed IDs. HMDD is a publicly accessible website (cmbi.bjmu.edu.cn/hmdd).

Inhibitory molecules of the invention can be administered to a cell, by any method known to one of skill in the art. For example, inhibitory molecules can be passively delivered to cells. Passive uptake can be modulated, for example, by the presence of a conjugate such as a polyethylene glycol moiety or a cholesterol moiety or any other hydrophobic moiety associated with the 5' terminus, the 3' terminus, or internal regions of the inhibitor. Other methods for inhibitor delivery include, but are not limited to transfection techniques (e.g., using forward for reverse transfection techniques) employing DEAE-Dextran, calcium phosphate, cationic lipids/liposomes, microinjection, electroporation, immunoporation, and coupling of the inhibitors to specific conjugates or ligands such as antibodies, peptides, antigens, or receptors. Other methods include the use of delivery reagents can be enhance uptake and/or delivery of the inhibitors, such as cationic lipids, and lipid-like delivery agents (Semple, et al, 2010, Nature Biotech. January 17, p. 1-7; Love et al, 2010, PNAS, v. 107, p. 1-6). Other methods include complexing the inhibitor with a lipid.

Inhibitory molecules of the invention can be administered in a dosage that is therapeutically effective to reduce symptoms of a disease, to reduce the amount and/or symptoms of a pathogen, and or to reduce the amount of siRNAs, long non-coding RNAs, miRNAs, and/or piRNAs that are being targeted. The dosages can vary from micrograms per kilogram to hundreds of milligrams per kilogram of a subject. As is known in the art, dosage will vary according to the mass of the mammal receiving the dose, the nature of the mammal receiving the dose, the severity of the disease or disorder, and the stability of the medicament in the serum of the subject, among other factors well known to persons of ordinary skill in the art. Results of the treatment can be ameliorative, palliative, prophylactic, and/or diagnostic of a particular disease or disorder. Suitable dosing regimens can be determined by, for example, administering varying amounts of one or more inhibitors in a pharmaceutically acceptable carrier or diluents by a pharmaceutically acceptable delivery route, and the amount of drug accumulated in the body of the recipient organism can be determined at various times following administration. Similarly the desired effect can be measured at various times following administration of the inhibitor and this data can be correlated with other pharmacokinetic data such as body or organ accumulation. Those of ordinary skill can determine optimum dosages, dosing regimens, and the like. The inhibitors can be administered in combination with other pharmaceuticals for treatment of a disease. In some embodiments, inhibitory molecules can be administered to a patient that has been exposed to a disease and/or to keep a patient from getting a disease they will be exposed to (proactively).

Inhibitory molecules can be administered using any route of administration known to one of skill in the art. For example, inhibitory molecules can be administered in a cream or ointment topically, an oral preparation such as a capsule or tablet or suspension or solution, and the like. The route of administration can be intravenous intramuscular, dermal, subdermal, cutaneous, subcutaneous, intranasal, oral, rectal, by eye drops, by tissue implantation of a device that releases the inhibitor at an advantageous location, such as near an organ or tissue or cell type harboring a target nucleic acid of interest.

VII. Quantifying Inhibitory Molecule Function

The method of assessing the level of inhibition or inactivation is not limited. Thus, the effects of any inhibitory molecules can be studied by one of any number of procedures. Methods include, but are not limited to, the biological assay 1 or 2 herein (Examples1-6), Northern analysis, RT PCR, expression profiling, and others. In some methods, a vector or plasmid encoding a reporter whose protein is easily assayed is used. The vector or plasmid is modified to contain the target site (e.g., the reverse complement of the mature long non-coding RNA, miRNA, piRNA, or siRNA) in the 5' UTR, ORF, or 3'UR of the sequence. Such reporter genes include but are not limited to alkaline phosphatase (AP), beta galactosidease (LacZ), chloramphenicol acetyltransferase (CAT), green fluorescent protein (GFP), variants of luciferase (Luc), and deriviatives thereof. In the absence of inhibitory molecules, endogenous (or exogenously added) miRNAs target the reporter mRNA for silencing (e.g., either by transcript cleavage or translation attenuation) thus leading to an overall low level of reporter expression. In contrast, in the presence of inhibitory molecules of the invention, miRNA, piRNA, or siRNA mediated targeting is suppressed, thus giving rise to a heightened level of reporter expression.

VIII. Self-Delivery Aspect of the Molecules

The invention also provides molecules which are capable of "self-delivery". "Self-delivery" refers to the ability of a molecule to efficiently cross a cell membrane in the absence of the addition of a transfection reagent (e.g., 293FECTIN™, OPTIFECT™, LIPOFECTIN®, LIPOFECTAMINE® 2000, etc.). "Self-delivery" may also be measured based upon a functional effect resulting from entry into a cell by the molecule (e.g., induction of apoptosis). Self-delivery may be in vitro or in vivo. Examples of in vitro self-delivery include instances where cells in a well of a microtiter or in a culture medium flask are exposed to molecules which efficiently cross the cell membrane in the absence of a transfection reagent.

As one skilled in the art would understand, it is generally not desirable to introduce molecules (e.g., nucleic acid molecules of the invention) into multicellular organisms (e.g., animals) in conjunction with a transfection reagent. Further, it is generally desirable to introduce the fewest possible number of compound, for example, into the blood stream of an animal required to achieve the desired goal (e.g., inhibition of miRNA function). Thus, the invention provides molecules which are designed to allow for in vivo self-delivery.

In many instances, molecules which are capable of self-delivery will contain a hydrophobic region, hydrophobic chemical entity or set of hydrophobic chemical entities. Further, when present, hydrophobic regions or hydrophobic chemical entities may be located anywhere on the molecules and may be attached to the molecules either covalently or non-covalently.

With respect to molecules of the type shown in FIG. 1 for reference, hydrophobic regions or hydrophobic chemical entities may be located, for examples, on the 3' terminus (attached to a hydroxyl group or a phosphate group) and/or 5' terminus (attached to a hydroxyl group or a phosphate group). Further, hydrophobic regions or hydrophobic chemical entities may be located in one or more loop region or attached to the sugar backbone of a stem (e.g., any one, two, three or all four stem regions) or the binding region. Thus, as an example, the invention includes molecules which contain hydrophobic regions or hydrophobic chemical entities located at the 3'terminus, loop 1, and loop 2.

The number of hydrophobic regions or hydrophobic chemical entities associated with each molecule capable of self-delivery can vary widely based upon factors such as the desired hydrophobic character of the final molecule and locations which contain the hydrophobic regions or entities. In specific embodiments, from about one to about fifty (e.g., from about one to about forty, from about one to about thirty, from about one to about twenty, from about one to about ten, from about two to about fifteen, from about two to about five, from about three to about eight, from about four to about ten, etc.) hydrophobic regions or hydrophobic chemical entities may be present on each molecule capable of self-delivery. These numbers may refer to averages of hydrophobic regions or hydrophobic chemical entities present on each molecule. This is so because molecules in a population may vary in the presence of functional groups as a result of factors such as incomplete chemical modification or post chemical modification reactions. In most instances, greater than 50% of the molecules in the population will have hydrophobic regions or hydrophobic chemical entities in all of the desired locations.

Hydrophobic regions or hydrophobic chemical entities may be either directly or indirectly (e.g., through a linker) linked to a group of a nucleic acid molecule. (For example, in example 7 multimeric inhibitors are described. Sterols or any other hydrophobic groups can be attached for example to the bridging, non-functional oligonucleotide, while the functional oligonucleotide with the antisense region—targeting miRNA—could be unmodified) One example of such a group is the 2' OH of ribose. Further, multiple (e.g., from about two to about twenty, from about two to about fifteen, from about two to about ten, from about two to about five, from about two to about three, from about three to about ten, from about four to about ten, etc.) groups of a nucleic acid molecule may contain the same or different hydrophobic regions or hydrophobic chemical entities, some, all or none or which may be connected to the nucleic acid molecule through one or more linkers. Also, a specified percentage (e.g., from about 10% to about 100%, from about 20% to about 100%, from about 30% to about 100%, from about 40% to about 100%, from about 50% to about 100%, from about 10% to about 20%, from about 10% to about 30%, from about 10% to about 40%, from about 10% to about 50%, etc.) of the nucleosides present may contain the same or different hydrophobic regions or hydrophobic chemical entities.

Hydrophobic chemical entities employed in the practice of the invention include lipids (e.g., steroids). Exemplary lipids can be simple lipids (esters of fatty acids with various alcohols); complex lipids such as phospholipids and glycolipids; derived lipids such as fatty acids, higher alcohols, lipid soluble vitamins, steroids, and hydrocarbons. To enhance the cellular uptake efficiency, the lipid may be a derived lipid, such as a fatty acid having from about 6 to about 50 (e.g., from about 10 to about 22, from about 12 to about 18, from about 6 to about 22, from about 6 to about 40, from about 10 to about 40, from about 20 to about 40, from about 20 to about 50, etc.) carbon atoms. Specific fatty acids which may be used in the practice of the invention include lauric acid, stearic acid, myristic acid, and palmitic acid. In addition, lipid conjugates such as cardiolipin, ceramides, and sphingolipids which can be attached to oligonucleotides.

Figure 22:
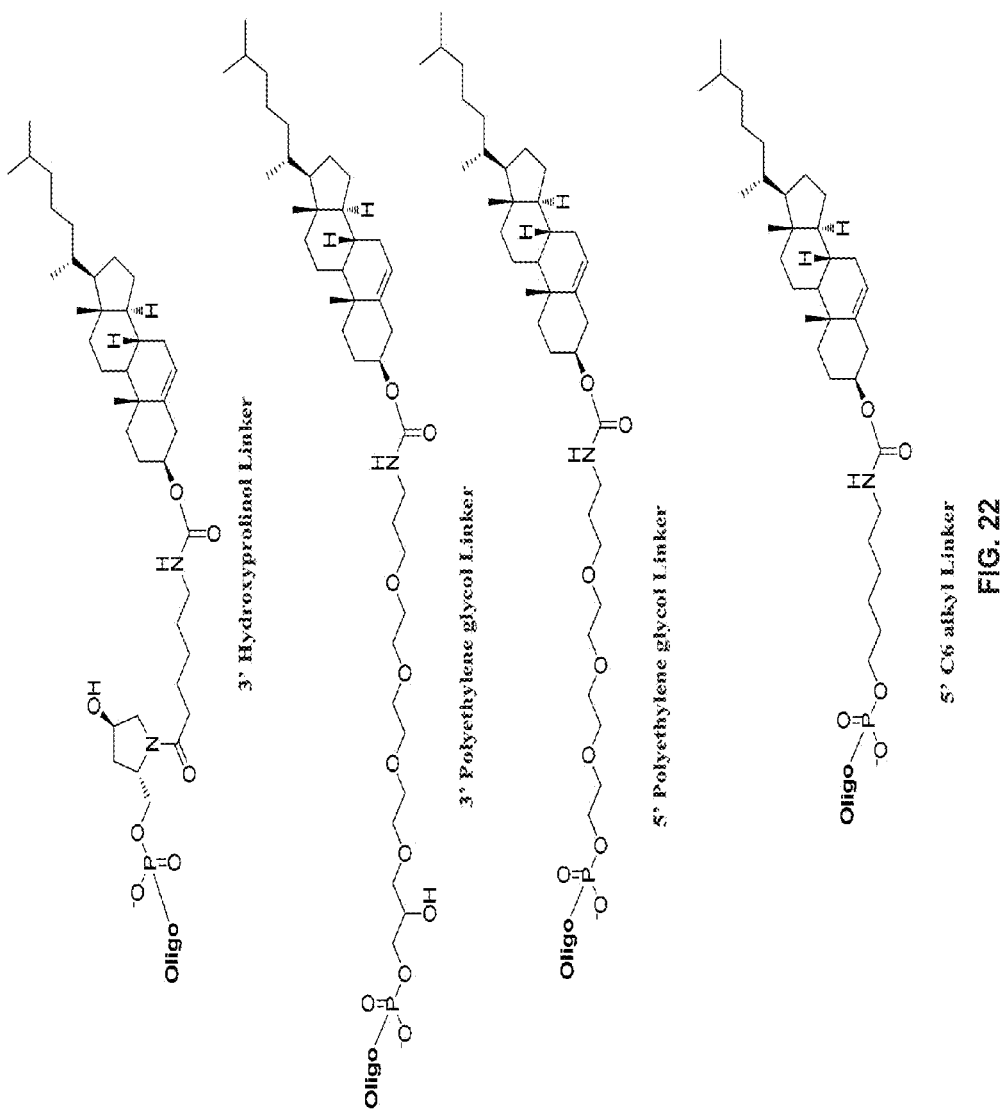
FIG. 22 shows a number of exemplary structures of miRNA inhibitors with cholesterol attachments for use in self-delivery applications.

Any number of different steroids may be used in the practice of the invention. Exemplary steroids include cholesterol, acebrochol, androsterone, 5-beta-cholanic acid, progesterone, aldosterone, dehydroaldosterone, isoandrosterone, esterone, estradiol, ergosterol, dehydroergosterol, lanosterol, 4-cholesten-3-one, guggulsterone, testosterone, nortestosterone, formestane, hydroxyecdysone, ketoestriol, corticosterone, dienestrol, dihydroxypregnanone, pregnanone, copornmon, equilenin, equilin, estriol, ethinylestradiol, mestranol, moxestrol, mytatrienediol, quinestradiol, quinestrol, helvolic acid, protostadiene, fusidic acid, cycloartenol, tricallol, cucurbitanin cedrelone, euphol, dammerenediol, parkeol, dexametasone, methylprednisolone, prednisolone, hydrocortisone, parametasone, betametasone, cortisone, fluocinonide, fluorometholone, halcinonide, and budesonide, Calciferol, Cholecalciferol, Deoxycholic acid. Cholic acid, Hydrodeoxycholic acid, Lithocholic acid, Ursodeoxycholic acid. Prednisone, Dehydrocholic acid, as well as any of these molecules further substituted with one or more hydroxyl, halogen, amino, alkylamino, alkyl, carboxylic acid, ester, amide, carbonyl, alkoxyl, or cyano groups. FIG. 22 provides a number of structures depicting attachment of cholesterol to the miRNAs of the invention.

Hydrophobic chemical entities employed in the practice of the invention include hydrocarbons with alkyl groups. As used herein, the term "alkyl" refers to a hydrocarbyl moiety that can be saturated or unsaturated, and substituted or unsubstituted. It may comprise moieties that are linear, branched, cyclic and/or heterocyclic, and contain functional groups such as ethers, ketones, aldehydes, carboxylates, etc. Exemplary alkyl groups include but are not limited to substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. The term alkyl also encompasses alkenyl groups, such as vinyl, allyl, aralkyl and alkynyl groups. The alkynyl groups may be substituted.

Substitutions within alkyl groups, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The substitutions within alkyl groups can, by way of example, also comprise modifications such as azo groups, keto groups, aldehyde groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Alkyl groups may contain halogens, sulfurs, thiols, thioethers, thioesters, amines, amides, ethers, esters, alcohols, oxygen, or the modifications listed above.

Further, alkyl groups may also contain hetero substitutions, which are substitutions of carbon atoms, by, for example, nitrogen, oxygen or sulfur. Heterocyclic substitutions refer to alkyl rings having one or more heteroatoms. Examples of heterocyclic moieties include but are not limited to morpholino, imidazole, and pyrrolidino. Alkyl groups may contain hetero substitutions or alkyl rings with one or more heteroatoms (i.e., heterocyclic substitutions).

Nucleic acid molecules with enhanced capability of crossing cell membranes in the absence of a transfection reagent are set out in U.S. Pat. Publ. 2008/0085869A1, the entire content of which is incorporated herein by reference.

Unmodified nucleic acid molecules have some ability to cross cell membranes. Thus, self-delivery refers to an increased ability to enter cells. Uptake can be measured from the quantitative perspective of the total amount of a molecule taken up or the qualitative perspective of functional activity associated with uptake. Qualitative uptake may not exactly correlate with quantitative uptake because the functional activities of molecules capable of self-delivery may vary from those not capable of self-delivery. Functional activities of two molecules can be compared by measurement of (1) total uptake of each molecule and (2) resulting activity. By such methods one can determine quantitative uptake from functional activity.

Regardless of how uptake is measured, the invention provides nucleic acid molecules capable of self-delivery. Nucleic acid molecules capable of self-delivery may be taken up by cells more than 40% (e.g., from about 40% to about 90%, from about 50% to about 90%, from about 60% to about 90%, from about 70% to about 90%, from about 75% to about 90%, from about 50% to about 98%, from about 60% to about 99%, from about 70% to about 99%, etc.) more efficiently than unmodified nucleic acid molecules (e.g., nucleic acid molecules represented in FIG. 1). In one embodiment, the invention provides nucleic acid molecules capable of self-delivery which are taken up at least 75% more efficiently than otherwise identical unmodified nucleic acid molecules. Quantification of uptake will generally be determined by quantification of the numbers of individual molecules (e.g., moles) present in cells.

The invention provides, in part, molecules which may be administered to a multicellular organism (e.g., a plant or animal) to achieve a specific intracellular effect (e.g., the inhibition of the function of a specific miRNA, such as MiR-122). As shown in Example 19, sterol conjugated molecules of the invention can be administered to animals, with the measurement of effect in a distant organ (i.e., liver in this instance). Thus, the invention provides methods for the systemic and organ specific delivery of molecules of the invention. The invention further provides methods for the treatment of disease.

The invention thus includes methods for delivering nucleic acid inhibitory molecules of the invention to cells of a multicellular organism. Such delivery may be local or systemic.

Local delivery of nucleic acid molecules (e.g., nucleic acid molecules of the invention) is well suited for afflictions where administration sites are easily accessible. Examples are such administration sites are skin and mucosal surfaces. Local delivery has the advantage of lessening potential side effects resulting from systemic administration. Further, local administration avoids first-pass hepatic clearance making it more likely that the therapeutic concentration is reached at the target site in sufficient concentrations to achieve the desired effect. Local delivery can be generally categorized into five main groups: mucosal (intranasal, intratracheal, intravaginal and intrarectal), intraocular, transdermal, intrathecal and intratumoral, any of which may be used in the practice of the invention. Local delivery also has the advantage that transfection reagents can often be readily used with limited effect on multicellular organisms. Thus, self-delivering and non-self-delivering may be easily used.

Systemic administration may be used to deliver nucleic acid molecules (e.g., nucleic acid molecules of the invention). In many instances, such delivery would be for the treatment of diseases (e.g., cancer, metabolic disorders, etc.) where the target sites are not easily accessible to local administration. Systemic administration can be performed through, for examples, intravenous, intraperitoneal, intramuscular, or subcutaneous injections. Intravenous administration, as an example, is the widely used, simple with respect to procedure, and results in rapid distribution of administered agent to various tissue sites.

The invention thus includes methods for administering and method involving administration of molecules of the invention to multicellular organisms (e.g., animals), as well as composition used in such administration. In some embodiments, such methods include method of treating afflictions/diseases.

The invention further includes pharmaceutical compositions comprising molecules of the invention, as well as admixtures comprising molecules of the invention and additional compounds for administration to multicellular organisms (e.g., buffers, excipients, etc).

In some embodiments, the invention includes compositions comprising (1) one or more molecules of the invention and (2) an excipient formulation, as well as methods for preparing such compositions and methods for administering such compounds to multicellular organisms. Exemplary excipients include polymers such as cyclodextrins, lipids, cationic lipids, polyamines, phospholipids, nanoparticles, receptors, ligands, and others.

In some embodiments, molecules of the invention as delivered to multicellular organisms as components of compositions including, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In specific embodiments, a pharmaceutically acceptable carrier is used such as a liposome or a transdermal enhancer.

Exemplary delivery systems of the invention include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Molecules of the invention may be formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see for example Ogris et al., 2001, *AAPA Pharm. Sci.*, 3, 1-11; Furgeson et al., 2003, *Bioconjugate Chem.*, 14, 840-847; Kunath et al., 2002, *Pharmaceutical Research*, 19, 810-817; Choi et al., 2001, *Bull. Korean Chem. Soc.*, 22, 46-52; Bettinger et al., 1999, *Bioconjugate Chem.*, 10, 558-561; Peterson et al., 2002, *Bioconjugate Chem.*, 13, 845-854; Erbacher et al., 1999, *Journal of Gene Medicine Preprint*, 1, 1-18; Godbey et al., 1999, *PNAS USA*, 96, 5177-5181; Godbey et al., 1999, *Journal of Controlled Release*, 60, 149-160; Diebold et al., 1999, *Journal of Biological Chemistry*, 274, 19087-19094; Thomas and Klibanov, 2002, PNAS USA, 99, 14640-14645; and Sagara, U.S. Pat. No. 6,586,524, the entire disclosure of which is incorporated by reference herein.

Molecule of the invention comprises a bioconjugate, for example a nucleic acid conjugate as described in Vargeese et al., U.S. Patent Publication No. 2003/0130186 A1, U.S. Pat. Nos. 6,528,631; 6,335,434; 6,235,886; 6,153,737; 5,214,136; 5,138,045, the entire disclosures of which are incorporated by reference herein.

Thus, the invention features a pharmaceutical composition comprising one or more molecules of the invention in an acceptable carrier, such as a stabilizer, buffer, and the like. Molecules of the invention can be administered and introduced to a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as creams, gels, sprays, oils and other suitable compositions for topical, dermal, or transdermal administration as is known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

As used herein, a pharmacological composition or formulation includes compositions or formulations in forms suitable for administration, e.g., systemic or local administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

Molecules of the invention may be administered to subjects by systemic administration in a pharmaceutically acceptable composition or formulation. "Systemic administration" includes in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes may be used to expose molecules of the invention to an accessible diseased tissue. The use of a liposome or other drug carrier comprising the compounds of the instant invention can potentially localize molecules of the invention, for example, in certain tissue types, such as the tissues of the reticular endothelial system (RES). In some instances, liposome formulations that can facilitate the association of molecules of the invention with the surface of cells, such as, lymphocytes and macrophages may also be useful. This approach can provide enhanced delivery of molecules of the invention to target cells by taking advantage of the specificity of macrophage and lymphocyte immune recognition of abnormal cells.

By "pharmaceutically acceptable formulation" or "pharmaceutically acceptable composition" is meant, a composition or formulation that allows for the effective distribution of molecules of the invention in the physical location most suitable for their desired activity. Non-limiting examples of agents suitable for formulation with the molecules of the invention include: P-glycoprotein inhibitors (such as Pluronic P85); biodegradable polymers, such as poly (DL-lactide-coglycolide) microspheres for sustained release delivery (Emerich, D F et al., 1999, *Cell Transplant,* 8, 47-58); and loaded nanoparticles, such as those made of polybutylcyanoacrylate. Other non-limiting examples of delivery strategies for molecules of the invention include material described in Boado et al., 1998, *J. Pharm. Sci.,* 87, 1308-1315; Tyler et al., 1999, *FEBS Lett.,* 421, 280-284; Pardridge et al., 1995, *PNAS USA.,* 92, 5592-5596; Boado, 1995, *Adv. Drug Delivery Rev.,* 15, 73-107; Aldrian-Herrada et al., 1998, *Nucleic Acids Res.,* 26, 4910-4916; and Tyler et al., 1999, *PNAS USA.,* 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta,* 1238, 86-90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat of a disease state (e.g., alleviate a symptom or inhibit a disease state mechanism). The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.01 mg/kg and 300 mg/kg body weight/day (e.g., from about 0.1 mg/kg to about 100 mg/kg, from about 0.5 mg/kg to about 100 mg/kg, from about 1 mg/kg to about 100 mg/kg, from about 5 mg/kg to about 100 mg/kg, from about 0.01 mg/kg to about 3 mg/kg, from about 0.01 mg/kg to about 1 mg/kg, from about 0.01 mg/kg to about 0.5 mg/kg, from about 0.01 mg/kg to about 0.1 mg/kg, from about 3 mg/kg to about 20 mg/kg, from about 2 mg/kg to about 40 mg/kg, from about 5 mg/kg to about 50 mg/kg, etc.) of active ingredients is administered to achieve the desired physiological effect (e.g., inhibition of microRNA activity).

The amount of a molecule of the invention administered to a multicellular organism will vary with the desired and/or required effect. For example, treatment of an affliction may require at least 70% inhibition of a microRNA in a specific tissue (e.g., prostate gland tissue). Thus, the invention includes methods for using molecules of the invention which yield a desired effect. The effect can be empirical (remission of a diseases state). The effect can also be measured through the measurement of the activity of one or more molecules targeted by molecules of the invention (e.g., microRNAs). In such instances, the invention provides methods for inhibition of target molecule activity within a multicellular organism where activity of one or more target molecules is inhibited by at least 30% (e.g., from about 30% to about 99%, from about 40% to about 99%, from about 50% to about 99%, from about 60% to about 99%, from about 70% to about 99%, from about 80% to about 99%, from about 30% to about 95%, from about 40% to about 95%, from about 60% to about 95%, from about 30% to about 90%, from about 40% to about 90%, from about 50% to about 90%, from about 60% to about 90%, from about 30% to about 85%, from about 40% to about 85%, from about 50% to about 85%, from about 60% to about 85%, from about 70% to about 90%, etc.).

Molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising one or more molecule of the invention and a pharmaceutically acceptable carrier. One or more molecules of the invention can be present in association with one or more non-toxic pharmaceutically acceptable carriers and/or diluents and/or adjuvants, and if desired other active ingredients. Pharmaceutical compositions containing molecules of the invention can be in a form suitable for oral use, for example, as tablets, troches, lozenges, aqueous or oily suspensions, dispersible powders or granules, emulsion, hard or soft capsules, or syrups or elixirs.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. Oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Pharmaceutical compositions can be in the form of a sterile injectable aqueous or oleaginous suspension. Such suspensions can be formulated according to the known art using those suitable dispersing or wetting agents and suspending agents that have been mentioned above. Sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids, such as oleic acid, may be used in the preparation of injectables.

Molecules of the invention can also be administered in the form of suppositories, e.g., for rectal administration of the drug. Such compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Molecules of the invention can be administered parenterally in a sterile medium. Molecules of the invention, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

For administration to non-human animals, molecules of the invention can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

Molecules of the invention can also be administered to a subject in combination with other therapeutic compounds to increase the overall therapeutic effect. In some instances, the use of multiple compounds to treat an indication can increase the beneficial effects while reducing the presence of side effects.

The invention also comprises compositions suitable for administering molecules of the invention to specific cell types. For example, the asialoglycoprotein receptor (ASGPr) (Wu and Wu, 1987, *J. Biol. Chem.* 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatenarry or monoatennary chains (Baenziger and Fiete, 1980, *Cell*, 22, 611-620; Connolly et al., 1982, *J. Biol. Chem.*, 257, 939-945). Lee and Lee, 1987, *Glycoconjugate J.*, 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, *J. Med. Chem.*, 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavailability, pharmacodynamics, and pharmacokinetic parameters can be modulated through the use of nucleic acid bioconjugates of the invention. Non-limiting examples of such bioconjugates are described in Vargeese et al., U.S. Patent Publication No. 2003/0130186 A1 and Matulic-Adamic et al., U.S. Pat. No. 7,833,992, the entire disclosure of which is incorporated by reference herein.

IX. Kits

Some embodiments of the invention provide kits for the inhibition of one or more target nucleic acid molecules (i.e., miRNAs) in a sample, including at least one hairpin inhibitor, at least one conjugated antisense inhibitory molecule, at least one multimeric inhibitory molecule, chimeric inhibitory molecules, and/or mixtures thereof. The kit can be used in any of the methods of using the miRNA inhibitory molecules known or disclosed herein. Some embodiments of the kit are used for inhibition of a long non-coding RNA, an miRNA, a piRNA, an siRNA, an mRNA, and/or an rRNA in a cell or organism. In some embodiments the kit is used to identify a treatment for a disease or to produce a treatment for a disease in a mammal.

Having described the invention with a degree of particularity, examples will now be provided. The following examples are intended to illustrate but not limit the invention.

EXAMPLES

The sequences and formats of the inhibitory molecules used in the following examples are presented in Tables 1A-1D. The codes for the modifications are shown in Table 1A. Briefly, RNA is designated by a capital letter (A, C, G, U); DNA is designated by a lower case letter (a, c, g, t); 2'OMe modification is designated by italics; locked nucleic acids (LNA) is designated by bold; 2'F is designated by a subscript "f"; phosphorothioate is designated by an underline; C6 amino is designated by a "N"; and 2'O-Propargyl G is designated by a "Y". Table 1B gives the sequences of the complementary sequences (the target sequences), Table 1C gives the formats and modifications for the inhibitors and Table 1D gives the corresponding sequences of the inhibitors.

The examples use the *Homo sapiens* (hsa) microRNA sequences hsa Mir21, hsa Mir let 7c, and hsa Mir 122 as the targets and various formats of inhibitory molecules are produced to inactivate and/or inhibit these mRNAs. The targets were chosen because they produce high levels of microRNAs, so varying amounts of inhibition can be quantitated. The general sequences of the target microRNAs are as follows: Mir-21: 5'-UAGCUUAUCAGACUGAUGUUGA-3' (SEQ ID NO:144), Let-7a: 5'-UGAGGUAGUAGGUUGUAUAGUU-3' (SEQ ID NO:145), Let-7c: 5'-UGAGGUAGUAGGUUGUAUGGUU-3' (SEQ ID NO:146), and Mir-122: 5'-UGGAGUGUGACAAUGGUGUUUG-3' (SEQ ID NO:147). Note that Let-7C and Let-7a are from the same family and have almost identical sequences. They differ by just one nucleotide shown in bold and highlighted in the sequences. Table 1B shows the specific complementary sequences and modifications used in the assays in the Examples.

TABLE 1B

Complementary Sequences

| Complementary sequence | Sequence Identifier |
|---|---|
| UCAACAUCAGUCUGAUAAGCUA | SEQ ID NO: 1 |
| UCAACAUCAGUCUGAUAAGCUA | SEQ ID NO: 2 |
| UCAACAUCAGUCUGAUAAGCUAc | SEQ ID NO: 3 |
| AACCAUACAACCUACUACCUCA | SEQ ID NO: 4 |
| AACCAUACAACCUACUACCUCA | SEQ ID NO: 5 |
| AACCAUACAACCUACUACCUCAc | SEQ ID NO: 6 |
| AACUAUACAACCUACUACCUCAt | SEQ ID NO: 7 |
| AACUAUACAACCUACUACCUCA | SEQ ID NO: 8 |
| AACCAUACAACCUACUACCUCAg | SEQ ID NO: 9 |
| ACAAACACCAUUGUCACACUCCAc | SEQ ID NO: 10 |
| ACAAACACCAUUGUCACACUCCA | SEQ ID NO: 11 |
| ACAAACACCAUUGUCACACUCCAc | SEQ ID NO: 12 |
| AACCAUACAACCUACUACCUCAg | SEQ ID NO: 13 |
| AACUAUACAACCUACUACCUCAY | SEQ ID NO: 14 |
| AACUAUACAACCUACUACCUCA-Chol | SEQ ID NO: 15 |
| UCAACAUCAGUCUGAUAAGCUAY | SEQ ID NO: 16 |
| UCAACAUCAGUCUGAUAAGCUA-Chol | SEQ ID NO: 17 |
| AACUAUACAACCUACTACCTCAt | SEQ ID NO: 18 |
| AACUGUACAAACUACUACCUCAt | SEQ ID NO: 19 |
| AAC$_f$U$_f$AU$_f$AC$_f$AAC$_f$C$_f$U$_f$AC$_f$U$_f$AC$_f$C$_f$U$_f$C$_f$At | SEQ ID NO: 20 |
| AAC$_f$U$_f$AU$_f$AC$_f$AAC$_f$C$_f$U$_f$AC$_f$U$_f$AC$_f$C$_f$U$_f$C$_f$At | SEQ ID NO: 21 |

The miRNA inhibitors (see Tables 1C and 1D) were chemically synthesized using standard phosphoramidite-based nucleoside monomers and established solid phase oligomerization cycles according to Beaucage, S. L. and Iyer, R. P. (*Tetrahedron*, 1993 (49) 6123; *Tetrahedron*, 1992 (48) 2223). RNA phosphoramidites were protected with 2'O-TBDMS groups. Synthesis of oligonucleotides was performed on a BioAutomation MerMade™ 192 or BioAutomation MerMade™ 12 synthesizer (BioAutomation Corp, Plano, Tex.). Eight equivalents of activator were used for every equivalent of phosphoramidite to provide a satisfactory stepwise coupling yield of >98% per base addition. Purification of the individual oligonucleotides for in vitro screening was carried out using high throughput desalting and alcohol precipitation techniques. Purification of the individual oligonucleotides for in vivo screening was performed with either anion exchange or reverse-phase prep HPLC (Agilent 1200 series) and oligonucleotides were desalted using a semi-permeable membrane. Analytical HPLC (ion exchange or reverse-phase) was used for determining single strand purity, MALDI mass spectrometry was used for determining oligonucleotide identity, and UV spectroscopy was used for quantitative determination of inhibitors. When a cytidine (C) nucleoside was modified as a bicyclo-sugar, the substituted nucleobase was a 5'methylated cytidine residue. When a uridine (U) nucleoside was modified as a bicyclo-sugar, the substituted nucleobase was a thymine (T) residue.

To test the mRNA inhibitors Biological Assay 1 and/or 2 were used (see Examples 1 and 3). For Biological Assay 1, HeLa cells were pre-plated at 10,000 per well in a 96-well plate. The next day 0.2 µl LIPOFECTAMINE® 2000 transfection agent (Life Technologies) was complexed with 40 ng of the luciferase expression plasmid (with the corresponding miRNA binding site for let7c, miR21, or let7a; Life Technologies), 40 ng of the βGal expression plasmid and 10, 20 or 100 nM of the microRNA inhibitors (of different designs). 24 hours later, the DUAL-LIGHT® assay was performed to determine how the microRNA inhibitors were able to upregulate luciferase expression compared to other commercially available microRNA inhibitors. The βGal plasmid (Life Technologies) was used to normalize for transfection efficiency.

The sequences of the microRNA inhibitors that were tested are shown in Table 1C, Table 1D and FIG. 10. The miRNA inhibitors were based on the following target-binding sequences: Anti-mir-21 (synthetic inhibitor, reverse-complement to natural sequence): 5'-UCAACAUCAGUCUGAUAAGCUA-3' (SEQ ID NO:148), Anti-let-7a (synthetic inhibitor, reverse-complement to natural sequence): 5'-AACUAUACAACCUACUACCUCA-3' (SEQ ID NO:149), Anti-let-7c (synthetic inhibitor, reverse-complement to natural sequence): 5'-AACCAUACAACCUACUACCUCA-3' (SEQ ID NO:152), Anti-miR-122 (synthetic inhibitor, reverse-complement to natural sequence): 5'-CAAACACCAUUGUCACACUCCA-3' (SEQ ID NO:150). The negative control (neg) had the sequence: 5'-AAGUGGAUAUUGUUGCCAUCA-3' (SEQ ID NO:151) and all of the nucleotides were 2'OMe. Inhibitor Y was purchased from Dharmacon. Inhibitor X was purchased from Exiqon. See Tables 1A-1D for sequences and formats of the targets, the inhibitors, and the controls X, Y, 2'-OMe, and Neg.

Example 1

Initial Testing of Hairpin miRNA Inhibitors

This example provides novel hairpin miRNA inhibitor (anti-miR) formats that enabled strong inhibition of endogenous miRNAs. Inhibitors were prepared for two different sequences: hsa mir21 and hsa mir let7c as discussed above. miRNA Inhibitors with non-nucleotide loops were chemically prepared using standard solid phase phosphoramidite chemistry procedures and instrumentation for synthesis, cleavage, and deprotection. The oligonucleotides were then purified utilizing precipitation, desalting, and solid-phase extraction. Purified oligonucleotides were analyzed using analytical HPLC and mass spectrometry.

The design of the inhibitors comprised the following (see FIG. 1): (i) a target binding region (BR) with perfect sequence complementarity to the guide strand of a mature miRNA made up of 21-23 2'-O-methyl modified nucleotides, and (ii) a flanking stem-loop structure at the 3', 5', or both 3' and 5' termini composed of 4-8 nucleotide long stems (stem I and stem II) covalently attached 5' to 3' by a non-nucleotide loop (loop L1) such as polyethylene glycol (other potential loops: alkane diol, styrene, stilbene, triazole, tetrazole, peptide, polyamide, polyester, dithiol, polyamine, polyether, peptide nucleic acid, cycloalkane, poly alkene, or aryl). Target binding sequences of the Hairpin (HP) inhibitors were as follows:

```
Anti-miR-21:
                                       (SEQ ID NO: 148)
    5'-UCAACAUCAGUCUGAUAAGCUA-3' (22nt), Anti-let-7c:
                                       (SEQ ID NO: 152)
    5'-AACCAUACAACCUACUACCUCA-3' (22 nt).
```

Figure 2:
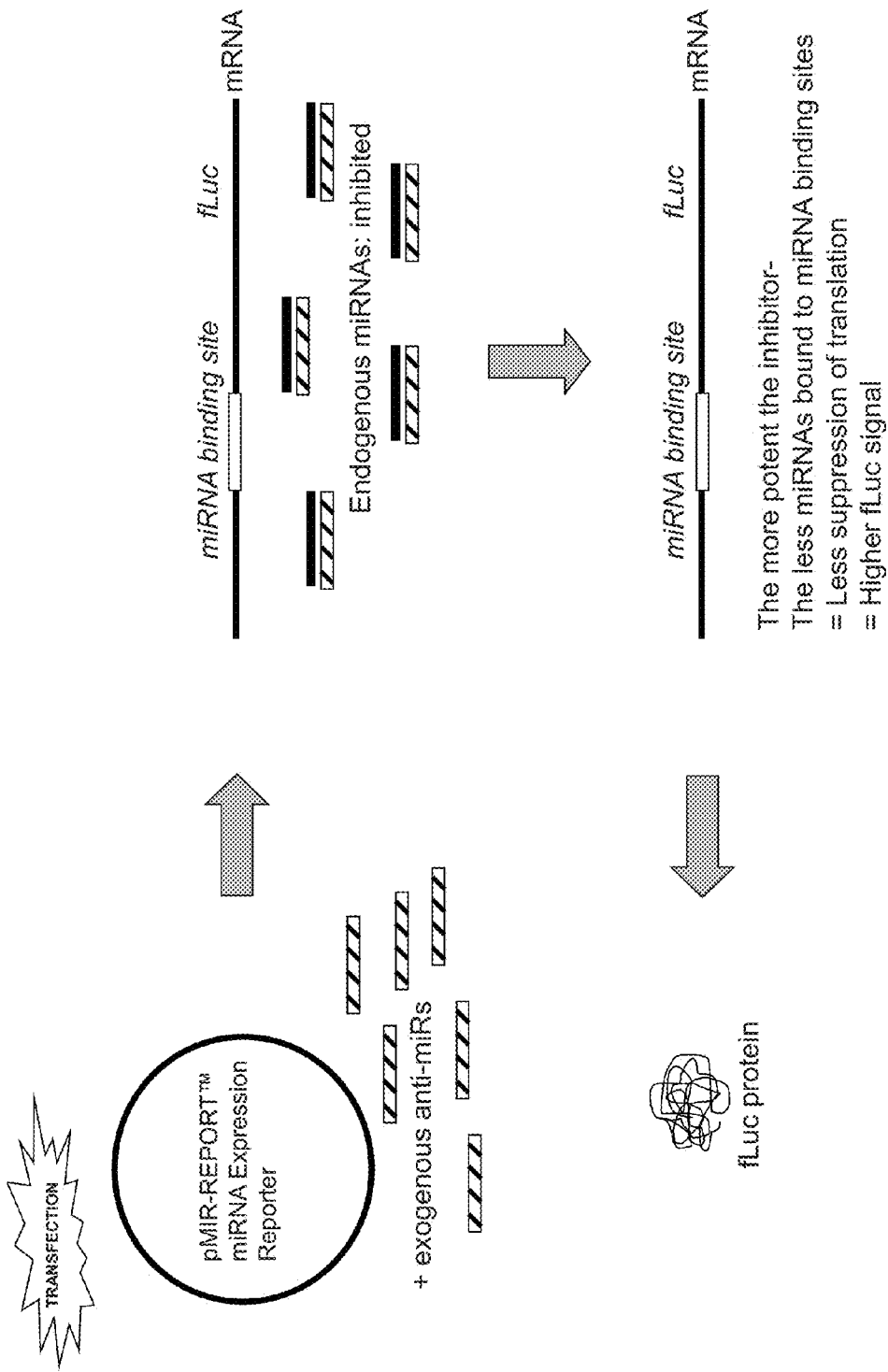
FIG. 2 shows a schematic depiction of one of the assays used for evaluation of performance of the miRNA inhibitors (anti-miRs). The figure shows the reporter (firefly luciferase) expression in the presence of endogenous microRNAs and exogenous anti-miRs. Anti-miRs bind and inhibit the miR-NAs and thus increase the firefly luciferase expression. All experiments were performed in triplicate.

The Biological assay 1 is a reporter system for assaying anti-miR potency using the pMIR-REPORT™ miRNA Expression Reporter Vector System (Life Technologies/Ambion, Austin, Tex.) (FIG. 2). This validated reporter system contained two mammalian expression vectors:

(i) The pMIR-REPORT™ Luciferase miRNA Expression Reporter Vector containing firefly luciferase (fLuc) under the control of a mammalian promoter/terminator system and a target cloning region downstream of the luciferase translation sequence. This vector was used for cloning and testing putative miRNA binding sites. It was also used to evaluate endogenous miRNA expression or the effects of either miRNA mimics (i.e., Pre-miR™ miRNA Precursors) or miRNA inhibitors (i.e., Anti-miR™ miRNA Inhibitors).

(ii) A second vector, pMIR-REPORT™ Beta-galactosidase Reporter Control Vector (Life Technologies) was used for normalization of transfection efficiency.

FIG. 2 shows a schematic depiction of the Biological assay 1 used for evaluation of the performance of the miRNA inhibitors (anti-miRs). The concentrations of the miRNA inhibitors upon transfection were 30, 3, and 0.3 nM. Initially, upon transfection of the pMIR-REPORT™ miRNA expression reporter encoding firefly luciferase (fLuc) as well as containing the binding site for the particular miRNA, mRNA was transcribed inside the cells. Endogenous miRNAs, naturally present inside the cells, bound this mRNA and suppressed translation of the firefly luciferase protein. As a result little or no fLuc was detected in the sample. The same effect was observed if negative control anti-miR (non-targeting sequence) was co-transfected with the pMIR-REPORT™ miRNA expression reporter. FIG. 2 shows the reporter expression in the presence of the exogenous anti-miRs (miRNA inhibitors). In order to evaluate the efficacy of the miRNA inhibitors, the antisense oligonucleotides were co-transfected with the pMIR-REPORT miRNA expression reporter. (A pMIR-REPORT™ Beta-galactosidase Reporter Control Vector was also transfected in each well for normalization of delivery efficiency.) mRNA was transcribed inside the cells, encoding firefly luciferase as well as containing the binding site for the particular miRNA. If the inhibitors bound and inactivated the endogenous miRNA (contained within Ago complex), no translational suppression of the firefly luciferase protein occurred. As a result, high levels of fLuc were detected in the sample. By comparing the reading with the negative control sample it was possible to calculate the average fold change for each anti-miR format evaluated, and to determine which anti-miR caused the maximum increase in the fLuc signal, i.e. was the most potent.

To test the hairpin (HP) anti-miRs, HeLa cells were pre-plated at 10,000 per well in a 96-well plate in Dulbecco's Modified Eagle Medium (DMEM) high glucose (Invitrogen) supplemented with 10% Fetal Bovine Serum (FBS) ((MediaTech, Inc.) and 1% Penicillin (5000 Units)-Streptomycin (5000 µg) (Invitrogen). The next day, 0.2 ul LIPOFECTAMINE® 2000 transfection agent was complexed with 40 ng of the pMIR-REPORT™ Luciferase miRNA Expression Reporter Vector (with the corresponding miRNA binding site: miR21, let7c, let7a, or miR23), 40 ng of the pMIR-REPORT™ Beta-Galactosidase Reporter Control Vector and 0.003-100 nM of the chemically synthesized anti-miR (of different designs). Twenty-four hours later, the DUAL-LIGHT® assay was performed to determine how the novel anti-miRs were able to up-regulate luciferase expression, compared to other anti-miRs. The other anti-miRs used were a 2'-OMe modified antisense oligonucleotide (2'-OMe), anti-miR Y (Dharmacon), and anti-miR X (Exiqon).

The Tropix® Dual-Light® Luminescent Reporter Gene Assay System for luciferase and β-galactosidase (Applied Biosystems, LLC, Foster City, Calif.) was used to quantitate firefly luciferase (fLuc) and β-galactosidase (β-gal) activity in the same sample. First, the luciferase reporter enzyme activity was quantitated with an enhanced luciferase reaction. Following a 30-60 minute incubation and addition of a light emission accelerator, β-galactosidase reporter enzyme activity was quantitated with GALACTON-PLUS® substrate. The wide dynamic range of this dual assay enabled accurate measurement of fLuc and β-galactosidase concentrations over seven orders of magnitude (femtogram to nanogram range).

By comparing the fLuc readings for specific anti-miR-transfected wells with the negative control anti-miR (non-targeting sequence)-transfected wells it was possible to calculate the average fold change for each anti-miR format evaluated, and determine which anti-miR caused the maximum increase in the fLuc signal, i.e. was the most potent. The average fold change was calculated in the following way: (fLuc activity anti-miR/βGal activity anti-miR)/(fLuc activity negative/βGal activity negative).

Figure 3A:
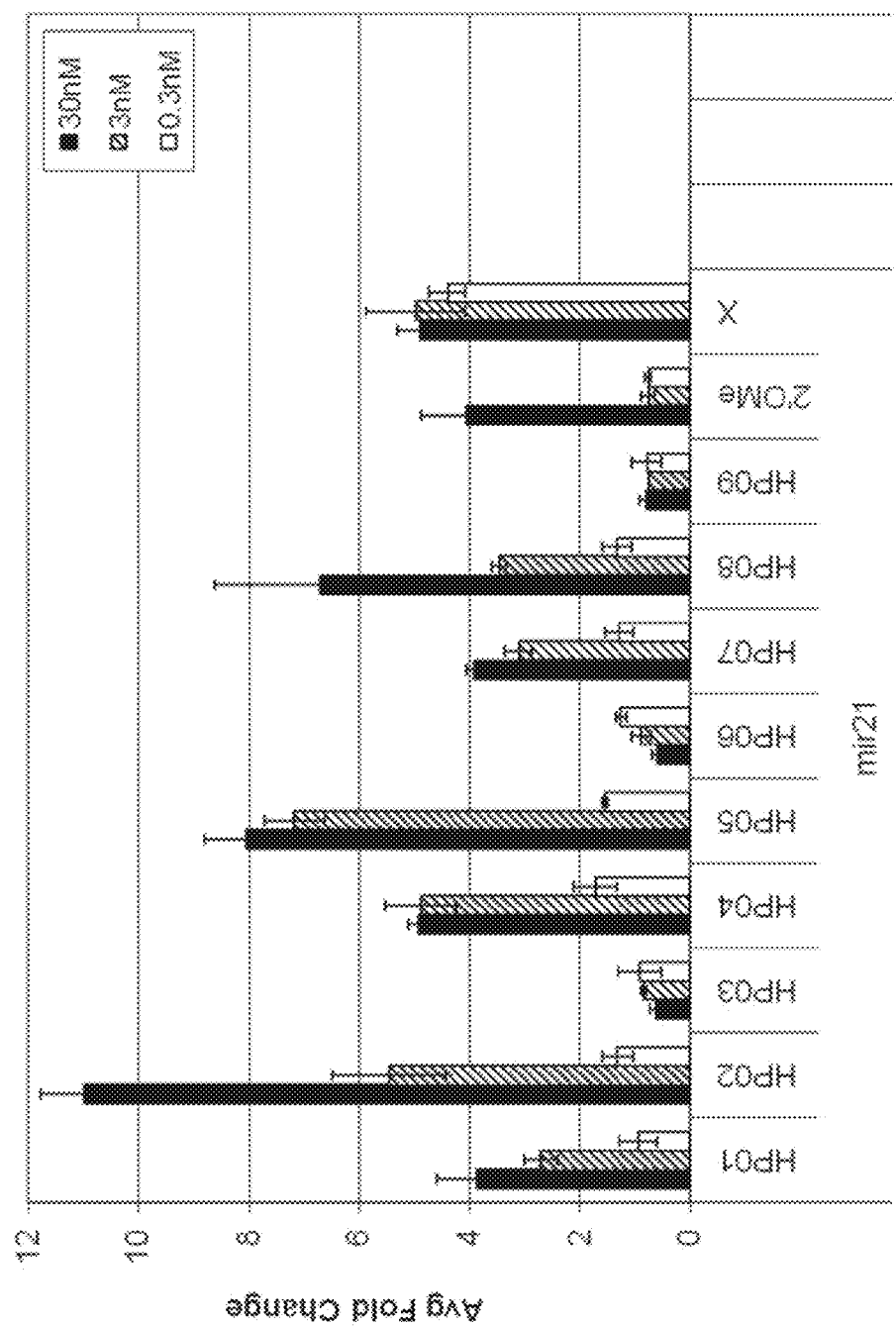
FIG. 3A and FIG. 3B show data derived from the Example 1 experiment in which the potency of the hairpin inhibitors HP#01-HP#09 was evaluated using the pMIR-REPORT™ miRNA expression reporter (miR21 or let7c target cloned), along with two controls: a 22 nt miRNA inhibitor with complete 2'-OMe modification (2'-OMe), and miRNA inhibitor X (Exiqon).
Figure 3B:
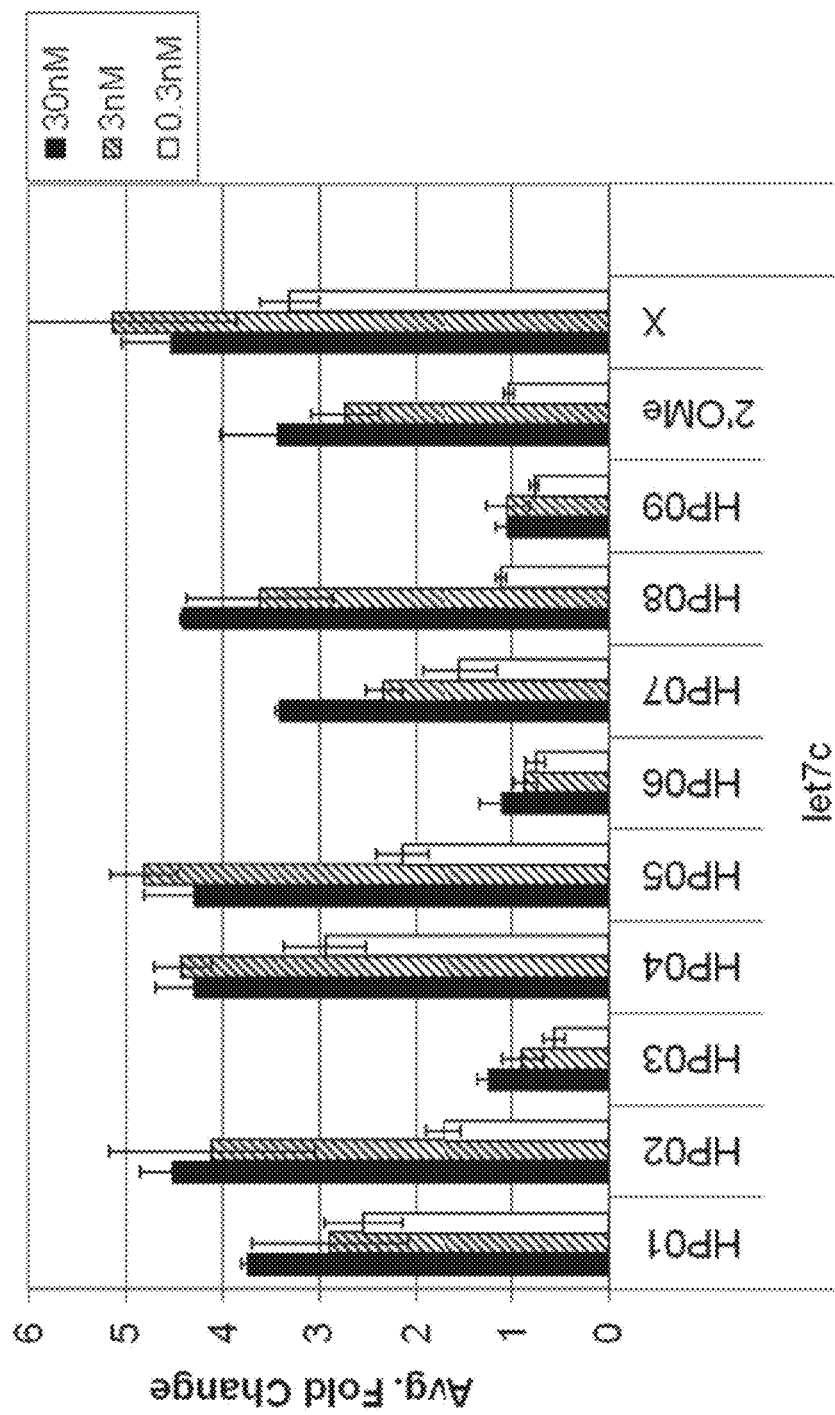

The activity of the hairpin inhibitors HP#01-HP#09 (see Tables 1A-1D for format and sequence of the inhibitors and targets) was evaluated using the pMIR-REPORT™ miRNA expression reporter (miR21 or let7c target cloned), along with two controls: a 22 nt miRNA inhibitor with complete 2'-O-methyl modification (2'-OMe), and miRNA inhibitor X (Exiqon) (FIG. 3A and FIG. 3B). HP#01-HP#09 in FIG. 3A and FIG. 3B included hairpin inhibitors with a 5'-loop, a 3'-loop or both 5' & 3'-loops; PEG3 (polyethyleneglycol polymer—3 monomeric units) or all-nucleotide loop; unmodified or 2'-OMe modified oligonucleotides (see also Tables 1A-1C for the sequences and formats).

The results of this experiment indicated the following: (1) Inhibitors with single loops (i.e., loops on only one end) were effective for inhibiting miRNA function; (2) Inhibitors with 5' loops were typically more potent than inhibitors with 3'-loop structures; (3) PEG loops performed better than the nucleotide loops for inhibitors with double loops and single loops; (4) 2'-OMe modified inhibitors were more potent than unmodified 2'-OH inhibitors (5'-loop, 3'-loop and 3'& 5' loops); and (5) LNA-modified antisense inhibitors worked better than 2'OMe-modified antisense inhibitors of the same length 22 nt. (Note: more versions of stems and loops were tested in Examples 2, 3, 9 and 10.)

Example 2

Effect of Linker Length, Linker Type and Stem Length on the Activity of the Hairpin Inhibitors Additional hairpin inhibitors were prepared similarly as described in Example 1 and assayed using the same in vitro reporter system to investigate the effect of the linker length, linker type, and stem length. As in Example 1, the efficiency of the hairpin inhibitors HP#10-HP#31, HP#5, and HP#8 was evaluated using the pMIR-REPORT™ miRNA expression reporter (miR21 or let7c target cloned), along with three controls: a 22 nt miRNA inhibitor with complete 2'-OMe modification (2'-OMe), and miRNA inhibitor X (Exiqon) and miRNA inhibitor Y (Dharmacon).

The formats of the HP#10-HP#31, HP#05, and HP#08 inhibitors are depicted in FIG. 1 with the following variations: a 5'-loop or a 3'-loop; 8 versions of non-nucleotide loops and all-nucleotide loop; 3, 4, 5 bp stem (see also Tables 1A-1D for formats and sequences).

Figure 4A:
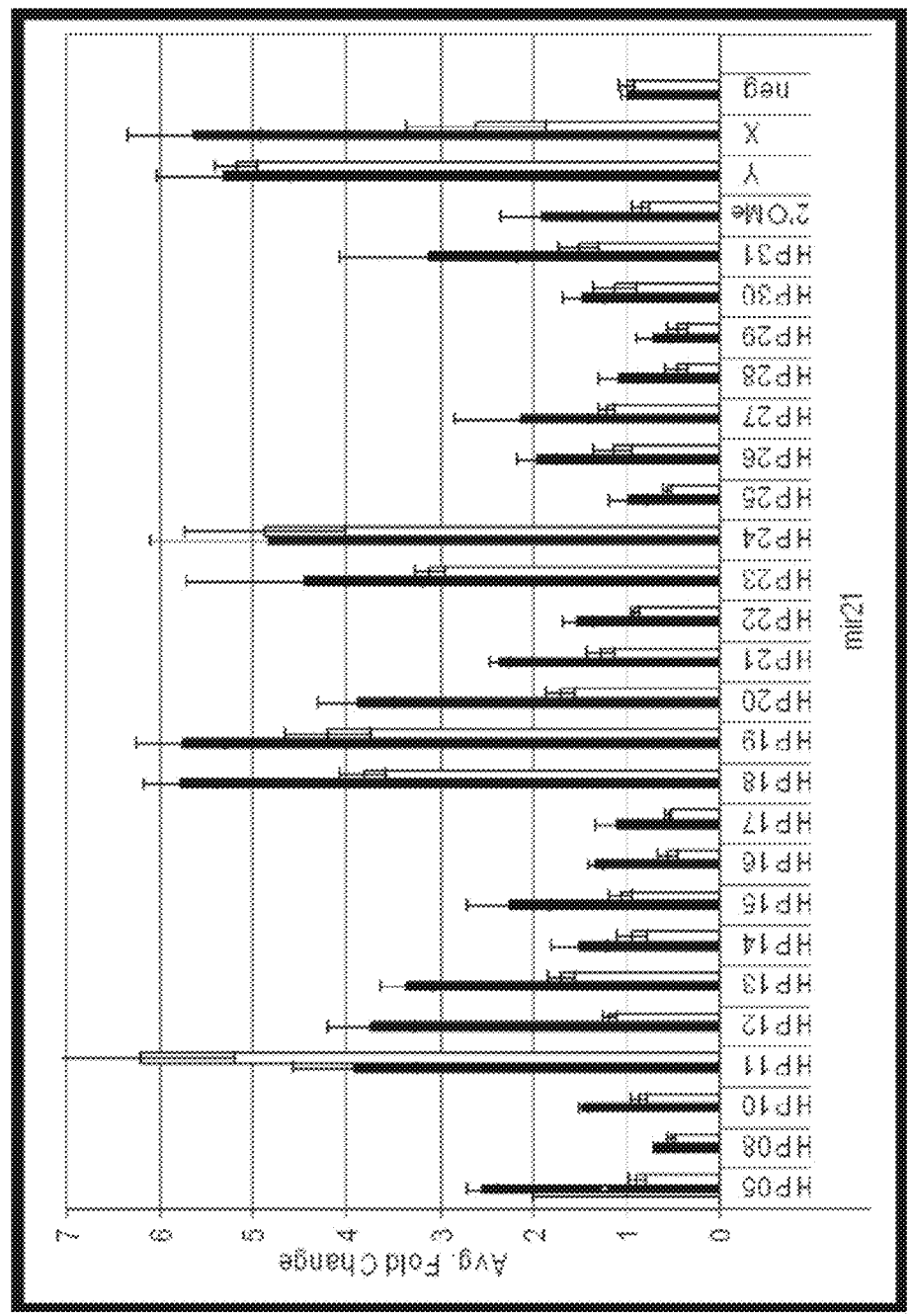
FIG. 4A and FIG. 4B show data derived from the Example 2 experiment in which the efficiency of the hairpin inhibitors HP#05, HP#08, and HP#10-HP#31 was evaluated using pMIR-REPORT™ miRNA expression reporter (miR21 or let7c target cloned), along with three controls: a 22 nt miRNA inhibitor with complete 2'-OMe modification (2'-OMe), miRNA inhibitor X (Exiqon) and miRNA inhibitor Y (Dharmacon).
Figure 4B:
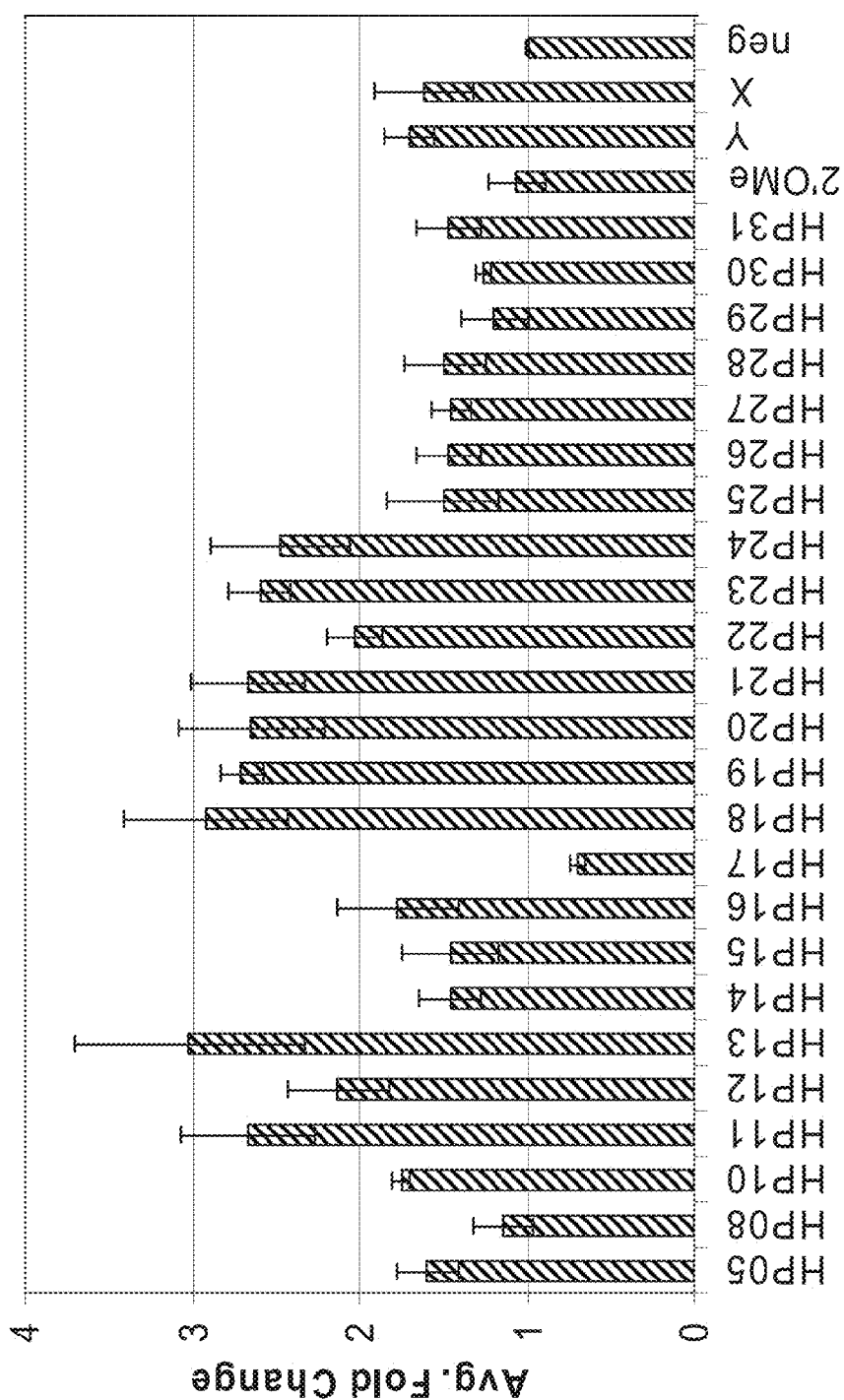

The results are shown in FIG. 4A and FIG. 4B and indicated the following: (1) Reverse complement oligonucleotides with 4-6 base-pair stems and non-nucleotide loops were potent inhibitors for in vitro loss of function studies of short (~22 nts) regulatory non-coding RNAs, particularly microRNAs (miRNAs); (2) In general, hairpin inhibitors of multiple designs (different loops, stems) very efficiently inhibited endogenous miRNAs and were more potent than the 2'-OMe modified miRNA inhibitor (2'-OMe), as well as miRNA inhibitor X (Exiqon) and miRNA inhibitor Y (Dharmacon); (3) Non-nucleotide loops were the same or better than all-nucleotide loops; L1-3, L7-8 (see Table 2) were best; (4) Inhibitors with 5' loops were more potent than inhibitors with 3'-loop structures; and (5) Inhibitors with longer stems (4-5 nt) were more potent than those with 3 nt stems.

Example 3

Evaluation of the Potency of Hairpin Inhibitors

The potency of the hairpin inhibitors HP#10-HP#31, HP#5, and HP#8 targeting let-7c miRNA was evaluated by quantification of the levels of HMGA2 mRNA expression with TAQMAN® assays, along with three controls: a 22 nt miRNA inhibitor with a complete 2'-OMe modification (2'-OMe), and miRNA inhibitor X (Exiqon) and miRNA inhibitor Y (Dharmacon).

The formats of the HP#10-HP#31 inhibitors are depicted in FIG. 1 and Tables 1A-1D. Variations of the hairpin inhibitors included: a 5'-loop or a 3'-loop; 8 versions of non-nucleotide loops and all-nucleotide loop; 3, 4, 5 bp stem.

From the literature it was known that one of the direct endogenous targets for miRNAs has-let7a and let7c, is the HMGA2 gene. A highly efficient assay was developed for measuring the endogenous gene expression levels to monitor potency of the miRNA inhibitors in vitro. Coupled with results from the reporter assays, this allowed for various conclusions regarding inhibitor formats.

The Biological Assay 2, an endogenous assay, was used as follows: To test the novel hairpin (HP) anti-miRs, HeLa cells were pre-plated at 6,000 per well in a 96-well plate. The next day, 0.15 ul LIPOFECTAMINE® RNAIMAX™ transfection agent was complexed with 0.3-100 nM of the chemically synthesized anti-miR (of different designs) and added to the cells. 24 hrs later, cells were lysed with CELLS-TO-CT™ lysis buffer (10 uL). HMGA2 mRNA levels were measured by qRT-PCR, using TAQMAN® Gene Expression CELLS-TO-CT™ kit (Applied Biosystems). A 20 μL RT reaction was set up using 1 μL of the lysate (37° C. for 60 minutes, 95° C. for 5 minutes, then 4° C.), followed by a 10 μL PCR reaction with a 2 μL cDNA input using an inventoried TAQMAN® gene expression assay for HMGA2#. Samples were normalized with the Eukaryotic 18S rRNA endogenous control.

By comparing the values for anti-let7 transfected wells with the negative control (non-targeting sequence) transfected wells it was possible to calculate the relative HMGA2 expression (anti-let7/negative) for each anti-miR format evaluated. The higher the relative HMGA2 expression—the more potent the miRNA inhibitor was.

Figure 5:
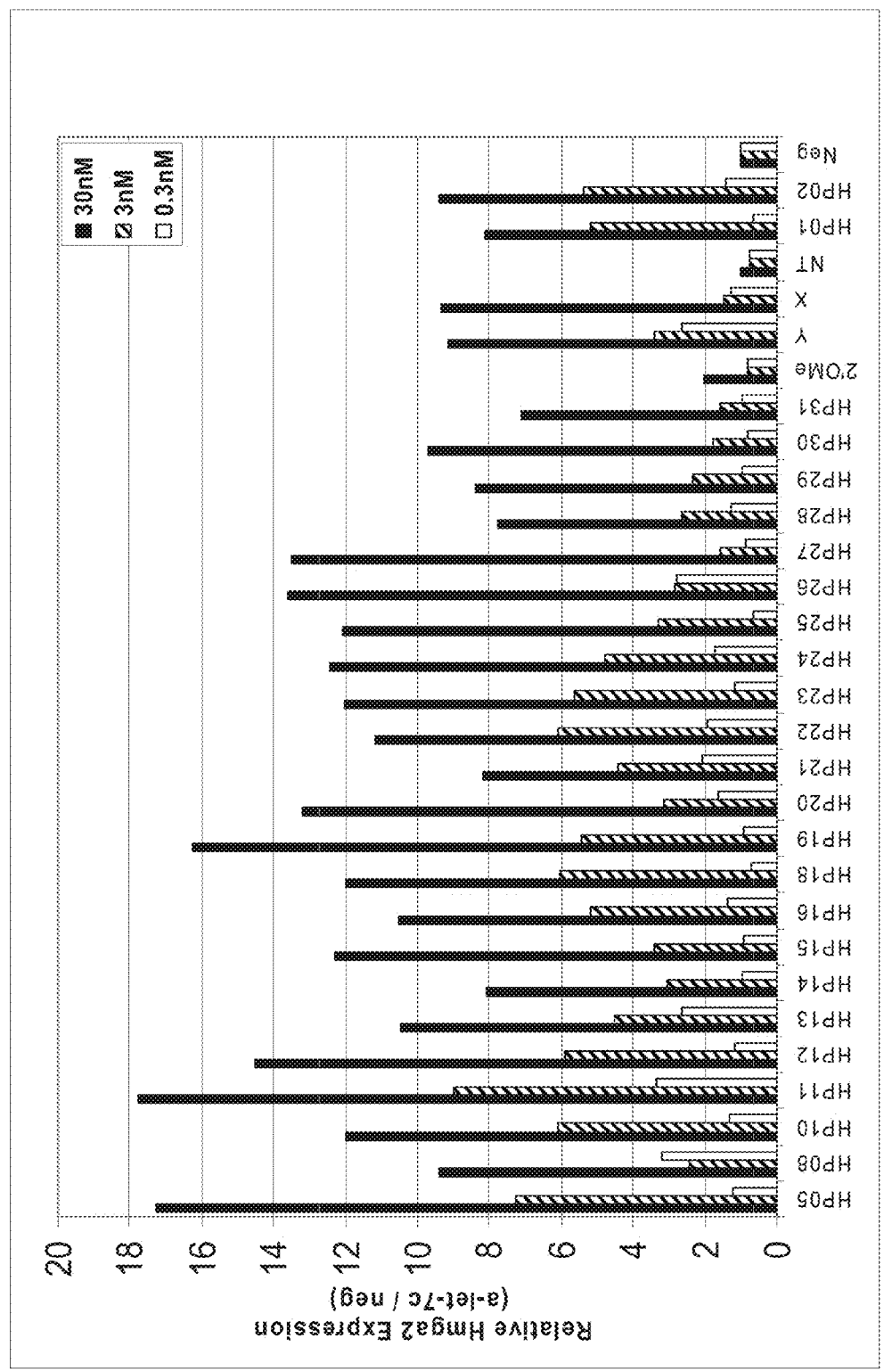
FIG. 5 shows data derived from the Example 3 experiment in which the potency of the hairpin inhibitors HP#05, HP#08, and HP#10-HP#31 targeting let-7c miRNA was evaluated by quantification of the levels of the endogenous HMGA2 mRNA transcript expression using TAQMAN® gene expression assays, along with three controls: a 22 nt miRNA inhibitor with complete 2'-OMe modification (2'-OMe), miRNA inhibitor X (Exiqon) and miRNA inhibitor Y (Dharmacon). The concentration of miRNA inhibitors upon transfection: 0.3, 3 and 30 nM. Increase of the HMGA2 mRNA levels is shown relative to negative control-transfected samples. All experiments were performed in triplicate.

The results (in FIG. 5) generally showed an increase of the HMGA2 mRNA levels relative to the negative control-transfected samples. More specifically, the results of this experiment indicated the following: (1) In general, HP inhibitors of multiple designs (different loops, stems) very efficiently inhibited endogenous miRNAs and were more potent than 2'-OMe modified miRNA inhibitor, as well as miRNA inhibitor X (Exiqon) and miRNA inhibitor Y (Dharmacon); (2) all non-nucleotide loops performed well (in particular L1 and L3), except L4, see Table 2 for loop structures; (3) inhibitors with 5' loops were more potent than inhibitors with 3'-loop structures; and (4) inhibitors with longer stems (>4 nt) were more potent than those with 3 nt stems.

Example 4

Evaluation of the Potency of Hairpin Inhibitor HP#24

The potency of the hairpin inhibitor HP#24 was evaluated by quantification of the fraction of the free endogenous miRNA (miR21 or let7c) with miRNA-specific TAQMAN® assays, along with three controls: a 22 nt miRNA inhibitor with complete 2'-OMe modification (2'-OMe), and miRNA inhibitor X (Exiqon) and miRNA inhibitor Y (Dharmacon).

Figure 6A:
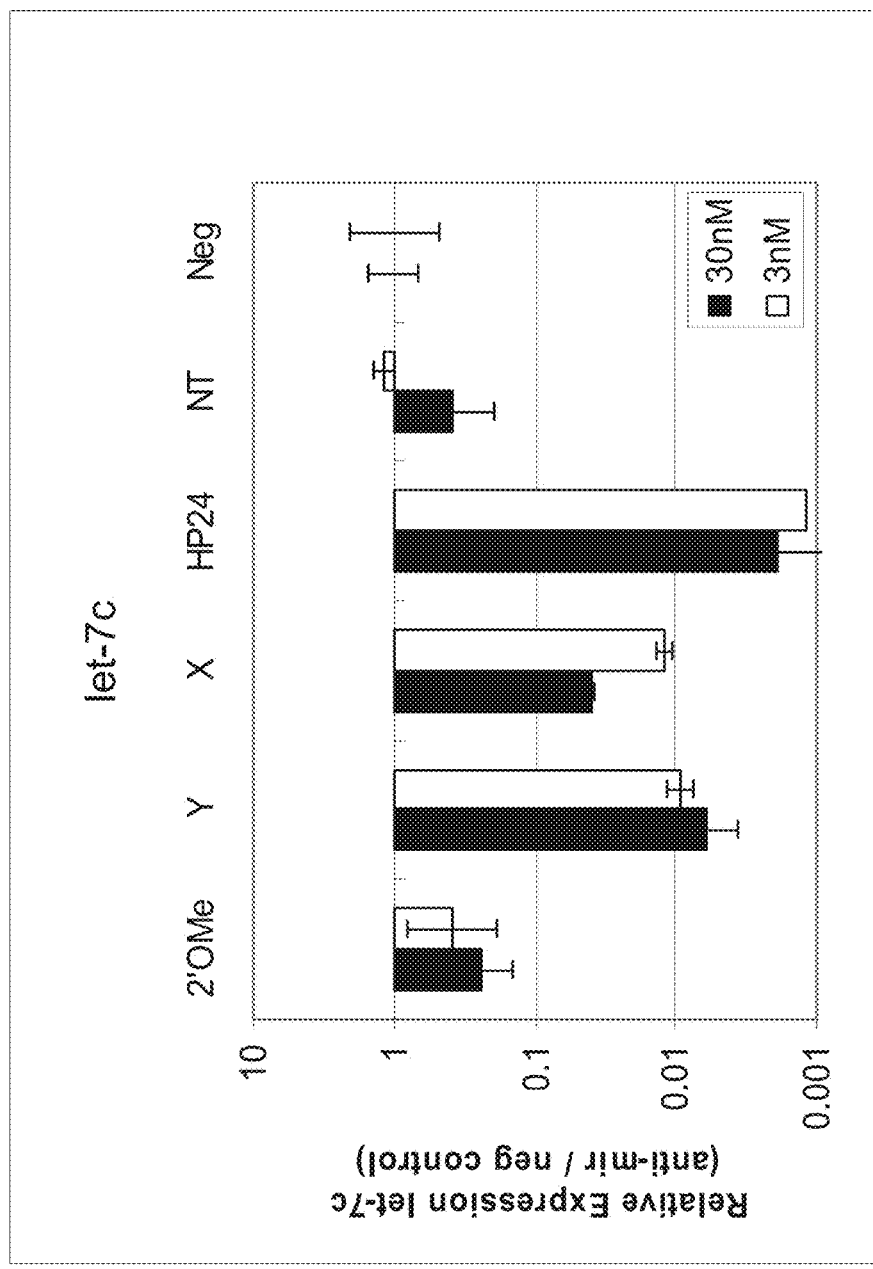
FIG. 6A and FIG. 6B show data derived from the Example 4 experiment in which the potency of the hairpin inhibitor HP#24 was evaluated by quantification of the fraction of the free endogenous miRNA (miR21 or let7c) using a TAQMAN® assay. Three inhibitor controls were used: a 22 nt miRNA inhibitor with complete 2'-OMe modification (2'-OMe), miRNA inhibitor X (Exiqon) and miRNA inhibitor Y (Dharmacon).
Figure 6B:
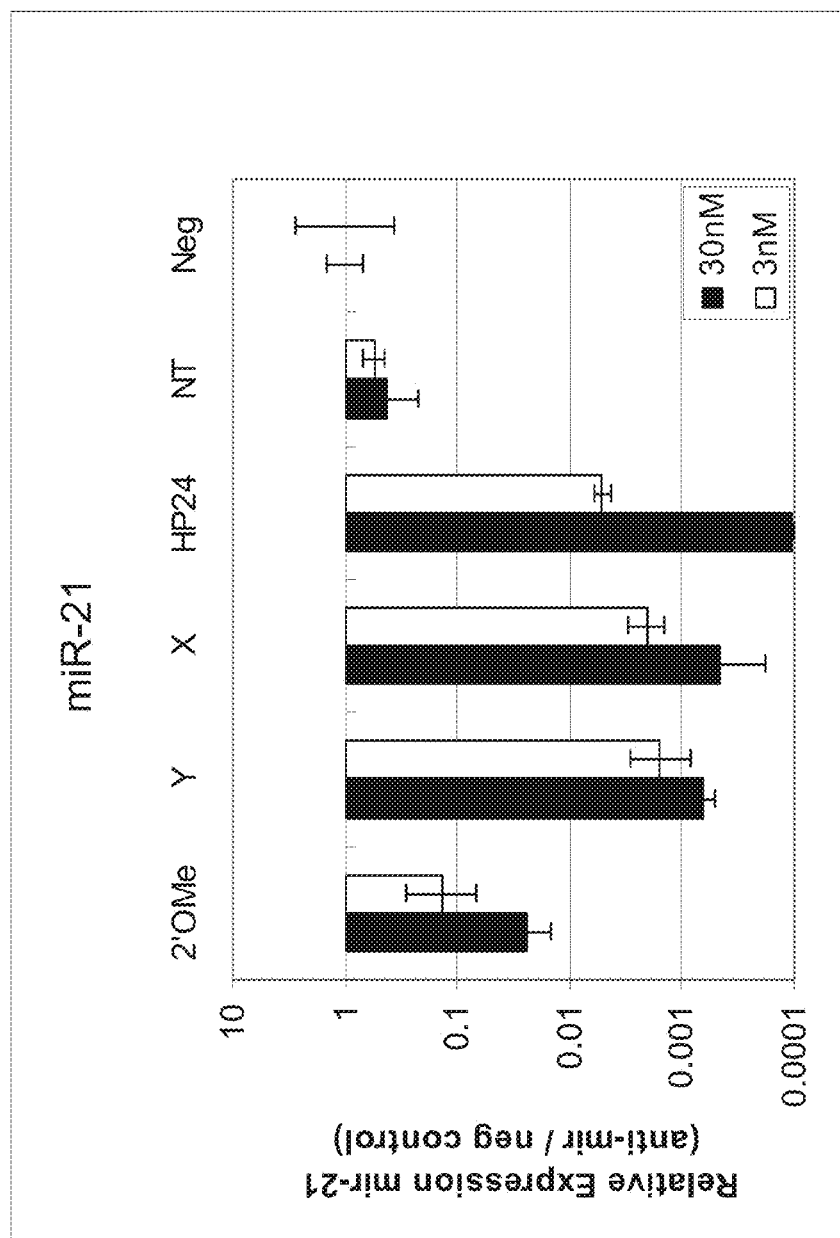

The format of the HP#24 inhibitor is depicted in FIG. 1 and Tables 1A-1D. The results are shown in FIG. 6A-FIG. 6B.

One of the approaches to measure the efficiency of miRNA inhibition with antisense oligonucleotides was to measure the fraction of endogenous miRNA remaining free (in the single-stranded form and thus accessible for primer binding) with TAQMAN® assays as follows:

Twenty four hours prior to transfection, HeLa cells were pre-plated at 250,000 cells per well in 2.3 mL. The next day, synthetic miRNA inhibitors (targeting has-let7c, miR21, and a negative control) were diluted in OptiMEM® medium (Invitrogen, Carlsbad, Calif.) up to 100 µL. 5 µL of LIPO-FECTAMINE® 2000 transfection agent (Invitrogen, Carlsbad, Calif.) was diluted in OptiMEM® medium up to 100 µL and incubated at room temperature for 5 minutes. Diluted transfection agent was mixed with the inhibitors, incubated at room temperature for 20 minutes, then the 200 µL complex was added to the cells. The final volume in the wells was 2.5 mL, and the miRNA inhibitor concentration was 3-100 nM.

At 24 hours post-transfection, cells were washed with 2 mL of PBS three times by rotating the plate to ensure coverage of the cells followed by treatment with 400 µL 0.05% trypsin for 3 minutes at 37° C., then the trypsin was inactivated by adding 1 mL of complete growth medium (DMEM+10% FBS). Media was swirled around and pipetted up and down to dislodge cell clumps. The cells were transferred to 1.5 mL Eppendorf tubes, pelleted at 800 g for 3 minutes, and the cell pellets were washed two times with 1 mL of PBS by flicking the tube to disrupt the pellet. The pellets were then lysed with 1.25 mL of the TAQMAN® MicroRNA CELLS-TO-CT™ lysis buffer (Applied Biosystems). The lysates were mixed by inverting the tubes five times and then incubated at room temperature for 8 minutes. The lysis reactions were stopped by adding 125 µL Stop Solution followed by inverting the tubes to mix and incubation at room temperature for another 2 minutes. Finally, RT and PCR were performed as described for quantification of endogenous miRNA levels.

The assay for quantification of miRNAs consisted of two steps: reverse transcription (RT) and PCR. The RT primer from TAQMAN® MicroRNA Assays features a stem-loop design (Applied Biosystems Inc., Foster City, Calif.) (Chen et al, 2005, v. 33, p. 1-9). A typical 10 µL RT reaction (Applied Biosystems) included either 10 nanogram of total purified RNA or 1 µL lysate prepared using the TAQMAN® MicroRNA Cells-to-CT™ kit and 50 nM of RT primer. After adding the enzyme mix (at final concentrations, 0.25 mM of each dNTP, 3.33 units/µL of MULTISCRIBE™ reverse transcriptase, 1×RT buffer, 0.25 units/µL of RNase inhibitor), the reaction mixture was incubated at 16° C. for 30 minutes, 42° C. for 30 minutes, 85° C. for 5 minutes, and then 4° C. Real-time PCR was performed using a standard TAQMAN® PCR protocol on an Applied Biosystems 7900HT Sequence Detection System. The 10 µL PCR reaction mixture included 1 µL RT product, 1× TAQMAN® Universal PCR Master Mix, 0.2 µM TAQMAN® probe, 1.5 µM forward primer, and 0.7 µM reverse primer. The reaction was incubated at 95° C. for 10 minutes, followed by 40 cycles of 95° C. for 15 seconds and 60° C. for 1 minute.

The data in FIG. 6A-FIG. 6B are presented in the form of a bar graphs and showed a decrease of the free miRNA levels (available for primer hybridization and thus detection)—relative to negative control-transfected samples for both targets. FIG. 6A shows the results for let-7c and FIG. 6B shows the mir-21 results. The results of this experiment indicated that the hairpin inhibitor HP#24 was more potent than the 2'-OMe modified miRNA inhibitor (2'-OMe), as well as miRNA inhibitor X (Exiqon) and miRNA inhibitor Y (Dharmacon).

This was the $3^{rd}$ biological assay that showed that HP inhibitors performed similarly or better than miRNA inhibitor X (Exiqon) and miRNA inhibitor Y (Dharmacon), and by far better than 2'-OMe antisense inhibitors.

Example 5

Evaluation of the Potency of Hairpin Inhibitor HP#79-HP#83

The efficiency of the hairpin inhibitors HP#79-HP#83 was evaluated using the pMIR-REPORT™ miRNA expression reporter (miR21, let7a or let7c target cloned), along with three controls: a 22 nt miRNA inhibitor with complete 2'-OMe modification (2'-OMe), and miRNA inhibitor X (Exiqon) and miRNA inhibitor Y (Dharmacon).

The formats of the HP inhibitors are depicted in FIG. 1 and Tables 1A-1D. The variables were inhibitors with a 5'-loop or a 3'-loop; 0, 1, or 2 nt between the antisense region and the stem-loop structure. Biological evaluation using pMIR-REPORT™ miRNA Expression Reporter Vector System was performed as described in Example 1.

Figure 7A:
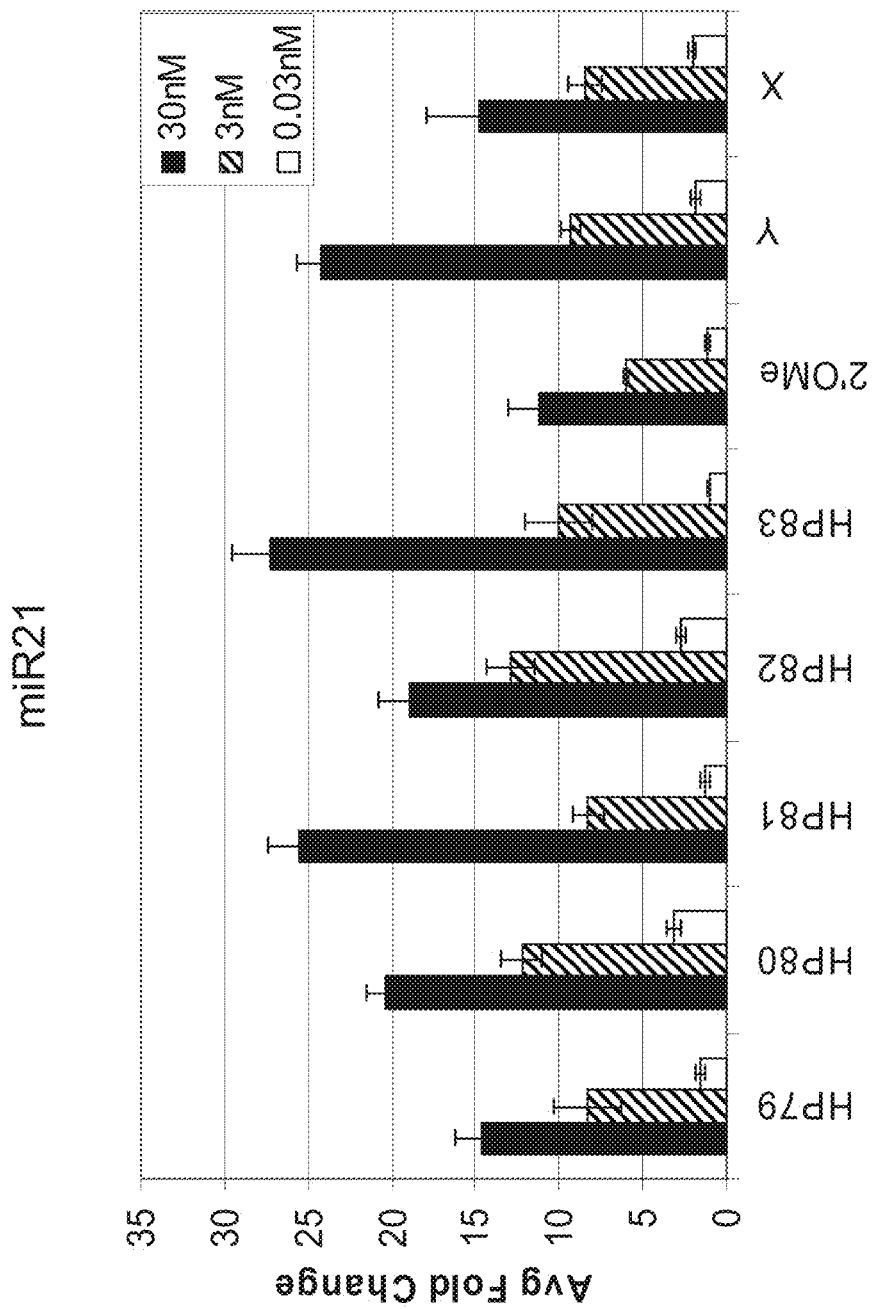
FIG. 7A-FIG. 7C show data derived from the Example 5 experiment in which the efficiency of the hairpin inhibitors HP#79-HP#83 was evaluated using a pMIR-REPORT™ miRNA expression reporter (miR21, let7a or let7c target cloned), along with three controls: a 22 nt miRNA inhibitor with complete 2'-OMe modification (2'-OMe), miRNA inhibitor X (Exiqon) and miRNA inhibitor Y (Dharmacon).
Figure 7B:
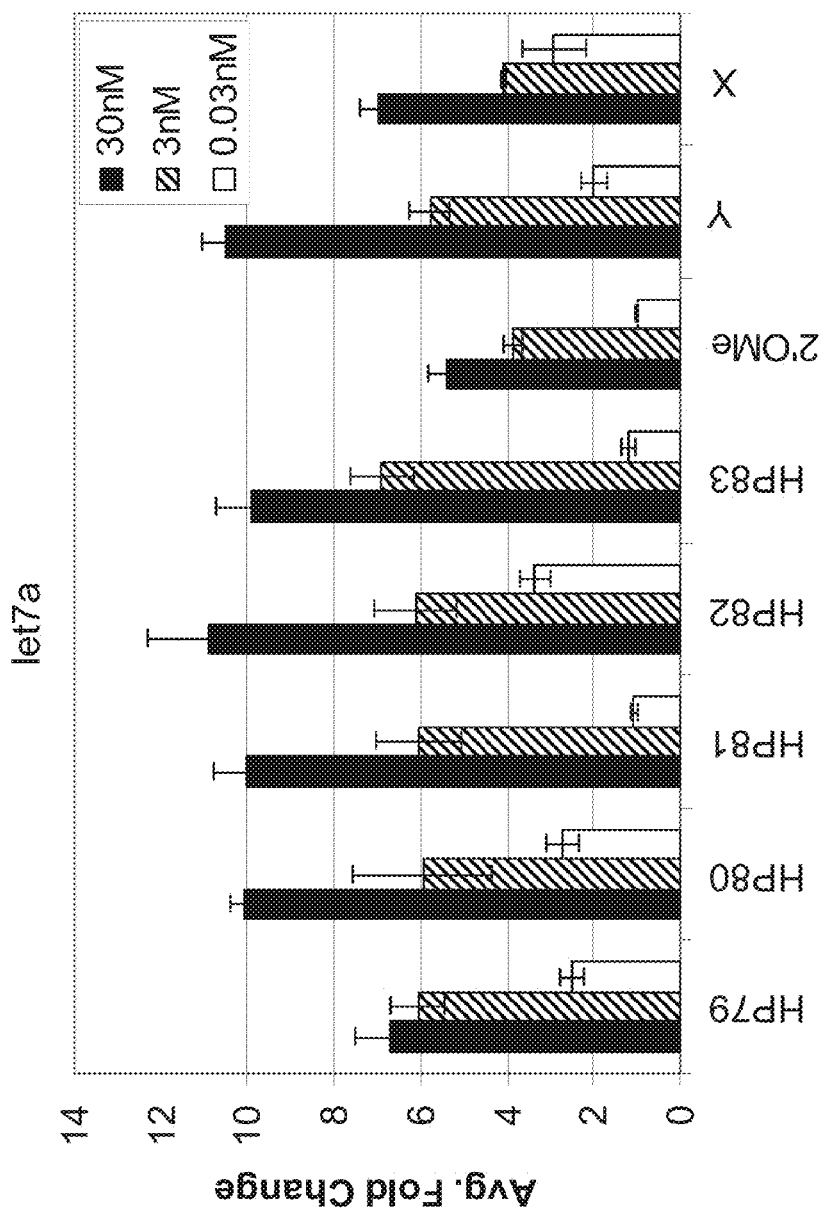
Figure 7C:
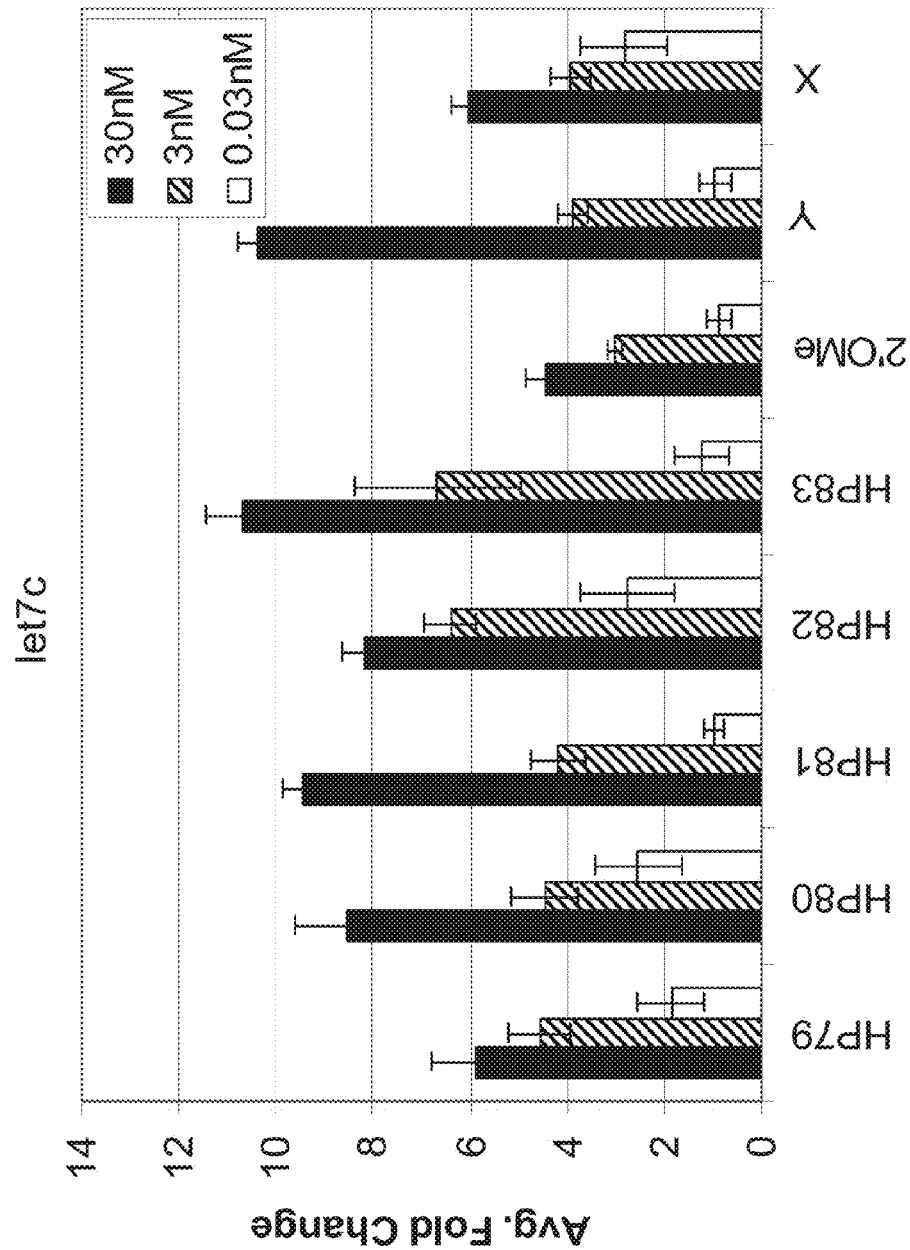

The results shown in FIG. 7A-FIG. 7C indicated the following: (1) For miRNA HP inhibitors with 5'-loops, introduction of an extra-nucleotide between the antisense region and the stem-loop structure did not reduce the inhibitor activity, i.e., the base stacking interaction with the miRNA strand was not crucial; (2) For HP inhibitors with 3-loops, introduction of an extra-nucleotide between the antisense region and the stem-loop structure enhanced the anti-miR activity (compare with Example1, where inhibitors with 3'-loops and 0 nt spacer were used); and (3) Overall, HP inhibitors of multiple designs very efficiently inhibited miR- NAs. Depending on the miRNA target and assay used (reporter, endogenous, etc) the best format varied.

Advantages of the Hairpin Inhibitors:

The hairpin inhibitors described herein utilizing an asymmetric design for the inhibitor, with a single stem loop at the 3' or 5' end of the antisense region and/or wherein the stem loop had a non-nucleotide loop were compared. The asymmetric design had more potency then the two commercially-available inhibitors used to compare. The hairpin inhibitors were 34-36 nucleotides long making the manufacturing of such molecules more feasible at a lower cost, especially if using a non-nucleotide loop. Contrary to current ideas, this suggests that the base-stacking interaction is not as crucial as was thought. Without being bound by a specific explanation for the increased potency of the asymmetric hairpin inhibitors, the process was likely driven primarily not by hybridization of the miRNA-antisense, but by the Ago protein (which contains an miRNA guide strand) which has certain template preferences (size, structure, etc). The natural targets of the Ago protein are certain mRNAs.

The addition of a 3' alkyl amino group somewhat enhanced potency at lower concentrations. Comparison of inhibitors with non-nucleotide loops at the 3' end prepared with and without a 3' alkyl amino group showed that inhibitors with alkyl amino modification demonstrated better activity at very low concentrations (0.03 nM).

Example 6

Evaluation of the Potency of Modified Antisense Inhibitors

The efficiency of the modified antisense oligonucleotide-based inhibitors BTM#03-BTM#22 was evaluated using pMIR-REPORT™ miRNA expression reporter (miR21, let7a or let7c target cloned), along with three controls: a 22 nt miRNA inhibitor with complete 2'-OMe modification (2'-OMe), and miRNA inhibitor X (Exiqon).

Figure 8A:
FIG. 8A-FIG. 8C show data derived from the Example 6 experiment in which the efficiency of the modified antisense oligonucleotide-based inhibitors BTM#03-BTM#07, and BTM#22 was evaluated using a pMIR-REPORT™ miRNA expression reporter (miR21, let7a or let7c target cloned), along with two controls: a 22 nt miRNA inhibitor with complete 2'-OMe modification (2'-OMe) and with miRNA inhibitor X (Exiqon).
Figure 8B:
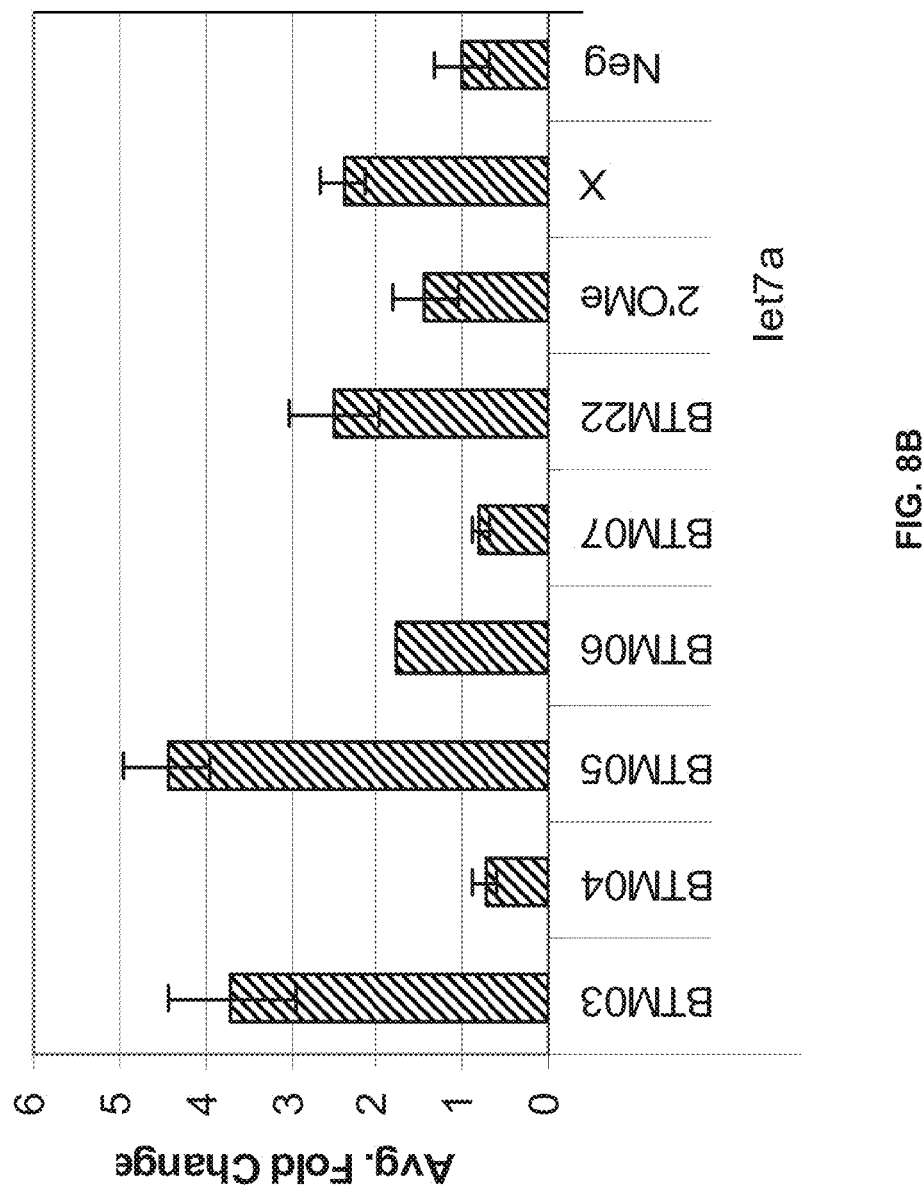
Figure 8C:
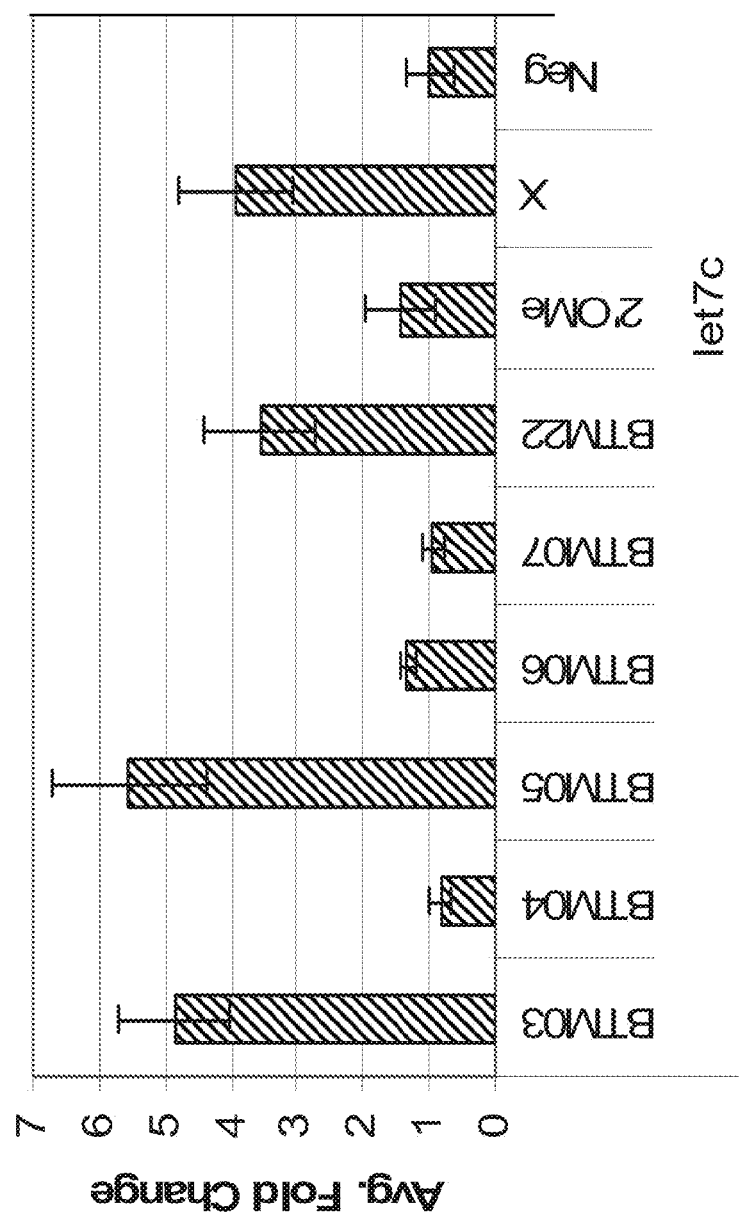

The formats of the antisense inhibitors are depicted in FIG. 1 and Tables 1A-1D. The variables were inhibitors with combinations of LNA, 2'-F, 2'-OMe modification; 21 nt versus 15 nt long antisense sequence. Synthesis of miRNA inhibitors and biological evaluation using pMIR-REPORT™ miRNA Expression Reporter Vector System was performed as described in Example 1. The results are shown in FIG. 8A-FIG. 8C.

miRNA inhibitors were prepared that were highly chemically modified (LNA, ENA and 2'-F combinations with 2'-OMe) without any hairpin structures- to compare the value of strong binding chemistry nucleotides. The results showed that: (1) LNA chemistry and LNA/2'-OMe, LNA/2'-F combinations were more effective at inhibition of miRNAs than 2'-OMe or 2'-F anti-miR modifications; (2) inhibitors with the full-length antisense sequence (21 nt) were significantly more potent than inhibitors with the shorter antisense region (15 nt); (3) modified 22 nt miRNA inhibitors were either as good or worse than the hairpin inhibitors in Examples 1 and 2); and (4) LNA modifications incorporated into the hairpin inhibitors may improve their potency. However, LNA modified molecules are challenging to synthesize and can be expensive.

Example 7

Evaluation of the Potency of Multimerized Inhibitors

Figure 11:
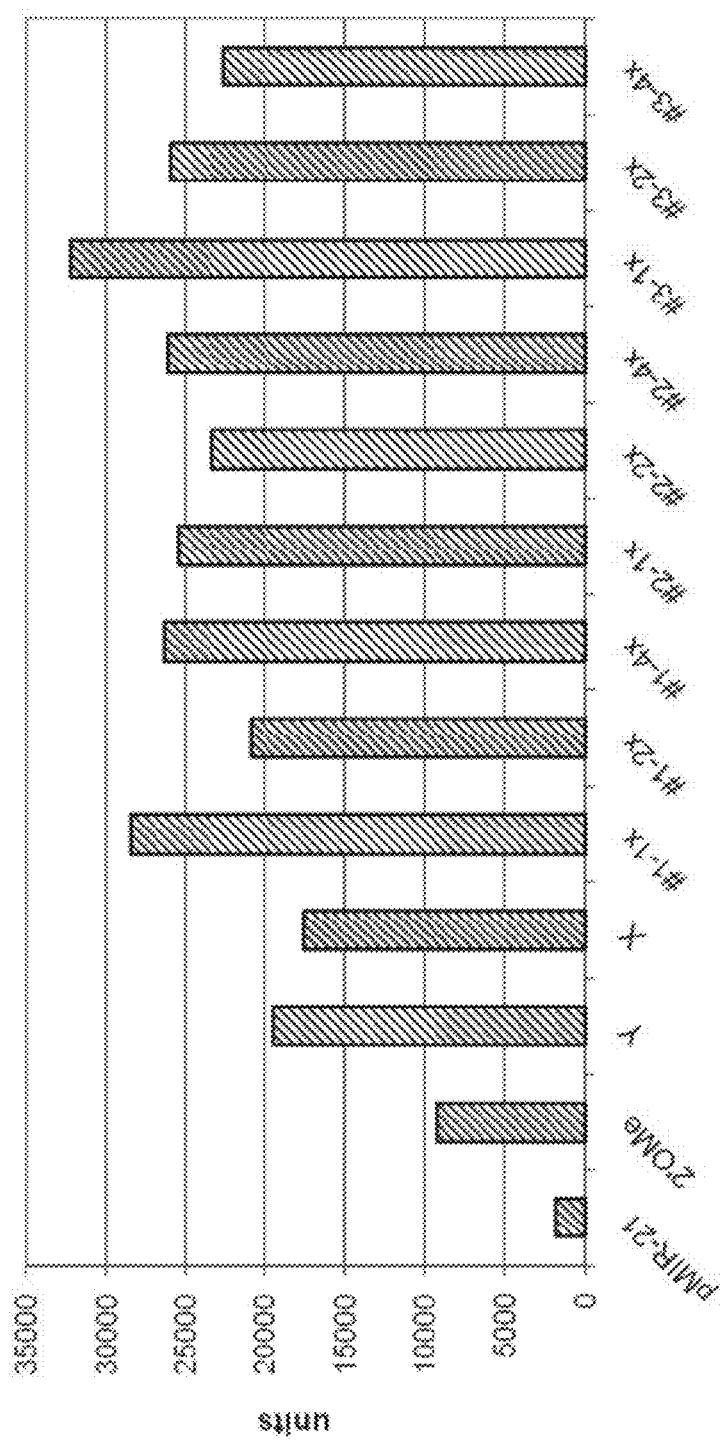
FIG. 11 shows data derived from the Example 7 experiment assaying the inhibitory activity of antisense oligonucleotide-based multimeric anti-miRs. #1, #2, and #3 refer to different annealing buffers. Buffer #1: 10 mM Tris-HCl pH 7.4, 100 mM NaCl. Buffer #2: 6 mM HEPES pH 7.4, 20 mM potassium acetate, 0.4 mM Magnesium acetate. Buffer#3: 10 mM Tris-HCl pH 8.0, 10 mM NaCl, 1 mM EDTA. 1×, 2×, and 4× refer to the molar excess of the "bridging" oligonucleotide over the long antisense oligonucleotide. The concentration of the inhibitor was 10 nM. Three controls are: a 22 nt miRNA inhibitor with complete 2'-OMe modification (2'-OMe), miRNA inhibitor X (Exiqon) and miRNA inhibitor Y (Dharmacon). All experiments were performed in triplicate.

The design of the miRNA inhibitor multimers targeting miR21 is depicted in FIG. 9 and FIG. 10. Biological evaluation using pMIR-REPORT™ miRNA Expression Reporter Vector System was performed as described in Example 1. The results are shown in FIG. 11.

Multimerized anti-miRs were designed and tested to determine their performance. As shown in FIG. 10, 30-45 nucleotide long anti-miRs were synthesized (enhanced with chemical modifications for stronger binding) so that the central 20-22 nt part was complementary to the target miRNA strand, and flanking sequences were used for multimeric complex formation. Upon addition of the "bridging" oligonucleotide (NBR2C:NBR1C in FIG. 9) (with or without LNA or other modifications to promote stronger interaction) the anti-miRs spontaneously formed multimeric complexes.

Multimeric Anti-miRs targeting mir21, prepared under different conditions, were co-transfected into HeLa cells at a concentration of 10 nM with the luciferase expression plasmid containing the mir21 binding site and βGal plasmid (used for normalization of transfection efficiency). 24 hours later the DUAL-LIGHT® Assay was performed to monitor the effect of the anti-miR on luciferase expression. Each anti-miR was normalized to the negative control anti-miR (NCa). Multimeric complex formation was as follows: Antisense oligonucleotide (with extra-sequences at the 3'-termini and 5'-termini-enabling complex formation, see FIG. 9 and FIG. 10) was annealed with the "bridging" oligonucleotide at 95° C. for 3 min, followed by a 1 hour incubation at 37° C. The designations #1, #2, and #3 of FIG. 11 refer to different annealing buffers. Buffer #1: 10 mM Tris-HCl pH 7.4, 100 mM NaCl. Buffer #2: 6 mM Hepes pH 7.4, 20 mM potassium acetate, 0.4 mM Magnesium acetate. Buffer#3: 10 mM Tris-HCl pH 8.0, 10 mM NaCl, 1 mM EDTA. The designations 1×, 2×, and 4× refer to the molar excess of the "bridging" oligonucleotide over the long antisense oligonucleotide. The multimeric miRNA inhibitors self assembled in the specified buffer. The number of multimers was dependent upon the type of buffer used and the molar excess of the bridging oligonucleotide.

These anti-miRs had several attractive features: (1) The large size closely mimicked the natural substrate—mRNA—and thus promoted very efficient binding with miRNA/Ago; (2) Multimers did not have secondary structure that could complicate complex formation with miRNAs—in contrast to "miRNA sponges" (long tandem antisense transcripts expressed from DNA vectors); (3) The termini of multimers had extra protection from RNases; (4) Packaging and in vitro delivery of the multimers was more efficient when using certain commercially available reagents (such as PEI=polyethyleneimine), because complexes are long and rigid similarly to dsDNA; and (5) The multimers were chemically synthesized so modifications could be incorporated, enabling strong interaction with the miRNA target (2'-OMe was used, but LNA or other molecules could be used)—in contrast to "miRNA sponges".

A long anti-miR to mir21 (45 nt)-the core 22-nt RNA, 2'OMe modified, flanked by 11 nt and 12 nt sequences, was also synthesized. The "bridging" oligonucleotide was 21 nt long, LNA was modified at every other position. Multimeric complexes were formed by mixing equal amounts of the long anti-miR and "bridging" oligonucleotide in annealing buffer (10 mM Tris pH 7.4, 100 mM NaCl), incubating at 95° C. for 3 minutes and cooling down at 37° C. for 1 hr. The biological evaluation using pMIR-REPORT™ miRNA Expression Reporter Vector System was performed as described in Example 1.

Initial evaluation of the performance of the multimers showed that they had better inhibitory activity than 2'-OMe anti-miRs, as well as miRNA inhibitor X (Exiqon) and miRNA inhibitor Y (Dharmacon) (FIG. 11).

Example 8

In Vivo Studies

Hairpin inhibitor miR122 was tested in vivo as follows: Mice (3 animals/group) were injected in the tail vein with 50 mg/kg anti-miR122 (with phosphorothioate modifications, without any delivery reagent), on 3 subsequent days, and sacrificed 24 h post 3rd injection. Levels of AldoA, Hfe2, Slc35a4, Lass6 mRNAs (reported targets for miR-122: Elmén et al, 2008 Nucl. Acids Res. v. 36, p. 1153-1162; Davis et al, Nucl. Acids Res. 2009 v. 37, p. 70-77) in their livers was quantified by qRT-PCR. Data normalized to untreated mice, and Let7—additional "neg control"—is shown. MiR122 5'HPp=s was the format HP#81, with complete phosphorothioate (P=S) modification of the target binding strand for in vivo use. MiR122 3'HPp=s was the format HP#83, with complete phosphorothioate (P=S) modification of the target binding strand for in vivo use (MiR122 5'HP format HP#81 w/o phosphorothioate modification did not show any activity).

Figure 12:
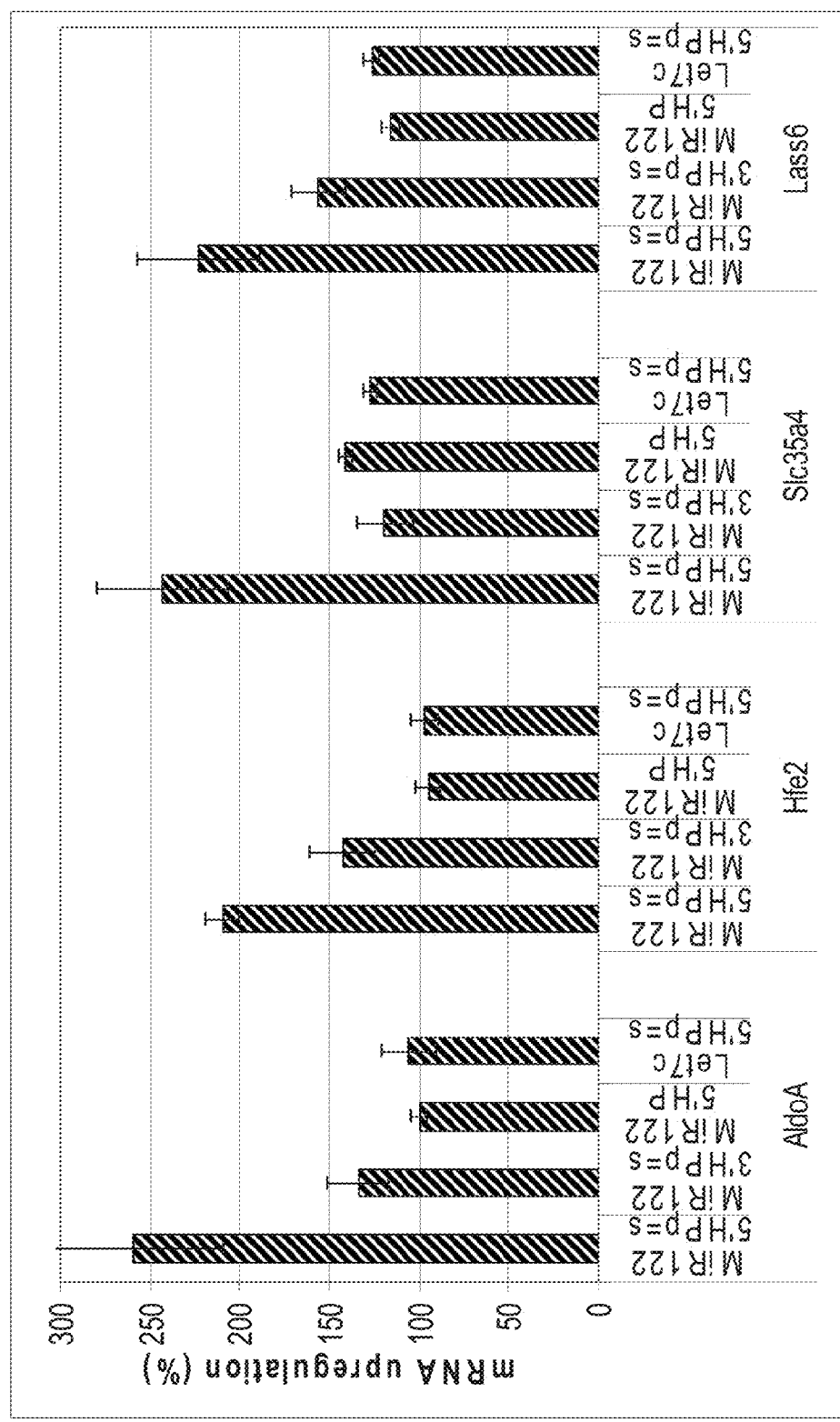
FIG. 12 shows the derepression of miR-122 target genes AldoA, Hfe2, Slc35a4, and Lass6 after miR-122 inhibition in mice. mRNA upregulation (%) is normalized to the negative control-injected mice. Three daily injections of 50 mg/kg of phosphorothioate (p=s) modified HP#81 and HP#83 miRNA inhibitors were used. All experiments were performed in triplicate.

The results in FIG. 12 showed the following: (1) miRNA inhibitors with phosphorothioate modifications could be used in in vivo experiments, and they induced robust inhibition of their targets in the liver, upon systemic tail vein administration. (2) phosphorothioate modifications were advantageous for in vivo experiments. Formats that were not self-deliverable in vivo could be successfully used with in vivo delivery reagents. (3) miRNA inhibitors with 5'-hairpin structures had better activity than inhibitors with 3'-hairpins in vitro and in vivo.

Example 9

Evaluation of the Potency of Hairpin Inhibitors

The potency of hairpin inhibitors HP#79, HP#81, HP#96, HP#85, HP#88, HP#93, and HP#96 targeting let-7a miRNA with CLICK-IT® loops (HP#85) or CLICK-IT® chemistry at the 3'-termini (HP#88; ready for conjugation of other molecules, e.g., cholesterol or dye label) were tested. See Tables 1A-1D for the format and sequence of the inhibitors and/or the targets. Click chemistry is a class of high yielding reactions for generating new compounds. The most popular reaction from the class is the copper catalyzed 1,3 dipolar cycloaddition between an alkyne and an azide to yield a substituted 1,2,3, triazole (also known as Huisgen cycloaddition). Potency was evaluated by quantification of the levels of HMGA2 mRNA expression with TAQMAN® assays, along with three controls: a 22 nt miRNA inhibitor with complete 2'-OMe anti-miRs, as well as miRNA inhibitor X (Exiqon) and miRNA inhibitor Y (Dharmacon) as discussed in Examples 1 and 4. The concentration of miRNA inhibitors upon transfection was 0.3, 3, 30 nM. Increase of the HMGA2 mRNA levels is shown relative to negative control-transfected samples. The increase in the firefly luciferase expression induced by miRNA inhibition (the Average fold change) was calculated in the following way: (fLuc activity anti-miR/βGal activity anti-miR)/(fLuc activity neg/βGal activity neg). (For details, see Example 1 Materials and Methods section.)

Figure 13:
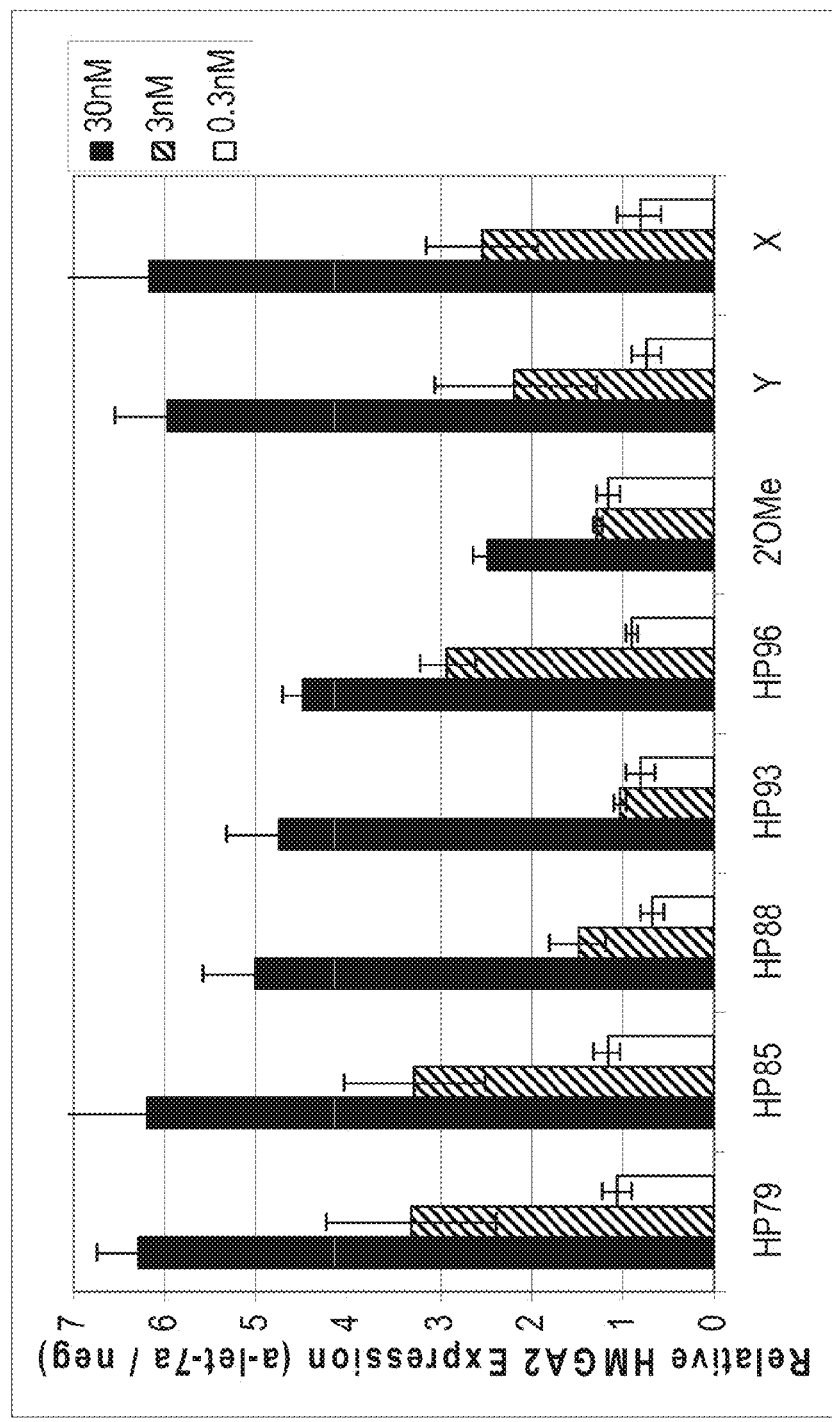
FIG. 13 shows the potency of the hairpin inhibitors HP#79, HP#85, HP#88, HP#93, and HP#96 targeting let-7a miRNA in Example 9. Potency was evaluated by quantification of the levels of HMGA2 mRNA expression with TAQMAN® assays, along with three controls: a 22 nt miRNA inhibitor with complete 2'-OMe modification (2'-OMe), miRNA inhibitor X (Exiqon) and miRNA inhibitor Y (Dharmacon). The concentration of miRNA inhibitors upon transfection: 0.3, 3, 30 nM. Increase of the HMGA2 mRNA levels is shown relative to negative control-transfected samples. All experiments were performed in triplicate.
Figure 14:
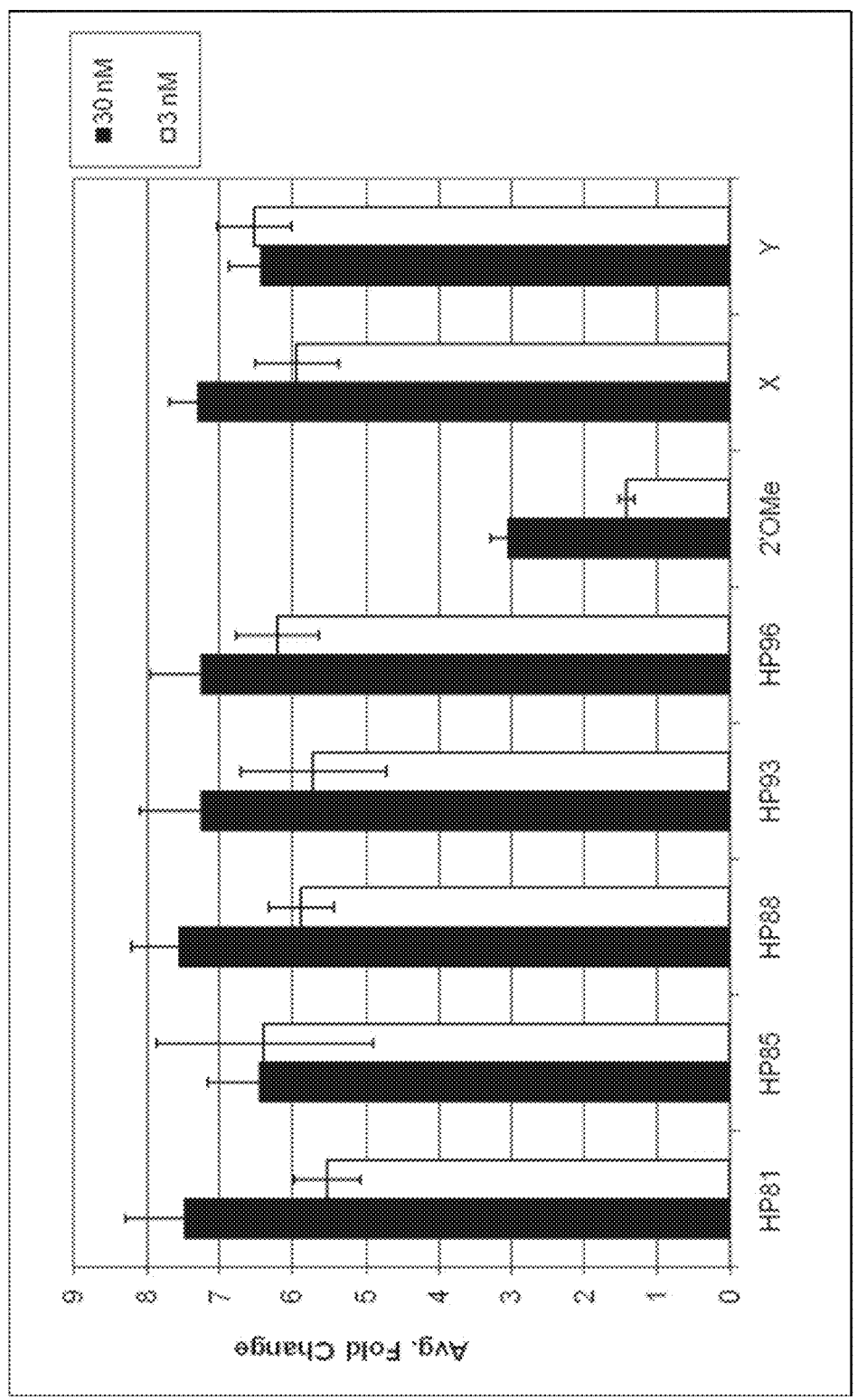
FIG. 14 shows the potency of the hairpin inhibitors HP#81, HP#85, HP#88, HP#93, and HP#96 in Example 9. Potency was evaluated using pMIR-REPORT™ miRNA expression reporter (miR21 target cloned), along with three controls: a 22 nt miRNA inhibitor with complete 2'-OMe modification (2'-OMe), miRNA inhibitor X (Exiqon) and miRNA inhibitor Y (Dharmacon). Concentrations of miRNA inhibitors upon transfection: 30, 3 nM. The increase in the firefly luciferase expression induced by miRNA inhibition (the Average fold change) was calculated in the following way: (fLuc activity anti-miR/βGal activity anti-miR)/(fLuc activity neg/βGal activity neg). All experiments were performed in triplicate.

The results in FIG. 13 and FIG. 14 showed that (1)—hairpin inhibitors synthesized with CLICK-IT® loops (HP#85) or CLICK-IT® chemistry at the 3'-termini (HP#88; ready for conjugation of other molecules, e.g. cholesterol or dye label) have the same potency as the HP inhibitors (2)—HP conjugates with cholesterol (HP#96) are functional, and the level of activity is similar to unconjugated HP. Cholesterol can enable in vitro and in vivo delivery of these inhibitors.

Example 10

Evaluation of the Potency of Hairpin Inhibitors

HP#89, HP#90, HP#91, HP#92: LNA and 2'F/2OMe modified hairpin inhibitors targeting let-7c miRNA were tested for potency by quantification of the levels of HMGA2 mRNA expression with TAQMAN® assays, along with three controls: a 2'-OMe anti-miR, as well as miRNA inhibitor X (Exiqon) and miRNA inhibitor Y (Dharmacon). See Tables 1A-1D for formats and sequences of the inhibitors and targets. The assays were performed as in Example 4. The concentration of the miRNA inhibitors tested upon transfection was 10 nM.

Figure 15:
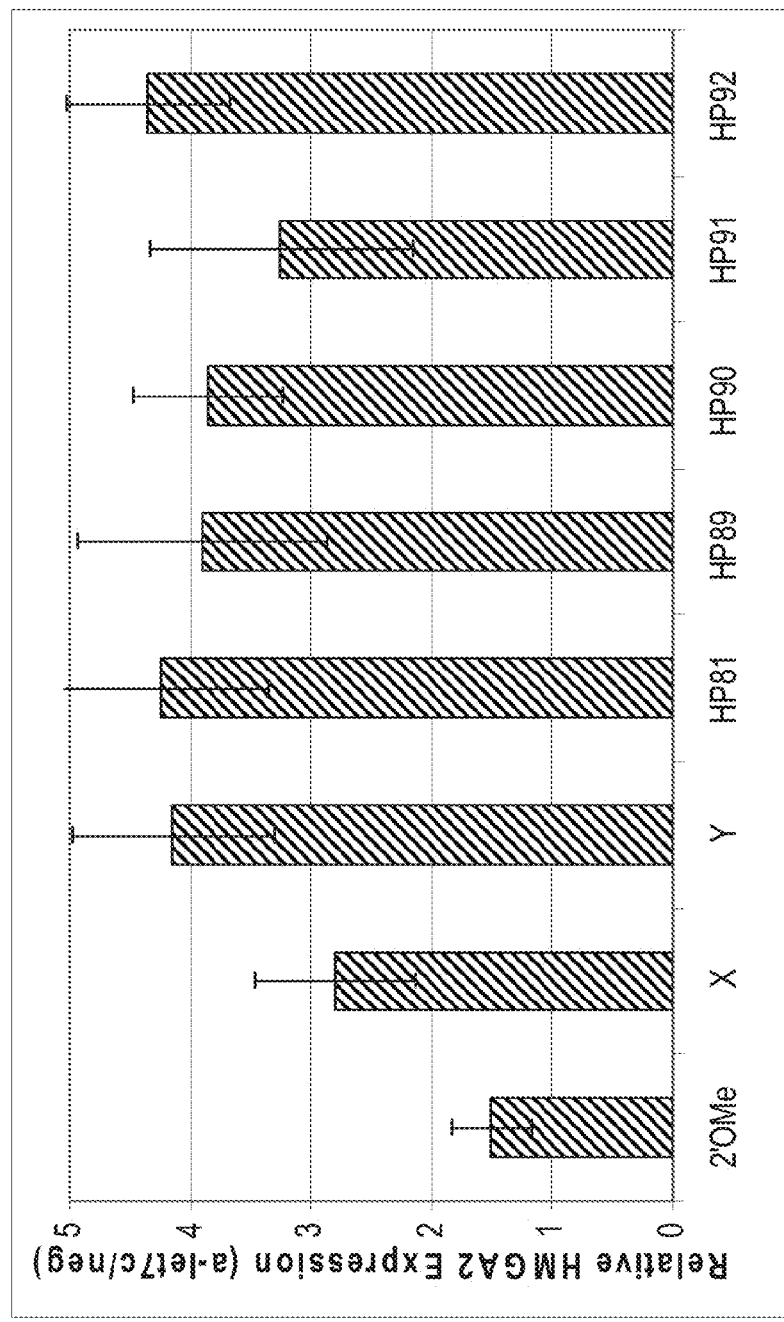
FIG. 15 shows the potency of the hairpin inhibitors HP#81 and HP#89-HP#92 targeting let-7c miRNA in Example 10. Potency was evaluated by quantification of the levels of HMGA2 mRNA expression using a TAQMAN® assay. Three controls were used: a 22 nt miRNA inhibitor with complete 2'-OMe modification (2'-OMe), miRNA inhibitor X (Exiqon) and miRNA inhibitor Y (Dharmacon). The concentration of miRNA inhibitors upon transfection: 10 nM. All experiments were performed in triplicate.

The results are shown in FIG. 15 where an increase of the HMGA2 mRNA levels is shown relative to the negative control-transfected samples. The results showed that (1) chemistries other than 2'-OMe can be used for HP inhibitors, and all of them are highly functional. However, LNA or other modifications did not result in superior performance of inhibitors, compared to 2'-OMe modifications. However, the activity of the inhibitors was at such a high level already, improvements may be very small or negligible. With hairpin structures 2'-OMe modifications perform very well, but for single-stranded antisense oligonucleotides the LNA-modified inhibitors were superior to 2'-OMe inhibitors. Thus, the modifications that enhanced activity varied for different structures. However, in all cases, the hairpin inhibitors were significantly better than "standard" 2'-OMe inhibitors (21 nt long) and X and Y inhibitors (Exiqon and Dharmacon).

Example 11

Synthesis of Inhibitor with Non-Nucleotide Loop L11 that Targets Let 7a miRNA Inhibitor HPX (SEQ ID NO:103) was synthesized with non-nucleotide loop L11 (see Table 2) via copper catalyzed Huisgen 1,3-dipolar cycloaddition. The miRNA inhibitor targeted Let 7a miRNA. However this method can be used to synthesize any type of inhibitor. The sequence and chemical structure of compound 1 is shown below. Synthesis was achieved using solid phase phosphoramidite synthesis on a MerMade™ 192 synthesizer. Standard coupling times and cycles were employed along with $I_2/H_2O$ oxidation and acetic anhydride capping on DNA T nucleoside loaded CPG columns 1 mole (Biosearch). 2'OMe phosphoramidites A, C, G, and U were purchased from Chemgenes, Inc and diluted with anhydrous acetonitrile prior to use. The phosphorohexyne moiety was installed using 5' alkyne modifier (Glen Research). After synthesis, the CPG was treated with a mixture of aqueous ammonia and methylamine for 15 minutes to cleave the oligonucleotide from the solid support. This mixture was further incubated for a period of 2.5 hours in the ammonia/methylamine solution to afford the removal of both the exocyclic amino protection groups (benzyl for A, acetyl for C, and dmf for G) as well as the cyanoethyl protecting groups from the phosphate backbone. The aqueous solution was dried via compressed air under elevated temperature to produce the crude product. The oligonucleotide was purified on anion exchange resin using an Agilent 1200 HPLC with NaClO$_4$ buffer as the eluent. The oligonucleotide was then desalted utilizing ultracentrifugation cartridges (Sartorius, 2000 MWCO) and the molecular weight of the oligonucleotide was verified with MALDI (Applied Biosystems).

(SEQ ID NO: 106)

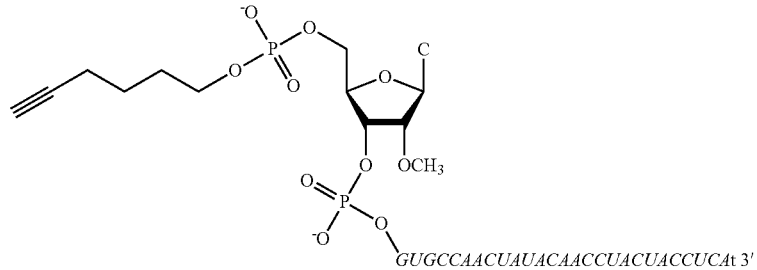

1

GUGCCAACUAUACAACCUACUACCUCAt 3'

The sequence and chemical structure of compound 2 is shown below. Synthesis was achieved using solid phase phosphoramidite synthesis on a MerMade™ 192 synthesizer. Standard coupling times and cycles were employed along with $I_2/H_2O$ oxidation and acetic anhydride capping on C6 phthalimido loaded CPG (Prime Synthesis) 500 nmole columns. 2'OMe phosphoramidites A, C, G, and U were purchased from Chemgenes, Inc and diluted with anhydrous acetonitrile prior to use. After synthesis, the CPG was treated with a mixture of aqueous ammonia and methylamine for 15 minutes to cleave the oligonucleotide from the solid support. This mixture was further incubated for a period of 2.5 hours in the ammonia/methylamine solution to afford the removal of both the exocyclic amino protection groups (benzyl for A, acetyl for C, and dmf for G) as well as the cyanoethyl protecting groups from the phosphate backbone. The aqueous solution was dried via compressed air under elevated temperature to produce the crude product. The oligonucleotide was purified on anion exchange resin using an Agilent 1200 HPLC with NaClO$_4$ buffer as the eluent. The oligonucleotide was then desalted utilizing ultracentrifugation cartridges (Sartorius, 2000 MWCO) and molecular weight of the oligonucleotide was verified with MALDI (Applied Biosystems).

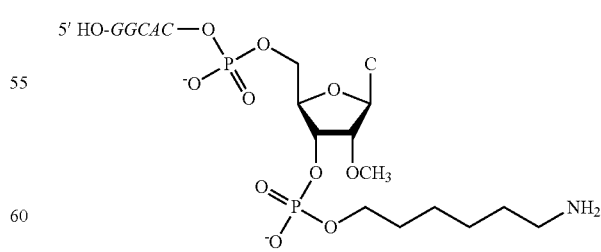

2

The sequence and chemical structure of compound 3 is shown below. Azidobutyrate NHS ester (Glen Research) in dimethylsulfoxide (15 μL, 0.17 M) was added to 0.5 umole of compound 2 in 100 mM sodium borate buffer. The solution was mixed using an orbital shaker at room temperature for a period of 4 hours. The oligonucleotide was purified on anion exchange resin using an Agilent 1200 HPLC with NaClO$_4$ buffer as the eluent. The oligonucleotide was then desalted utilizing ultracentrifugation cartridges (Sartorius, 2000 MWCO).

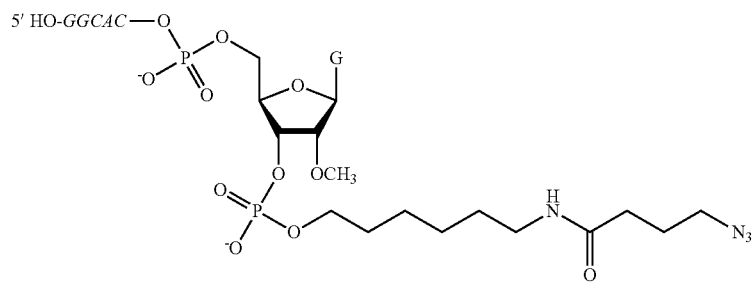

The sequence and chemical structure of miRNA Inhibitor SEQ ID NO:103 is shown below. CuSO$_4$ (10 µL, 0.1 M), butanone (20 µL), and Tris[(1-benzyl-1H-1,2,3-triazol-4-yl-methyl]amine (TBTA, 5 µL, 0.1 M) was added to a solution of 1 (0.05 mol, 0.7 mM) in phosphate buffered saline. After vortexing for 1 minute, compound 3 (84 µL, 0.9 M) and ascorbic acid (2 µL, 0.5 M) were added to the mixture and the solution was vortexed again for 1 minute. The solution was then mixed using an orbital shaker at room temperature for a period of 2 hours. The inhibitor was then desalted utilizing ultracentrifugation cartridges (Sartorius, 2000 MWCO) and molecular weight of the inhibitor was verified with MALDI (Applied Biosystems).

Example 12

Synthesis of Inhibitor with Non-nucleotide Loop L11 that Targets mir21 miRNA

Inhibitor HPX (SEQ ID NO:106) was synthesized with non-nucleotide loop L11 (see Table 2) via copper catalyzed Huisgen 1,3-Dipolar cycloaddition of the non-nucleotide loop. This inhibitor targets mir21 miRNA.

The sequence and chemical structure of compound 4 is shown below. Synthesis was achieved using solid phase phosphoramidite synthesis on a MerMade 192 synthesizer. Standard coupling times and cycles were employed along with I$_2$/H$_2$O oxidation and acetic anhydride capping on DNA C nucleoside loaded CPG columns 1 mole (Biosearch). 2'OMe phosphoramidites A, C, G, and U were purchased from Chemgenes, Inc and diluted with anhydrous acetonitrile prior to use. The phosphoro-hexyne moiety was installed using 5' Alkyne modifier (Glen Research). After synthesis, the CPG was treated with a mixture of aqueous ammonia and methylamine for 15 minutes to cleave the oligonucleotide from the solid support. This mixture was further incubated for a period of 2.5 hours in the ammonia/

SEQ ID NO: 103

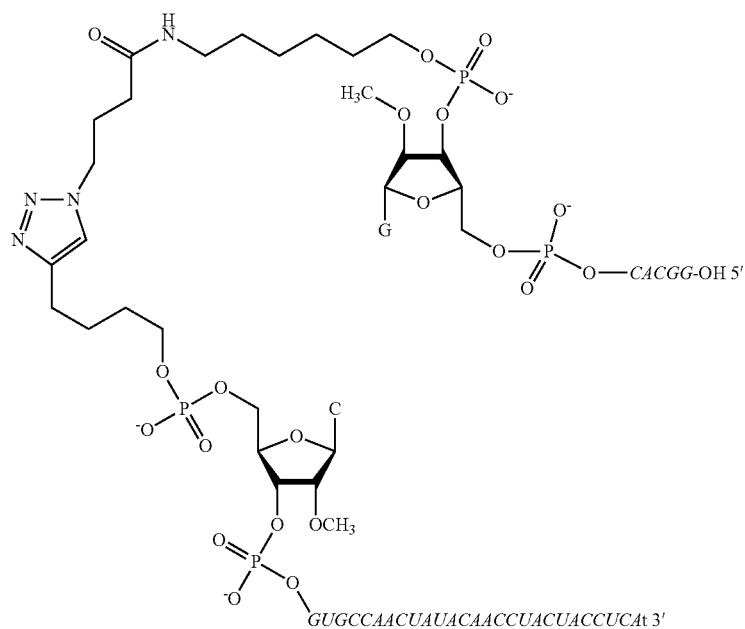

methylamine solution to afford the removal of both the exocyclic amino protection groups (benzyl for A, acetyl for C, and dmf for G) as well as the cyanoethyl protecting groups from the phosphate backbone. The aqueous solution was dried via compressed air under elevated temperature to produce the crude product. The oligo was purified on anion exchange resin using an Agilent 1200 HPLC with NaClO$_4$ buffer as the eluent. The oligonucleotide was then desalted utilizing ultracentrifugation cartridges (Sartorius, 2000 MWCO) and molecular weight of the oligonucleotide was verified with MALDI (Applied Biosystems).

4-yl)methyl]amine (TBTA, 5 µL, 0.1 M) was added to a solution of 4 (0.05 mol, 0.56 mM) in phosphate buffered saline. After vortexing for 1 minute, compound 3 from Example XI (84 µL, 0.9 M) and ascorbic acid (2 µL, 0.5 M) were added to the mixture and the solution was vortexed again for 1 minute. The solution was then mixed using an orbital shaker at room temperature for a period of 2 hours. The inhibitor was then desalted utilizing ultracentrifugation cartridges (Sartorius, 2000 MWCO) and molecular weight of the inhibitor was verified with MALDI (Applied Biosystems).

4

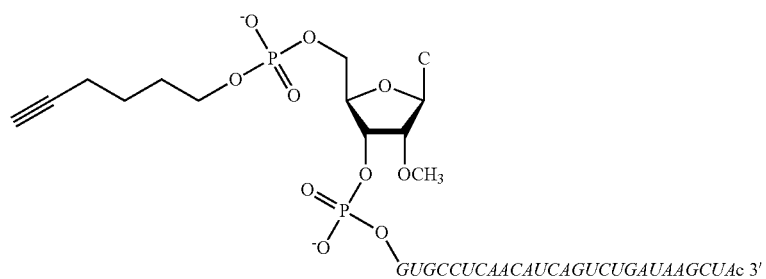

GUGCCUCAACAUCAGUCUGAUAAGCUAc 3' miRNA Inhibitor SEQ ID NO:154. CuSO$_4$ (10 µL, 0.1 M), butanone (20 µL), and Tris[(1-benzyl-1H-1,2,3-triazol-

30

(SEQ ID NO: 154)

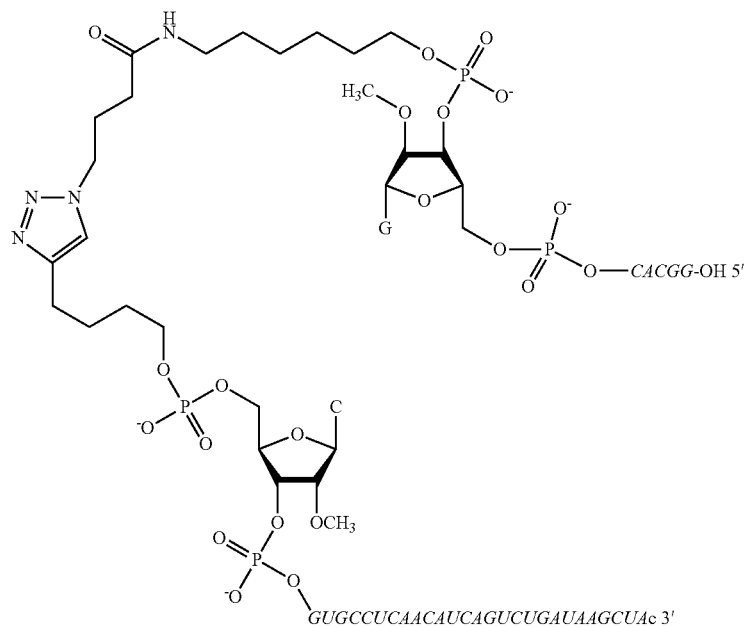

GUGCCUCAACAUCAGUCUGAUAAGCUAc 3'

Example 13

Effect of Loop Length on the Activity of the
Hairpin Inhibitors

Figure 16:
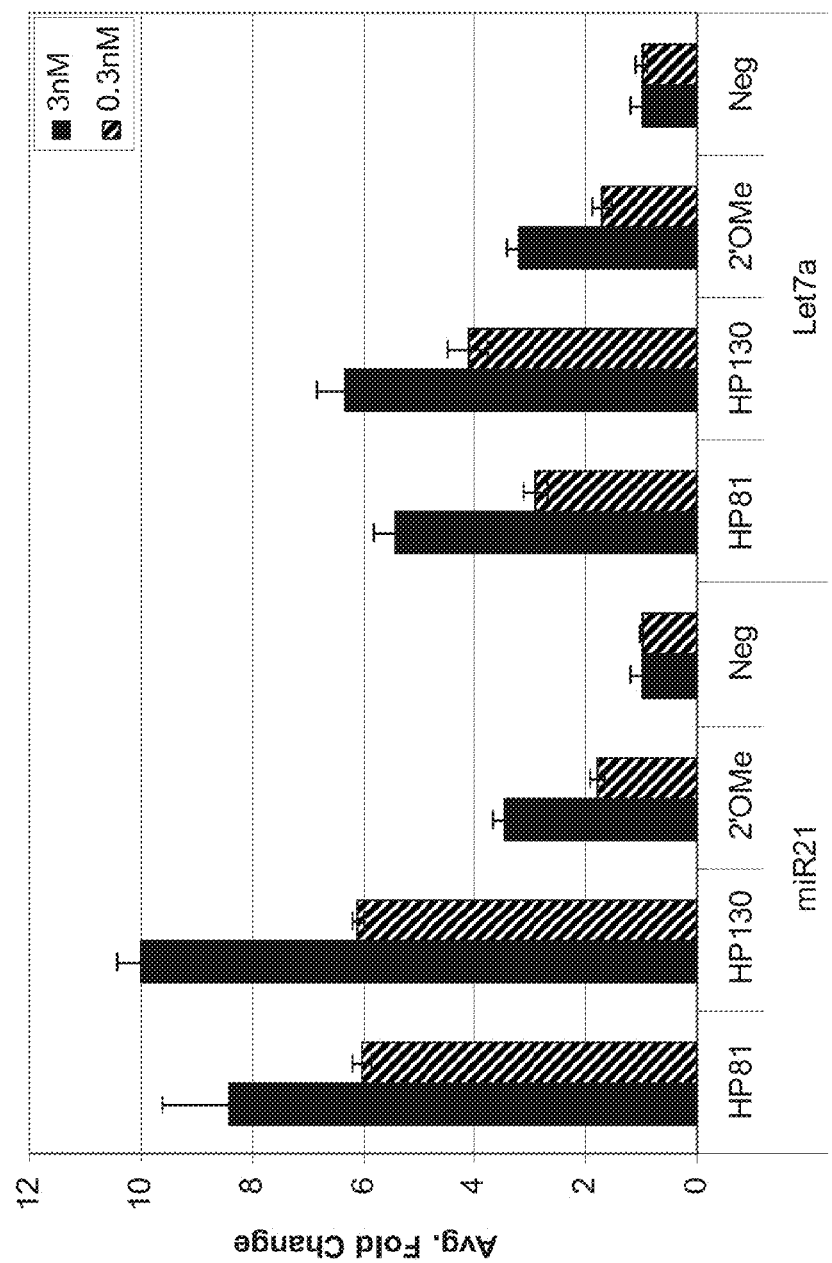
FIG. 16 shows data derived from the Example 13 experiment in which the potency of the hairpin inhibitors with a PEG6 vs a PEG5 loop was evaluated using the pMIR-REPORT™ miRNA expression reporter (miR21 or let7a target cloned), along with a 22 nt miRNA inhibitor with complete 2'-OMe modification (2'-OMe) control. The expression induced by miRNA inhibition is the Average fold change and is calculated in the following way: (fLuc activity anti-miR/βGal activity anti-miR)/(fLuc activity negative/βGal activity negative). Note: the higher the bars—the stronger the miRNA inhibition. The concentration of miRNA inhibitors upon transfection: 0.3 and 3 nM. All experiments were performed in triplicate.

Additional hairpin inhibitors with PEG5 loops and 6 bp stems were prepared similarly to those described in Example 1 and assayed using the same in vitro reporter system to investigate the effect of the loop length on the inhibitor potency. The efficiency of the hairpin inhibitors HP#130 (PEG5) was evaluated side by side with HP#81 (PEG6), using the pMIR-REPORT™ miRNA expression reporter (miR21 or let7a target cloned), along with a positive control—a 22 nt miRNA inhibitor with complete 2'-OMe modification (2'-OMe), and a negative control. The formats of the HP#130 and HP#81 inhibitors are depicted in FIG. 1. Note that the only difference was the length of their non-nucleotide loop. Thus, the sequence of HP#130 is the same as that of HP#81. In FIG. 16, the expression induced by miRNA inhibition was the Average fold change and was calculated in the following way: (fLuc activity anti-miR/βGal activity anti-miR)/(fLuc activity negative/βGal activity negative). Note: the higher the bars—the stronger miRNA inhibition. The concentration of the miRNA inhibitors upon transfection was 0.3 and 3 nM and all experiments were performed in triplicate.

The results in FIG. 16 indicated that microRNA inhibitors with PEG6 and PEG5 loops displayed about the same in vitro activity for miR21 and let7a targets, and both were superior to the standard antisense inhibitor without the stem-loop structure.

TABLE 3

Sequences in FIGs. 16-20

| FIG. | SEQ ID NO: | loop position | HR I | Linker (L-1) | HR II | HR III | Linker (L2) | HR IV | Target | Complementary sequence |
|---|---|---|---|---|---|---|---|---|---|---|
| 16 | 089 HP81 | 5' | GGCAC G | L3 | CGUGC C | na | na | na | mir 21 | SEQ ID NO: 003 |
| 16 | 139 HP130 | 5' | GGCAC G | L12 | CGUGC C | na | na | na | mir 21 | SEQ ID NO: 003 |
| 16 | 031 2'OMe | none | na | na | na | na | na | na | mir 21 | UCAACAUCAGUCUGAUAAGCUAN (SEQ ID NO: 31) |
| 16 | 064 Neg | | | | | | | | neg | AAGUGGAUAUUGUUGCCAUCAN (SEQ ID NO: 64) |
| 16 | 134 HP81 | 5' | GGCAC G | L3 | CGUGC C | na | na | na | let7a | SEQ ID NO: 007 |
| 16 | 140 HP130 | 5' | GGCAC G | L12 | CGUGC C | na | na | na | let7a | SEQ ID NO: 007 |
| 16 | 097 2'OMe | none | na | na | na | na | na | na | let7a | AACUAUACAACCUACUACCUCAN (SEQ ID NO: 97) |
| 16 | 064 Neg | | | | | | | | neg | AAGUGGAUAUUGUUGCCAUCAN (SEQ ID NO: 64) |
| 17 | 141 HP130 | 5' | GGCAC G | L12 | CGUGC C | na | na | na | mir122 | SEQ ID NO: 012 |
| 17 | 064 Neg | | | | | | | | neg | AAGUGGAUAUUGUUGCCAUCAN (SEQ ID NO: 64) |
| 18 | umod | | | | | | | | | |

TABLE 3-continued

Sequences in FIGs 16-20

| FIG. | SEQ ID NO: | loop position | HR I | Linker (L-1) | HR II | HR III | Linker (L2) | HR IV | Target | Complementary sequence |
|---|---|---|---|---|---|---|---|---|---|---|
| 18 | 031 | 2'OMe | none | na | na | na | na | na | mir 21 | UCAACAUCAGUCUGAUAAGCUAN (SEQ ID NO: 31) |
| 18 | 089 | HP81 | 5' | GGCACG | CGUGCC | na | L3 | na | mir 21 | SEQ ID NO: 003 |
| 18 | 091 | HP83 | 3' | na | na | UCCGUGC | L3 | GCACGg | mir 21 | SEQ ID NO: 001 |
| 18 | | Y umod | | | | | | | | mir 21 | SEQ ID NO: 003 |
| 18 | 041 | 2'OMe | none | na | na | na | na | na | let7c | AACCAUACAACCUACUACCCUCAN (SEQ ID NO: 41) |
| 18 | 100 | HP81 | 5' | GGCACG | L3 | CGUGCC | na | na | let7c | SEQ ID NO: 006 |
| 18 | 102 | HP83 | 3' | na | na | UCCGUGC | L3 | GCACGg | let7c | SEQ ID NO: 004 |
| 18 | | Y | | | | | | | | let7c | SEQ ID NO: 003 |
| 19 | 089 | HP81 | 5' | GGCACG | L3 | CGUGCC | na | na | mir 21 | SEQ ID NO: 003 |
| 19 | 064 | Neg | | | | | | | | neg | AAGUGGAUAUUGUUGCCAUCAN (SEQ ID NO: 64) |
| 19 | 134 | HP81 | 5' | GGCACG | L3 | CGUGCC | na | na | let7a | SEQ ID NO: 007 |
| 19 | 064 | Neg | | | | | | | | neg | AAGUGGAUAUUGUUGCCAUCAN (SEQ ID NO: 64) |

TABLE 3-continued

Sequences in FIGs 16-20

| FIG. | SEQ ID NO: | loop position | HR I | Linker (L-1) | HR II | HR III | Linker (L2) | HR IV | Target | Complementary sequence |
|---|---|---|---|---|---|---|---|---|---|---|
| 20 | 142 HP81 | 5' | GGCAC G | L3 | CGUGC C | na | na | na | mir 23a | GGAAUCCCUGGCAAUGUGAUc (SEQ ID NO: 156) |
| 20 | X | | | | | | | | | |
| 20 | 064 Neg | | | | | | | | | AAGUGGAUAUUGUUGCCAUCAN (SEQ ID NO: 64) |
| 20 | 089 HP81 | 5' | GGCAC G | L3 | CGUGC C | na | na | na | mir 21 | SEQ ID NO: 003 |
| 20 | X | | | | | | | | | |
| 20 | 064 Neg | | | | | | | | | AAGUGGAUAUUGUUGCCAUCAN (SEQ ID NO: 64) |
| 21 | 143 2'Ome | | | | | | | | mir122 | ACAAACACCAUUGUCACACUCCAN (SEQ ID NO: 157) |
| 21 | 144 HP81 | 5' | GGCAC G | L3 | CGUGC C | na | na | na | mir122 | SEQ ID NO: 012 |
| 21 | 145 Antago mir | | | | | | | | mir122 | ACAAACACCAUUGUCACACUCCA-Chol (SEQ ID NO: 162) |
| 21 | 064 Neg | | | | | | | | neg | AAGUGGAUAUUGUUGCCAUCAN (SEQ ID NO: 64) |
| 23 | 146 HP115 | 5' | GGCAC G | L3 | CGUGC C | na | na | na | mir122 | ACAAACACCAUUGUCACACUCCA-Chol (SEQ ID NO: 162) |

Example 14

Evaluation of the Potency of HP#130 (PEG5) Inhibitor

Figure 17:
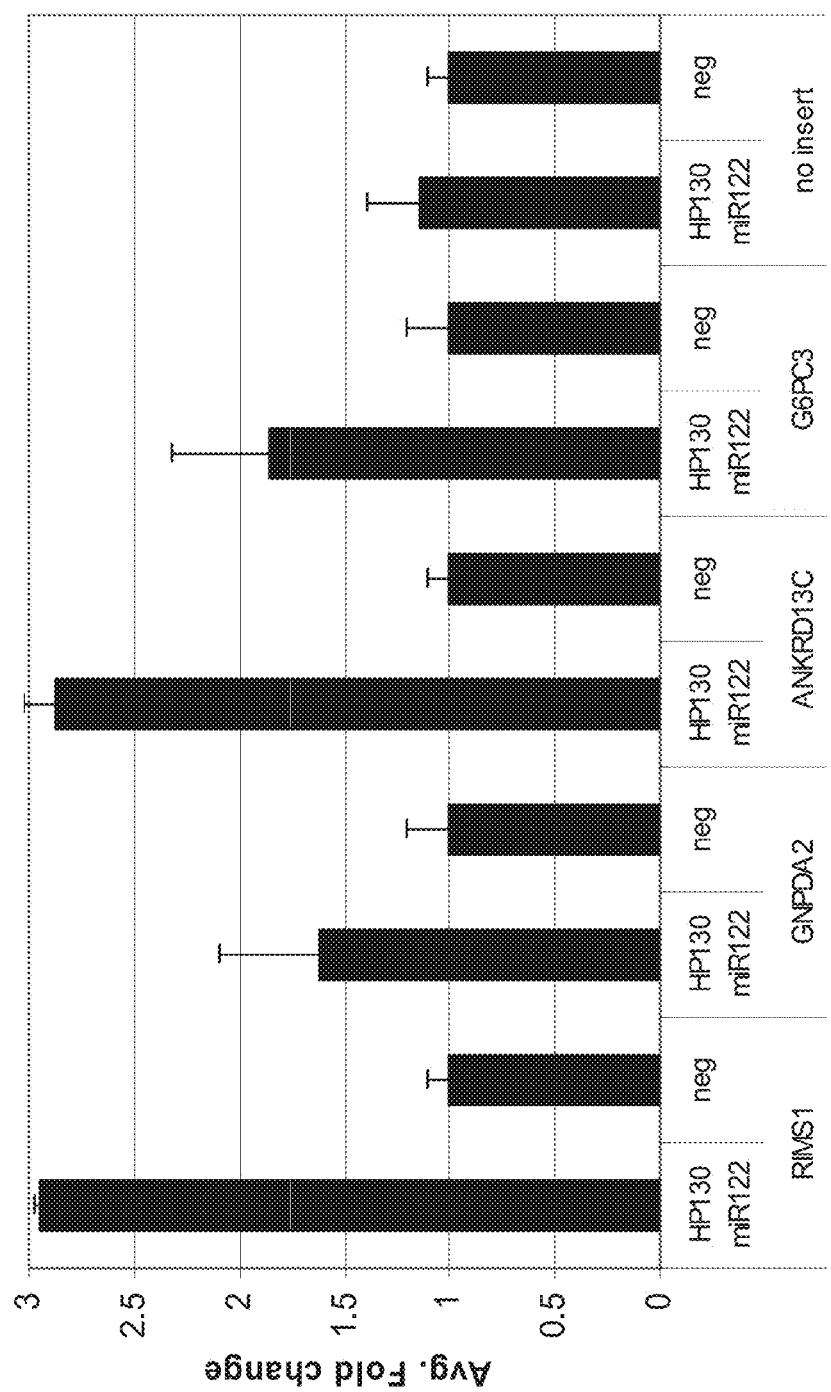
FIG. 17 shows data derived from the Example 14 experiment in which the potency of miR122-targeting HP#130 inhibitor (with a PEG5 loop) was evaluated in the exogenous assays. Four constructs were used with cloned natural targets for miR122—RIMS1, GNPDA2, ANKRD13C, and G6PC3 fragments. The expression induced by miRNA inhibition is the Average Fold change and is calculated in the following way: (fLuc activity anti-miR/βGal activity anti-miR)/(fLuc activity negative/βGal activity negative). The concentration of miRNA inhibitors upon transfection: 3 nM. All experiments were performed in triplicate.

The potency of the miR122-targeting HP#130 inhibitor with the PEG5 loop was evaluated in exogenous assays. The assays were similar to those described in Example 1. The only difference was that for miR 122, four constructs were used with cloned natural targets for miR122-RIMS1, GNPDA2, ANKRD13C, and G6PC3 fragments; in the above-described Examples #1-13, all in vitro reporters contained the cloned miRNA binding site fully complementary to the miRNA of interest. The HP#130 inhibitors were co-transfected with these constructs, and 24 h later the Luciferase signal was measured versus a negative control-enabling the determination of the potency of the inhibitors towards these four targets. The results are shown in FIG. 17. In the figure, the expression induced by miRNA inhibition was the Average Fold change and was calculated in the following way: (fLuc activity anti-miR/βGal activity anti-miR)/(fLuc activity negative/βGal activity negative). The concentration of miRNA inhibitors upon transfection was 3 nM. All experiments were performed in triplicate. The results in FIG. 17 indicated that the miR122 inhibitor was active on all four natural miR122 targets, displaying 1.5-3 fold upregulation.

Example 15

Detection of the HP#81 Hairpin Inhibitor with Small RNA TAQMAN® Assays

For in vitro and in vivo experiments, understanding the efficiency of miRNA inhibitor intracellular delivery, localization and distribution, helps to unravel the pathways and kinetics of the process. Small RNA TAQMAN® assays (Applied Biosystems/Life Technologies) enable accurate and robust quantification of small RNA molecules, including miRNA inhibitors. The purpose of this example was to explore whether chemical modifications and the 5'-hairpin structure would negatively impact the detection of these molecules. HP#81 inhibitors (with 5'-stem/loop and complete 2'-OMe modifications) were compared to the unmodified antisense oligonucleotides, antisense oligonucleotides with complete 2'-OMe modification, inhibitors with 3'-stem/loop and complete 2'-OMe modifications, and miRNA inhibitor Y (Dharmacon) featuring both 3'- and 5'-terminal loops and complete 2'-OMe modifications. The miRNA inhibitors in the above listed formats were synthesized for miR21 and let7c, and detected with TAQMAN® assays in a cell-free system.

The assay for quantification of miRNA inhibitors consisted of two steps: reverse transcription (RT) and PCR. The RT primer from TAQMAN® MicroRNA Assays features a stem-loop design (Applied Biosystems Inc., Foster City, Calif.). A typical 10 µL RT reaction included 0.5 pmol of miRNA inhibitor and 50 nM of RT primer. The anti-miR and stem loop primer mixture was heat denatured, incubated at 85° C. for 5 min, 60° C. for 5 min, and transferred to ice. After adding the enzyme mix (at final concentrations, 0.25 mM of each dNTP, 3.33 units/µL of MultiScribe™ reverse transcriptase, 1×RT buffer, 0.25 units/µL of RNase inhibitor), the reaction mixture was incubated at 16° C. for 30 minutes, 42° C. for 30 minutes, 85° C. for 5 minutes, and then 4° C. Real-time PCR was performed using a standard TAQMAN® PCR protocol on an Applied Biosystems 7900HT Sequence Detection System. The 10 µL PCR reaction mixture included 1 µL RT product, 1× TAQMAN® Universal PCR Master Mix, 0.2 µM TAQMAN® probe, 1.5 µM forward primer, and 0.7 µM reverse primer. The reaction was incubated at 95° C. for 10 minutes, followed by 40 cycles of 95° C. for 15 seconds and 60° C. for 1 minute.

Figure 18:
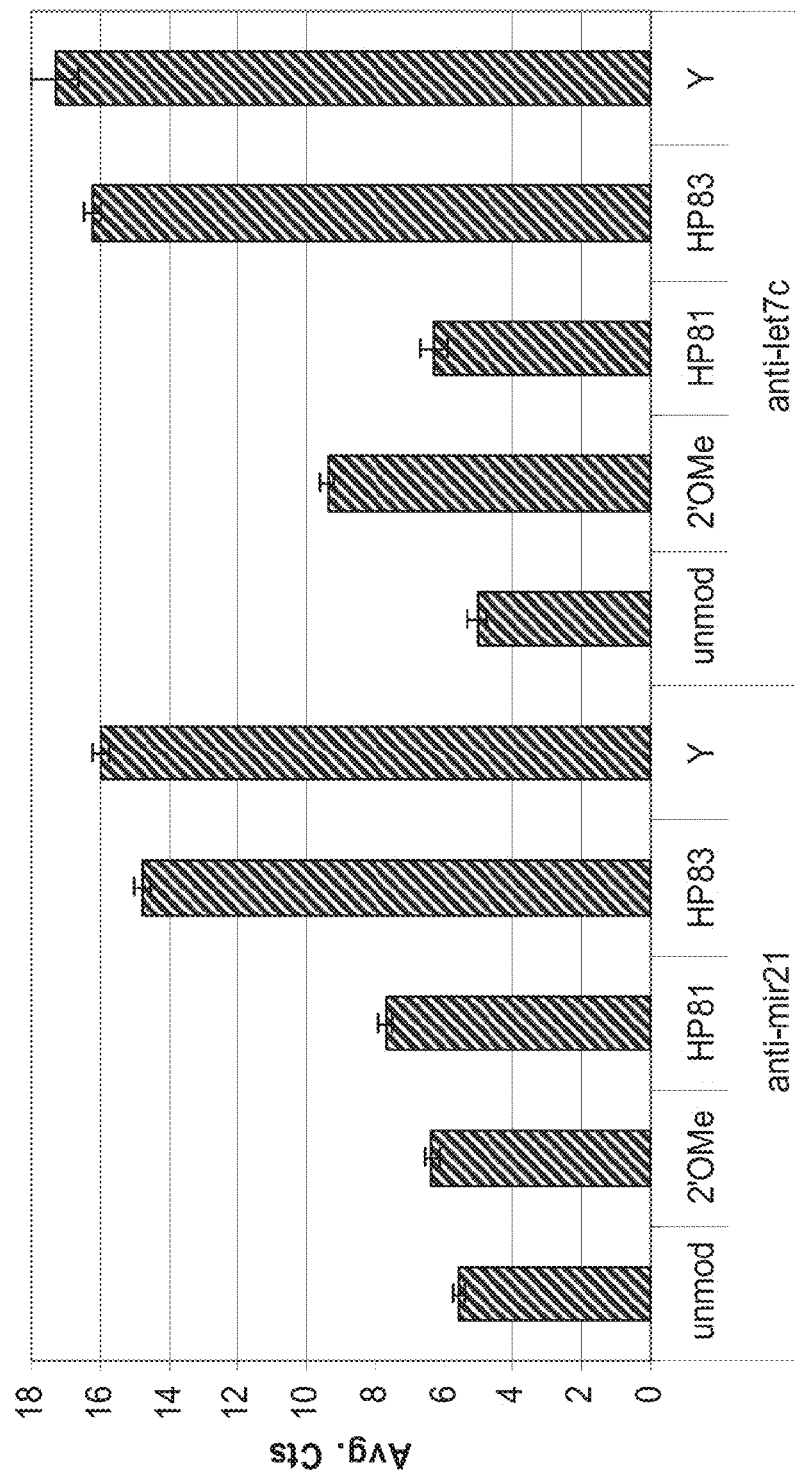
FIG. 18 shows data derived from the Example 15 experiment in which the detection of the hairpin inhibitors with Small RNA TAQMAN® assays was evaluated. HP#81 inhibitors (with 5'-stem/loop and 2'-OMe modifications) were compared to the unmodified antisense oligonucleotides (unmod), antisense oligonucleotides with complete 2'-OMe modification (2'OMe), inhibitors with 3'-stem/loop and complete 2'-OMe modifications (HP#83), and miRNA inhibitor Y (Dharmacon) featuring both 3'- and 5'-terminal loops and complete 2'-OMe modifications. The miRNA inhibitors in the above listed formats were synthesized for miR21 and let7c, and detected with Small RNA TAQMAN® assays in the cell-free system, in triplicates.

The results are shown in FIG. 18. As expected, the unmodified antisense oligonucleotides were detected most efficiently (as indicated by lowest Ct values). Antisense oligonucleotides with complete 2'-OMe modification were detected slightly less efficiently. HP#81 inhibitors (with 5'-stem/loop and complete 2'-OMe modifications) were also detected slightly less efficiently, with a Ct difference of <2 versus unmodified single-stranded RNA. Inhibitors with 3'-stem/loop and complete 2'-OMe modifications, and especially the miRNA inhibitor Y (Dharmacon) featuring both 3'- and 5'-terminal loops and complete 2'-OMe modifications were detected much less efficiently, presumably because the loop structure at the 3'-end interfered with RT primer binding and elongation. To summarize, HP#81 miRNA inhibitors were compatible with stem-loop RT primers and Small RNA TAQMAN® assays (LT) and thus could be easily traced and quantified in the in vitro and in vivo experiments.

Example 16

Specificity of the Hairpin Inhibitors

The specificity of the HP#81 inhibitors (with PEG6 loops and 6 bp stems) was studied. An inhibitor (HP#81 format, SEQ ID NO:89) for miR-21 was tested against its intended target, miR-21, as well as miR-31, let-7a, miR-106a, miR-23a, miR-19a, miR-17, and miR-24 targets. An inhibitor (HP#81 format, SEQ ID NO:134) for let-7a was tested against its intended target, let-7a, as well as miR-31, miR-21, miR-106a, miR-23a, miR-19a, miR-17, and miR-24 targets. The experimental conditions for these exogenous assays were similar to those described in Example 1.

Figure 19A:
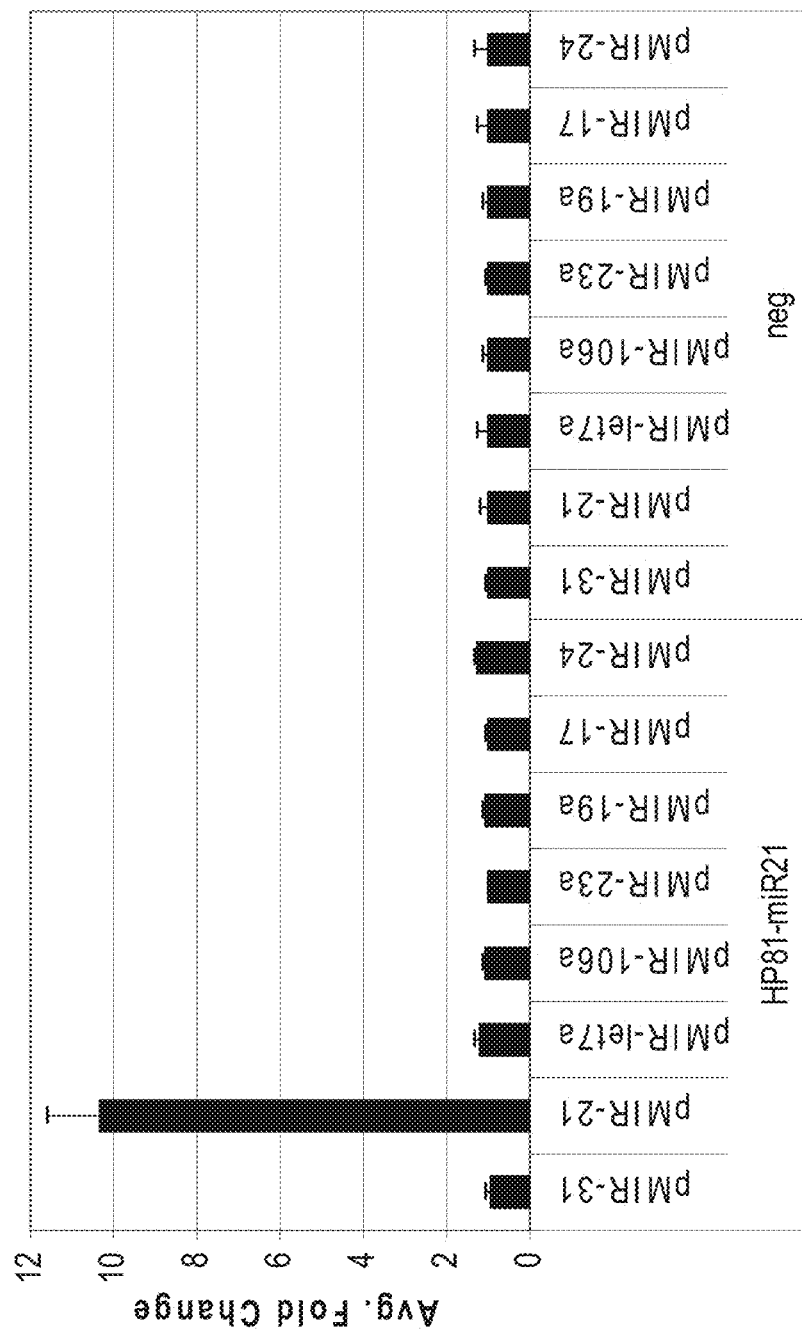
FIG. 19A and FIG. 19B show data derived from the Example 16 experiment in which the specificity of HP#81 inhibitors was studied in the exogenous assays. The inhibitor for miR-21 was tested against its intended target, miR-21, as well as miR-31, miR-let-7a, miR-106a, miR-23a, miR-19a, miR-17, and miR-24 targets. Inhibitor for let-7a was tested against its intended target, miR-let-7a, as well as miR-31, miR-21, miR-106a, miR-23a, miR-19a, miR-17, and miR-24 targets. The expression induced by miRNA inhibition is the Average Fold change and is calculated in the following way: (fLuc activity anti-miR/βGal activity anti-miR)/(fLuc activity negative/βGal activity negative). The concentration of miRNA inhibitors upon transfection: 3 nM. All experiments were performed in triplicate.
Figure 19:
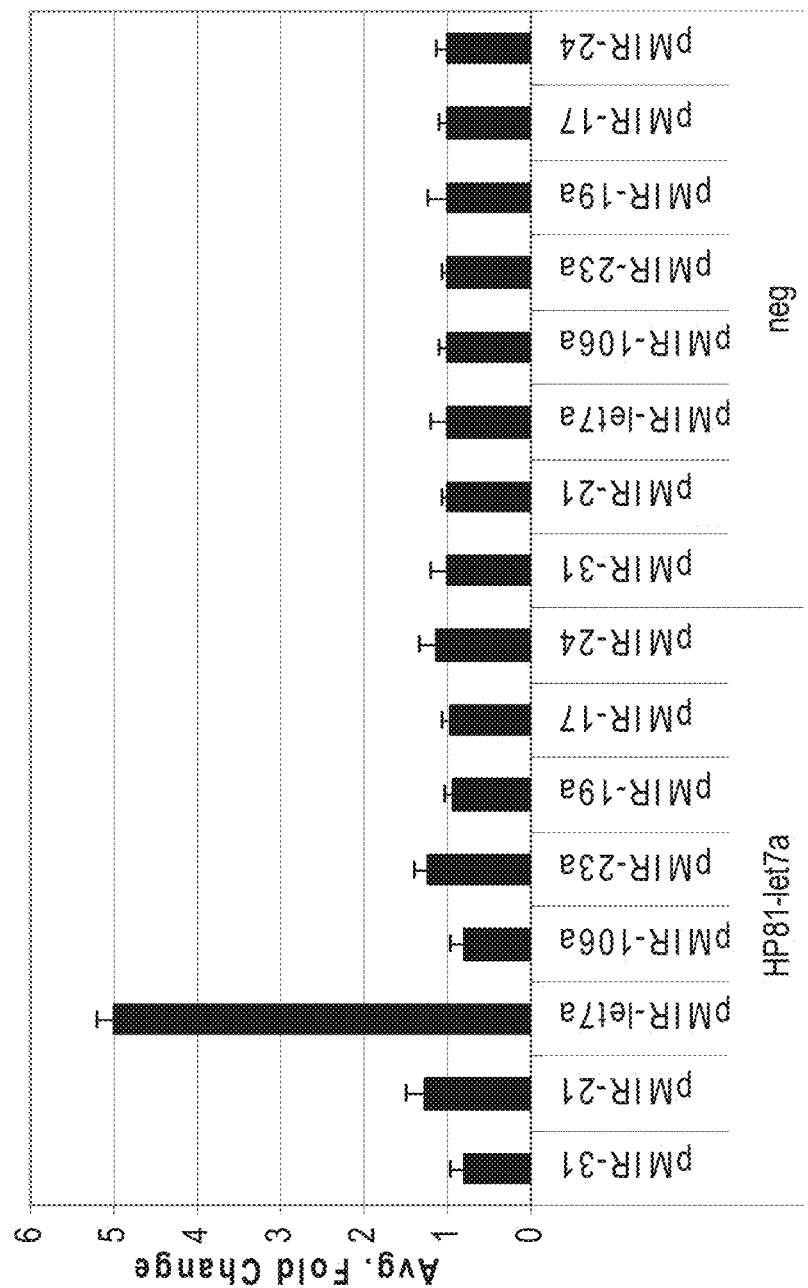

In FIG. 19A and FIG. 19B, the expression induced by miRNA inhibition was measured as the Average Fold change and was calculated in the following way: (fLuc activity anti-miR/βGal activity anti-miR)/(fLuc activity negative/βGal activity negative). The concentration of miRNA inhibitors upon transfection was 3 nM. All experiments were performed in triplicate. The results shown in FIG. 19A and FIG. 19B indicated the following: HP#81 microRNA inhibitors were specific to their intended target and did not affect the levels of the unrelated miRNA targets.

Example 17

Stability of the Hairpin Inhibitors

Long-term stability of the HP#81 inhibitors (with PEG6 loops and 6 bp stems) was evaluated. Water solutions (20 molar) of the inhibitors targeting miR-21 (SEQ ID NO:89) and miR-23a (SEQ ID NO:142) were stored at +4° C. for 1 week, 2 months and 1 year. Their potency was then evaluated side-by-side with miRNA inhibitor X (Exiqon) and negative control. The experimental conditions for these exogenous assays were similar to described in Example 1: miRNA inhibitors were co-transfected in HeLa cells with reporter constructs, and the Luciferase readout allowed determination of their potency towards endogenous miRNAs.

The expression induced by miRNA inhibition was the Average fold change and was calculated in the following way: (fLuc activity anti-miR/βGal activity anti-miR)/(fLuc activity negative/βGal activity negative). Note: the higher the bars—the stronger the miRNA inhibition. The concentration of miRNA inhibitors upon transfection: 0.3 and 3 nM. All experiments were performed in triplicate.

Figure 20A:
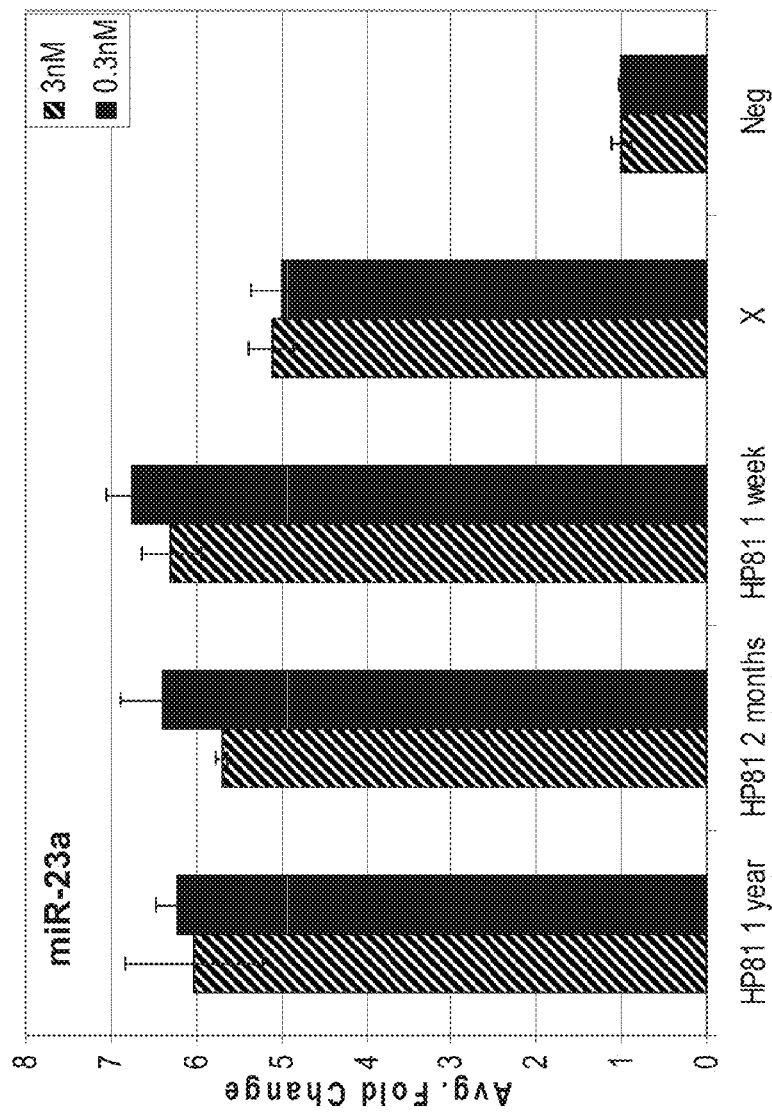
FIG. 20A and FIG. 20B show data derived from the Example 17 experiment in which the stability of the hairpin inhibitors HP#81 was studied. Water solutions (20 μmolar) of the inhibitors targeting miR-21 and miR-23a were stored at +4° C. for 1 week, 2 months and 1 year. Their potency was evaluated using the pMIR-REPORT™ miRNA expression reporter (miR21 or miR23a target cloned), along with miRNA inhibitor X (Exiqon).
Figure 20B:
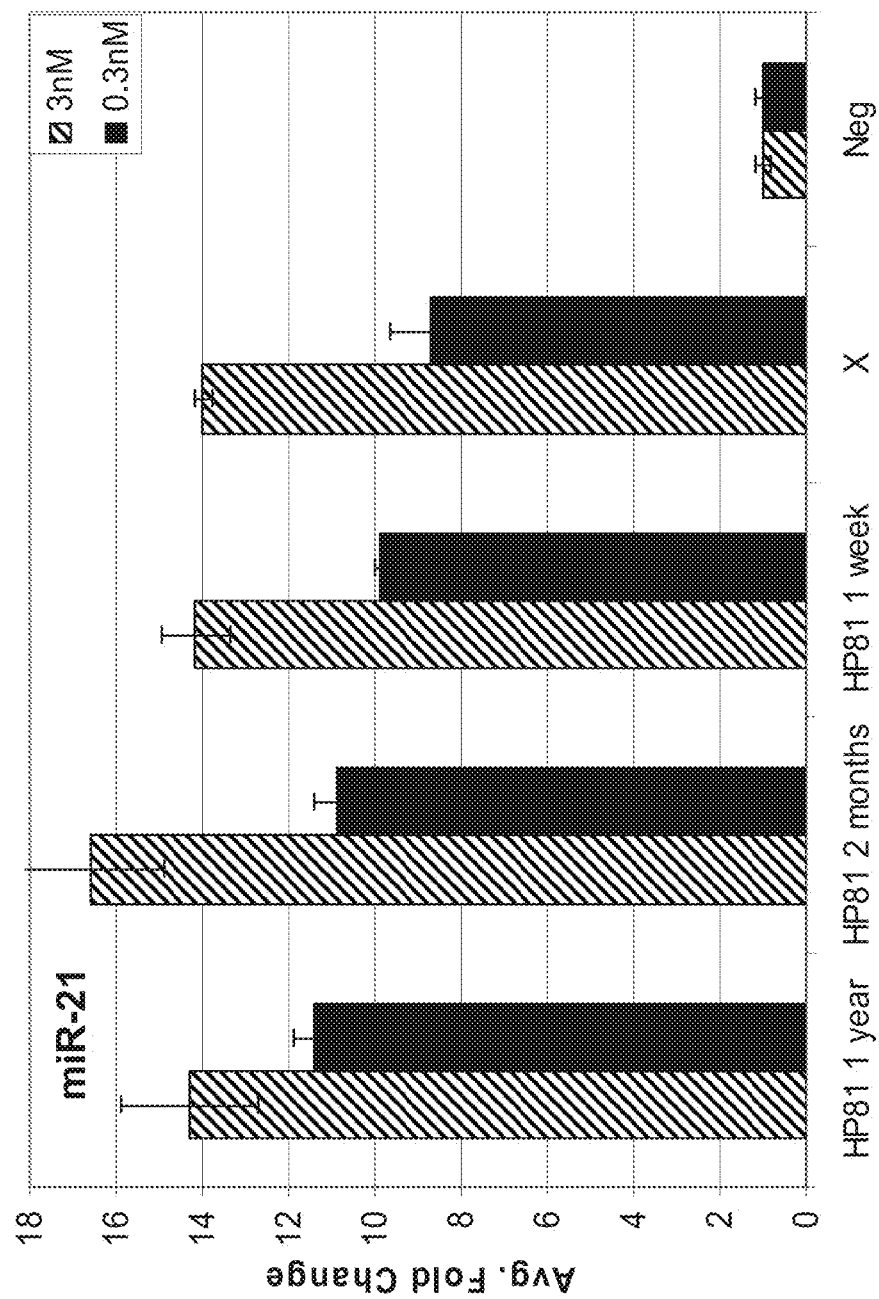

The results in FIG. 20A-FIG. 20B indicated that the HP#81 microRNA inhibitors were stable for prolonged periods of time, and there was no loss of potency after 1 year real-time storage of stock solutions in water, unfrozen, at +4° C.

Example 18

In Vivo Performance of the Hairpin Inhibitors

Hairpin inhibitor MiR122 was tested in vivo as follows: Mice (3 animals/group) were injected in the tail vein with 5 mg/kg HP#81 anti-miR122 (without p=s modifications) complexed with INVIVOFECTAMINE® 2.0 reagent (Life Technologies) according to the manufacturer's protocol, on 3 subsequent days, and sacrificed 24 h post 3rd injection.

The 2nd group of mice was similarly treated with single-stranded 2'-OMe miRNA inhibitors complexed with INVIVOFECTAMINE® 2.0 reagent.

The 3rd group of mice was injected with miR122 antagomirs (Krutzfeldt J. et al., *Nucl. Acids Res.* 2007 v. 35, p. 2885-2892) at 50 mg/kg, given three daily injections. MiR122 antagomirs were self-deliverable chemically modified siRNAs conjugated to cholesterol, and they were injected without any delivery reagent.

The 4th group of mice was a negative control and the mice were injected with negative control (non-targeting) miRNA inhibitor, complexed with INVIVOFECTAMINE® 2.0 reagent.

The 5th group of mice was the untreated group (normal uninjected animals). All experiments were performed with 3 animals per group. After the animals were sacrificed, levels of AldoA, Hfe2, Slc35a4, Lass6 mRNAs (reported targets for miR-122: see Elmén et al, 2008 *Nucl. Acids Res.* v. 36, p. 1153-1162; and Davis et al, *Nucl. Acids Res.* 2009 v. 37, p. 70-77) in the livers were quantified by qRT-PCR. mRNA upregulation was normalized to the negative control oligo-injected mice (=100%).

Figure 21:
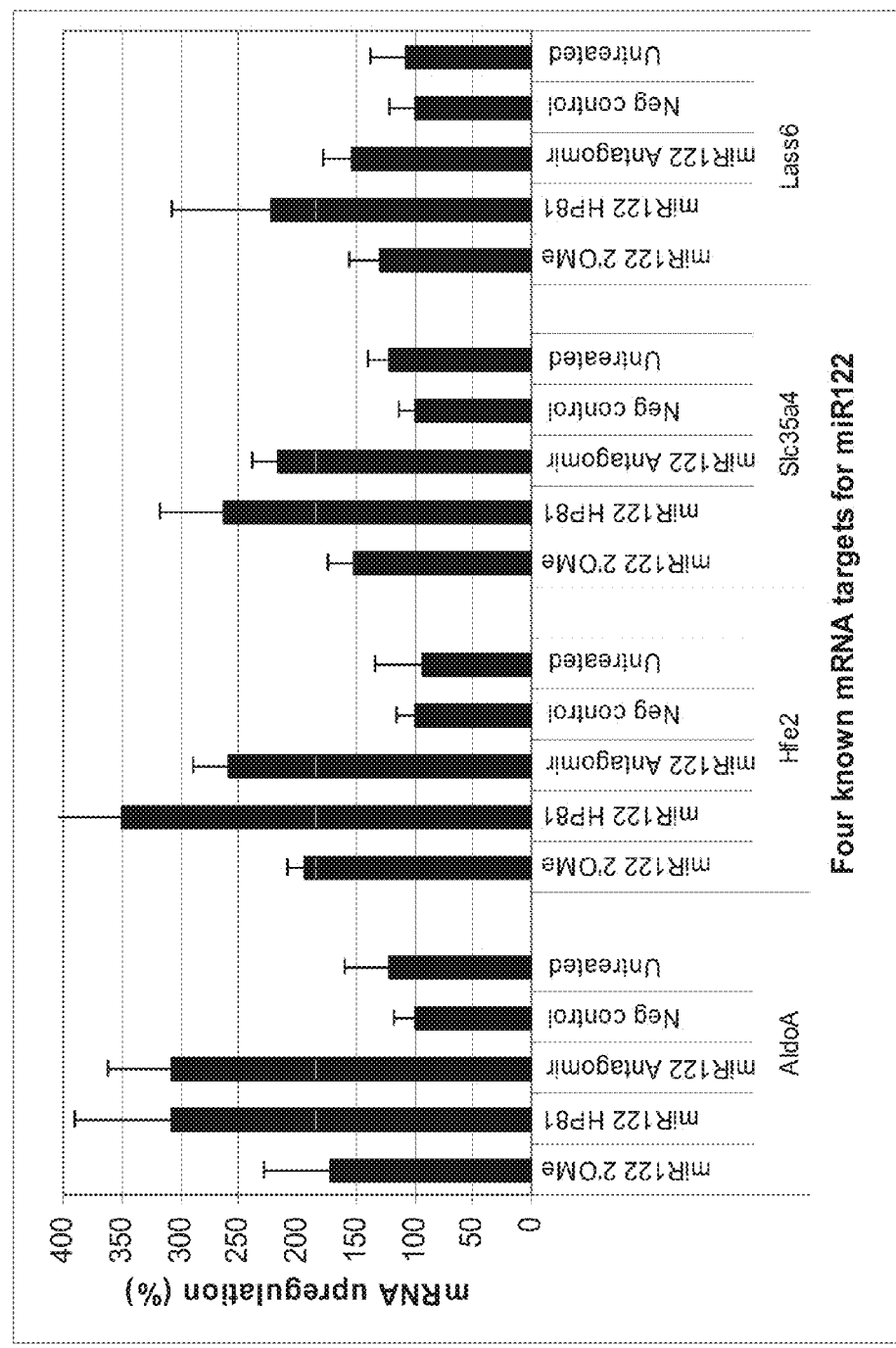
FIG. 21 shows data derived from the Example 18 experiment in which the derepression (upregulation) of miR-122 target genes AldoA, Hfe2, Slc35a4, and Lass6 after miR-122 inhibition in mice livers was achieved with the antisense oligonucleotides. Three daily injections of 5 mg/kg of HP#81 and 2'-OMe miRNA inhibitors were used, complexed with INVIVOFECTAMINE® 2.0 reagent. A separate group of mice was injected with miR122 antagomirs at 50 mg/kg, given in three daily injections. The negative control was mice injected with a negative control (non-targeting) miRNA inhibitor, complexed with INVIVOFECTAMINE® 2.0 Reagent. mRNA upregulation was normalized to the negative control oligo-injected mice (=100%). Untreated: normal uninjected animals. All experiments were performed with 3 animals per group.

The results in FIG. 21 showed the following: (1) miRNA inhibitors were efficiently delivered to the liver upon systemic tail vein administration with INVIVOFECTAMINE® 2.0 reagent and inhibited microRNA 122 as indicated by upregulation of four targets. (2) HP#81 inhibitors were superior to 2'-OMe antisense oligonucleotides. (3) HP#81 inhibitors delivered with INVIVOFECTAMINE® 2.0 reagent induced better miRNA inhibition compared to Antagomirs—despite the fact that antagomir conjugates were used at a 10-fold higher dose.

Example 19

In Vivo Performance of the Cholesterol-modified Hairpin Inhibitors

Figure 23:
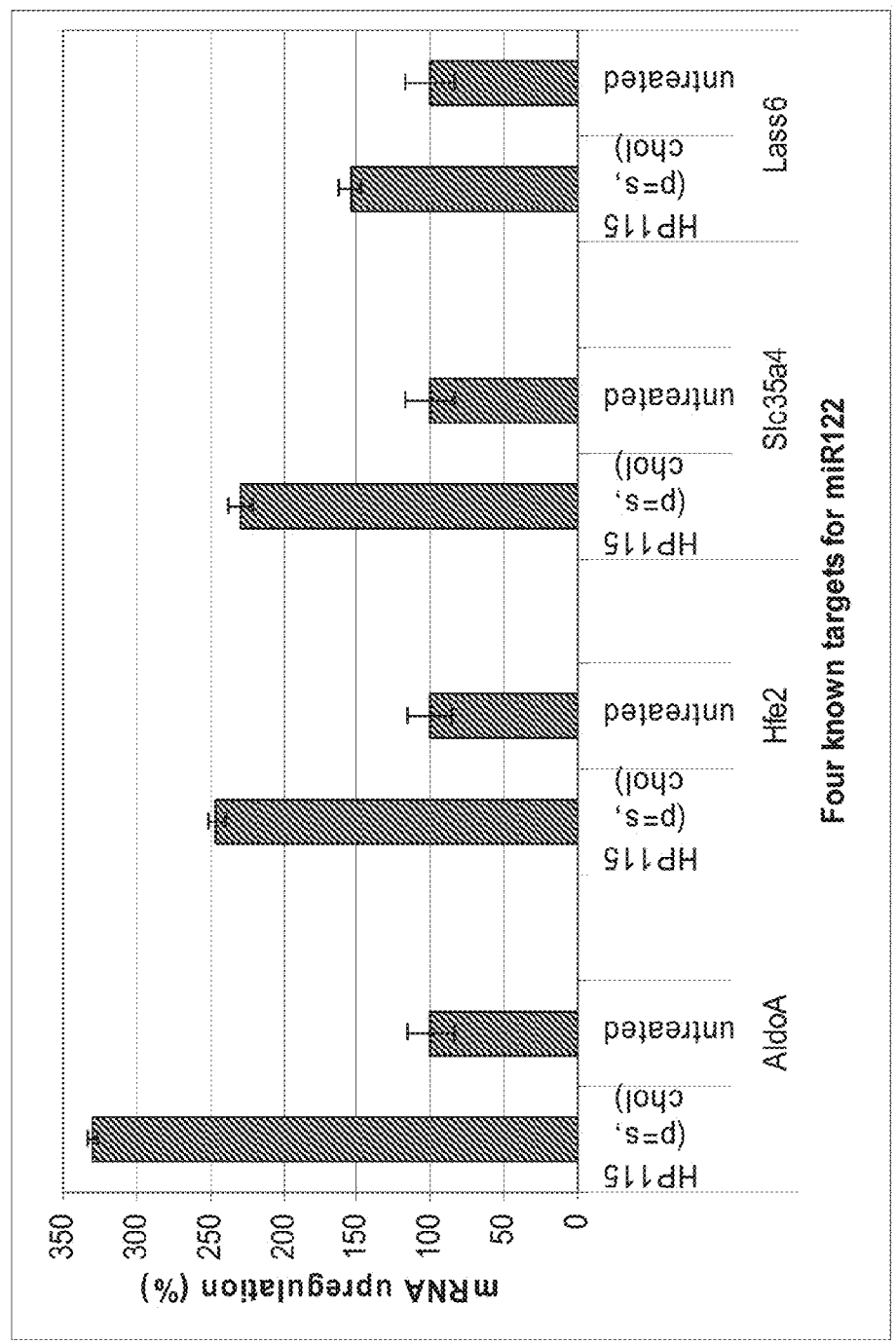
FIG. 23 shows data derived from the Example 17 experiment in which the derepression (upregulation) of miR-122 target genes AldoA, Hfe2, Slc35a4, and Lass6 was achieved after miR-122 inhibition in mice livers with the antisense oligonucleotides. Three daily injections of 50 mg/kg of HP#115 inhibitors were used. mRNA upregulation was normalized to the untreated mice (=100%). All experiments were performed with 3 animals per group.

Performance of the sterol-modified hairpin inhibitors for miR122 was evaluated in vivo. The format of miRNA inhibitor HP#115 (SEQ ID NO:146) is based on HP#81 but contains phosphorothioate modifications and is conjugated to cholesterol. Mice (3 animals/group) were injected in the tail vein with 50 mg/kg anti-miR122 HP#115 (without any delivery reagent), on 3 subsequent days, and sacrificed 24 h post 3rd injection. Levels of AldoA, Hfe2, Slc35a4, Lass6 mRNAs (four reported targets for miR-122: Elmén et al, 2008 *Nucl. Acids Res.* v. 36, p. 1153-1162; Davis et al, *Nucl. Acids Res.* 2009 v. 37, p. 70-77) in their livers were quantified by qRT-PCR. Data were normalized to untreated mice. The results in FIG. 23 showed the following: (1) miRNA inhibitors with cholesterol and limited phosphorothioate modifications could be used in in vivo experiments, and they induced robust inhibition of their targets in the liver, upon systemic tail vein administration, in the absence of any delivery reagents. Thus, the miRNA inhibitors showed the ability for self-delivery. In Example 20, the miRNA inhibitor-sterol conjugates are used for in vitro applications without delivery agents.

Example 20

In Vitro Use of miRNA Inhibitor-sterol Conjugates

Sterol conjugates of the miRNA inhibitors, such as HP#81 with limited phosphorothioate modifications and conjugated to cholesterol or any other sterol can have cell-penetrating properties, i.e. they can be used for in vitro experiments without delivery (transfection) reagents. Such sterol conjugates are used at 1 nanoMolar-10 microMolar concentrations, and, after incubation with the cells of interest, the amount of the oligonucleotide inside the cells is measured with Small RNA TAQMAN® assays (Cheng et al. (2009) Stem-loop RT-PCR quantification of siRNAs in vitro and in vivo. *Oligonucleotides,* 19, 203-208) and biological effects such as upregulation of the mRNA targets—are measured by qRT-PCR at 24-72 h post-transfection. Cells are typically maintained in the appropriate growth media containing up to 10% FBS, at 37° C., and depending on the cell type, the density is usually between about 1000-30,000 cells per well of a 96 well plate.

TABLE 1C

| FIG. | Seq ID | | loop position | HR I | Linker (L-1) | HR II | HR III | Linker (L2) | HR IV | Target | Complementary sequence |
|---|---|---|---|---|---|---|---|---|---|---|---|
| 3A | SEQ ID NO: 22 | HP01 | 5' and 3' | GCUG | AUCU | CAGC | GCUG | AUCU | CAGc | mir 21 | SEQ ID NO: 1 |
| 3A | SEQ ID NO: 23 | HP02 | 5' and 3' | GCUG | L1 | CAGC | GCUG | L1 | CAGc | mir 21 | SEQ ID NO: 1 |
| 3A | SEQ ID NO: 24 | HP03 | 5' and 3' | GCUG | L1 | CAGC | GCUG | L1 | CAGc | mir 21 | SEQ ID NO: 2 |
| 3A | SEQ ID NO: 25 | HP04 | 5' | GCUG | AUCU | CAGC | na | na | na | mir 21 | SEQ ID NO: 3 |
| 3A | SEQ ID NO: 26 | HP05 | 5' | GCUG | L1 | CAGC | na | na | na | mir 21 | SEQ ID NO: 3 |
| 3A | SEQ ID NO: 27 | HP06 | 5' | GCUG | L1 | CAGC | na | na | na | mir 21 | SEQ ID NO: 3 |
| 3A | SEQ ID NO: 28 | HP07 | 3' | na | na | na | GCUG | AUCU | CAGc | mir 21 | SEQ ID NO: 1 |
| 3A | SEQ ID NO: 29 | HP08 | 3' | na | na | na | GCUG | L1 | CAGc | mir 21 | SEQ ID NO: 1 |
| 3A | SEQ ID NO: 30 | HP09 | 3' | na | na | na | GCUG | L1 | CAGc | mir 21 | SEQ ID NO: 2 |
| 3A | SEQ ID NO: 31 | 2'OMe | None | na | na | na | na | na | na | mir 21 | UCAACAUCAGUCCUGAUAAGCUAN (SEQ ID NO: 31) |
| 3B | SEQ ID NO: 32 | HP01 | 5' and 3' | GCUG | AUCU | CAGC | GCUG | AUCU | CAGc | let7c | SEQ ID NO: 4 |
| 3B | SEQ ID NO: 33 | HP02 | 5' and 3' | GCUG | L1 | CAGC | GCUG | L1 | CAGc | let7c | SEQ ID NO: 4 |
| 3B | SEQ ID NO: 34 | HP03 | 5' and 3' | GCUG | L1 | CAGC | GCUG | L1 | CAGc | let7c | SEQ ID NO: 5 |
| 3B | SEQ ID NO: 35 | HP04 | 5' | GCUG | AUCU | CAGC | na | na | na | let7c | SEQ ID NO: 6 |
| 3B | SEQ ID NO: 36 | HP05 | 5' | GCUG | L1 | CAGC | na | na | na | let7c | SEQ ID NO: 6 |
| 3B | SEQ ID NO: 37 | HP06 | 5' | GCUG | L1 | CAGC | na | na | na | let7c | SEQ ID NO: 6 |
| 3B | SEQ ID NO: 38 | HP07 | 3' | na | na | na | GCUG | AUCU | CAGc | let7c | SEQ ID NO: 4 |
| 3B | SEQ ID NO: 39 | HP08 | 3' | na | na | na | GCUG | L1 | CAGc | let7c | SEQ ID NO: 4 |
| 3B | SEQ ID NO: 40 | HP09 | 3' | na | na | na | GCUG | L1 | CAGc | let7c | SEQ ID NO: 5 |
| 3B | SEQ ID NO: 41 | 2'OMe | None | na | na | na | na | na | na | let7c | AACCAUACAACCUACUACCUCAN (SEQ ID NO: 41) |
| 4A | SEQ ID NO: 26 | HP05 | 5' | GCUC | L1 | CAGC | na | na | na | mir 21 | SEQ ID NO: 3 |
| 4A | SEQ ID NO: 29 | HP08 | 3' | na | na | na | GCUG | L1 | CAGc | mir 21 | SEQ ID NO: 1 |

TABLE 1C-continued

Inhibitor Formats and Modifications

| FIG. | Seq ID | | loop position | HR I | Linker (L-1) | HR II | HR III | Linker (L2) | HR IV | Target | Complementary sequence |
|---|---|---|---|---|---|---|---|---|---|---|---|
| 4A | SEQ ID NO: 42 | HP10 | 5' | GCG | L1 | CGC | na | na | na | mir 21 | SEQ ID NO: 3 |
| 4A | SEQ ID NO: 43 | HP11 | 5' | GCGUG | L1 | CACGC | na | na | na | mir 21 | SEQ ID NO: 3 |
| 4A | SEQ ID NO: 44 | HP12 | 5' | UGGC | L1 | CAGC | na | na | na | mir 21 | SEQ ID NO: 3 |
| 4A | SEQ ID NO: 45 | HP13 | 5' | GCUG | AUUCU | CAGC | na | na | na | mir 21 | SEQ ID NO: 3 |
| 4A | SEQ ID NO: 46 | HP14 | 3' | na | na | na | GCG | L1 | CGc | mir 21 | SEQ ID NO: 1 |
| 4A | SEQ ID NO: 47 | HP15 | 3' | na | na | na | GCGUG | L1 | CACGc | mir 21 | SEQ ID NO: 1 |
| 4A | SEQ ID NO: 48 | HP16 | 3' | na | na | na | UGGC | L1 | CAGc | mir 21 | SEQ ID NO: 1 |
| 4A | SEQ ID NO: 49 | HP17 | 3' | na | na | na | GCUG | AUUCU | CAGc | mir 21 | SEQ ID NO: 1 |
| 4A | SEQ ID NO: 50 | HP18 | 5' | GCUG | L2 | CAGC | na | na | na | mir 21 | SEQ ID NO: 3 |
| 4A | SEQ ID NO: 51 | HP19 | 5' | GCUG | L3 | CAGC | na | na | na | mir 21 | SEQ ID NO: 3 |
| 4A | SEQ ID NO: 52 | HP20 | 5' | GCUG | L4 | CAGC | na | na | na | mir 21 | SEQ ID NO: 3 |
| 4A | SEQ ID NO: 53 | HP21 | 5' | GCUG | L5 | CAGC | na | na | na | mir 21 | SEQ ID NO: 3 |
| 4A | SEQ ID NO: 54 | HP22 | 5' | GCUG | L6 | CAGC | na | na | na | mir 21 | SEQ ID NO: 3 |
| 4A | SEQ ID NO: 55 | HP23 | 5' | GCUG | L7 | CAGC | na | na | na | mir 21 | SEQ ID NO: 3 |
| 4A | SEQ ID NO: 56 | HP24 | 5' | GCUG | L8 | CAGC | na | na | na | mir 21 | SEQ ID NO: 3 |
| 4A | SEQ ID NO: 57 | HP25 | 3' | na | na | na | GCUG | L2 | CAGc | mir 21 | SEQ ID NO: 1 |
| 4A | SEQ ID NO: 58 | HP26 | 3' | na | na | na | GCUG | L3 | CAGc | mir 21 | SEQ ID NO: 1 |
| 4A | SEQ ID NO: 59 | HP27 | 3' | na | na | na | GCUG | L4 | CAGc | mir 21 | SEQ ID NO: 1 |
| 4A | SEQ ID NO: 60 | HP28 | 3' | na | na | na | GCUG | L5 | CAGc | mir 21 | SEQ ID NO: 1 |
| 4A | SEQ ID NO: 61 | HP29 | 3' | na | na | na | GCUG | L6 | CAGc | mir 21 | SEQ ID NO: 1 |
| 4A | SEQ ID NO: 62 | HP30 | 3' | na | na | na | GCUG | L7 | CAGc | mir 21 | SEQ ID NO: 1 |
| 4A | SEQ ID NO: 63 | HP31 | 3' | na | na | na | GCUG | L8 | CAGc | mir 21 | SEQ ID NO: 1 |
| 4A | SEQ ID NO: 31 | 2'OMe | None | na | na | na | na | na | na | mir 21 | UCAACAUCAGUCUGAUAAGCUAN (SEQ ID NO: 31) |

TABLE 1C-continued

| FIG. | Seq ID | loop position | HR I | Linker (L-1) | HR II | HR III | Linker (L2) | HR IV | Target | Complementary sequence |
|---|---|---|---|---|---|---|---|---|---|---|
| 4A | SEQ ID NO: 64 | Y | | | | | | | mir 21 | AAGUGAUAUUGUUGCCAUCAN (SEQ ID NO: 64) |
| 4A | | X | | | | | | | mir 21 | |
| 4A | SEQ ID NO: 64 | Neg | None | na | na | na | na | na | neg | |
| 4B | SEQ ID NO: 36 | HP05 | 5' | GCUC | CAGC | na | TEG | na | let7c | SEQ ID NO: 6 |
| 4B | SEQ ID NO: 39 | HP08 | 3' | na | na | GCUG | TEG | CAGc | let7c | SEQ ID NO: 4 |
| 4B | SEQ ID NO: 65 | HP10 | 5' | GCG | L1 | CGC | na | na | let7c | SEQ ID NO: 6 |
| 4B | SEQ ID NO: 66 | HP11 | 5' | GCGUG | L1 | CACGC | na | na | let7c | SEQ ID NO: 6 |
| 4B | SEQ ID NO: 67 | HP12 | 5' | UGGC | L1 | CAGC | na | na | let7c | SEQ ID NO: 6 |
| 4B | SEQ ID NO: 68 | HP13 | 5' | GCUG | AUUCU | CAGC | na | na | let7c | SEQ ID NO: 6 |
| 4B | SEQ ID NO: 69 | HP14 | 3' | na | na | GCG | na | CGc | let7c | SEQ ID NO: 4 |
| 4B | SEQ ID NO: 70 | HP15 | 3' | na | na | GCGUG | L1 | CACGc | let7c | SEQ ID NO: 4 |
| 4B | SEQ ID NO: 71 | HP16 | 3' | na | na | UGGC | L1 | CAGc | let7c | SEQ ID NO: 4 |
| 4B | SEQ ID NO: 72 | HP17 | 3' | na | na | GCUG | AUUCU | CAGc | let7c | SEQ ID NO: 4 |
| 4B | SEQ ID NO: 73 | HP18 | 5' | GCUG | L2 | CAGC | na | na | let7c | SEQ ID NO: 6 |
| 4B | SEQ ID NO: 74 | HP19 | 5' | GCUG | L3 | CAGC | na | na | let7c | SEQ ID NO: 6 |
| 4B | SEQ ID NO: 75 | HP20 | 5' | GCUG | L4 | CAGC | na | na | let7c | SEQ ID NO: 6 |
| 4B | SEQ ID NO: 76 | HP21 | 5' | GCUG | L5 | CAGC | na | na | let7c | SEQ ID NO: 6 |
| 4B | SEQ ID NO: 77 | HP22 | 5' | GCUG | L6 | CAGC | na | na | let7c | SEQ ID NO: 6 |
| 4B | SEQ ID NO: 78 | HP23 | 5' | GCUG | L7 | CAGC | na | na | let7c | SEQ ID NO: 6 |
| 4B | SEQ ID NO: 79 | HP24 | 5' | GCUG | L8 | CAGC | na | na | let7c | SEQ ID NO: 6 |
| 4B | SEQ ID NO: 80 | HP25 | 3' | na | na | GCUG | L2 | CAGc | let7c | SEQ ID NO: 4 |
| 4B | SEQ ID NO: 81 | HP26 | 3' | na | na | GCUG | L3 | CAGc | let7c | SEQ ID NO: 4 |
| 4B | SEQ ID NO: 82 | HP27 | 3' | na | na | GCUG | L4 | CAGc | let7c | SEQ ID NO: 4 |

TABLE 1C-continued

| FIG. | Seq ID | | loop position | HR I | Linker (L-1) | HR II | HR III | Linker (L2) | HR IV | Target | Complementary sequence |
|---|---|---|---|---|---|---|---|---|---|---|---|
| 4B | SEQ ID NO: 83 | HP28 | 3' | na | na | na | GCUG | L5 | CAGc | let7c | SEQ ID NO: 4 |
| 4B | SEQ ID NO: 84 | HP29 | 3' | na | na | na | GCUG | L6 | CAGc | let7c | SEQ ID NO: 4 |
| 4B | SEQ ID NO: 85 | HP30 | 3' | na | na | na | GCUG | L7 | CAGc | let7c | SEQ ID NO: 4 |
| 4B | SEQ ID NO: 86 | HP31 | 3' | na | na | na | GCUG | L8 | CAGc | let7c | SEQ ID NO: 4 |
| 4B | SEQ ID NO: 41 | 2'OMe | None | na | na | na | na | na | na | let7c | AACCAUACAACCUACUACCUCAN (SEQ ID NO: 41) |
| 4B | | Y | | | | | | | | let7c | |
| 4B | | X | | | | | | | | let7c | |
| 4B | SEQ ID NO: 64 | neg | None | na | na | na | na | na | na | neg | AAGUGGAUAUUGUUGCCAUCAN (SEQ ID NO: 64) |
| 5 | SEQ ID NO: 36 | HP05 | 5' | GCUC | TEG | CAGC | na | na | na | let7c | SEQ ID NO: 6 |
| 5 | SEQ ID NO: 39 | HP08 | 3' | na | na | na | GCUG | TEG | CAGc | let7c | SEQ ID NO: 4 |
| 5 | SEQ ID NO: 65 | HP10 | 5' | GCG | L1 | CGC | na | na | na | let7c | SEQ ID NO: 6 |
| 5 | SEQ ID NO: 66 | HP11 | 5' | GCGUG | L1 | CACGC | na | na | na | let7c | SEQ ID NO: 6 |
| 5 | SEQ ID NO: 67 | HP12 | 5' | UGGC | L1 | CAGC | na | na | na | let7c | SEQ ID NO: 6 |
| 5 | SEQ ID NO: 68 | HP13 | 5' | GCUG | AUUCU | CAGC | na | na | na | let7c | SEQ ID NO: 6 |
| 5 | SEQ ID NO: 69 | HP14 | 3' | na | na | na | GCG | L1 | CGc | let7c | SEQ ID NO: 4 |
| 5 | SEQ ID NO: 70 | HP15 | 3' | na | na | na | GCGUG | L1 | CACGc | let7c | SEQ ID NO: 4 |
| 5 | SEQ ID NO: 71 | HP16 | 3' | na | na | na | UGGC | L1 | CAGc | let7c | SEQ ID NO: 4 |
| 5 | SEQ ID NO: 72 | HP17 | 3' | na | na | na | GCUG | AUUCU | CAGc | let7c | SEQ ID NO: 4 |
| 5 | SEQ ID NO: 73 | HP18 | 5' | GCUG | L2 | CAGC | na | na | na | let7c | SEQ ID NO: 6 |
| 5 | SEQ ID NO: 74 | HP19 | 5' | GCUG | L3 | CAGC | na | na | na | let7c | SEQ ID NO: 6 |
| 5 | SEQ ID NO: 75 | HP20 | 5' | GCUG | L4 | CAGC | na | na | na | let7c | SEQ ID NO: 6 |
| 5 | SEQ ID NO: 76 | HP21 | 5' | GCUG | L5 | CAGC | na | na | na | let7c | SEQ ID NO: 6 |
| 5 | SEQ ID NO: 77 | HP22 | 5' | GCUG | L6 | CAGC | na | na | na | let7c | SEQ ID NO: 6 |

TABLE 1C-continued

Inhibitor Formats and Modifications

| FIG. | Seq ID | | loop position | HR I | Linker (L-1) | HR II | HR III | Linker (L2) | HR IV | Target | Complementary sequence |
|---|---|---|---|---|---|---|---|---|---|---|---|
| 5 | SEQ ID NO: 78 | HP23 | 5' | GCUG | L7 | CAGC | na | na | na | let7c | SEQ ID NO: 6 |
| 5 | SEQ ID NO: 79 | HP24 | 5' | GCUG | L8 | CAGC | na | na | na | let7c | SEQ ID NO: 6 |
| 5 | SEQ ID NO: 80 | HP25 | 3' | na | na | na | GCUG | L2 | CAGc | let7c | SEQ ID NO: 4 |
| 5 | SEQ ID NO: 81 | HP26 | 3' | na | na | na | GCUG | L3 | CAGc | let7c | SEQ ID NO: 4 |
| 5 | SEQ ID NO: 82 | HP27 | 3' | na | na | na | GCUG | L4 | CAGc | let7c | SEQ ID NO: 4 |
| 5 | SEQ ID NO: 83 | HP28 | 3' | na | na | na | GCUG | L5 | CAGc | let7c | SEQ ID NO: 4 |
| 5 | SEQ ID NO: 84 | HP29 | 3' | na | na | na | GCUG | L6 | CAGc | let7c | SEQ ID NO: 4 |
| 5 | SEQ ID NO: 85 | HP30 | 3' | na | na | na | GCUG | L7 | CAGc | let7c | SEQ ID NO: 4 |
| 5 | SEQ ID NO: 86 | HP31 | 3' | na | na | na | GCUG | L8 | CAGc | let7c | SEQ ID NO: 4 |
| 5 | SEQ ID NO: 41 | 2'OMe | None | na | na | na | na | na | na | let7c | AACCAUACAACCUACUACCCUCAN (SEQ ID NO: 41) |
| 5 | | Y | | | | | | | | let7c | |
| 5 | | X | | | | | | | | let7c | |
| 5 | SEQ ID NO: 32 | HP01 | 5' and 3' | GCUG | AUCU | CAGC | GCUG | AUCU | CAGc | let7c | SEQ ID NO: 4 |
| 5 | SEQ ID NO: 33 | HP02 | 5' and 3' | GCUG | TEG | CAGC | GCUG | AUCU | CAGc | let7c | SEQ ID NO: 4 |
| 5 | SEQ ID NO: 64 | neg | None | na | na | na | na | na | na | neg | AAGUGGAUAUUGUUGCCAUCAN (SEQ ID NO: 64) |
| 6A | SEQ ID NO: 41 | 2'OMe | None | na | na | na | na | na | na | let7c | AACCAUACAACCUACUACCCUCAN (SEQ ID NO: 41) |
| 6A | | Y | | | | | | | | let7c | |
| 6A | | X | | | | | | | | let7c | |
| 6A | SEQ ID NO: 79 | HP24 | 5' | GCUG | L8 | CAGC | na | na | na | let7c | SEQ ID NO: 6 |
| 6A | | NT | | | | | | | | neg | |
| 6A | SEQ ID NO: 64 | Neg | None | na | na | na | na | na | na | neg | AAGUGGAUAUUGUUGCCAUCAN (SEQ ID NO: 64) |

TABLE 1C-continued

| FIG. | Seq ID | loop position | HR I | Linker (L-1) | HR II | HR III | Linker (L2) | HR IV | Target | Complementary sequence |
|---|---|---|---|---|---|---|---|---|---|---|
| 6B | SEQ ID NO: 31 2'OMe | None | na | na | na | na | na | na | mir 21 | UCAACAUCAGUCUGAUAAGCUAN (SEQ ID NO:3 1) |
| 6B | Y | | | | | | | | mir 21 | |
| 6B | X | | | | | | | | mir 21 | |
| 6B | SEQ ID NO: 56 HP24 | 5' | GCUG | L8 | CAGC | na | na | na | mir 21 | SEQ ID NO: 3 |
| 6B | NT | | | | | | | | mir 21 | |
| 6B | SEQ ID NO: 64 Neg | None | na | na | na | na | na | na | neg | AAGUGGAUAUUGUUGCCAUCAN (SEQ ID NO: 64) |
| 7A | SEQ ID NO: 87 HP79 | 5' | GGCACG | L3 | CGUGCCAU | na | na | na | mir 21 | SEQ ID NO: 3 |
| 7A | SEQ ID NO: 88 HP80 | 5' | GGCACG | L3 | CGUGCCA | na | na | na | mir 21 | SEQ ID NO: 3 |
| 7A | SEQ ID NO: 89 HP81 | 5' | GGCACG | L3 | CGUGCC | na | na | na | mir 21 | SEQ ID NO: 3 |
| 7A | SEQ ID NO: 90 HP82 | 3' | na | na | na | UCCGUGC | L3 | GCACGGN | mir 21 | SEQ ID NO: 1 |
| 7A | SEQ ID NO: 91 HP83 | 3' | na | na | na | UCCGUGC | L3 | GCACGg | mir 21 | SEQ ID NO: 1 |
| 7A | SEQ ID NO: 31 2'OMe | None | na | na | na | na | na | na | mir 21 | UCAACAUCAGUCUGAUAAGCUAN (SEQ ID NO: 31) |
| 7A | Y | | | | | | | | mir 21 | |
| 7A | X | | | | | | | | mir 21 | |
| 7B | SEQ ID NO: 92 HP79 | 5' | GGCACG | L3 | CGUGCCAU | na | na | na | let7a | SEQ ID NO: 7 |
| 7B | SEQ ID NO: 93 HP80 | 5' | GGCACG | L3 | CGUGCCA | na | na | na | let7a | SEQ ID NO: 7 |
| 7B | SEQ ID NO: 94 HP81 | 5' | GGCACG | L3 | CGUGCC | na | na | na | let7a | SEQ ID NO: 7 |
| 7B | SEQ ID NO: 95 HP82 | 3' | na | na | na | UCCGUGC | L3 | GCACGGN | let7a | SEQ ID NO: 8 |
| 7B | SEQ ID NO: 96 HP83 | 3' | na | na | na | UCCGUGC | L3 | GCACGg | let7a | SEQ ID NO: 8 |
| 7B | SEQ ID NO: 97 2'OMe | None | na | na | na | na | na | na | let7a | AACUAUACAACCUACUACCCUCAN (SEQ ID NO: 97) |
| 7B | Y | | | | | | | | let7a | |
| 7B | X | | | | | | | | let7a | |

TABLE 1C-continued

| FIG. | Seq ID | | loop position | Inhibitor Formats and Modifications | | | | | | Target | Complementary sequence |
|---|---|---|---|---|---|---|---|---|---|---|---|
| | | | | HR I | Linker (L-1) | HR II | HR III | Linker (L2) | HR IV | | |
| 7C | SEQ ID NO: 98 | HP79 | 5' | GGCACG | L3 | CGUGCCAU | na | na | na | let7c | SEQ ID NO: 9 |
| 7C | SEQ ID NO: 99 | HP80 | 5' | GGCACG | L3 | CGUGCCA | na | na | na | let7c | SEQ ID NO: 9 |
| 7C | SEQ ID NO: 100 | HP81 | 5' | GGCACG | L3 | CGUGCC | na | na | na | let7c | SEQ ID NO: 9 |
| 7C | SEQ ID NO: 101 | HP82 | 3' | na | na | na | UCCGUGC | L3 | GCACGGN | let7c | SEQ ID NO: 4 |
| 7C | SEQ ID NO: 102 | HP83 | 3' | na | na | na | UCCCUGC | L3 | GCACGg | let7c | SEQ ID NO: 4 |
| 7C | SEQ ID NO: 41 | 2'OMe | None | na | na | na | na | na | na | let7c | AACCAUACAACCUACUACCUCAN (SEQ ID NO: 41) |
| 7C | | Y | | | | | | | | let7c | |
| 7C | | X | | | | | | | | let7c | |
| 8A | SEQ ID NO: 103 | BTM03 | Na | na | na | na | na | na | na | mir21 | U$_1$C$_1$AAC$_1$AU$_1$C$_1$AGU$_1$C$_1$U$_1$GAU$_1$AAGC$_1$U$_1$A (SEQ ID NO: 153) |
| 8A | SEQ ID NO: 104 | BTM04 | Na | na | na | na | na | na | na | mir21 | U$_1$C$_1$AAC$_1$AU$_1$C$_1$AGU$_1$C$_1$U$_1$GAU$_1$AAGC$_1$U$_1$ (SEQ ID NO: 104) |
| 8A | SEQ ID NO: 105 | BTM05 | Na | na | na | na | na | na | na | mir21 | TCAACATCAGTCTGATAAGCTA (SEQ ID NO: 105) |
| 8A | SEQ ID NO: 106 | BTM06 | Na | na | na | na | na | na | na | mir21 | TCAACATCAGTCTGAT (SEQ ID NO: 155) |
| 8A | SEQ ID NO: 107 | BTM07 | Na | na | na | na | na | na | na | mir21 | U$_1$C$_1$AAC$_1$AU$_1$C$_1$AGU$_1$C$_1$U$_1$GAU$_1$AAGC$_1$U$_1$A (SEQ ID NO: 107) |
| 8A | SEQ ID NO: 108 | BTM22 | Na | na | na | na | na | na | na | mir21 | U$_1$C$_1$AAC$_1$AU$_1$C$_1$AGU$_1$C$_1$U$_1$GAU$_1$GAU$_1$AAGC$_1$U$_1$AN (SEQ ID NO: 108) |
| 8A | SEQ ID NO: 31 | 2'OMe | None | | | | | | | mir 21 | UCAACAUCAGUCUGAUAAGCUAN (SEQ ID NO: 31) |
| 8A | | X | | | | | | | | mir21 | |
| 8A | SEQ ID NO: 64 | Neg | | | | | | | | neg | AAGUGGAUAUUGUUGCCAUCAN (SEQ ID NO: 64) |

TABLE 1C-continued

| Inhibitor Formats and Modifications | | | | | | | | | | | |
|---|---|---|---|---|---|---|---|---|---|---|---|
| FIG. | Seq ID | | loop position | HR I | Linker (L-1) | HR II | HR III | Linker (L2) | HR IV | Target | Complementary sequence |
| 8B | SEQ ID NO: 109 | BTM03 | Na | na | na | na | na | na | na | let7a | $AAC_1U_1AU_1AC_1AAC_1C_1U_1AC_1U_1AC_1C_1U_1C_1A$ (SEQ ID NO: 109) |
| 8B | SEQ ID NO: 110 | BTM04 | Na | na | na | na | na | na | na | let7a | $AAC_1U_1AU_1AC_1AAC_1C_1U_1AC_1U_1$ (SEQ ID NO: 110) |
| 8B | SEQ ID NO: 111 | BTM05 | Na | na | na | na | na | na | na | let7a | AACTATACAACCTACTACCTCA (SEQ ID NO: 111) |
| 8B | SEQ ID NO: 112 | BTM06 | Na | na | na | na | na | na | na | let7a | AACTATACAACCTACT (SEQ ID NO: 112) |
| 8B | SEQ ID NO: 113 | BTM07 | Na | na | na | na | na | na | na | let7a | $AAC_1U_1AU_1AC_1AAC_1C_1U_1AC_1U_1AC_1C_1U_1C_1A$ (SEQ ID NO: 113) |
| 8B | SEQ ID NO: 114 | BTM22 | Na | na | na | na | na | na | na | let7a | $AAC_1U_1AU_1AC_1AAC_1C_1U_1AC_1U_1AC_1C_1U_1C_1AN$ (SEQ ID NO: 114) |
| 8B | SEQ ID NO: 97 | 2'OMe | None | na | na | na | na | na | na | let7a | *AACUAUACAACCUACUACCUCA*N (SEQ ID NO: 97) |
| 8B | | X | | | | | | | | let7a | |
| 8B | SEQ ID NO: 64 | Neg | | | | | | | | neg | *AAGUGGAUAUUGUUGCCAUCA*N (SEQ ID NO: 64) |
| 8C | SEQ ID NO: 115 | BTM03 | Na | na | na | na | na | na | na | let7c | $AAC_1C_1AU_1AC_1AAC_1C_1U_1AC_1U_1AC_1C_1U_1C_1A$ (SEQ ID NO: 115) |
| 8C | SEQ ID NO: 116 | BTM04 | Na | na | na | na | na | na | na | let7c | $AAC_1C_1AU_1AC_1AAC_1C_1U_1AC_1U_1$ (SEQ ID NO: 116) |
| 8C | SEQ ID NO: 117 | BTM05 | Na | na | na | na | na | na | na | let7c | AACCATACAACCTACTACCTCA (SEQ ID NO: 117) |
| 8C | SEQ ID NO: 118 | BTM06 | Na | na | na | na | na | na | na | let7c | AACCATACAACCTACT (SEQ ID NO: 118) |
| 8C | SEQ ID NO: 119 | BTM07 | Na | na | na | na | na | na | na | let7c | $AAC_1C_1AU_1AC_1AAC_1C_1U_1AC_1U_1AC_1C_1U_1C_1A$ (SEQ ID NO: 119) |
| 8C | SEQ ID NO: 120 | BTM22 | Na | na | na | na | na | na | na | let7c | $AAC_1C_1AU_1AC_1AAC_1C_1U_1AC_1U_1AC_1C_1U_1C_1AN$ (SEQ ID NO: 120) |
| 8C | SEQ ID NO: 41 | 2'OMe | None | na | na | na | na | na | na | let7c | *AACCAUACAACCUACUACCUCA*N (SEQ ID NO: 41) |

TABLE 1C-continued

| | | | | | Inhibitor Formats and Modifications | | | | | | |
|---|---|---|---|---|---|---|---|---|---|---|---|
| FIG. | Seq ID | | loop position | HR I | Linker (L-1) | HR II | HR III | Linker (L2) | HR IV | Target | Complementary sequence |
| 8C | SEQ ID NO: 64 | X | | | | | | | | let7c | |
| 8C | | Neg | | | | | | | | neg | AAGUGGAUAUUGUUGCCAUCAN (SEQ ID NO: 64) |
| 12 | SEQ ID NO: 120 | HP98 | 5' | GGCACG | L3 | CGUGCC | na | na | na | mir122 | SEQ ID NO: 10 |
| 12 | SEQ ID NO: 121 | HP101 | 3' | na | na | na | UCCGUGC | L3 | GCACGGN | mir122 | SEQ ID NO: 11 |
| 12 | SEQ ID NO: 122 | HP81 | 5' | GGCACG | L3 | CGUGCC | na | na | na | mir122 | SEQ ID NO: 12 |
| 12 | SEQ ID NO: 123 | HP98 | 5' | GGCACG | L3 | CGUGCC | na | na | na | let7c | SEQ ID NO: 13 |
| 13 | SEQ ID NO: 124 | HP79 | 5' | GGCACG | L3 | CGUGCCAU | na | na | na | let7a | SEQ ID NO: 7 |
| 13 | SEQ ID NO: 125 | HP85 | 5' | GGCACG | L11 | CGUGCC | na | na | na | let7a | SEQ ID NO: 7 |
| 13 | SEQ ID NO: 126 | HP88 | 5' | GGCACG | L3 | CGUGCC | na | na | na | let7a | SEQ ID NO: 14 |
| 13 | SEQ ID NO: 127 | HP93 | 5' | GGCACG | L10 | CGUGCC | na | na | na | let7a | SEQ ID NO: 7 |
| 13 | SEQ ID NO: 128 | HP96 | 5' | GGCACG | L3 | CGUGCC | na | na | na | let7a | SEQ ID NO: 15 |
| 13 | SEQ ID NO: 97 | 2'OMe | None | na | na | na | na | na | na | let7a | AACUAUACAACCUACUACCUCAN (SEQ ID NO: 97) |
| 13 | | Y | | | | | | | | let7a | |
| 13 | | X | | | | | | | | | |
| 14 | SEQ ID NO: 129 | HP81 | 5' | GGCACG | L3 | CGUGCC | na | na | na | mir 21 | SEQ ID NO: 3 |
| 14 | SEQ ID NO: 130 | HP85 | 5' | GGCACG | L11 | CGUGCC | na | na | na | mir 21 | SEQ ID NO: 3 |
| 14 | SEQ ID NO: 131 | HP88 | 5' | GGCACG | L3 | CGUGCC | na | na | na | mir 21 | SEQ ID NO: 16 |

TABLE 1C-continued

Inhibitor Formats and Modifications

| FIG. | Seq ID | | loop position | HR I | Linker (L-1) | HR II | HR III | Linker (L2) | HR IV | Target | Complementary sequence |
|---|---|---|---|---|---|---|---|---|---|---|---|
| 14 | SEQ ID NO: 132 | HP93 | 5' | GGCACG | L10 | CGUGCC | na | na | na | mir 21 | SEQ ID NO:3 |
| 14 | SEQ ID NO: 133 | HP96 | 5' | GGCACG | L3 | CGUGCC | na | na | na | mir 21 | SEQ ID NO:17 |
| 14 | SEQ ID NO: 31 | 2'OMe | None | na | na | na | na | na | na | mir 21 | UCAACAUCAGUCUGAUAAGCUAN (SEQ ID NO: 31) |
| 14 | | X | | | | | | | | mir 21 | |
| 14 | | Y | | | | | | | | mir 21 | |
| 15 | SEQ ID NO: 97 | 2'OMe | None | na | na | na | na | na | na | let7a | AACUAUACAACCUACUACCUCAN (SEQ ID NO: 97) |
| 15 | | X | | | | | | | | | |
| 15 | | Y | | | | | | | | | |
| 15 | SEQ ID NO: 134 | HP81 | 5' | GGCACG | L3 | CGUGCC | na | na | na | let7a | SEQ ID NO:7 |
| 15 | SEQ ID NO: 135 | HP89 | 5' | GGCACG | L3 | CGUGCC | na | na | na | let7a | SEQ ID NO:18 |
| 15 | SEQ ID NO: 136 | HP90 | 5' | GGCACG | L3 | CGUGCC | na | na | na | let7a | SEQ ID NO:19 |
| 15 | SEQ ID NO: 137 | HP91 | 5' | GGCACG | L3 | CGUGCC | na | na | na | let7a | SEQ ID NO:20 |
| 15 | SEQ ID NO: 138 | HP92 | 5' | GGCACG | L3 | CGUGCC | na | na | na | let7a | SEQ ID NO:21 |

TABLE 1D

| | | miRNA inhibitor | |
|---|---|---|---|
| FIG. | Sequence Identifier | Inhibitor sequence | |
| 3A | SEQ ID NO: 22 | *GCUGAUCUCAGCUCAACAUCAGUCUGAUAAGCUAGCUGAUCUCAGc* | HP01 |
| 3A | SEQ ID NO: 23 | *GCUG-L1-CAGCUCAACAUCAGUCUGAUAAGCUAGCUG-L1-CAGc* | HP02 |
| 3A | SEQ ID NO: 24 | *GCUG-L1-CAGCUCAACAUCAGUCUGAUAAGCUAGCUG-L1-CAGc* | HP03 |
| 3A | SEQ ID NO: 25 | *GCUGAUCUCAGCUCAACAUCAGUCUGAUAAGCUAc* | HP04 |
| 3A | SEQ ID NO: 26 | *GCUG-L1-CAGCUCAACAUCAGUCUGAUAAGCUAc* | HP05 |
| 3A | SEQ ID NO: 27 | *GCUG-L1-CAGCUCAACAUCAGUCUGAUAAGCUAc* | HP06 |
| 3A | SEQ ID NO: 28 | *UCAACAUCAGUCUGAUAAGCUAGCUGAUCUCAGc* | HP07 |
| 3A | SEQ ID NO: 29 | *UCAACAUCAGUCUGAUAAGCUAGCUG-L1-CAGc* | HP08 |
| 3A | SEQ ID NO: 30 | *UCAACAUCAGUCUGAUAAGCUAGCUG-L1-CAGc* | HP09 |
| 3A | SEQ ID NO: 31 | *UCAACAUCAGUCUGAUAAGCUAN* | 2'OMe |
| 3B | SEQ ID NO: 32 | *GCUGAUCUCAGCAACCAUACAACCUACUACCUCAGCUGAUCUCAGc* | HP01 |
| 3B | SEQ ID NO: 33 | *GCUG-L1-CAGCAACCAUACAACCUACUACCUCAGCUG-L1-CAGc* | HP02 |
| 3B | SEQ ID NO: 34 | *GCUG-L1-CAGCAACCAUACAACCUACUACCUCAGCUG-L1-CAGc* | HP03 |
| 3B | SEQ ID NO: 35 | *GCUGAUCUCAGCAACCAUACAACCUACUACCUCAc* | HP04 |
| 3B | SEQ ID NO: 36 | *GCUG-L1-CAGCAACCAUACAACCUACUACCUCAc* | HP05 |
| 3B | SEQ ID NO: 37 | *GCUG-L1-CAGCAACCAUACAACCUACUACCUCAc* | HP06 |
| 3B | SEQ ID NO: 38 | *AACCAUACAACCUACUACCUCAGCUGAUCUCAGc* | HP07 |
| 3B | SEQ ID NO: 39 | *AACCAUACAACCUACUACCUCAGCUG-L1-CAGc* | HP08 |
| 3B | SEQ ID NO: 40 | *AACCAUACAACCUACUACCUCAGCUG-L1-CAGc* | HP09 |
| 3B | SEQ ID NO: 41 | *AACCAUACAACCUACUACCUCAN* | 2'OMe |
| 4A | SEQ ID NO: 158 | *GCUC-L1-CAGCUCAACAUCAGUCUGAUAAGCUAc* | HP05 |
| 4A | SEQ ID NO: 29 | *UCAACAUCAGUCUGAUAAGCUAGCUG-L1-CAGc* | HP08 |
| 4A | SEQ ID NO: 42 | *GCG-L1-CGCUCAACAUCAGUCUGAUAAGCUAc* | HP10 |
| 4A | SEQ ID NO: 43 | *GCGUG-L1-CACGCUCAACAUCAGUCUGAUAAGCUAc* | HP11 |
| 4A | SEQ ID NO: 44 | *UGGC-L1-CAGCUCAACAUCAGUCUGAUAAGCUAc* | HP12 |
| 4A | SEQ ID NO: 45 | *GCUGAUUCUCAGCUCAACAUCAGUCUGAUAAGCUAc* | HP13 |
| 4A | SEQ ID NO: 46 | *UCAACAUCAGUCUGAUAAGCUAGCG-L1-CGc* | HP14 |
| 4A | SEQ ID NO: 47 | *UCAACAUCAGUCUGAUAAGCUAGCGUG-L1-CACGc* | HP15 |
| 4A | SEQ ID NO: 48 | *UCAACAUCAGUCUGAUAAGCUAUGGC-L1-CAGc* | HP16 |
| 4A | SEQ ID NO: 49 | *UCAACAUCAGUCUGAUAAGCUAGCUGAUUCUCAGc* | HP17 |
| 4A | SEQ ID NO: 50 | *GCUG-L2-CAGCUCAACAUCAGUCUGAUAAGCUAc* | HP18 |
| 4A | SEQ ID NO: 51 | *GCUG-L3-CAGCUCAACAUCAGUCUGAUAAGCUAc* | HP19 |
| 4A | SEQ ID NO: 52 | *GCUG-L4-CAGCUCAACAUCAGUCUGAUAAGCUAc* | HP20 |
| 4A | SEQ ID NO: 53 | *GCUG-L5-CAGCUCAACAUCAGUCUGAUAAGCUAc* | HP21 |
| 4A | SEQ ID NO: 54 | *GCUG-L6-CAGCUCAACAUCAGUCUGAUAAGCUAc* | HP22 |
| 4A | SEQ ID NO: 55 | *GCUG-L7-CAGCUCAACAUCAGUCUGAUAAGCUAc* | HP23 |
| 4A | SEQ ID NO: 56 | *GCUG-L8-CAGCUCAACAUCAGUCUGAUAAGCUAc* | HP24 |
| 4A | SEQ ID NO: 57 | *UCAACAUCAGUCUGAUAAGCUAGCUG-L2-CAGc* | HP25 |

TABLE 1D-continued miRNA inhibitor

| FIG. | Sequence Identifier | Inhibitor sequence | |
|---|---|---|---|
| 4A | SEQ ID NO: 58 | UCAACAUCAGUCUGAUAAGCUAGCUG-L3-CAGc | HP26 |
| 4A | SEQ ID NO: 59 | UCAACAUCAGUCUGAUAAGCUAGCUG-L4-CAGc | HP27 |
| 4A | SEQ ID NO: 60 | UCAACAUCAGUCUGAUAAGCUAGCUG-L5-CAGc | HP28 |
| 4A | SEQ ID NO: 61 | UCAACAUCAGUCUGAUAAGCUAGCUG-L6-CAGc | HP29 |
| 4A | SEQ ID NO: 62 | UCAACAUCAGUCUGAUAAGCUAGCUG-L7-CAGc | HP30 |
| 4A | SEQ ID NO: 63 | UCAACAUCAGUCUGAUAAGCUAGCUG-L8-CAGc | HP31 |
| 4A | SEQ ID NO: 31 | UCAACAUCAGUCUGAUAAGCUAN | 2'OMe |
| 4A | SEQ ID NO: 64 | AAGUGGAUAUUGUUGCCAUCAN | Neg |
| 4B | SEQ ID NO: 160 | GCUC-L1-CAGCAACCAUACAACCUACUACCUCAc | HP05 |
| 4B | SEQ ID NO: 39 | AACCAUACAACCUACUACCUCAGCUGiCAGc | HP08 |
| 4B | SEQ ID NO: 65 | GCG-L1-CGCAACCAUACAACCUACUACCUCAc | HP10 |
| 4B | SEQ ID NO: 66 | GCGUG-L1-CACGCAACCAUACAACCUACUACCUCAc | HP11 |
| 4B | SEQ ID NO: 67 | UGGC-D-CAGCAACCAUACAACCUACUACCUCAc | HP12 |
| 4B | SEQ ID NO: 68 | GCUGAUUCUCAGCAACCAUACAACCUACUACCUCAc | HP13 |
| 4B | SEQ ID NO: 69 | AACCAUACAACCUACUACCUCAGCG-L1-CGc | HP14 |
| 4B | SEQ ID NO: 70 | AACCAUACAACCUACUACCUCAGCGUG-L1-CACGc | HP15 |
| 4B | SEQ ID NO: 71 | AACCAUACAACCUACUACCUCAUGGC-L1-CAGc | HP16 |
| 4B | SEQ ID NO: 72 | AACCAUACAACCUACUACCUCAGCUGAUUCUCAGc | HP17 |
| 4B | SEQ ID NO: 73 | GCUG-L2-CAGCAACCAUACAACCUACUACCUCAc | HP18 |
| 4B | SEQ ID NO: 74 | GCUG-L3-CAGCAACCAUACAACCUACUACCUCAc | HP19 |
| 4B | SEQ ID NO: 75 | GCUG-L4-CAGCAACCAUACAACCUACUACCUCAc | HP20 |
| 4B | SEQ ID NO: 76 | GCUG-L5-CAGCAACCAUACAACCUACUACCUCAc | HP21 |
| 4B | SEQ ID NO: 77 | GCUG-L6-CAGCAACCAUACAACCUACUACCUCAc | HP22 |
| 4B | SEQ ID NO: 78 | GCUG-L7-CAGCAACCAUACAACCUACUACCUCAc | HP23 |
| 4B | SEQ ID NO: 79 | GCUG-L8-CAGCAACCAUACAACCUACUACCUCAc | HP24 |
| 4B | SEQ ID NO: 80 | AACCAUACAACCUACUACCUCAGCUG-L2-CAGc | HP25 |
| 4B | SEQ ID NO: 81 | AACCAUACAACCUACUACCUCAGCUG-L3-CAGc | HP26 |
| 4B | SEQ ID NO: 82 | AACCAUACAACCUACUACCUCAGCUG-L4-CAGc | HP27 |
| 4B | SEQ ID NO: 83 | AACCAUACAACCUACUACCUCAGCUG-L5-CAGc | HP28 |
| 4B | SEQ ID NO: 84 | AACCAUACAACCUACUACCUCAGCUG-L6-CAGc | HP29 |
| 4B | SEQ ID NO: 85 | AACCAUACAACCUACUACCUCAGCUG-L7-CAGc | HP30 |
| 4B | SEQ ID NO: 86 | AACCAUACAACCUACUACCUCAGCUG-L8-CAGc | HP31 |
| 4B | SEQ ID NO: 41 | AACCAUACAACCUACUACCUCAN | 2'OMe |
| 4B | SEQ ID NO: 64 | AAGUGGAUAUUGUUGCCAUCAN | neg |
| 5 | SEQ ID NO: 36 | GCUC-L1-CAGCAACCAUACAACCUACUACCUCAc | HP05 |
| 5 | SEQ ID NO: 39 | AACCAUACAACCUACUACCUCAGCUG-L1-CAGc | HP08 |
| 5 | SEQ ID NO: 65 | GCG-L1-CGCAACCAUACAACCUACUACCUCAc | HP10 |
| 5 | SEQ ID NO: 66 | GCGUG-L1-CACGCAACCAUACAACCUACUACCUCAc | HP11 |

TABLE 1D-continued miRNA inhibitor

| FIG. | Sequence Identifier | Inhibitor sequence | |
|---|---|---|---|
| 5 | SEQ ID NO: 67 | UGGC-L1-CAGCAACCAUACAACCUACUACCUCAc | HP12 |
| 5 | SEQ ID NO: 68 | GCUGAUUCUCAGCAACCAUACAACCUACUACCUCAc | HP13 |
| 5 | SEQ ID NO: 69 | AACCAUACAACCUACUACCUCAGCG-L1-CGc | HP14 |
| 5 | SEQ ID NO: 70 | AACCAUACAACCUACUACCUCAGCGUG-L1-CACGc | HP15 |
| 5 | SEQ ID NO: 71 | AACCAUACAACCUACUACCUCAUGGC-L1-CAGc | HP16 |
| 5 | SEQ ID NO: 72 | AACCAUACAACCUACUACCUCAGCUGAUUCUCAGc | HP17 |
| 5 | SEQ ID NO: 73 | GCUG-L2-CAGCAACCAUACAACCUACUACCUCAc | HP18 |
| 5 | SEQ ID NO: 74 | GCUG-L3-CAGCAACCAUACAACCUACUACCUCAc | HP19 |
| 5 | SEQ ID NO: 75 | GCUG-L4-CAGCAACCAUACAACCUACUACCUCAc | HP20 |
| 5 | SEQ ID NO: 76 | GCUG-L5-CAGCAACCAUACAACCUACUACCUCAc | HP21 |
| 5 | SEQ ID NO: 77 | GCUG-L6-CAGCAACCAUACAACCUACUACCUCAc | HP22 |
| 5 | SEQ ID NO: 78 | GCUG-L7-CAGCAACCAUACAACCUACUACCUCAc | HP23 |
| 5 | SEQ ID NO: 79 | GCUG-L8-CAGCAACCAUACAACCUACUACCUCAc | HP24 |
| 5 | SEQ ID NO: 80 | AACCAUACAACCUACUACCUCAGCUG-L2-CAGc | HP25 |
| 5 | SEQ ID NO: 81 | AACCAUACAACCUACUACCUCAGCUG-L3-CAGc | HP26 |
| 5 | SEQ ID NO: 82 | AACCAUACAACCUACUACCUCAGCUG-L4-CAGc | HP27 |
| 5 | SEQ ID NO: 83 | AACCAUACAACCUACUACCUCAGCUG-L5-CAGc | HP28 |
| 5 | SEQ ID NO: 84 | AACCAUACAACCUACUACCUCAGCUG-L6-CAGc | HP29 |
| 5 | SEQ ID NO: 85 | AACCAUACAACCUACUACCUCAGCUG-L7-CAGc | HP30 |
| 5 | SEQ ID NO: 86 | AACCAUACAACCUACUACCUCAGCUG-L8-CAGc | HP31 |
| 5 | SEQ ID NO: 41 | AACCAUACAACCUACUACCUCAN | 2'OMe |
| 5 | SEQ ID NO: 32 | GCUGAUCUCAGCAACCAUACAACCUACUACCUCAGCUGAUCUCAGc | HP01 |
| 5 | SEQ ID NO: 159 | GCUG-L1-CAGCAACCAUACAACCUACUACCUCAGCUGAUCUCAGc | HP02 |
| 5 | SEQ ID NO: 64 | AAGUGGAUAUUGUUGCCAUCAN | neg |
| 6A | SEQ ID NO: 41 | AACCAUACAACCUACUACCUCAN | 2'OMe |
| 6A | SEQ ID NO: 79 | GCUG-L8-CAGCAACCAUACAACCUACUACCUCAc | HP24 |
| 6A | SEQ ID NO: 64 | AAGUGGAUAUUGUUGCCAUCAN | Neg |
| 6B | SEQ ID NO: 31 | UCAACAUCAGUCUGAUAAGCUAN | 2'OMe |
| 6B | SEQ ID NO: 56 | GCUG-L8-CAGCUCAACAUCAGUCUGAUAAGCUAc | HP24 |
| 6B | SEQ ID NO: 64 | AAGUGGAUAUUGUUGCCAUCAN | Neg |
| 7A | SEQ ID NO: 87 | GGCACG-L3-CGUGCCAUUCAACAUCAGUCUGAUAAGCUAc | HP79 |
| 7A | SEQ ID NO: 88 | GGCACG-L3-CGUGCCAUCAACAUCAGUCUGAUAAGCUAc | HP80 |
| 7A | SEQ ID NO: 89 | GGCACG-L3-CGUGCCUCAACAUCAGUCUGAUAAGCUAc | HP81 |
| 7A | SEQ ID NO: 90 | UCAACAUCAGUCUGAUAAGCUACCGUGC-L3-GCACGGN | HP82 |
| 7A | SEQ ID NO: 91 | UCAACAUCAGUCUGAUAAGCUACCGUGC-L3-GCACGg | HP83 |
| 7A | SEQ ID NO: 31 | UCAACAUCAGUCUGAUAAGCUAN | 2'OMe |
| 7B | SEQ ID NO: 92 | GGCACG-L3-CGUGCCAUAACUAUACAACCUACUACCUCAt | HP79 |
| 7B | SEQ ID NO: 93 | GGCACG-L3-CGUGCCAAACUAUACAACCUACUACCUCAt | HP80 |

TABLE 1D-continued miRNA inhibitor

| FIG. | Sequence Identifier | Inhibitor sequence | |
|---|---|---|---|
| 7B | SEQ ID NO: 94 | *GGCACG*-L3-*CGUGCCAACUAUACAACCUACUACCUCA*t | HP81 |
| 7B | SEQ ID NO: 95 | *AACUAUACAACCUACUACCUCAUCCGUGC*-L3-*GCACGG*N | HP82 |
| 7B | SEQ ID NO: 96 | *AACUAUACAACCUACUACCUCAUCCGUGC*-L3-*GCACG*g | HP83 |
| 7B | SEQ ID NO: 97 | *AACUAUACAACCUACUACCUCA*N | 2'OMe |
| 7C | SEQ ID NO: 98 | *GGCACG*-L3-*CGUGCCAUAACCAUACAACCUACUACCUCA*g | HP79 |
| 7C | SEQ ID NO: 99 | *GGCACG*-L3-*CGUGCCAAACCAUACAACCUACUACCUCA*g | HP80 |
| 7C | SEQ ID NO: 100 | *GGCACG*-L3-*CGUGCCAACCAUACAACCUACUACCUCA*g | HP81 |
| 7C | SEQ ID NO: 101 | *AACCAUACAACCUACUACCUCAUCCGUGC*-L3-*GCACGG*N | HP82 |
| 7C | SEQ ID NO: 102 | *AACCAUACAACCUACUACCUCAUCCGUGC*-L3-*GCACG*g | HP83 |
| 7C | SEQ ID NO: 41 | *AACCAUACAACCUACUACCUCA*N | 2'OMe |
| 8A | SEQ ID NO: 153 | $U_1C_1$AAC$_1$AU$_1C_1$AGU$_1C_1U_1$GAU$_1$AAGC$_1U_1$A | BTM03 |
| 8A | SEQ ID NO: 104 | $U_1C_1$AAC$_1$AU$_1C_1$AGU$_1C_1U_1$GAU$_1$ | BTM04 |
| 8A | SEQ ID NO: 105 | TCAACATCAGTCTGATAAGCTA | BTM05 |
| 8A | SEQ ID NO: 155 | TCAACATCAGTCTGAT | BTM06 |
| 8A | SEQ ID NO: 107 | $U_1C_1$AAC$_1$AU$_1C_1$AGU$_1C_1U_1$GAU$_1$AAGC$_1U_1$A | BTM07 |
| 8A | SEQ ID NO: 108 | $U_1C_1$AAC$_1$AU$_1C_1$AGU$_1C_1U_1$GAU$_1$AAGC$_1U_1$AN | BTM22 |
| 8A | SEQ ID NO: 31 | *UCAACAUCAGUCUGAUAAGCUA*N | 2'OMe |
| 8A | SEQ ID NO: 64 | *AAGUGGAUAUUGUUGCCAUCA*N | Neg |
| 8B | SEQ ID NO: 109 | AAC$_1U_1$AU$_1$AC$_1$AAC$_1C_1U_1$AC$_1U_1$AC$_1C_1U_1C_1$A | BTM03 |
| 8B | SEQ ID NO: 110 | AAC$_1U_1$AU$_1$AC$_1$AAC$_1C_1U_1$AC$_1U_1$ | BTM04 |
| 8B | SEQ ID NO: 111 | AACTATACAACCTACTACCTCA | BTM05 |
| 8B | SEQ ID NO: 112 | AACTATACAACCTACT | BTM06 |
| 8B | SEQ ID NO: 113 | AAC$_1U_1$AU$_1$AC$_1$AAC$_1C_1U_1$AC$_1U_1$AC$_1C_1U_1C_1$A | BTM07 |
| 8B | SEQ ID NO: 114 | AAC$_1U_1$AU$_1$AC$_1$AAC$_1C_1U_1$AC$_1U_1$AC$_1C_1U_1C_1$AN | BTM22 |
| 8B | SEQ ID NO: 97 | *AACUAUACAACCUACUACCUCA*N | 2'OMe |
| 8B | SEQ ID NO: 64 | *AAGUGGAUAUUGUUGCCAUCA*N | Neg |
| 8C | SEQ ID NO: 115 | AAC$_1C_1$AU$_1$AC$_1$AAC$_1C_1U_1$AC$_1U_1$AC$_1C_1U_1C_1$A | BTM03 |
| 8C | SEQ ID NO: 116 | AAC$_1C_1$AU$_1$AC$_1$AAC$_1C_1U_1$AC$_1U_1$ | BTM04 |
| 8C | SEQ ID NO: 117 | AACCATACAACCTACTACCTCA | BTM05 |
| 8C | SEQ ID NO: 118 | AACCATACAACCTACT | BTM06 |
| 8C | SEQ ID NO: 119 | AAC$_1C_1$AU$_1$AC$_1$AAC$_1C_1U_1$AC$_1U_1$AC$_1C_1U_1C_1$A | BTM07 |
| 8C | SEQ ID NO: 120 | AAC$_1C_1$AU$_1$AC$_1$AAC$_1C_1U_1$AC$_1U_1$AC$_1C_1U_1C_1$AN | BTM22 |
| 8C | SEQ ID NO: 41 | *AACCAUACAACCUACUACCUCA*N | 2'OMe |
| 8C | SEQ ID NO: 64 | *AAGUGGAUAUUGUUGCCAUCA*N | Neg |
| 12 | SEQ ID NO: 161 | *GGCACG*-L3-*CGUGCC<u>ACAAACACCAUUGUCACACUCCA</u>*c | HP98 |
| 12 | SEQ ID NO: 121 | <u>*ACAAACACCAUUGUCACACUCCA*</u>*UCCGUGC*-L3-*GCACGG*N | HP101 |
| 12 | SEQ ID NO: 122 | *GGCACG*-L3-*CGUGCCACAAACACCAUUGUCACACUCCA*c | HP81 |
| 12 | SEQ ID NO: 123 | *GGCACG*-L3-*CGUGCC<u>AACCAUACAACCUACUACCUCA</u>*g | HP98 |

TABLE 1D-continued miRNA inhibitor

| FIG. | Sequence Identifier | Inhibitor sequence | |
|---|---|---|---|
| 13 | SEQ ID NO: 124 | GGCACG-L3-CGUGCCAUAACUAUACAACCUACUACCUCAt | HP79 |
| 13 | SEQ ID NO: 125 | GGCACG-L11-CGUGCCAACUAUACAACCUACUACCUCAt | HP85 |
| 13 | SEQ ID NO: 126 | GGCACG-L3-CGUGCCAACUAUACAACCUACUACCUCAY | HP88 |
| 13 | SEQ ID NO: 127 | GGCACG-L10-CGUGCCAACUAUACAACCUACUACCUCAt | HP93 |
| 13 | SEQ ID NO: 128 | GGCACG-L3-CGUGCCAACUAUACAACCUACUACCUCA-Chol | HP96 |
| 13 | SEQ ID NO: 97 | AACUAUACAACCUACUACCUCAN | 2'OMe |
| 14 | SEQ ID NO: 129 | GGCACG-L3-CGUGCCUCAACAUCAGUCUGAUAAGCUAc | HP81 |
| 14 | SEQ ID NO: 130 | GGCACG-L11-CGUGCCUCAACAUCAGUCUGAUAAGCUAc | HP85 |
| 14 | SEQ ID NO: 131 | GGCACG-L3-CGUGCCUCAACAUCAGUCUGAUAAGCUAY | HP88 |
| 14 | SEQ ID NO: 132 | GGCACG-L10-CGUGCCUCAACAUCAGUCUGAUAAGCUAc | HP93 |
| 14 | SEQ ID NO: 133 | GGCACG-L3-CGUGCCUCAACAUCAGUCUGAUAAGCUA-Chol | HP96 |
| 14 | SEQ ID NO: 31 | UCAACAUCAGUCUGAUAAGCUAN | 2'OMe |
| 15 | SEQ ID NO: 97 | AACUAUACAACCUACUACCUCAN | 2'OMe |
| 15 | SEQ ID NO: 134 | GGCACG-L3-CGUGCCAACUAUACAACCUACUACCUCAt | HP81 |
| 15 | SEQ ID NO: 135 | GGCACG-L3-CGUGCCAACUAUACAACCUACTACCTCAt | HP89 |
| 15 | SEQ ID NO: 136 | GGCACG-L3-CGUGCCAACUGUACAAACUACUACCUCAt | HP90 |
| 15 | SEQ ID NO: 137 | GGCACG-L3-CGUGCCAAC$_1$U$_1$AU$_1$AC$_1$AAC$_1$C$_1$U$_1$AC$_1$U$_1$AC$_1$C$_1$U$_1$C$_1$At | HP91 |
| 15 | SEQ ID NO: 138 | GGCACG-L3-CGUGCCAAC$_1$U$_1$AU$_1$AC$_1$AAC$_1$C$_1$U$_1$AC$_1$U$_1$AC$_1$C$_1$U$_1$C$_1$At | HP92 |

35

Although the invention has been described with reference to the above example, it will be understood that modifications and variations are encompassed within the spirit and scope of the invention. Accordingly, the invention is limited only by the following claims. The entire contents of all patents, published patent applications, and other references cited herein are hereby expressly incorporated herein in their entireties by reference.

What is claimed is:

1. A multimeric nucleic acid inhibitory molecule capable of binding at least one target nucleic acid molecule under physiological conditions, the multimeric nucleic acid inhibitory molecule comprising
two to one hundred of first oligonucleotides having structure B2A

B2A    _____

NBR1  S1  BR  S2  NBR2 and
at least one second oligonucleotide B2B,

B2B    _____

NBR2C       NBR1C wherein each of the first oligonucleotides B2A comprises at least one target nucleic acid molecule binding region BR, at least two regions NBR1 and NBR2 which will not hybridize to the at least one target nucleic acid molecule and wherein NBR1 will not hybridize to NBR2, and optional spacers S1 and S2,
wherein at least one second oligonucleotide B2B comprises a region NBR1C that is capable of hybridizing under physiological conditions to NBR1 of at least one of the first oligonucleotides B2A and a region NBR2C that is capable of hybridizing under physiological conditions to NBR2 of a second of the first oligonucleotides B2A,
wherein, when hybridized, the NBR1 region of the at least one first oligonucleotide B2A is annealed to the NBR1C region of the at least one second oligonucleotide B2B, and the NBR2C region of the at least one second oligonucleotide B2B is annealed to an NBR2 region of the second of the first oligonucleotides B2A molecule wherein the multimeric nucleic acid inhibitory molecule comprises a nicked head to tail configuration of the B2A molecules with both single-stranded (BR) and double-stranded regions (NBR1/NBR1C) and (NBR2/NBR2C).

2. The multimeric nucleic acid inhibitory molecule of claim 1, wherein at least one of first oligonucleotides B2A comprises at least one of spacer S1 and S2 wherein the at least one spacer comprises at least one nucleotide having a purine base, a pyrimidine base, or no base (abasic).

3. The multimeric nucleic acid inhibitory molecule of claim 1, wherein the at least one target nucleic acid molecule is a long non-coding RNA or a short non-coding RNA.

4. The multimeric nucleic acid inhibitory molecule of claim 1, wherein each first oligonucleotide B2A is 30 nucleotides to 200 nucleotides in length.

5. The multimeric nucleic acid inhibitory molecule of claim 1, wherein the at least one second oligonucleotide is 6 nucleotides to 50 nucleotides in length.

6. The multimeric nucleic acid inhibitory molecule of claim 1, wherein single-stranded region BR of first oligonucleotides B2A is complementary to all or a portion of the at least one target nucleic acid molecule.

7. The multimeric nucleic acid inhibitory molecule of claim 3, wherein the short non-coding RNA is chosen from a microRNA, Piwi-interacting RNA, small interfering RNA, and a ribosomal RNA.

8. The multimeric nucleic acid inhibitory molecule of claim 1, comprising at least one nucleotide modification chosen from 2'OMe, 2'OAllyl, 2'O-propargyl, 2'O-alkyl, 2'fluoro, 2'arabino, 2'xylo, 2'fluoro arabino, phosphorothioate, phosphorodithioate, 2'amino, 5-alkyl-substituted pyrimidine, 5-halo-substituted pyrimidine, alkyl-substituted purine, halo-substituted purine, bicyclic nucleotides, 2'MOE, LNA, and combinations thereof.

9. The multimeric nucleic acid inhibitory molecule of claim 1, wherein the molecule further comprises one or more nucleotides on either end of the molecule.

10. The multimeric nucleic acid inhibitory molecule of claim 1, wherein the target binding nucleic acid segment is about 60 to about 100% complementary to all or a portion of at least one target nucleic acid.

11. A method for inhibiting the function of a target RNA or DNA molecule, the method comprising contacting the target RNA or DNA molecule with the nucleic acid inhibitory molecule of claim 1.

12. A method for treatment of a disease, comprising administering an amount of the inhibitory molecule of claim 1 in an amount effective to treat a disease, wherein treatment of the disease comprises reducing the symptoms of a disease.

13. The method of claim 12, further comprising complexing the inhibitory molecule with a cellular delivery agent.

14. The method of claim 12, wherein the disease is chosen from cancer, Alzheimer's disease, diabetes, and viral infections.

15. The multimeric nucleic acid inhibitory molecule of claim 1, further comprising a sterol moiety for self-delivery.

16. The multimeric nucleic acid inhibitory molecule of claim 1, comprising at least two first oligonucleotides having structure B2A, wherein each binding region of the at least two first oligonucleotides binds one or more target nucleic acid molecules.

17. The multimeric nucleic acid inhibitory molecule of claim 1, comprising mixtures of first oligonucleotides having structure B2A molecules, the B2A molecules having multiple binding regions, each binding region complementary to one or more target nucleic acid molecules.

18. The multimeric nucleic acid inhibitory molecule of claim 1, comprising a mixture of RNA and DNA.

19. The multimeric nucleic acid inhibitory molecule of claim 1, comprising a mixture of modified and unmodified RNA or modified and unmodified DNA.

20. The multimeric nucleic acid inhibitory molecule of claim 1, wherein the target binding region has 80-100% complementarity with the at least one target nucleic acid.

* * * * *

SEQUENCE LISTING

```
<160> NUMBER OF SEQ ID NOS: 162

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 1
ucaacaucag ucugauaagc ua                                              22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
```
ucaacaucag ucugauaagc ua                                              22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'OMe modified

<400> SEQUENCE: 3
ucaacaucag ucugauaagc uac                                             23

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 4
aaccauacaa ccuacuaccu ca                                              22

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aaccauacaa ccuacuaccu ca                                              22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'OMe modified

<400> SEQUENCE: 6
aaccauacaa ccuacuaccu cac                                             23

<210> SEQ ID NO 7
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'OMe modified

<400> SEQUENCE: 7
aacuauacaa ccuacuaccu cat                                              23

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 8
aacuauacaa ccuacuaccu ca                                               22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'OMe modified

<400> SEQUENCE: 9
aaccauacaa ccuacuaccu cag                                              23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(23)
<223> OTHER INFORMATION: 2'OMe modified
<220> FEATURE:
<221> NAME/KEY: misc_feature
<222> LOCATION: (1)..(23)
<223> OTHER INFORMATION: Phosphorothioate linkage

<400> SEQUENCE: 10
acaaacacca uugucacacu ccac                                             24

<210> SEQ ID NO 11
<211> LENGTH: 23
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: 2'OMe modified
<220> FEATURE:
<221> NAME/KEY: misc_feature
<222> LOCATION: (1)..(23)
<223> OTHER INFORMATION: Phosphorothioate linkage

<400> SEQUENCE: 11
acaaacacca uugucacacu cca                                              23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(23)
<223> OTHER INFORMATION: 2'OMe modified

<400> SEQUENCE: 12
acaaacacca uugucacacu ccac                                             24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'OMe modified
<220> FEATURE:
<221> NAME/KEY: misc_feature
<222> LOCATION: (1)..(22)
<223> OTHER INFORMATION: Phosphorothioate linkage

<400> SEQUENCE: 13
aaccauacaa ccuacuaccu cag                                              23

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified
<220> FEATURE:
<221> NAME/KEY: modified_base
<222> LOCATION: (23)..(23)
<223> OTHER INFORMATION: 2'O-Propargyl modified

<400> SEQUENCE: 14
```

```
aacuauacaa ccuacuaccu cag                                              23
```

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 15

```
aacuauacaa ccuacuaccu ca                                               22
```

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: 2'OMe modified
<220> FEATURE:
<221> NAME/KEY: modified_base
<222> LOCATION: (23)..(23)
<223> OTHER INFORMATION: 2'O-Propargyl modified

<400> SEQUENCE: 16

```
ucaacaucag ucugauaagc uag                                              23
```

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 17

```
ucaacaucag ucugauaagc ua                                               22
```

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(13)
<223> OTHER INFORMATION: 2'OMe modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base

```
<222> LOCATION: (15)..(15)
<223> OTHER INFORMATION: 2'OMe modified
<220> FEATURE:
<221> NAME/KEY: modified_base
<222> LOCATION: (16)..(16)
<223> OTHER INFORMATION: Locked nucleic acid
<220> FEATURE:
<221> NAME/KEY: modified_base
<222> LOCATION: (17)..(17)
<223> OTHER INFORMATION: 2'OMe modified
<220> FEATURE:
<221> NAME/KEY: modified_base
<222> LOCATION: (18)..(18)
<223> OTHER INFORMATION: Locked nucleic acid
<220> FEATURE:
<221> NAME/KEY: modified_base
<222> LOCATION: (19)..(19)
<223> OTHER INFORMATION: 2'OMe modified
<220> FEATURE:
<221> NAME/KEY: modified_base
<222> LOCATION: (20)..(20)
<223> OTHER INFORMATION: Locked nucleic acid
<220> FEATURE:
<221> NAME/KEY: modified_base
<222> LOCATION: (21)..(21)
<223> OTHER INFORMATION: 2'OMe modified
<220> FEATURE:
<221> NAME/KEY: modified_base
<222> LOCATION: (22)..(22)
<223> OTHER INFORMATION: Locked nucleic acid

<400> SEQUENCE: 18
aacuauacaa ccuactacct cat                                            23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(3)
<223> OTHER INFORMATION: Locked nucleic acid
<220> FEATURE:
<221> NAME/KEY: modified_base
<222> LOCATION: (4)..(4)
<223> OTHER INFORMATION: 2'OMe modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'OMe modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'OMe modified
<220> FEATURE:
<221> NAME/KEY: modified_base
<222> LOCATION: (9)..(9)
<223> OTHER INFORMATION: Locked nucleic acid
<220> FEATURE:
```

```
<221> NAME/KEY: modified_base
<222> LOCATION: (10)..(22)
<223> OTHER INFORMATION: 2'OMe modified

<400> SEQUENCE: 19
aacuguacaa acuacuaccu cat                                              23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: 2'OMe modified
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: 2'OMe modified
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: 2'OMe modified

<400> SEQUENCE: 20
aacuauacaa ccuacuaccu cat                                              23

<210> SEQ ID NO 21
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 21
aacuauacaa ccuacuaccu cat                                           23

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(45)
```

<223> OTHER INFORMATION: 2'OMe modified

<400> SEQUENCE: 22
gcugaucuca gcucaacauc agucugauaa gcuagcugau cucagc            46

<210> SEQ ID NO 23
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: 2'OMe modified

<400> SEQUENCE: 23
cagcucaaca ucagucugau aagcuagcug            30

<210> SEQ ID NO 24
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: 2'OMe modified
<220> FEATURE:
<221> NAME/KEY: modified_base
<222> LOCATION: (27)..(30)
<223> OTHER INFORMATION: 2'OMe modified

<400> SEQUENCE: 24
cagcucaaca ucagucugau aagcuagcug            30

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(34)
<223> OTHER INFORMATION: 2'OMe modified

<400> SEQUENCE: 25
gcugaucuca gcucaacauc agucugauaa gcuac            35

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

```
<400> SEQUENCE: 26
cagcucaaca ucagucugau aagcuac                                           27

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'OMe modified

<400> SEQUENCE: 27
cagcucaaca ucagucugau aagcuac                                           27

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(33)
<223> OTHER INFORMATION: 2'OMe modified

<400> SEQUENCE: 28
ucaacaucag ucugauaagc uagcugaucu cagc                                   34

<210> SEQ ID NO 29
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 29
ucaacaucag ucugauaagc uagcug                                            26

<210> SEQ ID NO 30
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(26)
<223> OTHER INFORMATION: 2'OMe modified

<400> SEQUENCE: 30
ucaacaucag ucugauaagc uagcug                                            26
```

```
<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 31
ucaacaucag ucugauaagc ua                                              22

<210> SEQ ID NO 32
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(45)
<223> OTHER INFORMATION: 2'OMe modified

<400> SEQUENCE: 32
gcugaucuca gcaaccauac aaccuacuac cucagcugau cucagc                    46

<210> SEQ ID NO 33
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: 2'OMe modified

<400> SEQUENCE: 33
cagcaaccau acaaccuacu accucagcug                                      30

<210> SEQ ID NO 34
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: 2'OMe modified
<220> FEATURE:
<221> NAME/KEY: modified_base
<222> LOCATION: (27)..(30)
<223> OTHER INFORMATION: 2'OMe modified

<400> SEQUENCE: 34
cagcaaccau acaaccuacu accucagcug                                      30

<210> SEQ ID NO 35
<211> LENGTH: 35
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(34)
<223> OTHER INFORMATION: 2'OMe modified

<400> SEQUENCE: 35
gcugaucuca gcaaccauac aaccuacuac cucac                                 35

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 36
cagcaaccau acaaccuacu accucac                                          27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(4)
<223> OTHER INFORMATION: 2'OMe modified

<400> SEQUENCE: 37
cagcaaccau acaaccuacu accucac                                          27

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(33)
<223> OTHER INFORMATION: 2'OMe modified

<400> SEQUENCE: 38
aaccauacaa ccuacuaccu cagcugaucu cagc                                  34

<210> SEQ ID NO 39
<211> LENGTH: 26

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 39
aaccauacaa ccuacuaccu cagcug                                           26

<210> SEQ ID NO 40
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(26)
<223> OTHER INFORMATION: 2'OMe modified

<400> SEQUENCE: 40
aaccauacaa ccuacuaccu cagcug                                           26

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 41
aaccauacaa ccuacuaccu ca                                               22

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(25)
<223> OTHER INFORMATION: 2'OMe modified

<400> SEQUENCE: 42
cgcucaacau cagucugaua agcuac                                           26

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (1)..(27)
<223> OTHER INFORMATION: 2'OMe modified

<400> SEQUENCE: 43
cacgcucaac aucagucuga uaagcuac                                             28

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 44
cagcucaaca ucagucugau aagcuac                                              27

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(35)
<223> OTHER INFORMATION: 2'OMe modified

<400> SEQUENCE: 45
gcugauucuc agcucaacau cagucugaua agcuac                                    36

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: 2'OMe modified

<400> SEQUENCE: 46
ucaacaucag ucugauaagc uagcg                                                25

<210> SEQ ID NO 47
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(27)
<223> OTHER INFORMATION: 2'OMe modified
```

```
<400> SEQUENCE: 47
ucaacaucag ucugauaagc uagcgug                                              27

<210> SEQ ID NO 48
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 48
ucaacaucag ucugauaagc uauggc                                               26

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(34)
<223> OTHER INFORMATION: 2'OMe modified

<400> SEQUENCE: 49
ucaacaucag ucugauaagc uagcugauuc ucagc                                     35

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 50
cagcucaaca ucagucugau aagcuac                                              27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 51
```
cagcucaaca ucagucugau aagcuac                                           27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 52
cagcucaaca ucagucugau aagcuac                                           27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 53
cagcucaaca ucagucugau aagcuac                                           27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 54
cagcucaaca ucagucugau aagcuac                                           27

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 55
cagcucaaca ucagucugau aagcuac                                    27

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 56
cagcucaaca ucagucugau aagcuac                                    27

<210> SEQ ID NO 57
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 57
ucaacaucag ucugauaagc uagcug                                     26

<210> SEQ ID NO 58
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 58
ucaacaucag ucugauaagc uagcug                                     26

<210> SEQ ID NO 59
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 59
ucaacaucag ucugauaagc uagcug                                     26

<210> SEQ ID NO 60
<211> LENGTH: 26
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 60
ucaacaucag ucugauaagc uagcug                                            26

<210> SEQ ID NO 61
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 61
ucaacaucag ucugauaagc uagcug                                            26

<210> SEQ ID NO 62
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 62
ucaacaucag ucugauaagc uagcug                                            26

<210> SEQ ID NO 63
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 63
ucaacaucag ucugauaagc uagcug                                            26

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'OMe modified

<400> SEQUENCE: 64
aaguggauau uguugccauc a                                                 21
```

```
<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(25)
<223> OTHER INFORMATION: 2'OMe modified

<400> SEQUENCE: 65
cgcaaccaua caaccuacua ccucac                                          26

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(27)
<223> OTHER INFORMATION: 2'OMe modified

<400> SEQUENCE: 66
cacgcaacca uacaaccuac uaccucac                                        28

<210> SEQ ID NO 67
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 67
cagcaaccau acaaccuacu accucac                                         27

<210> SEQ ID NO 68
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(35)
<223> OTHER INFORMATION: 2'OMe modified

<400> SEQUENCE: 68
```
gcugauucuc agcaaccaua caaccuacua ccucac        36

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: 2'OMe modified

<400> SEQUENCE: 69
aaccauacaa ccuacuaccu cagcg        25

<210> SEQ ID NO 70
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(27)
<223> OTHER INFORMATION: 2'OMe modified

<400> SEQUENCE: 70
aaccauacaa ccuacuaccu cagcgug        27

<210> SEQ ID NO 71
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 71
aaccauacaa ccuacuaccu cauggc        26

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(34)
<223> OTHER INFORMATION: 2'OMe modified

<400> SEQUENCE: 72
aaccauacaa ccuacuaccu cagcugauuc ucagc        35

<210> SEQ ID NO 73
<211> LENGTH: 27
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 73
cagcaaccau acaaccuacu accucac                                            27

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 74
cagcaaccau acaaccuacu accucac                                            27

<210> SEQ ID NO 75
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 75
cagcaaccau acaaccuacu accucac                                            27

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 76
cagcaaccau acaaccuacu accucac                                            27

<210> SEQ ID NO 77
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 77
cagcaaccau acaaccuacu accucac                                              27

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 78
cagcaaccau acaaccuacu accucac                                              27

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 79
cagcaaccau acaaccuacu accucac                                              27

<210> SEQ ID NO 80
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 80
aaccauacaa ccuacuaccu cagcug                                               26

<210> SEQ ID NO 81
<211> LENGTH: 26
<212> TYPE: RNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (1)..(26)
<223> OTHER INFORMATION: 2'OMe modified

<400> SEQUENCE: 81
aaccauacaa ccuacuaccu cagcug                                              26

<210> SEQ ID NO 82
<211> LENGTH: 26
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (1)..(26)
<223> OTHER INFORMATION: 2'OMe modified

<400> SEQUENCE: 82
aaccauacaa ccuacuaccu cagcug                                              26

<210> SEQ ID NO 83
<211> LENGTH: 26
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (1)..(26)
<223> OTHER INFORMATION: 2'OMe modified

<400> SEQUENCE: 83
aaccauacaa ccuacuaccu cagcug                                              26

<210> SEQ ID NO 84
<211> LENGTH: 26
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (1)..(26)
<223> OTHER INFORMATION: 2'OMe modified

<400> SEQUENCE: 84
aaccauacaa ccuacuaccu cagcug                                              26

<210> SEQ ID NO 85
<211> LENGTH: 26
<212> TYPE: RNA
<213> ORGANISM: Artificial Sequence
<220> FEATURE:
<223> OTHER INFORMATION: Description of Artificial Sequence: Synthetic
        oligonucleotide
<220> FEATURE:
<221> NAME/KEY: modified_base
<222> LOCATION: (1)..(26)
<223> OTHER INFORMATION: 2'OMe modified

<400> SEQUENCE: 85
aaccauacaa ccuacuaccu cagcug                                              26

```
<210> SEQ ID NO 86
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(26)
<223> OTHER INFORMATION: 2'OMe modified

<400> SEQUENCE: 86
aaccauacaa ccuacuaccu cagcug                                        26

<210> SEQ ID NO 87
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(30)
<223> OTHER INFORMATION: 2'OMe modified

<400> SEQUENCE: 87
cgugccauuc aacaucaguc ugauaagcua c                                  31

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'OMe modified

<400> SEQUENCE: 88
cgugccauca acaucagucu gauaagcuac                                    30

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 89
cgugccucaa caucagucug auaagcuac                                     29

<210> SEQ ID NO 90
<211> LENGTH: 29
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified

<400> SEQUENCE: 90
ucaacaucag ucugauaagc uauccgugc                                        29

<210> SEQ ID NO 91
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified

<400> SEQUENCE: 91
ucaacaucag ucugauaagc uauccgugc                                        29

<210> SEQ ID NO 92
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(30)
<223> OTHER INFORMATION: 2'OMe modified

<400> SEQUENCE: 92
cgugccauaa cuauacaacc uacuaccuca t                                     31

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'OMe modified

<400> SEQUENCE: 93
cgugccaaac uauacaaccu acuaccucat                                       30

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 94
cgugccaacu auacaaccua cuaccucat                                              29

<210> SEQ ID NO 95
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified

<400> SEQUENCE: 95
aacuauacaa ccuacuaccu cauccgugc                                              29

<210> SEQ ID NO 96
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified

<400> SEQUENCE: 96
aacuauacaa ccuacuaccu cauccgugc                                              29

<210> SEQ ID NO 97
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: 2'OMe modified

<400> SEQUENCE: 97
aacuauacaa ccuacuaccu ca                                                     22

<210> SEQ ID NO 98
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(30)
<223> OTHER INFORMATION: 2'OMe modified
```

<400> SEQUENCE: 98
cgugccauaa ccauacaacc uacuaccuca g    31

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'OMe modified

<400> SEQUENCE: 99
cgugccaaac cauacaaccu acuaccucag    30

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 100
cgugccaacc auacaaccua cuaccucag    29

<210> SEQ ID NO 101
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified

<400> SEQUENCE: 101
aaccauacaa ccuacuaccu cauccgugc    29

<210> SEQ ID NO 102
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified

<400> SEQUENCE: 102
aaccauacaa ccuacuaccu cauccgugc    29

```
<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(27)
<223> OTHER INFORMATION: 2'OMe modified

<400> SEQUENCE: 103
gugccaacua uacaaccuac uaccucat                                            28

<210> SEQ ID NO 104
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'F modified
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(15)
<223> OTHER INFORMATION: Locked nucleic acid
<220> FEATURE:
<221> NAME/KEY: modified_base
<222> LOCATION: (16)..(16)
<223> OTHER INFORMATION: 2'F modified

<400> SEQUENCE: 104
ucaacaucag ucugau                                                         16

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'OMe modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'OMe modified
<220> FEATURE:
<221> NAME/KEY: modified_base
<222> LOCATION: (7)..(8)
<223> OTHER INFORMATION: Locked nucleic acid
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: Locked nucleic acid
<220> FEATURE:
<221> NAME/KEY: modified_base
<222> LOCATION: (14)..(15)
<223> OTHER INFORMATION: 2'OMe modified
<220> FEATURE:
<221> NAME/KEY: modified_base
<222> LOCATION: (16)..(16)
<223> OTHER INFORMATION: Locked nucleic acid
<220> FEATURE:
<221> NAME/KEY: modified_base
<222> LOCATION: (17)..(19)
<223> OTHER INFORMATION: 2'OMe modified
<220> FEATURE:
<221> NAME/KEY: modified_base
<222> LOCATION: (20)..(21)
<223> OTHER INFORMATION: Locked nucleic acid
<220> FEATURE:
<221> NAME/KEY: modified_base
<222> LOCATION: (22)..(22)
<223> OTHER INFORMATION: 2'OMe modified

<400> SEQUENCE: 105
tcaacatcag tctgataagc ta                                           22

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(27)
<223> OTHER INFORMATION: 2'OMe modified

<400> SEQUENCE: 106
gugccaacua uacaaccuac uaccucat                                     28

<210> SEQ ID NO 107
<211> LENGTH: 22
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified
<220> FEATURE:
<221> NAME/KEY: modified_base
<222> LOCATION: (3)..(4)
<223> OTHER INFORMATION: 2'OMe modified
<220> FEATURE:
<221> NAME/KEY: modified_base
<222> LOCATION: (5)..(5)
<223> OTHER INFORMATION: 2'F modified
<220> FEATURE:
<221> NAME/KEY: modified_base
<222> LOCATION: (6)..(6)
<223> OTHER INFORMATION: 2'OMe modified
<220> FEATURE:
<221> NAME/KEY: modified_base
<222> LOCATION: (7)..(8)
<223> OTHER INFORMATION: 2'F modified
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(15)
<223> OTHER INFORMATION: 2'OMe modified
<220> FEATURE:
<221> NAME/KEY: modified_base
<222> LOCATION: (16)..(16)
<223> OTHER INFORMATION: 2'F modified
<220> FEATURE:
<221> NAME/KEY: modified_base
<222> LOCATION: (17)..(19)
<223> OTHER INFORMATION: 2'OMe modified
<220> FEATURE:
<221> NAME/KEY: modified_base
<222> LOCATION: (20)..(21)
<223> OTHER INFORMATION: 2'F modified
<220> FEATURE:
<221> NAME/KEY: modified_base
<222> LOCATION: (22)..(22)
<223> OTHER INFORMATION: 2'OMe modified

<400> SEQUENCE: 107
ucaacaucag ucugauaagc ua                                          22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'F modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'F modified
<220> FEATURE:
```

```
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(15)
<223> OTHER INFORMATION: Locked nucleic acid
<220> FEATURE:
<221> NAME/KEY: modified_base
<222> LOCATION: (16)..(16)
<223> OTHER INFORMATION: 2'F modified
<220> FEATURE:
<221> NAME/KEY: modified_base
<222> LOCATION: (17)..(19)
<223> OTHER INFORMATION: Locked nucleic acid
<220> FEATURE:
<221> NAME/KEY: modified_base
<222> LOCATION: (20)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 108
ucaacaucag ucugauaagc ua                                            22

<210> SEQ ID NO 109
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
```

```
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 109
aacuauacaa ccuacuaccu ca                                              22

<210> SEQ ID NO 110
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified

<400> SEQUENCE: 110
aacuauacaa ccuacu                                                     16
```

```
<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'OMe modified
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
<223> OTHER INFORMATION: Locked nucleic acid
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: Locked nucleic acid
<220> FEATURE:
<221> NAME/KEY: modified_base
<222> LOCATION: (17)..(17)
<223> OTHER INFORMATION: 2'OMe modified
<220> FEATURE:
<221> NAME/KEY: modified_base
<222> LOCATION: (18)..(21)
<223> OTHER INFORMATION: Locked nucleic acid
<220> FEATURE:
<221> NAME/KEY: modified_base
<222> LOCATION: (22)..(22)
<223> OTHER INFORMATION: 2'OMe modified

<400> SEQUENCE: 111
aactatacaa cctactacct ca                                             22

<210> SEQ ID NO 112
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'OMe modified
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
<223> OTHER INFORMATION: Locked nucleic acid
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: Locked nucleic acid

<400> SEQUENCE: 112
aactatacaa cctact                                                   16

<210> SEQ ID NO 113
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: 2'OMe modified
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
```

```
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: 2'OMe modified
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: 2'OMe modified

<400> SEQUENCE: 113
aacuauacaa ccuacuaccu ca                                              22

<210> SEQ ID NO 114
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified
```

```
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 114
aacuauacaa ccuacuaccu ca                                              22

<210> SEQ ID NO 115
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 115
```
aaccauacaa ccuacuaccu ca                                              22

<210> SEQ ID NO 116
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified

<400> SEQUENCE: 116
aaccauacaa ccuacu                                                     16

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'OMe modified

```
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
<223> OTHER INFORMATION: Locked nucleic acid
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: Locked nucleic acid
<220> FEATURE:
<221> NAME/KEY: modified_base
<222> LOCATION: (17)..(17)
<223> OTHER INFORMATION: 2'OMe modified
<220> FEATURE:
<221> NAME/KEY: modified_base
<222> LOCATION: (18)..(21)
<223> OTHER INFORMATION: Locked nucleic acid
<220> FEATURE:
<221> NAME/KEY: modified_base
<222> LOCATION: (22)..(22)
<223> OTHER INFORMATION: 2'OMe modified

<400> SEQUENCE: 117
aaccatacaa cctactacct ca                                        22

<210> SEQ ID NO 118
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'OMe modified
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
```

-continued

```
<223> OTHER INFORMATION: Locked nucleic acid
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: Locked nucleic acid

<400> SEQUENCE: 118
aaccatacaa cctact                                                 16

<210> SEQ ID NO 119
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'OMe modified
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: 2'OMe modified
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: 2'OMe modified
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: 2'OMe modified
<220> FEATURE:
<221> NAME/KEY: modified_base
<222> LOCATION: (18)..(21)
<223> OTHER INFORMATION: 2'F modified
<220> FEATURE:
```

<221> NAME/KEY: modified_base
<222> LOCATION: (22)..(22)
<223> OTHER INFORMATION: 2'OMe modified

<400> SEQUENCE: 119
aaccauacaa ccuacuaccu ca                                          22

<210> SEQ ID NO 120
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'F modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'F modified
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (8)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(16)
<223> OTHER INFORMATION: 2'F modified
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (18)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 120
aaccauacaa ccuacuaccu ca                                          22

<210> SEQ ID NO 121
<211> LENGTH: 30
<212> TYPE: RNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: 2'OMe modified
<220> FEATURE:
<221> NAME/KEY: misc_feature
<222> LOCATION: (1)..(23)
<223> OTHER INFORMATION: Phosphorothioate linkage

<400> SEQUENCE: 121
acaaacacca uugucacacu ccauccgugc                               30

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'OMe modified

<400> SEQUENCE: 122
cgugccacaa acaccauugu cacacuccac                               30

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified
<220> FEATURE:
<221> NAME/KEY: misc_feature
<222> LOCATION: (7)..(28)
<223> OTHER INFORMATION: Phosphorothioate linkage

<400> SEQUENCE: 123
cgugccaacc auacaaccua cuaccucag                                29

<210> SEQ ID NO 124
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(30)
<223> OTHER INFORMATION: 2'OMe modified

<400> SEQUENCE: 124
cgugccauaa cuauacaacc uacuaccuca t                             31

```
<210> SEQ ID NO 125
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 125
cgugccaacu auacaaccua cuaccucat                                          29

<210> SEQ ID NO 126
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(28)
<223> OTHER INFORMATION: 2'OMe modified
<220> FEATURE:
<221> NAME/KEY: modified_base
<222> LOCATION: (29)..(29)
<223> OTHER INFORMATION: 2'O-Propargyl modified

<400> SEQUENCE: 126
cgugccaacu auacaaccua cuaccucag                                          29

<210> SEQ ID NO 127
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 127
cgugccaacu auacaaccua cuaccucat                                          29

<210> SEQ ID NO 128
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(28)
<223> OTHER INFORMATION: 2'OMe modified

<400> SEQUENCE: 128
cgugccaacu auacaaccua cuaccuca                                           28
```

```
<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 129
cgugccucaa caucagucug auaagcuac                                       29

<210> SEQ ID NO 130
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 130
cgugccucaa caucagucug auaagcuac                                       29

<210> SEQ ID NO 131
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(29)
<223> OTHER INFORMATION: 2'OMe modified
<220> FEATURE:
<221> NAME/KEY: modified_base
<222> LOCATION: (29)..(29)
<223> OTHER INFORMATION: 2'O-Propargyl modified

<400> SEQUENCE: 131
cgugccucaa caucagucug auaagcuag                                       29

<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 132
cgugccucaa caucagucug auaagcuac                                       29
```

<210> SEQ ID NO 133
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(28)
<223> OTHER INFORMATION: 2'OMe modified

<400> SEQUENCE: 133
cgugccucaa caucagucug auaagcua                                           28

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(28)
<223> OTHER INFORMATION: 2'OMe modified

<400> SEQUENCE: 134
cgugccaacu auacaaccua cuaccucat                                          29

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(19)
<223> OTHER INFORMATION: 2'OMe modified
<220> FEATURE:
<221> NAME/KEY: modified_base
<222> LOCATION: (20)..(20)
<223> OTHER INFORMATION: Locked nucleic acid
<220> FEATURE:
<221> NAME/KEY: modified_base
<222> LOCATION: (21)..(21)
<223> OTHER INFORMATION: 2'OMe modified
<220> FEATURE:
<221> NAME/KEY: modified_base
<222> LOCATION: (22)..(22)
<223> OTHER INFORMATION: Locked nucleic acid
<220> FEATURE:
<221> NAME/KEY: modified_base
<222> LOCATION: (23)..(23)
<223> OTHER INFORMATION: 2'OMe modified
<220> FEATURE:
<221> NAME/KEY: modified_base
<222> LOCATION: (24)..(24)
<223> OTHER INFORMATION: Locked nucleic acid
<220> FEATURE:
<221> NAME/KEY: modified_base
<222> LOCATION: (25)..(25)
<223> OTHER INFORMATION: 2'OMe modified
<220> FEATURE:
<221> NAME/KEY: modified_base
<222> LOCATION: (26)..(26)
<223> OTHER INFORMATION: Locked nucleic acid
<220> FEATURE:
<221> NAME/KEY: modified_base
<222> LOCATION: (27)..(27)
<223> OTHER INFORMATION: 2'OMe modified
<220> FEATURE:
<221> NAME/KEY: modified_base
<222> LOCATION: (28)..(28)
<223> OTHER INFORMATION: Locked nucleic acid

<400> SEQUENCE: 135
cgugccaacu auacaaccua ctacctcat                29

<210> SEQ ID NO 136
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'OMe modified
<220> FEATURE:
<221> NAME/KEY: modified_base
<222> LOCATION: (9)..(9)
<223> OTHER INFORMATION: Locked nucleic acid
<220> FEATURE:
<221> NAME/KEY: modified_base
<222> LOCATION: (10)..(10)
<223> OTHER INFORMATION: 2'OMe modified
<220> FEATURE:
<221> NAME/KEY: modified_base
<222> LOCATION: (11)..(11)
<223> OTHER INFORMATION: Locked nucleic acid
<220> FEATURE:
<221> NAME/KEY: modified_base
<222> LOCATION: (12)..(12)
<223> OTHER INFORMATION: 2'OMe modified
<220> FEATURE:
<221> NAME/KEY: modified_base
<222> LOCATION: (13)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'OMe modified
<220> FEATURE:
<221> NAME/KEY: modified_base
<222> LOCATION: (15)..(15)
<223> OTHER INFORMATION: Locked nucleic acid
<220> FEATURE:
<221> NAME/KEY: modified_base
<222> LOCATION: (16)..(28)
<223> OTHER INFORMATION: 2'OMe modified

<400> SEQUENCE: 136
cgugccaacu guacaaacua cuaccucat                29

<210> SEQ ID NO 137
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:

```
<221> NAME/KEY: modified_base
<222> LOCATION: (1)..(8)
<223> OTHER INFORMATION: 2'OMe modified
<220> FEATURE:
<221> NAME/KEY: modified_base
<222> LOCATION: (9)..(10)
<223> OTHER INFORMATION: 2'F modified
<220> FEATURE:
<221> NAME/KEY: modified_base
<222> LOCATION: (11)..(11)
<223> OTHER INFORMATION: 2'OMe modified
<220> FEATURE:
<221> NAME/KEY: modified_base
<222> LOCATION: (12)..(12)
<223> OTHER INFORMATION: 2'F modified
<220> FEATURE:
<221> NAME/KEY: modified_base
<222> LOCATION: (13)..(13)
<223> OTHER INFORMATION: 2'OMe modified
<220> FEATURE:
<221> NAME/KEY: modified_base
<222> LOCATION: (14)..(14)
<223> OTHER INFORMATION: 2'F modified
<220> FEATURE:
<221> NAME/KEY: modified_base
<222> LOCATION: (15)..(16)
<223> OTHER INFORMATION: 2'OMe modified
<220> FEATURE:
<221> NAME/KEY: modified_base
<222> LOCATION: (17)..(19)
<223> OTHER INFORMATION: 2'F modified
<220> FEATURE:
<221> NAME/KEY: modified_base
<222> LOCATION: (20)..(20)
<223> OTHER INFORMATION: 2'OMe modified
<220> FEATURE:
<221> NAME/KEY: modified_base
<222> LOCATION: (21)..(22)
<223> OTHER INFORMATION: 2'F modified
<220> FEATURE:
<221> NAME/KEY: modified_base
<222> LOCATION: (23)..(23)
<223> OTHER INFORMATION: 2'OMe modified
<220> FEATURE:
<221> NAME/KEY: modified_base
<222> LOCATION: (24)..(27)
<223> OTHER INFORMATION: 2'F modified
<220> FEATURE:
<221> NAME/KEY: modified_base
<222> LOCATION: (28)..(28)
<223> OTHER INFORMATION: 2'OMe modified

<400> SEQUENCE: 137
cgugccaacu auacaaccua cuaccucat                                      29

<210> SEQ ID NO 138
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'OMe modified
<220> FEATURE:
<221> NAME/KEY: modified_base
<222> LOCATION: (7)..(8)
<223> OTHER INFORMATION: Locked nucleic acid
<220> FEATURE:
<221> NAME/KEY: modified_base
<222> LOCATION: (9)..(10)
<223> OTHER INFORMATION: 2'F modified
```

```
<220> FEATURE:
<221> NAME/KEY: modified_base
<222> LOCATION: (11)..(11)
<223> OTHER INFORMATION: Locked nucleic acid
<220> FEATURE:
<221> NAME/KEY: modified_base
<222> LOCATION: (12)..(12)
<223> OTHER INFORMATION: 2'F modified
<220> FEATURE:
<221> NAME/KEY: modified_base
<222> LOCATION: (13)..(13)
<223> OTHER INFORMATION: Locked nucleic acid
<220> FEATURE:
<221> NAME/KEY: modified_base
<222> LOCATION: (14)..(14)
<223> OTHER INFORMATION: 2'F modified
<220> FEATURE:
<221> NAME/KEY: modified_base
<222> LOCATION: (15)..(16)
<223> OTHER INFORMATION: Locked nucleic acid
<220> FEATURE:
<221> NAME/KEY: modified_base
<222> LOCATION: (17)..(19)
<223> OTHER INFORMATION: 2'F modified
<220> FEATURE:
<221> NAME/KEY: modified_base
<222> LOCATION: (20)..(20)
<223> OTHER INFORMATION: Locked nucleic acid
<220> FEATURE:
<221> NAME/KEY: modified_base
<222> LOCATION: (21)..(22)
<223> OTHER INFORMATION: 2'F modified
<220> FEATURE:
<221> NAME/KEY: modified_base
<222> LOCATION: (23)..(23)
<223> OTHER INFORMATION: Locked nucleic acid
<220> FEATURE:
<221> NAME/KEY: modified_base
<222> LOCATION: (24)..(27)
<223> OTHER INFORMATION: 2'F modified
<220> FEATURE:
<221> NAME/KEY: modified_base
<222> LOCATION: (28)..(28)
<223> OTHER INFORMATION: Locked nucleic acid

<400> SEQUENCE: 138
cgugccaacu auacaaccua cuaccucat                                            29

<210> SEQ ID NO 139
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(33)
<223> OTHER INFORMATION: 2'OMe modified

<400> SEQUENCE: 139
acugcgaacc aucaacauca gucugauaag cuagaauccu uuauc                          45

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gguucgcagu gauaaaggau u                                                    21
```

```
<210> SEQ ID NO 141
<211> LENGTH: 90
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)..(33)
<223> OTHER INFORMATION: 2'OMe modified
<220> FEATURE:
<221> NAME/KEY: modified_base
<222> LOCATION: (57)..(78)
<223> OTHER INFORMATION: 2'OMe modified

<400> SEQUENCE: 141
acugcgaacc aucaacauca gucugauaag cuagaauccu uuaucacugc gaaccaucaa      60
caucagucug auaagcuaga auccuuuauc                                      90

<210> SEQ ID NO 142
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142 aauuugc                                                                7

<210> SEQ ID NO 143
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143 gcaaauu                                                                7

<210> SEQ ID NO 144
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uagcuuauca gacugauguu ga                                              22

<210> SEQ ID NO 145
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ugagguagua gguuguauag uu                                              22

<210> SEQ ID NO 146
<211> LENGTH: 22
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 146
ugagguagua gguuguaugg uu                                              22

<210> SEQ ID NO 147
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uggaguguga caauguguu ug                                               22

<210> SEQ ID NO 148
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ucaacaucag ucugauaagc ua                                              22

<210> SEQ ID NO 149
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
aacuauacaa ccuacuaccu ca                                              22

<210> SEQ ID NO 150
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
caaacaccau ugucacacuc ca                                              22

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
aaguggauau uguugccauc a                                               21

<210> SEQ ID NO 152
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 152
aaccauacaa ccuacuaccu ca                                              22

<210> SEQ ID NO 153
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'F modified
<220> FEATURE:
<221> NAME/KEY: modified_base
<222> LOCATION: (3)..(4)
<223> OTHER INFORMATION: Locked nucleic acid
<220> FEATURE:
<221> NAME/KEY: modified_base
<222> LOCATION: (5)..(5)
<223> OTHER INFORMATION: 2'F modified
<220> FEATURE:
<221> NAME/KEY: modified_base
<222> LOCATION: (6)..(6)
<223> OTHER INFORMATION: Locked nucleic acid
<220> FEATURE:
<221> NAME/KEY: modified_base
<222> LOCATION: (7)..(8)
<223> OTHER INFORMATION: 2'F modified
<220> FEATURE:
<221> NAME/KEY: modified_base
<222> LOCATION: (9)..(10)
<223> OTHER INFORMATION: Locked nucleic acid
<220> FEATURE:
<221> NAME/KEY: modified_base
<222> LOCATION: (11)..(13)
<223> OTHER INFORMATION: 2'F modified
<220> FEATURE:
<221> NAME/KEY: modified_base
<222> LOCATION: (14)..(15)
<223> OTHER INFORMATION: Locked nucleic acid
<220> FEATURE:
<221> NAME/KEY: modified_base
<222> LOCATION: (16)..(16)
<223> OTHER INFORMATION: 2'F modified
<220> FEATURE:
<221> NAME/KEY: modified_base
<222> LOCATION: (17)..(19)
<223> OTHER INFORMATION: Locked nucleic acid
<220> FEATURE:
<221> NAME/KEY: modified_base
<222> LOCATION: (20)..(21)
<223> OTHER INFORMATION: 2'F modified
<220> FEATURE:
<221> NAME/KEY: modified_base
<222> LOCATION: (22)..(22)
<223> OTHER INFORMATION: Locked nucleic acid

<400> SEQUENCE: 153
ucaacaucag ucugauaagc ua                                              22

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

-continued

```
      Synthetic oligonucleotide
<220> FEATURE:
<221> NAME/KEY: modified_base
<222> LOCATION: (1)..(27)
<223> OTHER INFORMATION: 2'OMe modified

<400> SEQUENCE: 154
gugccucaac aucagucuga uaagcuac                                              28

<210> SEQ ID NO 155
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(4)
<223> OTHER INFORMATION: 2'OMe modified
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (6)..(6)
<223> OTHER INFORMATION: 2'OMe modified
<220> FEATURE:
<221> NAME/KEY: modified_base
<222> LOCATION: (7)..(8)
<223> OTHER INFORMATION: Locked nucleic acid
<220> FEATURE:
<221> NAME/KEY: modified_base
<222> LOCATION: (9)..(10)
<223> OTHER INFORMATION: 2'OMe modified
<220> FEATURE:
<221> NAME/KEY: modified_base
<222> LOCATION: (11)..(13)
<223> OTHER INFORMATION: Locked nucleic acid
<220> FEATURE:
<221> NAME/KEY: modified_base
<222> LOCATION: (14)..(15)
<223> OTHER INFORMATION: 2'OMe modified
<220> FEATURE:
<221> NAME/KEY: modified_base
<222> LOCATION: (16)..(16)
<223> OTHER INFORMATION: Locked nucleic acid

<400> SEQUENCE: 155
tcaacatcag tctgat                                                           16

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(21)
<223> OTHER INFORMATION: 2'OMe modified

<400> SEQUENCE: 156
```
ggaaaucccu ggcaauguga uc                                                     22

<210> SEQ ID NO 157
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(23)
<223> OTHER INFORMATION: 2'OMe modified

<400> SEQUENCE: 157
acaaacacca uugucacacu cca                                                    23

<210> SEQ ID NO 158
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 158
cagcucaaca ucagucugau aagcuac                                                27

<210> SEQ ID NO 159
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(37)
<223> OTHER INFORMATION: 2'OMe modified

<400> SEQUENCE: 159
cagcaaccau acaaccuacu accucagcug aucucagc                                    38

<210> SEQ ID NO 160
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(26)
<223> OTHER INFORMATION: 2'OMe modified

<400> SEQUENCE: 160
cagcaaccau acaaccuacu accucac                                                27

```
<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'OMe modified
<220> FEATURE:
<221> NAME/KEY: misc_feature
<222> LOCATION: (7)..(29)
<223> OTHER INFORMATION: Phosphorothioate linkage

<400> SEQUENCE: 161
cgugccacaa acaccauugu cacacuccac                                           30

<210> SEQ ID NO 162
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: modified_base
<222> LOCATION: (1)..(23)
<223> OTHER INFORMATION: 2'OMe modified
<220> FEATURE:
<221> NAME/KEY: misc_feature
<222> LOCATION: (21)..(23)
<223> OTHER INFORMATION: Phosphorothioate linkage

<400> SEQUENCE: 162
acaaacacca uugucacacu cca                                                  23
```